(12) United States Patent
Meng

(10) Patent No.: US 9,447,084 B2
(45) Date of Patent: Sep. 20, 2016

(54) ANTIPARISITIC AND PESTICIDAL ISOXAZOLINE COMPOUNDS

(71) Applicant: MERIAL LIMITED, Duluth, GA (US)

(72) Inventor: Charles Q Meng, Grayson, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/528,172

(22) Filed: Oct. 30, 2014

(65) Prior Publication Data

US 2015/0126523 A1 May 7, 2015

Related U.S. Application Data

(60) Provisional application No. 61/898,578, filed on Nov. 1, 2013.

(51) Int. Cl.
| | |
|---|---|
| *C07D 413/12* | (2006.01) |
| *C07D 413/14* | (2006.01) |
| *A01N 43/80* | (2006.01) |
| *C07D 413/10* | (2006.01) |

(52) U.S. Cl.
CPC ............. *C07D 413/12* (2013.01); *A01N 43/80* (2013.01); *C07D 413/10* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 7,662,972 B2 | 2/2010 | Mita et al. | |
| 7,951,828 B1 | 5/2011 | Mita et al. | |
| 7,964,204 B2 | 6/2011 | Lahm et al. | |
| 8,053,452 B2 | 11/2011 | Mita et al. | |
| 8,119,671 B2 | 2/2012 | Mita et al. | |
| 8,242,283 B2 | 8/2012 | Mita et al. | |
| 8,318,757 B2 | 11/2012 | Mita et al. | |
| 8,410,153 B2 | 4/2013 | Lahm et al. | |
| 8,618,126 B2 | 12/2013 | Le Hir de Fallois et al. | |
| 2007/0066617 A1* | 3/2007 | Mita et al. | 514/241 |
| 2010/0137372 A1 | 6/2010 | Ihara et al. | |
| 2010/0179194 A1* | 7/2010 | Mihara et al. | 514/340 |
| 2010/0179195 A1 | 7/2010 | Lahm et al. | |
| 2010/0279999 A1 | 11/2010 | Renold et al. | |
| 2011/0245274 A1 | 10/2011 | Nanchen et al. | |
| 2012/0238517 A1 | 9/2012 | Cassayre et al. | |
| 2012/0324604 A1 | 12/2012 | Dutton et al. | |
| 2013/0085064 A1 | 4/2013 | Hoegger et al. | |
| 2013/0338197 A1 | 12/2013 | Mita et al. | |

FOREIGN PATENT DOCUMENTS

| | | |
|---|---|---|
| WO | 2008/122375 | 10/2008 |
| WO | 2010/025998 | 3/2010 |
| WO | 2012/163959 | 12/2012 |
| WO | 2013/050302 | 4/2013 |

* cited by examiner

*Primary Examiner* — Emily Bernhardt
(74) *Attorney, Agent, or Firm* — Judy Jarecki-Black; John Ezcurra; Merial, Inc.

(57) ABSTRACT

The present invention relates to novel and inventive isoxazoline of formula (I) and salts thereof:

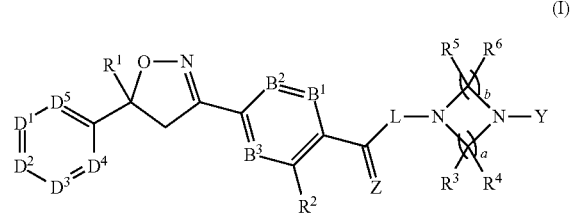

wherein variables $D^1$, $D^2$, $D^3$, $D^4$, $D^5$, $R^1$, $B^1$, $B^2$, $B^3$, $R^2$, $R^3$, $R^4$, $R^5$, $R^6$, Y, Z, L, a and b are described herein are as defined in the description. The invention also relates to parasiticidal and pesticidal compositions comprising the isoxazoline compounds of formula (I), processes for their preparation and their uses to prevent or treat parasitic infections or infestations in animals and as pesticides.

30 Claims, No Drawings

ANTIPARISITIC AND PESTICIDAL ISOXAZOLINE COMPOUNDS

CROSS REFERENCE TO RELATED APPLICATIONS

This application claims the benefit of priority to U.S. Provisional Patent Application No. 61/898,578 filed Nov. 1, 2013, which is incorporated herein by reference in its entirety.

INCORPORATION BY REFERENCE

The foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to novel and inventive parasiticidal and pesticidal isoxazoline compounds of formula (I):

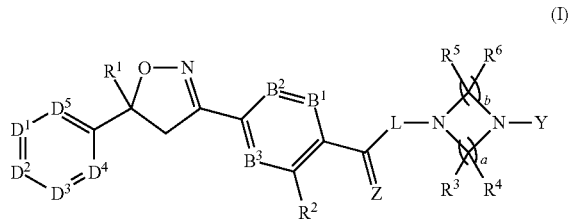

wherein, $D^1$, $D^2$, $D^3$, $D^4$, $D^5$, $B^1$, $B^2$, $B^3$, $R^1$, $R^2$, $R^3$, $R^4$, $R^5$, $R^6$, Y, Z, L, a and b are as defined below, and compositions comprising at least one compound of formula (I) in combination with a pharmaceutically acceptable or agriculturally acceptable carrier. The invention also relates to uses of the compounds and methods comprising the compounds for the treatment and prevention of parasitic infections or infestations and for controlling pests in crops, plants, plant propagation material and material derived from wood.

BACKGROUND OF THE INVENTION

Animals such as mammals and birds are often susceptible to parasite infestations/infections. These parasites may be ectoparasites, such as insects, and endoparasites such as nematodes and other worms. Domesticated animals, such as cats and dogs, are often infested with one or more of the following ectoparasites:
  fleas (e.g. *Ctenocephalides* spp., such as *Ctenocephalides felis* and the like);
  ticks (e.g. *Rhipicephalus* spp., *Ixodes* spp., *Dermacentor* spp., *Amblyoma* spp., and the like);
  mites (e.g. *Demodex* spp., *Sarcoptes* spp., *Otodectes* spp., and the like);
  lice (e.g. *Trichodectes* spp., *Cheyletiella* spp., *Linognathus* spp. and the like);
  mosquitoes (*Aedes* spp., *Culex* spp., *Anopheles* spp. and the like); and
  flies (*Hematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borrelioses (Lyme disease caused by *Borrelia burgdorferi*), babesiosis (or piroplasmoses caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, a parasite which is prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting companion animals and poultry. Other parasites which occur in the gastrointestinal tract of animals and humans include *Ancylostoma*, *Necator*, *Ascaris*, *Strongyloides*, *Trichinella*, *Capillaria*, *Toxocara*, *Toxascaris*, *Trichiris*, *Enterobius* and parasites which are found in the blood or other tissues and organs such as filarial worms and the extra intestinal stages of *Strogyloides*, *Toxocara* and *Trichinella*. Various patent publications have described isoxazoline derivatives having pesticidal properties, compositions comprising these compounds and use of the compounds in the fields of agriculture and veterinary medicine.

International Patent Publication Nos. WO2009/072621, WO 2009/001942, WO 2009/024541, WO 2009/035004, WO 2008/108448, WO 2005/085216, WO 2007/075459, WO 2007/079162, WO 2008/150393, WO 2008/154528, WO 2009/002809, WO 2009/003075, WO 2009/045999, WO 2009/051956, WO 2009/02451, WO 2008/122375, WO 2007/125984, WO 2008/130651, WO 2009/022746, JP 2008/133273, WO 2008/126665, WO 2009/049846 and WO 2008/019760 describe pesticidal isoxazoline derivatives, compositions comprising the compounds and uses of the compounds against parasites and pests that harm animals and plants.

More recently, International Patent Publication Nos. WO 2009/141093, WO 2010/027051, WO 2010/005048, WO 2009/049845, WO 2009/04946, WO 2010/020521, WO 2010/020522, WO 2010/070068, WO 2010/084067, WO 2010/086225, WO 2010/108733, WO2010/070068, WO2010/079077, WO 2010/072781, WO2010/112545, WO2009/025983, WO2009/126668 and WO2010/090344 and Japanese Patent Publication Nos. JP2010/235590 and JP2010/168367 have also described isoxazoline derivatives having pesticidal activity and compositions comprising these compounds.

WO 2009/097992 describes arylpyrrolines with pesticidal activity, and WO 2008/128711 and WO 2010/043315, describes aryl pyrrolidines that are active against pests. WO 2009/112275 describes condensed ring aryl compounds with pesticidal activity.

Although some of these publications describe compounds containing a substituted isoxazoline ring having pesticidal and parasiticidal properties, none of the foregoing publications describe compounds of formula (I), that possess parasiticidal and pesticidal activity, particularly for controlling endoparasites or ectoparasites in or on animals.

The foregoing documents and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

SUMMARY OF THE INVENTION

The present invention provides novel and inventive isoxazoline compounds of formula (I), (IA), (IB), (IC), (ID) and (IE) shown below that are biologically active against parasites that harm animals and against pests that damage crops, plants, plant propagation material and material derived from wood. Accordingly, the application provides parasiticidal and pesticidal compositions comprising the isoxazoline compounds in combination with a pharmaceutically acceptable carrier or an agriculturally acceptable carrier. The present invention also provides methods for the treatment or prevention of a parasitic infection or infestation in an animal and for controlling pests that harm plants, plant propagation material and material derived from wood, which comprise administering an effective amount of a compound of the invention to the animal or to the plants, or the soil in which the infected plant grows, or the wood-derived material, with a pesticidally effective amount of a compound of formula (I).

A first object of the invention is to provide parasiticidal and pesticidal novel and inventive isoxazoline compounds of formulae (I), (IA), (IB), (IC), (ID) and (IE):

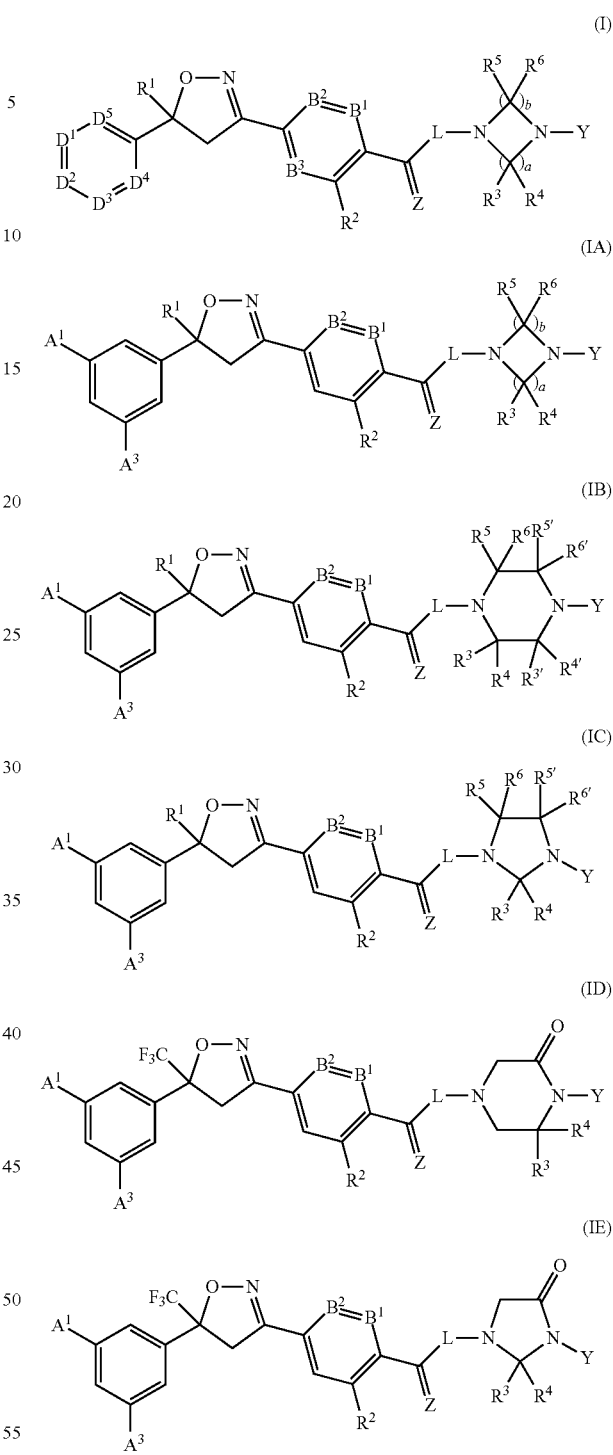

wherein variables $D^1$, $D^2$, $D^3$, $D^4$, $D^5$, $R^1$, $A^1$, $A^3$, $B^1$, $B^2$, $B^3$, $R^2$, $R^3$, $R^{3'}$, $R^4$, $R^{4'}$, $R^5$, $R^{5'}$, $R^6$, $R^{6'}$, Y, Z, L, a and b are described herein.

Further, this invention provides for antiparasitic compositions for the treatment or prevention of parasitic infections and infestations in animals comprising a parasiticidally effective amount of at least one compound of formula (I), (IA), (IB), (IC), (ID) or (IE), or a veterinarily acceptable salt thereof, in combination with a pharmaceutically acceptable carrier. The compositions may be formulated for oral, subcutaneous, parenteral, and topical administration including spot-on and pour-on administration.

Another object of the invention is to provide pesticidal compositions comprising at least one compound of formula (I), (IA), (IB), (IC), (ID) or (IE), or a pesticidally acceptable salt thereof, for combating pests that are harmful to plants, plant propagation material or material derived from wood in combination with a pesticidally effective carrier.

Another object of the invention is to provide veterinary compositions comprising at least one compound of formula (I), (IA), (IB), (IC), (ID) or (IE), or a veterinarily acceptable salt thereof, for combating parasites comprising a parasiticidally effective amount of the compounds of the invention, or veterinarily acceptable salts thereof, in combination with one more other active agent and a veterinarily acceptable carrier or diluent.

Another object of the invention is to provide agricultural compositions comprising at least one compound of formula (I), (IA), (IB), (IC), (ID) or (IE), or an agriculturally acceptable salt thereof, for combating pests comprising a pesticidally effective amount of the compounds of the invention, or agriculturally acceptable salts thereof, in combination with one more other active agent and an agriculturally acceptable carrier or diluent.

Another object of the invention is to provide plant propagation material (e.g. seed), comprising at least one compound of formula (I), (IA), (IB), (IC), (ID) or (IE) or agriculturally acceptable salts thereof, and plant propagation material that has been treated with at least one compound of formula (I), (IA), (IB), (IC), (ID) or (IE), or an agriculturally acceptable salt thereof, or a composition comprising the compound.

Another object of this invention is to provide methods of treatment and prevention of parasitic infections or infestations in or on an animal, which comprise treating the infected animal with a parasiticidally effective amount of a compound of formula (I), (IA), (IB), (IC), (ID) or (IE), or a veterinarily acceptable salt thereof.

Another object of this invention is to provide methods for combating pests on crops, plants, plant propagation material or material derived from wood, which comprises treating the infected plant, or the soil in which the infected plant grows, or the wood-derived material with a pesticidally effective amount of a compound of formula (I), (IA), (IB), (IC), (ID) or (IE), or a pesticidally acceptable salt thereof.

Another object of the invention is to provide methods for combating or controlling pests at a locus (excluding an animal), comprising administering a pesticidally or parasiticidally effective amount of a compound of formula (I), (IA), (IB), (IC), (ID) or (IE), or veterinarily or agriculturally acceptable salts thereof, to the locus.

Another object of the invention is to provide use of a compound of formula (I), (IA), (IB), (IC), (ID) or (IE), or a veterinarily acceptable salt thereof, for use in the treatment or prevention of a parasitic infection or infestation in or on an animal. Still another object of the invention is use of a compound of formula (I), (IA), (IB), (IC), (ID) or (IE), or a veterinarily acceptable salt thereof, in the preparation of a medicament for the treatment or prevention of a parasitic infestation or infection in or on an animal. In still another embodiment, the invention provides a compound of formula Still another object of this invention is to provide processes for the preparation of isoxazoline compounds of formula (I), (I), (IA), (IB), (IC), (ID) or (IE).

The present invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass isoxazoline compounds that have been previously disclosed in the art.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention. These and other embodiments are disclosed or are obvious from and encompassed by, the following Detailed Description.

DETAILED DESCRIPTION OF THE INVENTION

The novel and inventive isoxazoline compounds of formula (I), (IA), (IB), (IC), (ID) and (IE) of the invention have been found to have superior activity against pests, including parasites that cause harm to animals, and pests that damage plants, plant propagation material and material containing wood or derived from wood. Accordingly, the compounds of the invention have been found useful for preventing and treating a parasitic infestation/infection in an animal and for controlling and eradicating pests that damage plants, plant propagation material and material derived from wood.

The present invention provides novel and inventive isoxazoline compounds and compositions comprising the compounds. Furthermore, the invention provides methods for preventing and/or treating a parasitic infestation or infection in an animal, and the use of the compounds for treating a parasitic infestation or infection in an animal or the use of the compounds in the manufacture of a medicament for treating a parasitic infestation or infection in an animal.

In one embodiment, the invention provides novel and inventive isoxazoline compounds that are exceptionally potent against ectoparasites that harm animals. Thus, the compounds described herein may be used to treat and prevent parasitic infestations in animals.

In another embodiment, the present invention provides uses of the compounds for controlling and eradicating pests that cause damage to plants, plant propagation material and material derived from wood. In still another embodiment, the present invention provides uses of the isoxazoline compounds to control environmental pests.

A first object of the invention is to provide parasiticidal and pesticidal novel and inventive isoxazoline compounds of formula (I):

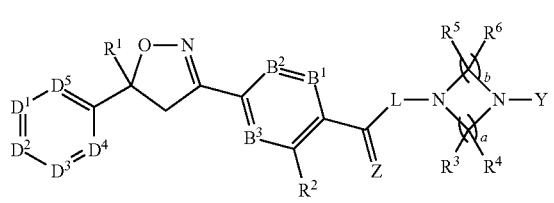

(I)

wherein:

each of $D^1$, $D^2$, $D^3$, $D^4$ and $D^5$ are independently N or $C-A^1$, $C-A^2$, $C-A^3$, $C-A^4$ and $C-A^5$, respectively, with the proviso that at most only three of $D^1$, $D^2$, $D^3$, $D^4$ and $D^5$ may be simultaneously N;

$R^1$ is halogen, alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of hydroxy, amino, alkyl- or di(alkyl)amino, alkoxy, haloalkoxy, alkylthio or haloalkylthio;

$A^1$, $A^2$, $A^3$, $A^4$ and $A^5$ are independently hydrogen, halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, —CN or —$NO_2$;

$B^1$, $B^2$ and $B^3$ are independently N or C—X;

each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —$NO_2$; or two adjacent X together form a 5- or 6-membered ring together with the carbon atoms to which they are bonded by forming —$CH_2CH_2CH_2$—, —CH═CH—CH═CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH═N— or —SCH═N—, $R^2$ is hydrogen, halogen, alkyl, haloalkyl, alkenyl, haloalkenyl, alkynyl, haloalkynyl, hydroxy, alkoxy, amino, alkyl- or dialkylamino, —CN or —$NO_2$;

$R^3$, $R^4$, $R^5$ and $R^6$ are each independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^3$ and $R^4$ together with the carbon atom to which they are bonded together form C═W; or $R^5$ and $R^6$ together with the carbon atom to which they are bonded together form C═W, with the proviso that at least one of $R^3$ and $R^4$ together or $R^5$ and $R^6$ together form the group C═W;

$R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$— or —CN; or Y is Y-1, Y-2, Y-3, Y-4, Y-5, Y-6, Y-7, Y-8, Y-9, Y-10, Y-11, Y-12 or Y-13, wherein # signifies the point of attachment;

Y-1

Y-2

Y-3

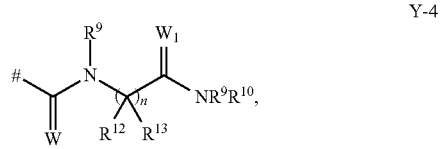

Y-4

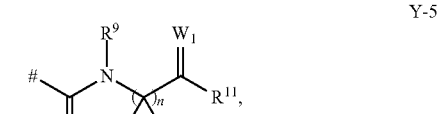

Y-5

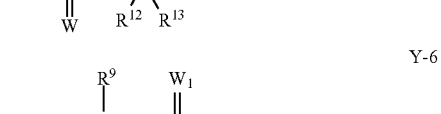

Y-6

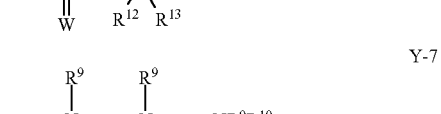

Y-7

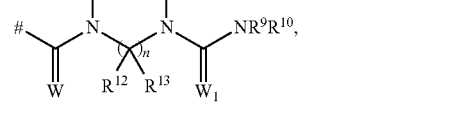

Y-8

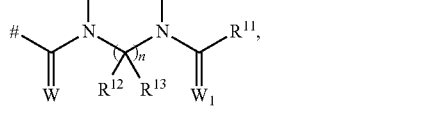

Y-9

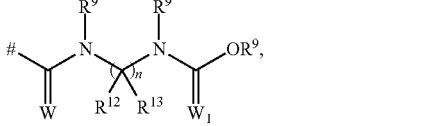

Y-10

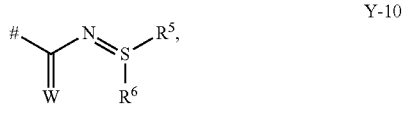

Y-11

-continued

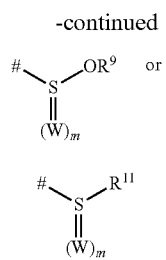

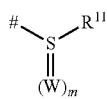

wherein each $R^9$, $R^{10}$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)-$, $R_7S(O)_2-$, $R_7C(O)-$, $R_7R_8NC(O)-$, $R_7OC(O)-$, $R_7C(O)O-$, $R_7C(O)NR_8-$;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^{12}$ and $R^{13}$ together with the carbon atom to which they are bonded together form C=W;

W, $W_1$ and Z are independently O, S or $NR^7$;

L is a direct bond, $-CR^3R^4-$, $-NR^8-$ or $-O-$;

a is 1, 2 or 3;

b is 1, 2 or 3;

n is 1, 2, 3 or 4; and m is 0, 1 or 2.

In one embodiment of formula (I), $D^1$, $D^2$, $D^3$, $D^4$ and $D^5$ are each $C-A^1$, $C-A^2$, $C-A^3$, $C-A^4$ and $C-A^5$, respectively.

In one embodiment of formula (I), $B^1$, $B^2$ and $B^3$ are C—H.

In one embodiment of formula (I), $B^1$ and $B^2$ are each independently C—X and the two adjacent X together with the carbon atoms to which they are attached form a 5- or 6-membered ring by forming —CH=CH—CH=CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—.

In another embodiment of formula (I), $B^1$ and $B^2$ are each independently C—X and the two adjacent X together with the carbon atoms to which they are attached form a naphthalene ring by forming —CH=CH—CH=CH—.

In yet another embodiment of formula (I), $R^2$ is hydrogen and $B^1$ and $B^2$ are each independently C—X and the two adjacent X together with the carbon atoms to which they are attached form a naphthalene ring by forming —CH=CH—CH=CH—.

In one embodiment of formula (I), $R^3$ and $R^4$ together form a carbonyl group C=O.

In still another embodiment, $R^5$ and $R^6$ together form a carbonyl group C=O.

In another embodiment of formula (I), a is 1 or 2; b is 1 or 2, wherein a+b is 3 or 4;

$R^3$ and $R^4$ together C=O and $R^5$ and $R^6$ together both form C=O.

In another embodiment of formula (I), $R^1$ is alkyl or haloalkyl. In another embodiment, $R^1$ is $C_1$-$C_4$ alkyl or $C_1$-$C_4$haloalkyl. In another embodiment, $R^1$ is $CF_3$.

In another embodiment of formula (I), $D^1$, $D^2$, $D^3$, $D^4$ and $D^5$ are each $C-A^1$, $C-A^2$, $C-A^3$, $C-A^4$ and $C-A^5$, respectively; $A^2$, $A^4$ and $A^5$ are hydrogen; and A and $A^3$ are independently halogen, alkyl or haloalkyl. In an embodiment, $A^2$ is hydrogen; and $A^1$ and $A^3$ are independently halogen, $C_1$-$C_4$ alkyl or $C_1$-$C_4$ haloalkyl.

In another embodiment of formula (I), $D^1$, $D^2$, $D^3$, $D^4$ and $D^5$ are each $C-A^1$, $C-A^2$, $C-A^3$, $C-A^4$ and $C-A^5$, respectively; $A^2$, $A^4$ and $A^5$ are hydrogen; $A^1$ and $A^3$ are independently halogen, $C_1$-$C_4$ alkyl or $C_1$-$C_4$ haloalkyl; and $R^1$ is $C_1$-$C_4$ alkyl or $C_1$-$C_4$haloalkyl. In yet another embodiment of formula (I), $A^2$, $A^4$ and $A^5$ are hydrogen; $A^1$ and $A^3$ are independently chloro, fluoro or $CF_3$; and $R^1$ is $CF_3$.

In another embodiment of formula (I), $D^1$ is N; $D^2$, $D^3$, $D^4$ and $D^5$ are each $C-A^2$, $C-A^3$, $C-A^4$ and $C-A^5$, respectively; $A^2$, $A^4$ and $A^5$ are hydrogen; $A^3$ is independently halogen, $C_1$-$C_4$ alkyl or $C_1$-$C_4$ haloalkyl; and $R^1$ is $C_1$-$C_4$ alkyl or $C_1$-$C_4$haloalkyl. In yet another embodiment of formula (I), $D^1$ is N; $D^2$, $D^3$, $D^4$ and $D^5$ are each $C-A^2$, $C-A^3$, $C-A^4$ and $C-A^5$, respectively; $A^2$, $A^4$ and $A^5$ are hydrogen; $A^3$ is chloro, fluoro or $CF_3$; and $R^1$ is $CF_3$.

In another embodiment of formula (I), $D^3$ is N; $D^1$, $D^2$, $D^4$ and $D^5$ are each $C-A^1$, $C-A^2$, $C-A^4$ and $C-A^5$, respectively; $A^2$, $A^4$ and $A^5$ are hydrogen; $A^1$ is independently halogen, $C_1$-$C_4$ alkyl or $C_1$-$C_4$ haloalkyl; and $R^1$ is $C_1$-$C_4$ alkyl or $C_1$-$C_4$haloalkyl. In yet another embodiment of formula (I), $D^3$ is N; $D^1$, $D^2$, $D^4$ and $D^5$ are each $C-A^1$, $C-A^2$, $C-A^4$ and $C-A^5$, respectively; $A^2$, $A^4$ and $A^5$ are hydrogen; A is chloro, fluoro or $CF_3$; and $R^1$ is $CF_3$.

In yet another embodiment of formula (I), $D^1$ and $D^3$ are N; $D^2$, $D^4$ and $D^5$ are each $C-A^2$, $C-A^4$ and $C-A^5$, respectively; $A^4$ and $A^5$ are hydrogen; $A^2$ is hydrogen, halogen, $C_1$-$C_4$ alkyl or $C_1$-$C_4$ haloalkyl; and $R^1$ is $C_1$-$C_4$ alkyl or $C_1$-$C_4$haloalkyl. In yet another embodiment of formula (I), $D^1$ and $D^3$ are N; $D^2$, $D^4$ and $D^5$ are each $C-A^2$, $C-A^4$ and $C-A^5$, respectively; $A^4$ and $A^5$ are hydrogen; $A^2$ is hydrogen, chloro, fluoro or $CF_3$; and $R^1$ is $CF_3$.

In another embodiment of formula (I), $R^2$ is hydrogen, halogen, alkyl or haloalkyl. In still another embodiment, $R^2$ is halogen, $C_1$-$C_4$ alkyl or $C_1$-$C_4$haloalkyl. In another embodiment, $R^2$ is methyl or $CF_3$. In another embodiment, $R^2$ is hydrogen.

In another embodiment of formula (I), $B^1$, $B^2$ and $B^3$ are C—H; $D^1$, $D^2$, $D^3$, $D^4$ and $D^5$ are each respectively $C-A^1$, $C-A^2$, $C-A^3$, $C-A^4$ or C-A; $A^2$, $A^4$ and $A^5$ are hydrogen; $A^1$ and $A^3$ are independently chloro, fluoro or $CF_3$; $R^1$ is $CF_3$; and $R^2$ is methyl or $CF_3$.

In another embodiment of formula (I), $B^1$, $B^2$ and $B^3$ are C—H; $D^1$, $D^2$, $D^3$, $D^4$ and $D^5$ are each $C-A^1$, $C-A^2$, $C-A^3$, $C-A^4$ and $C-A^5$, respectively; $A^2$, $A^4$ and $A^5$ are hydrogen; $A^1$ and $A^3$ are independently chloro, fluoro or $CF_3$; $R^1$ is $CF_3$; $R^2$ is methyl or $CF_3$; a is 1 or 2; and b is 1, 2 or 3.

In another embodiment of formula (I), $B^3$ is C—H; $B^1$ and $B^2$ are C—X where each X together form a 5- or 6-membered ring together with the carbon to which they are attached by forming —CH=CH—CH=CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—; $D^1$, $D^2$, $D^3$, $D^4$ and $D^5$ are each respectively $C-A^1$, $C-A^2$, $C-A^3$, $C-A^4$ and C-A; $A^2$, $A^4$ and $A^5$ are hydrogen; $A^1$ and $A^3$ are independently chloro, fluoro or $CF_3$; $R^1$ is $CF_3$; and $R^2$ is methyl or $CF_3$.

In another embodiment of formula (I), $B^3$ is C—H; $B^1$ and $B^2$ are C—X where each X together form a naphthalene ring together with the carbon to which they are attached by forming —CH=CH—CH=CH—; $D^1$, $D^2$, $D^3$, $D^4$ and $D^5$ are each C-$A^1$, C-$A^2$, C-$A^3$, C-$A^4$ and C-$A^5$, respectively; $A^2$, $A^4$ and $A^5$ are hydrogen; $A^1$ and $A^3$ are independently chloro, fluoro or $CF_3$; $R^1$ is $CF_3$; $R^2$ is methyl or $CF_3$; a is 1 or 2; and b is 1, 2 or 3.

In yet another embodiment of formula (I), Y is alkyl, haloalkyl, alkenyl, haloalkenyl, alkynyl or haloalkynyl each of which is unsubstituted or substituted with one or more of hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$.

In another embodiment, Y is $C_1$-$C_6$alkyl or $C_1$-$C_6$haloalkyl. In still another embodiment, Y is methyl, ethyl, propyl, 1-methylethyl, butyl, 1-methylpropyl, 2-methylpropyl or 1,1-dimethylethyl.

In another embodiment of formula (I), Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (I), Y is Y-1, Y-2, Y-3, Y-4, Y-5, Y-6, Y-7, Y-8, Y-9, Y-10, Y-11, Y-12 or Y-13.

In still another embodiment, Y is Y-1, Y-4, Y-5, Y-6. In another embodiment, Y is Y is Y-2, Y-3, Y-7, Y-8 or Y-9. In another embodiment, Y is Y-10, Y-11, Y-12 or Y-13.

In one embodiment of formula (I), Y is Y-1, Y-4, Y-5 or Y-6, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment of formula (I), Y is Y-2, Y-3, Y-7, Y-8 or Y-9, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment, Y is Y-1 wherein W is O; and $R^9$ and $R^{10}$ are independently hydrogen, $C_1$-$C_4$alkyl, $C_1$-$C_4$haloalkyl, $C_1$-$C_4$thioalkyl or $C_1$-$C_4$alkylthioalkyl.

In yet another embodiment, Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In another embodiment, Y is Y-4, wherein W and $W_1$ are O; $R^9$ and $R^{10}$ are independently hydrogen, $C_1$-$C_4$alkyl or $C_1$-$C_4$haloalkyl; $R^{12}$ and $R^{13}$ are hydrogen; and n is 1 or 2.

In another embodiment, Y is Y-4, wherein W and $W_1$ are O; $R^9$ and $R^{10}$ are independently hydrogen or $C_1$-$C_4$haloalkyl; $R^{12}$ and $R^{13}$ are hydrogen; and n is 1.

In still another embodiment of formula (I), Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In an embodiment, $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently halogen, alkyl or haloalkyl;

$B^1$, $B^2$ and $B^3$ are C—H; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In an embodiment, $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently halogen, alkyl or haloalkyl;

$B^3$ is C—H; $B^1$ and $B^2$ are C—X where each X together form a 5- or 6-membered ring together with the carbon to which they are attached by forming —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In another embodiment, $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently halogen, alkyl or haloalkyl;

$B^1$, $B^2$ and $B^3$ are C—H; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment, $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently halogen, alkyl or haloalkyl;

$B^3$ is C—H; $B^1$ and $B^2$ are C—X where each X together form —CH=CH—CH=CH— to form a naphthalene ring together with the carbon atoms to which they are bonded; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or at least one of $R^5$ and $R^6$ together form the group C=W; and Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment, $D^1$, $D^2$, $D^3$, $D^4$ and $D^5$ are each $C-A^1$, $C-A^2$, $C-A^3$, $C-A^4$ and $C-A^5$, respectively;

$A^2$, $A^4$ and $A^5$ are hydrogen; $A^1$ and $A^3$ are independently halogen, alkyl or haloalkyl;

$B^1$, $B^2$ and $B^3$ are C—H; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment, $D^1$, $D^2$, $D^3$, $D^4$ and $D^5$ are each $C-A^1$, $C-A^2$, $C-A^3$, $C-A^4$ and $C-A^5$, respectively;

$A^2$, $A^4$ and $A^5$ are hydrogen; $A^1$ and $A^3$ are independently halogen, alkyl or haloalkyl;

$B^3$ is C—H; $B^1$ and $B^2$ are C—X where each X together form —CH=CH—CH=CH— to form a naphthalene ring together with the carbon atoms to which they are bonded; $R^1$ is alkyl or haloalkyl; $R^2$ is hydrogen, halogen, alkyl or haloalkyl;

Z is O;

L is a bond or —$NR^8$—;

$R^3$, $R^4$, $R^5$ and $R^6$ are each independently hydrogen, halogen, alkyl or haloalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment of formula (I), $D^1$, $D^2$, $D^3$, $D^4$ and $D^5$ are each C-A, $C-A^2$, $C-A^3$, $C-A^4$ and $C-A^5$, respectively;

$A^2$, $A^4$ and $A^5$ are hydrogen; and $A^1$ and $A^3$ are independently halogen, $C_1$-$C_4$ alkyl or $C_1$-$C_4$ haloalkyl;

$B^1$, $B^2$ and $B^3$ are C—H; $R^1$ is $C_1$-$C_4$ alkyl or $C_1$-$C_4$haloalkyl; $R^2$ is hydrogen, halogen, $C_1$-$C_4$ alkyl or $C_1$-$C_4$haloalkyl;

Z is O;

L is a bond or —$NR^8$—;

$R^3$, $R^4$, $R^5$ and $R^6$ are each hydrogen, halogen or $C_1$-$C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In still another embodiment of formula (I), $D^1$, $D^2$, $D^3$, $D^4$ and $D^5$ are each $C-A^1$, $C-A^2$, $C-A^3$, $C-A^4$ and $C-A^5$, respectively;

$A^2$, $A^4$ and $A^5$ are hydrogen; and $A^1$ and $A^3$ are independently halogen, $C_1$-$C_4$ alkyl or $C_1$-$C_4$ haloalkyl;

$B^3$ is C—H; $B^1$ and $B^2$ are C—X where each X together form —CH=CH—CH=CH— to form a naphthalene ring together with the carbon atoms to which they are bonded;

$R^1$ is $C_1$-$C_4$ alkyl or $C_1$-$C_4$haloalkyl; $R^2$ is hydrogen, halogen, $C_1$-$C_4$ alkyl or $C_1$-$C_4$haloalkyl;

Z is O;

L is a bond or —$NR^8$—;

$R^3$, $R^4$, $R^5$ and $R^6$ are each hydrogen, halogen or $C_1$-$C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In another embodiment of formula (I), $D^1$, $D^2$, $D^3$, $D^4$ and $D^5$ are each $C-A^1$, $C-A^2$, $C-A^3$, $C-A^4$ and $C-A^5$, respectively;

$A^2$, $A^4$ and $A^5$ are hydrogen; and $A^1$ and $A^3$ are independently halogen, $C_1$-$C_4$ alkyl or $C_1$-$C_4$ haloalkyl;

$B^1$, $B^2$ and $B^3$ are C—H; $R^1$ is $C_1$-$C_4$ alkyl or $C_1$-$C_4$haloalkyl; $R^2$ is hydrogen, halogen, $C_1$-$C_4$ alkyl or $C_1$-$C_4$haloalkyl;

Z is O;

L is a bond or —$NR^8$—;

$R^3$, $R^4$, $R^5$ and $R^6$ are each hydrogen, halogen or $C_1$-$C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In another embodiment of formula (I), $D^1$, $D^2$, $D^3$, $D^4$ and $D^5$ are each $C-A^1$, $C-A^2$, $C-A^3$, $C-A^4$ and $C-A^5$, respectively;

$A^2$, $A^4$ and $A^5$ are hydrogen; and $A^1$ and $A^3$ are independently halogen, $C_1$-$C_4$ alkyl or $C_1$-$C_4$ haloalkyl;

$B^3$ is C—H; $B^1$ and $B^2$ are C—X where each X together form —CH=CH—CH=CH— to form a naphthalene ring together with the carbon atoms to which they are bonded;

$R^1$ is $C_1$-$C_4$ alkyl or $C_1$-$C_4$haloalkyl; $R^2$ is hydrogen, halogen, $C_1$-$C_4$ alkyl or $C_1$-$C_4$haloalkyl;

Z is O;

L is a bond or —$NR^8$—;

$R^3$, $R^4$, $R^5$ and $R^6$ are each hydrogen, halogen or $C_1$-$C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; and $A^1$ and $A^3$ are independently halogen, $C_1\text{-}C_4$ alkyl or $C_1\text{-}C_4$ haloalkyl;

$B^1$, $B^2$ and $B^3$ are C—H;

$R^1$ is $C_1\text{-}C_4$ alkyl or $C_1\text{-}C_4$ haloalkyl;

$R^2$ is hydrogen, halogen, $C_1\text{-}C_4$ alkyl or $C_1\text{-}C_4$ haloalkyl;

Z is O;

L is a bond or —$NR^8$—;

each $R^3$, $R^4$, $R^5$ and $R^6$ are each hydrogen, halogen or $C_1\text{-}C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-2, Y-3, Y-7, Y-8 or Y-9, wherein W and $W_1$ are O; $R^9$, $R^{10}$ and $R^{11}$ are independently hydrogen, $C_1\text{-}C_4$alkyl, $C_1\text{-}C_4$haloalkyl, $C_1\text{-}C_4$thioalkyl or $C_1\text{-}C_4$alkylthio $C_1\text{-}C_4$alkyl; $R^{12}$ and $R^{13}$ are hydrogen; and n is 1 or 2.

In yet another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; and $A^1$ and $A^3$ are independently halogen, $C_1\text{-}C_4$ alkyl or $C_1\text{-}C_4$ haloalkyl;

$B^3$ is C—H; $B^1$ and $B^2$ are C—X where each X together form —CH=CH—CH=CH— to form a naphthalene ring together with the carbon atoms to which they are bonded;

$R^1$ is $C_1\text{-}C_4$ alkyl or $C_1\text{-}C_4$haloalkyl;

$R^2$ is hydrogen, halogen, $C_1\text{-}C_4$ alkyl or $C_1\text{-}C_4$haloalkyl;

Z is O;

L is a bond or —$NR^8$—;

each $R^3$, $R^4$, $R^5$ and $R^6$ are each hydrogen, halogen or $C_1\text{-}C_4$alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-2, Y-3, Y-7, Y-8 or Y-9, wherein W and $W_1$ are O; $R^9$, $R^{10}$ and $R^{11}$ are independently hydrogen, $C_1\text{-}C_4$alkyl, $C_1\text{-}C_4$haloalkyl, $C_1\text{-}C_4$thioalkyl or $C_1\text{-}C_4$alkylthio $C_1\text{-}C_4$alkyl; $R^{12}$ and $R^{13}$ are hydrogen; and n is 1 or 2.

In another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; $A^1$ and $A^3$ are independently chloro, fluoro or $CF_3$;

$R^1$ is $CF_3$;

$B^1$, $B^2$ and $B^3$ are C—H;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is methyl, ethyl, propyl, 1-methylethyl, butyl, 1-methylpropyl, 2-methylpropyl or 1,1-dimethylethyl.

In another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; $A^1$ and $A^3$ are independently chloro, fluoro or $CF_3$;

$R^1$ is $CF_3$;

$B^3$ is C—H; $B^1$ and $B^2$ are C—X where each X together form —CH=CH—CH=CH— to form a naphthalene ring together with the carbon atoms to which they are bonded;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is methyl, ethyl, propyl, 1-methylethyl, butyl, 1-methylpropyl, 2-methylpropyl or 1,1-dimethylethyl.

In another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; $A^1$ and $A^3$ are independently chloro, fluoro or $CF_3$;

$R^1$ is $CF_3$;

$B^1$, $B^2$ and $B^3$ are C—H; $R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; $A^1$ and $A^3$ are independently chloro, fluoro or $CF_3$;

$R^1$ is $CF_3$;

$B^3$ is C—H; $B^1$ and $B^2$ are C—X where each X together form —CH=CH—CH=CH— to form a naphthalene ring together with the carbon atoms to which they are bonded;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In yet another embodiment of formula (I), $D^1$, $D^2$, $D^3$, $D^4$ and $D^5$ are each $C\text{-}A^1$, $C\text{-}A^2$, $C\text{-}A^3$, $C\text{-}A^4$ and $C\text{-}A^5$, respectively;

$A^2$, $A^4$ and $A^5$ are hydrogen; $A^1$ and $A^3$ are independently chloro, fluoro or $CF_3$;

$R^1$ is $CF_3$;

$B^1$, $B^2$ and $B^3$ are C—H; $R^2$ is methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (I), $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; A and $A^3$ are independently chloro, fluoro or $CF_3$;

$R^1$ is $CF_3$;

$B^1$, $B^2$ and $B^3$ are C—H; $R^2$ is methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In yet another embodiment of formula (I), $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently chloro, fluoro or $CF_3$;

$R^1$ is $CF_3$;

$B^3$ is C—H; $B^1$ and $B^2$ are C—X where each X together form —CH=CH—CH=CH— to form a naphthalene ring together with the carbon atoms to which they are bonded;

$R^2$ is methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (I), $D^1$, $D^2$, $D^3$, $D^4$ and $D^5$ are each C-$A^1$, C-$A^2$, C-$A^3$, C-$A^4$ and C-$A^5$, respectively;

$A^2$, $A^4$ and $A^5$ are hydrogen; $A^1$ and $A^3$ are independently chloro, fluoro or $CF_3$;

$R^1$ is $CF_3$;

$B^3$ is C—H; $B^1$ and $B^2$ are C—X where each X together form —CH=CH—CH=CH— to form a naphthalene ring together with the carbon atoms to which they are bonded;

$R^2$ is hydrogen;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In another embodiment, the invention provides parasiticidal and pesticidal isoxazoline compounds of formula (IA):

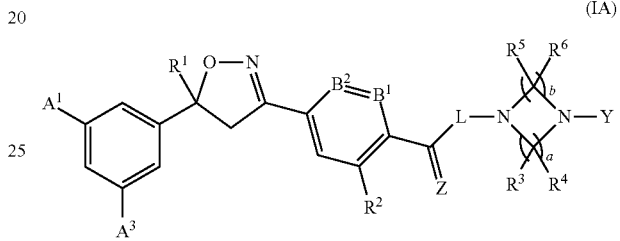

(IA)

wherein:

$R_1$ is halogen, alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of hydroxy, amino, alkyl- or di(alkyl)amino, alkoxy, haloalkoxy, alkylthio or haloalkylthio;

$A^1$ and $A^3$ are independently hydrogen, halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, —CN or —$NO_2$;

$B^1$ and $B^2$ are independently N or C—X;

each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —$NO_2$; or two adjacent X together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—;

$R^2$ is hydrogen, halogen, alkyl, haloalkyl, alkenyl, haloalkenyl, alkynyl, haloalkynyl, hydroxy, alkoxy, amino, alkyl- or dialkylamino, —CN or —$NO_2$;

$R^3$, $R^4$, $R^5$ and $R^6$ are each independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W;

$R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

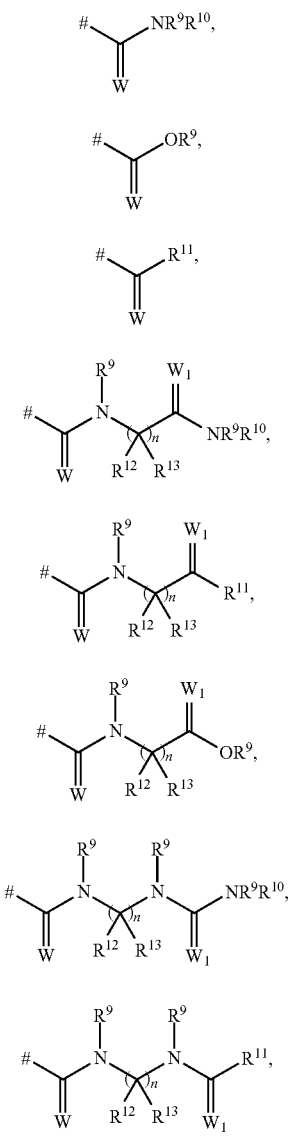

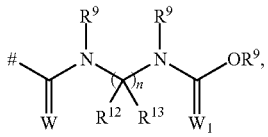
Y-9

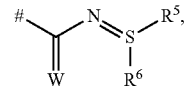
Y-10

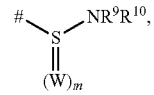
Y-11

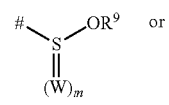
Y-12

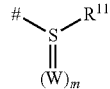
Y-13 wherein each $R^9$, $R^{10}$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)$—, $R_7S(O)_2$—, $R_7C(O)$—, $R_7R_8NC(O)$—, $R_7OC(O)$—, $R_7C(O)O$—, $R_7C(O)NR_8$—;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^{12}$ and $R^{13}$ together with the carbon atom to which they are bonded together form C=W;

W, $W_1$ and Z are independently O, S or $NR^7$;

L is a direct bond, —$CR^3R^4$—, —$NR^8$— or —O—;

a is 1, 2 or 3;

b is 1, 2 or 3;

n is 1, 2, 3 or 4; and m is 0, 1 or 2.

In one embodiment of formula (IA), $B^1$ and $B^2$ are CH.

In another embodiment of formula (IA), $B^1$ and $B^2$ are C—X and each X together form —CH=CH—CH=CH— to form a naphthalene ring together with the carbon atoms to which they are bonded.

In one embodiment of formula (IA), $R^3$ and $R^4$ together form a carbonyl group C=O.

In still another embodiment, $R^5$ and $R^6$ together form a carbonyl group C=O.

In another embodiment of formula (IA), a is 1 or 2; b is 1 or 2, wherein a+b is 3 or 4; $R^3$ and $R^4$ together C=O and $R^5$ and $R^6$ together both form C=O.

In another embodiment of formula (IA), $R^1$ is alkyl or haloalkyl. In another embodiment, $R^1$ is $C_1$-$C_4$ alkyl or $C_1$-$C_4$ haloalkyl. In another embodiment, $R^1$ is $CF_3$.

In another embodiment of formula (IA), $A^1$ and $A^3$ are independently halogen, alkyl or haloalkyl. In an embodiment, $A^1$ and $A^3$ are independently halogen, $C_1$-$C_4$ alkyl or $C_1$-$C_4$ haloalkyl.

In another embodiment of formula (IA), $A^1$ and $A^3$ are independently halogen, $C_1$-$C_4$ alkyl or $C_1$-$C_4$ haloalkyl; and $R^1$ is $C_1$-$C_4$ alkyl or $C_1$-$C_4$ haloalkyl. In yet another embodiment of formula (IA), $A^1$ and $A^3$ are independently chloro, fluoro or $CF_3$; and $R^1$ is $CF_3$.

In another embodiment of formula (IA), $R^2$ is halogen, alkyl or haloalkyl. In still another embodiment, $R^2$ is hydrogen, halogen, $C_1$-$C_4$ alkyl or $C_1$-$C_4$ haloalkyl. In another embodiment, $R^2$ is methyl or $CF_3$.

In another embodiment of formula (IA), $A^1$ and $A^3$ are independently chloro, fluoro or $CF_3$; $R^1$ is $CF_3$; and $R^2$ is methyl or $CF_3$.

In another embodiment of formula (IA), $A^1$ and $A^3$ are independently chloro, fluoro or $CF_3$; $R^1$ is $CF_3$; $R^2$ is methyl or $CF_3$; a is 1 or 2; and b is 1, 2 or 3.

In yet another embodiment of formula (IA), Y is alkyl, haloalkyl, alkenyl, haloalkenyl, alkynyl or haloalkynyl each of which is unsubstituted or substituted with one or more of hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$.

In another embodiment, Y is $C_1$-$C_6$alkyl or $C_1$-$C_6$haloalkyl. In still another embodiment, Y is methyl, ethyl, propyl, 1-methylethyl, butyl, 1-methylpropyl, 2-methylpropyl or 1,1-dimethylethyl.

In another embodiment of formula (IA), Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (IA), Y is Y-1, Y-2, Y-3, Y-4, Y-5, Y-6, Y-7, Y-8, Y-9, Y-10, Y-11, Y-12 or Y-13.

In still another embodiment, Y is Y-1, Y-4, Y-5, Y-6. In another embodiment, Y is Y is Y-2, Y-3, Y-7, Y-8 or Y-9. In yet another embodiment, Y is Y-2, Y-3, Y-7, Y-8 or Y-9. In another embodiment, Y is Y-10, Y-11, Y-12 or Y-13.

In one embodiment of formula (IA), Y is Y-1, Y-4, Y-5 or Y-6, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment of formula (IA), Y is Y-2, Y-3, Y-7, Y-8 or Y-9, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment, Y is Y-1 wherein W is O; and $R^9$ and $R^{10}$ are independently hydrogen, $C_1$-$C_4$alkyl, $C_1$-$C_4$haloalkyl, $C_1$-$C_4$thioalkyl or $C_1$-$C_4$alkylthioalkyl. In yet another embodiment, Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In another embodiment, Y is Y-4, wherein W and $W_1$ are O; $R^9$ and $R^{10}$ are independently hydrogen, $C_1$-$C_4$alkyl or $C_1$-$C_4$haloalkyl; $R^{12}$ and $R^{13}$ are hydrogen; and n is 1 or 2. In another embodiment, Y is Y-4, wherein W and $W_1$ are O; $R^9$ and $R^{10}$ are independently hydrogen or $C_1$-$C_4$haloalkyl; $R^{12}$ and $R^{13}$ are hydrogen; and n is 1. In still another embodiment of formula (IA), Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In an embodiment, $A^1$ and $A^3$ are independently halogen, alkyl or haloalkyl;
$B^1$ and $B^2$ are CH;
$R^1$ is alkyl or haloalkyl;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In an embodiment, $A^1$ and $A^3$ are independently halogen, alkyl or haloalkyl;
$B^1$ and $B^2$ are C—X and each X together form —CH=CH—CH=CH— to form a naphthalene ring together with the carbon atoms to which they are bonded;
$R^1$ is alkyl or haloalkyl;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and Y is $C_1$-$C_6$alkyl or $C_1$-$C_6$haloalkyl.

In another embodiment, $A^1$ and $A^3$ are independently halogen, alkyl or haloalkyl; $B^1$ and $B^2$ are C—H;
$R^1$ is alkyl or haloalkyl;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment, $A^1$ and $A^3$ are independently halogen, alkyl or haloalkyl;
$B^1$ and $B^2$ are C—X and each X together form —CH=CH—CH=CH— to form a naphthalene ring together with the carbon atoms to which they are bonded;
$R^1$ is alkyl or haloalkyl;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment, $A^1$ and $A^3$ are independently halogen, alkyl or haloalkyl;
$R^1$ is alkyl or haloalkyl;

$B^1$ and $B^2$ are C—H;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment, $A^1$ and $A^3$ are independently halogen, alkyl or haloalkyl; $R^1$ is alkyl or haloalkyl;
$B^1$ and $B^2$ are C—X and each X together form —CH=CH—CH=CH— to form a naphthalene ring together with the carbon atoms to which they are bonded;
$R^2$ is hydrogen, halogen, alkyl or haloalkyl;
Z is O;
L is a bond or —$NR^8$—;
$R^3$, $R^4$, $R^5$ and $R^6$ are each independently hydrogen, halogen, alkyl or haloalkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment of formula (IA), $A^1$ and $A^3$ are independently halogen, $C_1$-$C_4$ alkyl or $C_1$-$C_4$ haloalkyl;
$B^1$ and $B^2$ are C—H;
$R^1$ is $C_1$-$C_4$ alkyl or $C_1$-$C_4$haloalkyl;
$R^2$ is hydrogen, halogen, $C_1$-$C_4$ alkyl or $C_1$-$C_4$haloalkyl;
Z is O;
L is a bond or —$NR^8$—;
$R^3$, $R^4$, $R^5$ and $R^6$ are each hydrogen, halogen or $C_1$-$C_4$ alkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is $C_1$-$C_6$alkyl or $C_1$-$C_6$haloalkyl.

In still another embodiment of formula (IA), $A^1$ and $A^3$ are independently halogen, $C_1$-$C_4$ alkyl or $C_1$-$C_4$ haloalkyl;
$B^1$ and $B^2$ are C—X and each X together form —CH=CH—CH=CH— to form a naphthalene ring together with the carbon atoms to which they are bonded;
$R^1$ is $C_1$-$C_4$ alkyl or $C_1$-$C_4$haloalkyl;
$R^2$ is hydrogen, halogen, $C_1$-$C_4$ alkyl or $C_1$-$C_4$haloalkyl;
Z is O;
L is a bond or —$NR^8$—;
$R^3$, $R^4$, $R^5$ and $R^6$ are each hydrogen, halogen or $C_1$-$C_4$ alkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is $C_1$-$C_6$alkyl or $C_1$-$C_6$haloalkyl.

In another embodiment of formula (IA), $A^1$ and $A^3$ are independently halogen, $C_1$-$C_4$ alkyl or $C_1$-$C_4$haloalkyl;
$B^1$ and $B^2$ are C—H;
$R^1$ is $C_1$-$C_4$ alkyl or $C_1$-$C_4$haloalkyl;
$R^2$ is hydrogen, halogen, $C_1$-$C_4$ alkyl or $C_1$-$C_4$haloalkyl;
Z is O;
L is a bond or —$NR^8$—;
$R^3$, $R^4$, $R^5$ and $R^6$ are each hydrogen, halogen or $C_1$-$C_4$ alkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and
n is 1 or 2.

In another embodiment of formula (IA), $A^1$ and $A^3$ are independently halogen, $C_1$-$C_4$ alkyl or $C_1$-$C_4$haloalkyl;
$B^1$ and $B^2$ are C—X and each X together form —CH=CH—CH=CH— to form a naphthalene ring together with the carbon atoms to which they are bonded;
$R^1$ is $C_1$-$C_4$ alkyl or $C_1$-$C_4$haloalkyl;
$R^2$ is hydrogen, halogen, $C_1$-$C_4$ alkyl or $C_1$-$C_4$haloalkyl;
Z is O;
L is a bond or —$NR^8$—;
$R^3$, $R^4$, $R^5$ and $R^6$ are each hydrogen, halogen or $C_1$-$C_4$ alkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and
n is 1 or 2.

In yet another embodiment of formula (IA), $A^1$ and $A^3$ are independently halogen, $C_1$-$C_4$ alkyl or $C_1$-$C_4$haloalkyl;
$B^1$ and $B^2$ are C—H;
$R^1$ is $C_1$-$C_4$ alkyl or $C_1$-$C_4$haloalkyl;
$R^2$ is hydrogen, halogen, $C_1$-$C_4$ alkyl or $C_1$-$C_4$haloalkyl;
Z is O;
L is a bond or —$NR^8$—;
each $R^3$, $R^4$, $R^5$ and $R^6$ are each hydrogen, halogen or $C_1$-$C_4$ alkyl; or
$R^3$ and $R^4$ together with the carbon atom to which they are bonded together form C=W; or
$R^5$ and $R^6$ together with the carbon atom to which they are bonded together form C=W, with the proviso that at least one of $R^3$ and $R^4$ together or $R^5$ and $R^6$ together form the group C=W; and
Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IA), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$ haloalkyl;

$R^2$ is hydrogen, halogen, $C_1$-$C_4$ alkyl or $C_1$-$C_4$ haloalkyl;

Z is O;

L is a bond or —$NR^8$—;

each $R^3$, $R^4$, $R^5$ and $R^6$ are each hydrogen, halogen or $C_1$-$C_4$ alkyl; or $R^3$ and $R^4$ together with the carbon atom to which they are bonded together form C=W; or $R^5$ and $R^6$ together with the carbon atom to which they are bonded together form C=W, with the proviso that at least one of $R^3$ and $R^4$ together or $R^5$ and $R^6$ together form the group C=W; and Y is Y-2, Y-3, Y-7, Y-8 or Y-9, wherein W and $W_1$ are O; $R^9$, $R^{10}$ and $R^{11}$ are independently hydrogen, $C_1$-$C_4$ alkyl, $C_1$-$C_4$ haloalkyl, $C_1$-$C_4$ thioalkyl or $C_1$-$C_4$ alkylthio $C_1$-$C_4$ alkyl; $R^{12}$ and $R^{13}$ are hydrogen; and n is 1 or 2.

In another embodiment of formula (IA), $A^1$ and $A^3$ are independently chloro, fluoro or $CF_3$;

$B^1$ and $B^2$ are C—H;

$R^1$ is $CF_3$;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is methyl, ethyl, propyl, 1-methylethyl, butyl, 1-methylpropyl, 2-methylpropyl or 1,1-dimethylethyl.

In another embodiment of formula (IA), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;

$R^1$ is $CF_3$;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is methyl, ethyl, propyl, 1-methylethyl, butyl, 1-methylpropyl, 2-methylpropyl or 1,1-dimethylethyl.

In another embodiment of formula (IA), $A^1$ and $A^3$ are independently chloro, fluoro or $CF_3$;

$B^1$ and $B^2$ are C—H;

$R^1$ is $CF_3$; $R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (IA), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;

$R^1$ is $CF_3$; $R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In yet another embodiment of formula (IA), $A^1$ and $A^3$ are independently chloro, fluoro or $CF_3$;

$B^1$ and $B^2$ are C—H;

$R^1$ is $CF_3$;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IA), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;

$R^1$ is $CF_3$;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IA), $A^1$ and $A^3$ are independently chloro, fluoro or $CF_3$;

$B^1$ and $B^2$ are C—H;

$R^1$ is $CF_3$;

$R^2$ is methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In yet another embodiment of formula (IA), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;

$R^1$ is $CF_3$;

$R^2$ is hydrogen, methyl or $CF_3$;

Z is O;

L is a bond or —NH—;

$R^3$, $R^4$, $R^5$ and $R^6$ are each independently hydrogen or halogen; or $R^3$ and $R^4$ together with the carbon atom to which they are bonded together form C=O; or $R^5$ and $R^6$ together with the carbon atom to which they are bonded together form C=O, with the proviso that at least one of $R^3$ and $R^4$ together or $R^5$ and $R^6$ together form the group C=O; and Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In still another embodiment, the invention provides parasiticidal and pesticidal isoxazoline compounds of formula (IB):

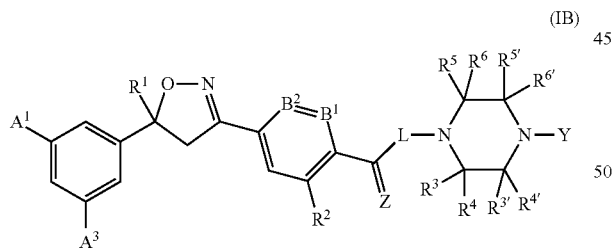

(IB)

wherein:

$R_1$ is alkyl, haloalkyl, alkenyl, haloalkenyl, alkynyl, haloalkynyl;

$A^1$ and $A^3$ are independently hydrogen, halogen, alkyl, haloalkyl, alkenyl, haloalkenyl, alkynyl or haloalkynyl;

$B^1$ and $B^2$ are independently N or C—X;

each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —$NO_2$; or two adjacent X together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—;

$R^2$ is hydrogen, halogen, alkyl, haloalkyl, alkenyl, haloalkenyl, alkynyl or haloalkynyl;

$R^3$, $R^4$, $R^{3'}$, $R^{4'}$, $R^5$, $R^6$, $R^{5'}$ and $R^{6'}$ are each independently hydrogen, halogen, alkyl, haloalkyl, alkenyl, haloalkenyl, alkynyl or haloalkynyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W;

$R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13, wherein # signifies the point of attachment;

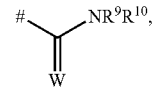

Y-1

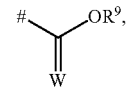

Y-2

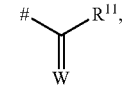

Y-3

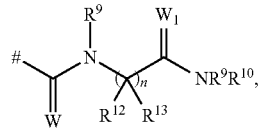

Y-4

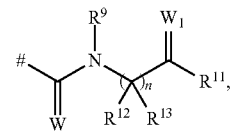

Y-5

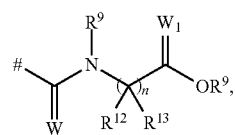

Y-6

-continued

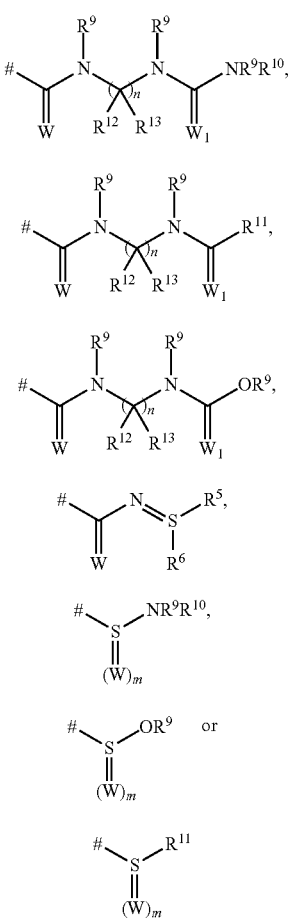

wherein each $R^9$, $R^{10}$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)—$, $R_7S(O)_2—$, $R_7C(O)—$, $R_7R_8NC(O)—$, $R_7OC(O)—$, $R_7C(O)O—$, $R_7C(O)NR_8—$;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^{12}$ and $R^{13}$ together with the carbon atom to which they are bonded together form C=W;

W, $W_1$ and Z are independently O, S or $NR^7$;

L is a direct bond, $—CR^3R^4—$, $—NR^8—$ or $—O—$;

n is 1, 2, 3 or 4; and m is 0, 1 or 2.

In one embodiment of formula (IB), $R^3$ and $R^4$ together form a carbonyl group C=O.

In another embodiment of formula (IB), $R^{3'}$ and $R^{4'}$ together form a carbonyl group C=O.

In still another embodiment, $R^5$ and $R^6$ together form a carbonyl group C=O.

In yet another embodiment of formula (IB), $R^{5'}$ and $R^{6'}$ together form a carbonyl group C=O.

In another embodiment of formula (IB), $R^3$ and $R^4$ together form C=O and $R^5$ and $R^6$ together both form C=O.

In another embodiment of formula (IB), $R^{3'}$ and $R^{4'}$ together form C=O and $R^{5'}$ and $R^{6'}$ together both form C=O.

In another embodiment of formula (IB), $R^3$ and $R^4$ together form C=O and $R^{5'}$ and $R^{6'}$ together both form C=O.

In still another embodiment of formula (IB), $R^{3'}$ and $R^{4'}$ together form C=O and $R^5$ and $R^6$ together both form C=O.

In another embodiment of formula (IB), $R^1$ is alkyl or haloalkyl. In another embodiment, $R^1$ is $C_1$-$C_4$ alkyl or $C_1$-$C_4$haloalkyl. In another embodiment, $R^1$ is $CF_3$.

In another embodiment of formula (IB), $A^1$ and $A^3$ are independently halogen, alkyl or haloalkyl. In an embodiment, $A^1$ and $A^3$ are independently halogen, $C_1$-$C_4$ alkyl or $C_1$-$C_4$ haloalkyl.

In another embodiment of formula (IB), $A^1$ and $A^3$ are independently halogen, $C_1$-$C_4$ alkyl or $C_1$-$C_4$haloalkyl; and $R^1$ is $C_1$-$C_4$ alkyl or $C_1$-$C_4$haloalkyl.

In yet another embodiment of formula (IA), A and $A^3$ are independently chloro, fluoro or $CF_3$; and $R^1$ is $CF_3$.

In one embodiment, $B^1$ and $B^2$ are C—H. In another embodiment, $B^1$ and $B^2$ are independently N or C—X; each X is independently hydrogen, alkyl, haloalkyl; or two adjacent X together form —CH=CH—CH=CH— to form a naphthalene ring together with the carbon atoms to which they are bonded;

In another embodiment of formula (IB), $R^2$ is hydrogen, halogen, alkyl or haloalkyl. In still another embodiment, $R^2$ is hydrogen, halogen, $C_1$-$C_4$ alkyl or $C_1$-$C_4$haloalkyl. In another embodiment, $R^2$ is methyl or $CF_3$.

In another embodiment of formula (IB), $A^1$ and $A^3$ are independently chloro, fluoro or $CF_3$; $R^1$ is $CF_3$; and $R^2$ is methyl or $CF_3$.

In another embodiment of formula (IB), $A^1$ and $A^3$ are independently chloro, fluoro or $CF_3$; $R^1$ is $CF_3$; $R^2$ is methyl or $CF_3$; a is 1 or 2; and b is 1, 2 or 3.

In another embodiment of formula (IB), $A^1$ and $A^3$ are independently chloro, fluoro or $CF_3$; $B^1$ and $B^2$ are C—H; $R^1$ is $CF_3$; and $R^2$ is hydrogen, methyl or $CF_3$.

In another embodiment of formula (IB), $A^1$ and $A^3$ are independently chloro, fluoro or $CF_3$; $B^1$ and $B^2$ are C—H; $R^1$ is $CF_3$; $R^2$ is hydrogen, methyl or $CF_3$; a is 1 or 2; and b is 1, 2 or 3.

In another embodiment of formula (IB), $A^1$ and $A^3$ are independently chloro, fluoro or $CF_3$; $B^1$ and $B^2$ are C—X and each X together form —CH=CH—CH=CH— to form a naphthalene ring together with the carbon atoms to which they are bonded; $R^1$ is $CF_3$; and $R^2$ is hydrogen, methyl or $CF_3$.

In another embodiment of formula (IB), $A^1$ and $A^3$ are independently chloro, fluoro or $CF_3$; $B^1$ and $B^2$ are C—X and each X together form —CH=CH—CH=CH— to form a naphthalene ring together with the carbon atoms to which they are bonded; $R^1$ is $CF_3$; $R^2$ is hydrogen, methyl or $CF_3$; a is 1 or 2; and b is 1, 2 or 3.

In yet another embodiment of formula (IB), Y is alkyl, haloalkyl, alkenyl, haloalkenyl, alkynyl or haloalkynyl each of which is unsubstituted or substituted with one or more of hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)—$, $R_7S$ (O)$_2$—, R$_7$C(O)—, R$_7$R$_8$NC(O)—, R$_7$OC(O)—, R$_7$C(O)O—, R$_7$C(O)NR$_8$—, —CN or —NO$_2$.

In another embodiment, Y is C$_1$-C$_6$alkyl or C$_1$-C$_6$haloalkyl. In still another embodiment, Y is methyl, ethyl, propyl, 1-methylethyl, butyl, 1-methylpropyl, 2-methylpropyl or 1,1-dimethylethyl.

In another embodiment of formula (I), Y is CF$_3$, —CH$_2$CF$_3$, —CF$_2$CF$_3$, —CH$_2$CH$_2$CF$_3$, —CH$_2$CF$_2$CF$_3$, —CF$_2$CF$_2$CF$_3$, —CH$_2$CH$_2$CH$_2$CF$_3$, —CH$_2$CH$_2$CF$_2$CF$_3$, —CH$_2$CF$_2$CF$_2$CF$_3$ or —CF$_2$CF$_2$CF$_2$CF$_3$.

In another embodiment of formula (IB), Y is Y-1, Y-2, Y-3, Y-4, Y-5, Y-6, Y-7, Y-8, Y-9, Y-10, Y-11, Y-12 or Y-13.

In still another embodiment of formula (IB), Y is Y-1, Y-4, Y-5, Y-6. In another embodiment, Y is Y is Y-2, Y-3, Y-7, Y-8 or Y-9. In another embodiment, Y is Y-10, Y-11, Y-12 or Y-13.

In one embodiment of formula (IB), Y is Y-1, Y-4, Y-5 or Y-6, wherein W and W$_1$ are O; R$^9$, R$^{10}$ and R$^{11}$ are independently hydrogen, alkyl, haloalkyl, thioalkyl or alkylthioalkyl; R$^{12}$ and R$^{13}$ are hydrogen; and n is 1 or 2.

In another embodiment of formula (IB), Y is Y-2, Y-3, Y-7, Y-8 or Y-9, wherein W and W$_1$ are O; R$^9$, R$^{10}$ and R$^{11}$ are independently hydrogen, alkyl, haloalkyl, thioalkyl or alkylthioalkyl; R$^{12}$ and R$^{13}$ are hydrogen; and n is 1 or 2.

In still another embodiment of formula (IB), Y is Y-1 wherein W is O; and R$^9$ and R$^{10}$ are independently hydrogen, C$_1$-C$_4$alkyl, C$_1$-C$_4$haloalkyl, C$_1$-C$_4$thioalkyl or C$_1$-C$_4$alkylthioalkyl. In yet another embodiment, Y is Y-1 wherein W is O; and R$^9$ and R$^{10}$ are independently hydrogen, —CH$_2$CH$_2$SH, —CH$_2$CH$_2$SCH$_3$ or —CH$_2$CH$_2$SCF$_3$.

In another embodiment of formula (IB), Y is Y-4, wherein W and W$_1$ are O; R$^9$ and R$^{10}$ are independently hydrogen, C$_1$-C$_4$alkyl or C$_1$-C$_4$haloalkyl; R$^{12}$ and R$^{13}$ are hydrogen; and n is 1 or 2. In another embodiment, Y is Y-4, wherein W and W$_1$ are O; R$^9$ and R$^{10}$ are independently hydrogen or C$_1$-C$_4$haloalkyl; R$^{12}$ and R$^{13}$ are hydrogen; and n is 1. In still another embodiment of formula (IB), Y is Y-4, wherein W and W$_1$ are O; R$^9$ and R$^{10}$ are independently hydrogen or —CH$_2$CF$_3$; R$^{12}$ and R$^{13}$ are hydrogen; and n is 1.

In an embodiment of formula (IB), A$^1$ and A$^3$ are independently halogen, alkyl or haloalkyl;
B$^1$ and B$^2$ are C—H;
R$^1$ is alkyl or haloalkyl;
R$^2$ is hydrogen, halogen, alkyl or haloalkyl;
Z is O;
L is a bond or —NR$^7$—;
R$^3$, R$^4$, R$^{3'}$, R$^{4'}$, R$^5$, R$^6$, R$^{5'}$ and R$^{6'}$ are each independently hydrogen, halogen, alkyl or haloalkyl; or
R$^3$ and R$^4$ and/or R$^{3'}$ and R$^{4'}$ together with the carbon atom to which they are bonded together form C=W; and/or
R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W; and Y is C$_1$-C$_6$alkyl or C$_1$-C$_6$haloalkyl.

In an embodiment of formula (IB), A$^1$ and A$^3$ are independently halogen, alkyl or haloalkyl;
B$^1$ and B$^2$ are C—X and each X together form —CH=CH—CH=CH— to form a naphthalene ring together with the carbon atoms to which they are bonded;
R$^1$ is alkyl or haloalkyl;
R$^2$ is hydrogen, halogen, alkyl or haloalkyl;
Z is O;
L is a bond or —NR$^7$—;
R$^3$, R$^4$, R$^{3'}$, R$^{4'}$, R$^5$, R$^6$, R$^{5'}$ and R$^{6'}$ are each independently hydrogen, halogen, alkyl or haloalkyl; or
R$^3$ and R$^4$ and/or R$^{3'}$ and R$^{4'}$ together with the carbon atom to which they are bonded together form C=W; and/or
R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W; and Y is C$_1$-C$_6$alkyl or C$_1$-C$_6$haloalkyl.

In another embodiment of formula (IB), A$^1$ and A$^3$ are independently halogen, alkyl or haloalkyl;
B$^1$ and B$^2$ are C—H;
R$^1$ is alkyl or haloalkyl;
R$^2$ is hydrogen, halogen, alkyl or haloalkyl;
Z is O;
L is a bond or —NR$^7$—;
R$^3$ and R$^4$ and/or R$^{3'}$ and R$^{4'}$ together with the carbon atom to which they are bonded together form C=W; and/or
R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W; and
Y is Y-1, Y-4, Y-5 or Y-6, in which W and W$_1$ are O, R$^9$, R$^{10}$ and R$^{11}$ are independently hydrogen, alkyl, haloalkyl, thioalkyl or alkylthioalkyl; R$^{12}$ and R$^{13}$ are hydrogen; and n is 1 or 2.

In another embodiment of formula (IB), A$^1$ and A$^3$ are independently halogen, alkyl or haloalkyl;
B$^1$ and B$^2$ are C—X and each X together form —CH=CH—CH=CH— to form a naphthalene ring together with the carbon atoms to which they are bonded;
R$^1$ is alkyl or haloalkyl;
R$^2$ is hydrogen, halogen, alkyl or haloalkyl;
Z is O;
L is a bond or —NR$^7$—;
R$^3$ and R$^4$ and/or R$^{3'}$ and R$^{4'}$ together with the carbon atom to which they are bonded together form C=W; and/or
R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W; and
Y is Y-1, Y-4, Y-5 or Y-6, in which W and W$_1$ are O, R$^9$, R$^{10}$ and R$^{11}$ are independently hydrogen, alkyl, haloalkyl, thioalkyl or alkylthioalkyl; R$^{12}$ and R$^{13}$ are hydrogen; and n is 1 or 2.

In yet another embodiment of formula (IB), A$^1$ and A$^3$ are independently halogen, alkyl or haloalkyl;
B$^1$ and B$^2$ are C—H;
R$^1$ is alkyl or haloalkyl;
R$^2$ is hydrogen, halogen, alkyl or haloalkyl;
Z is O;
L is a bond or —NR$^7$—;
R$^3$, R$^4$, R$^{3'}$, R$^{4'}$, R$^5$, R$^6$, R$^{5'}$ and R$^{6'}$ are each independently hydrogen, halogen, alkyl or haloalkyl; or
R$^3$ and R$^4$ and/or R$^{3'}$ and R$^{4'}$ together with the carbon atom to which they are bonded together form C=W; and/or
R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W; and
Y is Y is Y-2, Y-3, Y-7, Y-8 or Y-9, in which W and W$_1$ are O; R$^9$, R$^{10}$ and R$^{11}$ are independently hydrogen, alkyl, haloalkyl, thioalkyl or alkylthioalkyl; R$^{12}$ and R$^{13}$ are hydrogen; and n is 1 or 2.

In yet another embodiment of formula (IB), $A^1$ and $A^3$ are independently halogen, alkyl or haloalkyl;

$B^1$ and $B^2$ are C—X and each X together form —CH=CH—CH=CH— to form a naphthalene ring together with the carbon atoms to which they are bonded;

$R^1$ is alkyl or haloalkyl;

$R^2$ is hydrogen, halogen, alkyl or haloalkyl;

Z is O;

L is a bond or —$NR^7$—;

$R^3$, $R^4$, $R^{3'}$, $R^{4'}$, $R^5$, $R^6$, $R^{5'}$ and $R^{6'}$ are each independently hydrogen, halogen, alkyl or haloalkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment of formula (IB), $A^1$ and $A^3$ are independently halogen, $C_1$-$C_4$ alkyl or $C_1$-$C_4$ haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is $C_1$-$C_6$alkyl or $C_1$-$C_6$haloalkyl.

In still another embodiment of formula (IB), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is $C_1$-$C_6$alkyl or $C_1$-$C_6$haloalkyl.

In another embodiment of formula (IB), $A^1$ and $A^3$ are independently halogen, $C_1$-$C_4$ alkyl or $C_1$-$C_4$haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In another embodiment of formula (IB), $A^1$ and $A^3$ are independently halogen, $C_1$-$C_4$ alkyl or $C_1$-$C_4$haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IB), $A^1$ and $A^3$ are independently halogen, $C_1$-$C_4$ alkyl or $C_1$-$C_4$ haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

each $R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IB), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

each $R^3$, $R^4$, $R^{3'}$, $R^{4'}$, $R^5$, $R^6$, $R^{5'}$ and $R^{6'}$ are each hydrogen, halogen or $C_1$-$C_4$ alkyl; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In another embodiment of formula (IB), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is methyl, ethyl, propyl, 1-methylethyl, butyl, 1-methylpropyl, 2-methylpropyl or 1,1-dimethylethyl.

In another embodiment of formula (IB), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is methyl, ethyl, propyl, 1-methylethyl, butyl, 1-methylpropyl, 2-methylpropyl or 1,1-dimethylethyl.

In another embodiment of formula (IB), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (IB), $A^1$ and $A^3$ are independently chloro, fluoro or $CF_3$;

$B^1$ and $B^2$ are C—X and each X together form —CH=CH—CH=CH— to form a naphthalene ring together with the carbon atoms to which they are bonded;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In yet another embodiment of formula (IB), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IB), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IB), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^{3'}$, $R^{4'}$, $R^5$, $R^6$, $R^{5'}$ and $R^{6'}$ are hydrogen; or
$R^3$ and $R^4$ and/or $R^{3'}$ and $R^{4'}$ together with the carbon atom to which they are bonded together form C=W; and/or
$R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In yet another embodiment of formula (IB), $A^1$ and $A^3$ are independently chloro, fluoro or CF$_3$;

$B^1$ and $B^2$ are C—X and each X together form —CH=CH—CH=CH— to form a naphthalene ring together with the carbon atoms to which they are bonded;

$R^1$ is CF$_3$;

$R^2$ is hydrogen, methyl or CF$_3$;

Z is O;

L is a bond or —NH—;

$R^3$, $R^4$, $R^{3'}$, $R^{4'}$, $R^5$, $R^6$, $R^{5'}$ and $R^{6'}$ are hydrogen; or $R^3$ and $R^4$ and/or $R^{3'}$ and $R^{4'}$ together with the carbon atom to which they are bonded together form C=W; and/or $R^5$ and $R^6$ and/or $R^{5'}$ and $R^{6'}$ together with the carbon atom to which they are bonded together form C=W, with the proviso that at least one of $R^3$ and $R^4$, $R^{3'}$ and $R^{4'}$, $R^5$ and $R^6$, or $R^{5'}$ and $R^{6'}$, together with the carbon atom to which they are attached form the group C=W; and Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In still another embodiment, the invention provides parasiticidal and pesticidal compounds of formula IC):

(IC)

wherein:

$R_1$ is alkyl, haloalkyl, alkenyl, haloalkenyl, alkynyl, haloalkynyl;

$A^1$ and $A^3$ are independently hydrogen, halogen, alkyl, haloalkyl, alkenyl, haloalkenyl, alkynyl or haloalkynyl;

$B^1$ and $B^2$ are independently N or C—X;

each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —NO$_2$; or two adjacent X together form a 5- or 6-membered ring together with the carbon atoms to which they are bonded by forming —CH$_2$CH$_2$CH$_2$—, —CH=CH—CH=CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—;

$R^2$ is hydrogen, halogen, alkyl, haloalkyl, alkenyl, haloalkenyl, alkynyl or haloalkynyl;

$R^3$, $R^4$, $R^5$, $R^6$, $R^{5'}$ and $R^{6'}$ are each independently hydrogen, halogen, alkyl, haloalkyl, alkenyl, haloalkenyl, alkynyl or haloalkynyl; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$ together with the carbon atom to which they are attached form the group C=W;

$R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

Y-1

Y-2

Y-3

Y-4

Y-5

Y-6

Y-7

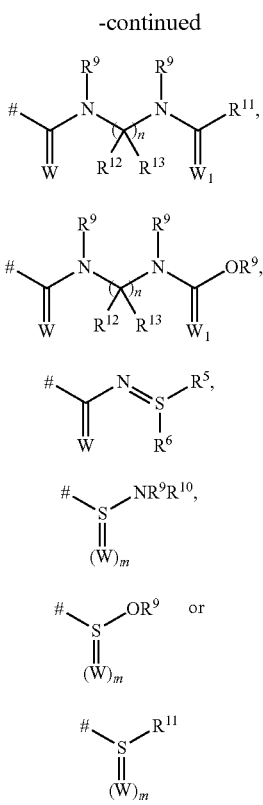

Y-8

Y-9

Y-10

Y-11

Y-12

Y-13 wherein each $R^9$, $R^{10}$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)$—, $R_7S(O)_2$—, $R_7C(O)$—, $R_7R_8NC(O)$—, $R_7OC(O)$—, $R_7C(O)O$—, $R_7C(O)NR_8$—;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl; or $R^{12}$ and $R^{13}$ together with the carbon atom to which they are bonded together form C=W;

W, $W_1$ and Z are independently O, S or $NR^7$;

L is a direct bond, —$CR^3R^4$—, —$NR^8$— or —O—;

n is 1, 2, 3 or 4; and m is 0, 1 or 2.

In one embodiment of formula (IC), $R^3$ and $R^4$ together form a carbonyl group C=O.

In another embodiment, $R^5$ and $R^6$ together form a carbonyl group C=O.

In yet another embodiment of formula (IC), $R^{5'}$ and $R^{6'}$ together form a carbonyl group C=O.

In another embodiment of formula (IC), $R^3$ and $R^4$ together form C=O and $R^5$ and $R^6$ together form C=O.

In another embodiment of formula (IC), $R^3$ and $R^4$ together form C=O and $R^{5'}$ and $R^{6'}$ together form C=O.

In another embodiment of formula (IC), $R^1$ is alkyl or haloalkyl. In another embodiment, $R^1$ is $C_1$-$C_4$ alkyl or $C_1$-$C_4$haloalkyl. In another embodiment, $R^1$ is $CF_3$.

In another embodiment of formula (IC), $A^1$ and $A^3$ are independently halogen, alkyl or haloalkyl. In an embodiment, $A^1$ and $A^3$ are independently halogen, $C_1$-$C_4$ alkyl or $C_1$-$C_4$ haloalkyl.

In another embodiment of formula (IC), $A^1$ and $A^3$ are independently halogen, $C_1$-$C_4$ alkyl or $C_1$-$C_4$haloalkyl; and $R^1$ is $C_1$-$C_4$ alkyl or $C_1$-$C_4$haloalkyl.

In yet another embodiment of formula (IC), $A^1$ and $A^3$ are independently chloro, fluoro or $CF_3$; and $R^1$ is $CF_3$.

In another embodiment of formula (IC), $A^1$ and $A^3$ are independently halogen, $C_1$-$C_4$ alkyl or $C_1$-$C_4$haloalkyl; $B^1$ and $B^2$ are C—H; and $R^1$ is $C_1$-$C_4$ alkyl or $C_1$-$C_4$haloalkyl.

In yet another embodiment of formula (IC), $A^1$ and $A^3$ are independently chloro, fluoro or $CF_3$; $B^1$ and $B^2$ are C—H; and $R^1$ is $CF_3$.

In another embodiment of formula (IC), $A^1$ and $A^3$ are independently halogen, $C_1$-$C_4$ alkyl or $C_1$-$C_4$ haloalkyl; $B^1$ and $B^2$ are C—X and each X together form —CH=CH—CH=CH— to form a naphthalene ring together with the carbon atoms to which they are bonded; and $R^1$ is $C_1$-$C_4$ alkyl or $C_1$-$C_4$haloalkyl.

In yet another embodiment of formula (IC), $A^1$ and $A^3$ are independently chloro, fluoro or $CF_3$; $B^1$ and $B^2$ are C—X and each X together form —CH=CH—CH=CH— to form a naphthalene ring together with the carbon atoms to which they are bonded; and $R^1$ is $CF_3$.

In another embodiment of formula (IC), $R^2$ is hydrogen, halogen, alkyl or haloalkyl. In still another embodiment, $R^2$ is hydrogen, halogen, $C_1$-$C_4$ alkyl or $C_1$-$C_4$haloalkyl. In another embodiment, $R^2$ is methyl or $CF_3$.

In another embodiment of formula (IC), $A^1$ and $A^3$ are independently chloro, fluoro or $CF_3$; $R^1$ is $CF_3$; and $R^2$ is hydrogen, methyl or $CF_3$.

In yet another embodiment of formula (IC), Y is alkyl, haloalkyl, alkenyl, haloalkenyl, alkynyl or haloalkynyl each of which is unsubstituted or substituted with one or more of hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$.

In another embodiment, Y is $C_1$-$C_6$alkyl or $C_1$-$C_6$haloalkyl. In still another embodiment, Y is methyl, ethyl, propyl, 1-methylethyl, butyl, 1-methylpropyl, 2-methylpropyl or 1,1-dimethylethyl.

In another embodiment of formula (IC), Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (IC), Y is Y-1, Y-2, Y-3, Y-4, Y-5, Y-6, Y-7, Y-8, Y-9, Y-10, Y-11, Y-12 or Y-13. In still another embodiment of formula (IC), Y is Y-1, Y-4, Y-5, Y-6. In another embodiment, Y is Y-2, Y-3, Y-7, Y-8 or Y-9. In another embodiment, Y is Y-10, Y-11, Y-12 or Y-13.

In one embodiment of formula (IC), Y is Y-1, Y-4, Y-5 or Y-6, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment of formula (IC), Y is Y-2, Y-3, Y-7, Y-8 or Y-9, wherein W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment of formula (IC), Y is Y-1 wherein W is O; and $R^9$ and $R^{10}$ are independently hydrogen, $C_1$-$C_4$alkyl, $C_1$-$C_4$haloalkyl, $C_1$-$C_4$thioalkyl or $C_1$-$C_4$alkylthioalkyl. In yet another embodiment, Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In another embodiment of formula (IC), Y is Y-4, wherein W and $W_1$ are O; $R^9$ and $R^{10}$ are independently hydrogen, $C_1$-$C_4$alkyl or $C_1$-$C_4$haloalkyl; $R^{12}$ and $R^{13}$ are hydrogen; and n is 1 or 2. In another embodiment, Y is Y-4, wherein W and $W_1$ are O; $R^9$ and $R^{10}$ are independently hydrogen or $C_1$-$C_4$haloalkyl; $R^{12}$ and $R^{13}$ are hydrogen; and n is 1. In still another embodiment of formula (IC), Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In an embodiment of formula (IC), $A^1$ and $A^3$ are independently halogen, alkyl or haloalkyl;

$B^1$ and $B^2$ are C—H;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'}$ are each independently hydrogen, halogen, alkyl or haloalkyl; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is $C_1$-$C_6$alkyl or $C_1$-$C_6$haloalkyl.

In an embodiment of formula (IC), $A^1$ and $A^3$ are independently halogen, alkyl or haloalkyl;

$B^1$ and $B^2$ are C—X and each X together form —CH=CH—CH=CH— to form a naphthalene ring together with the carbon atoms to which they are bonded;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'}$ are each independently hydrogen, halogen, alkyl or haloalkyl; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is $C_1$-$C_6$alkyl or $C_1$-$C_6$haloalkyl.

In another embodiment of formula (IC), $A^1$ and $A^3$ are independently halogen, alkyl or haloalkyl;

$B^1$ and $B^2$ are C—H;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'''}$ are each independently hydrogen, halogen, alkyl or haloalkyl; or $R^3$ and $R^4$ and/or $R^5$ and $R^6$ and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In another embodiment of formula (IC), $A^1$ and $A^3$ are independently halogen, alkyl or haloalkyl;

$B^1$ and $B^2$ are C—X and each X together form —CH=CH—CH=CH— to form a naphthalene ring together with the carbon atoms to which they are bonded;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'''}$ are each independently hydrogen, halogen, alkyl or haloalkyl; or $R^3$ and $R^4$ and/or $R^5$ and $R^6$ and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-1, Y-4, Y-5 or Y-6, in which W and $W_1$ are O, $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment of formula (IC), $A^1$ and $A^3$ are independently halogen, alkyl or haloalkyl;

$B^1$ and $B^2$ are C—H;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'''}$ are each independently hydrogen, halogen, alkyl or haloalkyl; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In yet another embodiment of formula (IC), $A^1$ and $A^3$ are independently halogen, alkyl or haloalkyl;

$B^1$ and $B^2$ are C—X and each X together form —CH=CH—CH=CH— to form a naphthalene ring together with the carbon atoms to which they are bonded;

$R^1$ is alkyl or haloalkyl;

$R^2$ is hydrogen, halogen, alkyl or haloalkyl;

Z is O;

L is a bond or —$NR^7$—;

$R^3$, $R^4$, $R^5$, $R^6$, $R^{5'}$ and $R^{6'''}$ are each independently hydrogen, halogen, alkyl or haloalkyl; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y is Y-2, Y-3, Y-7, Y-8 or Y-9, in which W and $W_1$ are O; $R^9$, $R^{10}$ and $R^{11}$ are independently hydrogen, alkyl, haloalkyl, thioalkyl or alkylthioalkyl; $R^{12}$ and $R^{13}$ are hydrogen; and n is 1 or 2.

In still another embodiment of formula (IC), $A^1$ and $A^3$ are independently halogen, $C_1$-$C_4$ alkyl or $C_1$-$C_4$ haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is $C_1$-$C_6$alkyl or $C_1$-$C_6$haloalkyl.

In still another embodiment of formula (IC), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is $C_1$-$C_6$alkyl or $C_1$-$C_6$haloalkyl.

In another embodiment of formula (IC), $A^1$ and $A^3$ are independently halogen, $C_1$-$C_4$ alkyl or $C_1$-$C_4$ haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In another embodiment of formula (IC), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

$R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IC), $A^1$ and $A^3$ are independently halogen, $C_1$-$C_4$ alkyl or $C_1$-$C_4$ haloalkyl;

$B^1$ and $B^2$ are C—H;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

each $R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IC), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^1$ is $C_1$-$C_4$ alkyl or $C_1$-$C_4$haloalkyl;

$R^2$ is hydrogen, halogen, $C_1$-$C_4$ alkyl or $C_1$-$C_4$haloalkyl;

Z is O;

L is a bond or —$NR^7$—;

each $R^3$, $R^4$, $R^5$, $R^6$, $R^{5'}$ and $R^{6'}$ are each hydrogen or halogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In another embodiment of formula (IC), $A^1$ and $A^3$ are independently chloro, fluoro or $CF_3$;

$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is methyl, ethyl, propyl, 1-methylethyl, butyl, 1-methylpropyl, 2-methylpropyl or 1,1-dimethylethyl.

In another embodiment of formula (IC), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is methyl, ethyl, propyl, 1-methylethyl, butyl, 1-methylpropyl, 2-methylpropyl or 1,1-dimethylethyl.

In another embodiment of formula (IC), $A^1$ and $A^3$ are independently chloro, fluoro or $CF_3$;
$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (IC), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In yet another embodiment of formula (IC), $A^1$ and $A^3$ are independently chloro, fluoro or $CF_3$;
$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IC), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or
$R^5$ and $R^6$ together with the carbon atom to which they are bonded together form C=W; and/or
$R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (IC), $A^1$ and $A^3$ are independently chloro, fluoro or $CF_3$;
$B^1$ and $B^2$ are C—H;
$R^1$ is $CF_3$;
$R^2$ is hydrogen, methyl or $CF_3$;
Z is O;
L is a bond or —NH—;
$R^3$, $R^4$, $R^5$, $R^6$, $R^{5'}$ and $R^{6'}$ are each hydrogen; or
$R^3$ and $R^4$ together with the carbon atom to which they are bonded together form C=W; and/or R⁵ and R⁶ together with the carbon atom to which they are bonded together form C=W; and/or R⁵' and R⁶' together with the carbon atom to which they are bonded together form C=W, with the proviso that at least one of R³ and R⁴, R⁵ and R⁶ or R⁵' and R⁶', together with the carbon atom to which they are attached form the group C=W; and Y is Y-4, wherein W and $W_1$ are O; $R^9$ and $R^{10}$ are independently hydrogen or —CH₂CF₃; $R^{12}$ and $R^{13}$ are hydrogen; and n is 1.

In yet another embodiment of formula (IC), $A^1$ and $A^3$ are independently chloro, fluoro or CF₃;

$B^1$ and $B^2$ are C—X and each X together form —CH=CH—CH=CH— to form a naphthalene ring together with the carbon atoms to which they are bonded;

$R^1$ is CF₃;

$R^2$ is hydrogen, methyl or CF₃;

Z is O;

L is a bond or —NH—;

$R^3$, $R^4$, $R^5$, $R^6$, $R^{5'}$ and $R^{6'}$ are each hydrogen; or $R^3$ and $R^4$ together with the carbon atom to which they are bonded together form C=W; and/or $R^5$ and $R^6$ together with the carbon atom to which they are bonded together form C=W; and/or $R^{5'}$ and $R^{6'}$ together with the carbon atom to which they are bonded together form C=W, with the proviso that at least one of $R^3$ and $R^4$, $R^5$ and $R^6$ or $R^{5'}$ and $R^{6'}$, together with the carbon atom to which they are attached form the group C=W; and Y is Y-4, wherein W and $W_1$ are O; $R^9$ and $R^{10}$ are independently hydrogen or —CH₂CF₃; $R^{12}$ and $R^{13}$ are hydrogen; and n is 1.

In another embodiment, the invention provides compounds of formula (ID):

(ID)

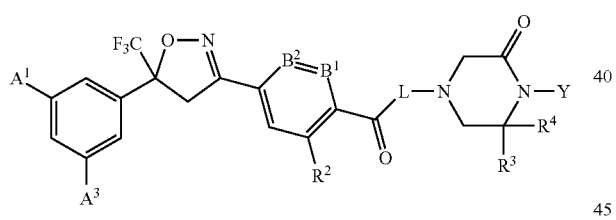

wherein:

$A^1$ and $A^3$ are independently halogen or $C_1$-$C_4$haloalkyl;

$B^1$ and $B^2$ are independently N or C—X;

each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —NO₂; or two adjacent X together form a 5- or 6-membered ring together with the carbon atoms to which they are bonded by forming —CH₂CH₂CH₂—, —CH=CH—CH=CH—, —CH₂CH₂O—, —CH₂OCH₂—, —OCH₂O—, —CH₂CH₂S—, —CH₂SCH₂—, —SCH₂S—, —CH₂CH₂CH₂CH₂—, —CH₂CH₂CH₂O—, —CH₂CH₂OCH₂—, —CH₂OCH₂O—, —OCH₂CH₂O—, —OCH₂CH₂S—, —SCH₂CH₂S—, —OCH=N— or —SCH=N—;

$R^2$ is hydrogen, $C_1$-$C_4$alkyl or $C_1$-$C_4$ haloalkyl;

$R^3$ and $R^4$ are independently hydrogen, $C_1$-$C_4$alkyl, $C_1$-$C_4$haloalkyl or halogen; or $R^3$ and $R^4$ together with the carbon atom to which they are bonded for the group C=O;

Y is hydrogen, $C_1$-$C_4$alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO₂; or Y is Y-1, Y-2, Y-3, Y-4, Y-5, Y-6, Y-7, Y-8, Y-9, Y-10, Y-11, Y-12 or Y-13, wherein # signifies the point of attachment;

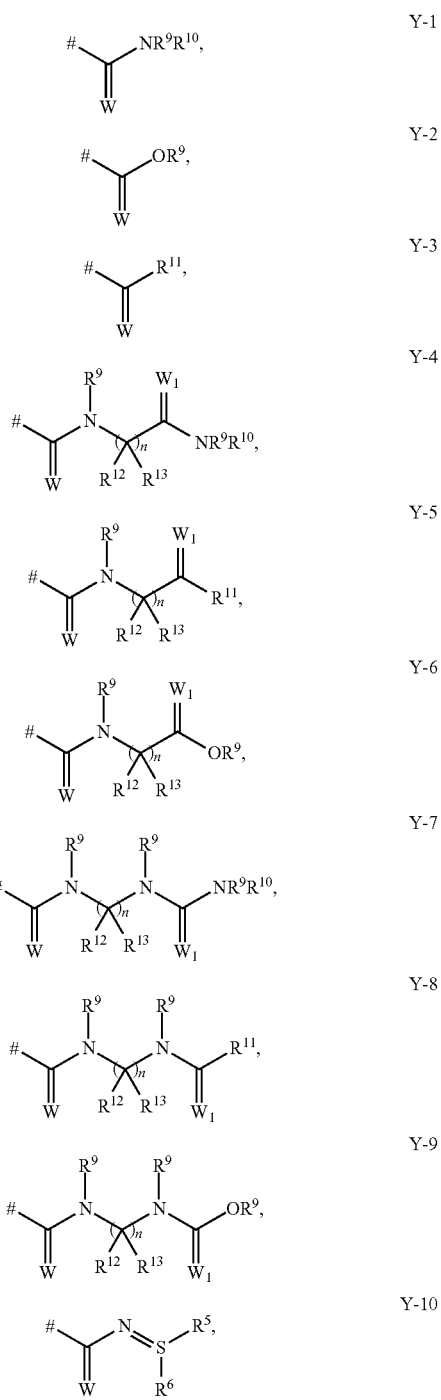

-continued

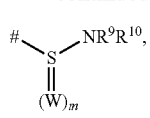
Y-11

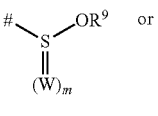
Y-12

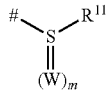
Y-13 wherein $R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;

$R^9$ and $R^{10}$ are independently hydrogen, $C_1$-$C_4$ alkyl, $C_1$-$C_4$haloalkyl, thio-$C_1$-$C_4$-alkyl or $C_1$-$C_4$alkylthio-$C_1$-$C_4$-alkyl;

each $R^{11}$ is independently hydrogen, $C_1$-$C_4$alkyl or $C_1$-$C_4$haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;

each $R^{12}$ and $R^{13}$ is independently hydrogen or $C_1$-$C_4$alkyl;

W and $W_1$ are O;

L is a direct bond, —$CR^3R^4$—, —$NR^8$— or —O—;

n is 1, 2, 3 or 4; and m is 0, 1 or 2.

In one embodiment, $R^3$ and $R^4$ are hydrogen. In another embodiment, $R^3$ and $R^4$ together with the carbon atom to which they are bonded for the group C=O.

In one embodiment of formula (ID), $A^1$ and $A^3$ are independently halogen, alkyl or haloalkyl. In an embodiment, $A^1$ and $A^3$ are independently halogen, $C_1$-$C_4$alkyl or $C_1$-$C_4$ haloalkyl.

In one embodiment, $B^1$ and $B^2$ are C—H. In another embodiment, $B^1$ and $B^2$ are C—X and each X together form —CH=CH—CH=CH— to form a naphthalene ring together with the carbon atoms to which they are bonded.

In another embodiment of formula (ID), $A^1$ and $A^3$ are independently chloro, fluoro, $C_1$-$C_4$ alkyl or $C_1$-$C_4$ haloalkyl. In yet another embodiment of formula (IA), $A^1$ and $A^3$ are independently chloro, fluoro or $CF_3$.

In another embodiment of formula (ID), $A^1$ and $A^3$ are independently chloro, fluoro, $C_1$-$C_4$ alkyl or $C_1$-$C_4$ haloalkyl; and $B^1$ and $B^2$ are C—H. In another embodiment of formula (ID), $A^1$ and $A^3$ are independently chloro, fluoro, $C_1$-$C_4$ alkyl or $C_1$-$C_4$ haloalkyl; and $B^1$ and $B^2$ are C—X where each X together form —CH=CH—CH=CH— to form a naphthalene ring together with the carbon atoms to which they are bonded.

In yet another embodiment of formula (IA), $A^1$ and $A^3$ are independently chloro, fluoro or $CF_3$; and $B^1$ and $B^2$ are C—H. In still another embodiment of formula (IA), $A^1$ and $A^3$ are independently chloro, fluoro or $CF_3$; and $B^1$ and $B^2$ are C—X and each X together form —CH=CH—CH=CH— to form a naphthalene ring together with the carbon atoms to which they are bonded.

In another embodiment of formula (ID), $R^2$ is hydrogen, halogen, alkyl or haloalkyl. In still another embodiment, $R^2$ is hydrogen, halogen, $C_1$-$C_4$ alkyl or $C_1$-$C_4$haloalkyl. In another embodiment, $R^2$ is methyl or $CF_3$.

In another embodiment of formula (ID), $A^1$ and $A^3$ are independently chloro, fluoro or $CF_3$; and $R^2$ is methyl or $CF_3$. In another embodiment of formula (ID), $A^1$ and $A^3$ are independently chloro, fluoro or $CF_3$; $B^1$ and $B^2$ are C—H; and $R^2$ is methyl or $CF_3$. In another embodiment of formula (ID), $A^1$ and $A^3$ are independently chloro, fluoro or $CF_3$; $B^1$ and $B^2$ are C—X and each X together form —CH=CH—CH=CH— to form a naphthalene ring together with the carbon atoms to which they are bonded; and $R^2$ is methyl or $CF_3$.

In yet another embodiment of formula (ID), Y is $C_1$-$C_6$alkyl or $C_1$-$C_6$haloalkyl. In still another embodiment, Y is methyl, ethyl, propyl, 1-methylethyl, butyl, 1-methylpropyl, 2-methylpropyl or 1,1-dimethylethyl. In another embodiment of formula (IC), Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$. In another embodiment of formula (ID), Y is Y-1, Y-2, Y-3, Y-4, Y-5, Y-6, Y-7, Y-8, Y-9, Y-10, Y-11, Y-12 or Y-13.

In still another embodiment of formula (ID), Y is Y-1, Y-4, Y-5, Y-6. In another embodiment, Y is Y-2, Y-3, Y-7, Y-8 or Y-9. In another embodiment, Y is Y-10, Y-11, Y-12 or Y-13.

In one embodiment of formula (ID), Y is Y-1, Y-4, Y-5 or Y-6, wherein W and $W_1$ are O; $R^9$, $R^{10}$ and $R^{11}$ are independently hydrogen, $C_1$-$C_4$alkyl, haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In another embodiment of formula (ID), Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In still another embodiment of formula (ID), Y is Y-1 wherein W is O; and $R^9$ and $R^{10}$ are independently hydrogen, $C_1$-$C_4$alkyl, $C_1$-$C_4$haloalkyl, $C_1$-$C_4$thioalkyl or $C_1$-$C_4$alkylthioalkyl. In yet another embodiment, Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In another embodiment of formula (ID), Y is Y-4, wherein W and $W_1$ are O; $R^9$ and $R^{10}$ are independently hydrogen, $C_1$-$C_4$alkyl or $C_1$-$C_4$haloalkyl; $R^{12}$ and $R^{13}$ are hydrogen; and n is 1 or 2. In another embodiment, Y is Y-4, wherein W and $W_1$ are O; $R^9$ and $R^{10}$ are independently hydrogen or $C_1$-$C_4$haloalkyl; $R^{12}$ and $R^{13}$ are hydrogen; and n is 1. In still another embodiment of formula (ID), Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In an embodiment of formula (ID), $A^1$ and $A^3$ are independently halogen, $C_1$-$C_4$alkyl or $C_1$-$C_4$haloalkyl;

$B^1$ and $B^2$ are C—H;

$R^2$ is hydrogen, halogen, $C_1$-$C_4$alkyl or $C_1$-$C_4$haloalkyl;

L is a bond or —$NR^7$—; and

Y is $C_1$-$C_6$alkyl or $C_1$-$C_6$haloalkyl.

In an embodiment of formula (ID), $A^1$ and $A^3$ are independently halogen, $C_1$-$C_4$alkyl or $C_1$-$C_4$haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$alkyl or $C_1$-$C_4$haloalkyl;

L is a bond or —$NR^7$—; and

Y is $C_1$-$C_6$alkyl or $C_1$-$C_6$haloalkyl.

In another embodiment of formula (ID), $A^1$ and $A^3$ are independently halogen, $C_1$-$C_4$alkyl or $C_1$-$C_4$haloalkyl;

B$^1$ and B$^2$ are C—H;
R$^2$ is hydrogen, halogen, C$_1$-C$_4$alkyl or C$_1$-C$_4$haloalkyl;
L is a bond or —NR$^7$—; and
Y is Y-1, Y-4, Y-5 or Y-6, in which W and W$_1$ are O, R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$-alkyl; R$^{12}$ and R$^{13}$ are hydrogen; and n is 1 or 2.

In another embodiment of formula (ID), A$^1$ and A$^3$ are independently halogen, C$_1$-C$_4$alkyl or C$_1$-C$_4$haloalkyl;
B$^1$ and B$^2$ are C—X and each X together form —CH=CH—CH=CH— to form a naphthalene ring together with the carbon atoms to which they are bonded;
R$^2$ is hydrogen, halogen, C$_1$-C$_4$alkyl or C$_1$-C$_4$haloalkyl;
L is a bond or —NR$^7$—; and
Y is Y-1, Y-4, Y-5 or Y-6, in which W and W$_1$ are O, R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$-alkyl; R$^{12}$ and R$^{13}$ are hydrogen; and n is 1 or 2.

In yet another embodiment of formula (ID), A$^1$ and A$^3$ are independently halogen, C$_1$-C$_4$alkyl or C$_1$-C$_4$haloalkyl;
B$^1$ and B$^2$ are C—H;
R$^2$ is hydrogen, halogen, C$_1$-C$_4$alkyl or C$_1$-C$_4$haloalkyl;
L is a bond or —NR$^7$—; and
Y is Y is Y-2, Y-3, Y-7, Y-8 or Y-9, in which W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$-alkyl; R$^{12}$ and R$^{13}$ are hydrogen; and n is 1 or 2.

In yet another embodiment of formula (ID), A$^1$ and A$^3$ are independently halogen, C$_1$-C$_4$alkyl or C$_1$-C$_4$haloalkyl;
B$^1$ and B$^2$ are C—X and each X together form —CH=CH—CH=CH— to form a naphthalene ring together with the carbon atoms to which they are bonded;
R$^2$ is hydrogen, halogen, C$_1$-C$_4$alkyl or C$_1$-C$_4$haloalkyl;
L is a bond or —NR$^7$—; and
Y is Y is Y-2, Y-3, Y-7, Y-8 or Y-9, in which W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$-alkyl; R$^{12}$ and R$^{13}$ are hydrogen; and n is 1 or 2.

In still another embodiment of formula (ID), A$^1$ and A$^3$ are independently halogen, C$_1$-C$_4$ alkyl or C$_1$-C$_4$ haloalkyl;
B$^1$ and B$^2$ are C—H;
R$^2$ is hydrogen, halogen, C$_1$-C$_4$ alkyl or C$_1$-C$_4$haloalkyl;
L is a bond or —NR$^7$—; and
Y is C$_1$-C$_6$alkyl or C$_1$-C$_6$haloalkyl.

In still another embodiment of formula (ID), A$^1$ and A$^3$ are independently halogen, C$_1$-C$_4$ alkyl or C$_1$-C$_4$haloalkyl;
B$^1$ and B$^2$ are independently N or C—X;
each X is independently hydrogen, alkyl, haloalkyl; or two adjacent X together form —CH=CH—CH=CH— to form a naphthalene ring together with the carbon atoms to which they are bonded;
R$^2$ is hydrogen, halogen, C$_1$-C$_4$ alkyl or C$_1$-C$_4$haloalkyl;
L is a bond or —NR$^7$—; and
Y is C$_1$-C$_6$alkyl or C$_1$-C$_6$haloalkyl.

In another embodiment of formula (ID), A$^1$ and A$^3$ are independently halogen, C$_1$-C$_4$ alkyl or C$_1$-C$_4$haloalkyl;
B$^1$ and B$^2$ are C—H;
R$^2$ is hydrogen, halogen, C$_1$-C$_4$ alkyl or C$_1$-C$_4$haloalkyl;
L is a bond or —NR$^7$—; and
Y is Y-1, Y-4, Y-5 or Y-6 in which W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$alkyl; R$^{12}$ and R$^{13}$ are hydrogen; and n is 1 or 2.

In another embodiment of formula (ID), A$^1$ and A$^3$ are independently halogen, C$_1$-C$_4$ alkyl or C$_1$-C$_4$haloalkyl;
B$^1$ and B$^2$ are C—X and each X together form —CH=CH—CH=CH— to form a naphthalene ring together with the carbon atoms to which they are bonded;
R$^2$ is hydrogen, halogen, C$_1$-C$_4$ alkyl or C$_1$-C$_4$haloalkyl;
L is a bond or —NR$^7$—; and
Y is Y-1, Y-4, Y-5 or Y-6 in which W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio-C$_1$-C$_4$alkyl; R$^{12}$ and R$^{13}$ are hydrogen; and n is 1 or 2.

In yet another embodiment of formula (ID), A$^1$ and A$^3$ are independently halogen, C$_1$-C$_4$ alkyl or C$_1$-C$_4$ haloalkyl;
B$^1$ and B$^2$ are C—H;
R$^2$ is hydrogen, halogen, C$_1$-C$_4$ alkyl or C$_1$-C$_4$haloalkyl;
L is a bond or —NR$^7$—; and
Y is Y-2, Y-3, Y-7, Y-8 or Y-9, wherein W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio C$_1$-C$_4$alkyl; R$^{12}$ and R$^{13}$ are hydrogen; and n is 1 or 2.

In yet another embodiment of formula (ID), A$^1$ and A$^3$ are independently halogen, C$_1$-C$_4$ alkyl or C$_1$-C$_4$ haloalkyl;
B$^1$ and B$^2$ are C—X and each X together form —CH=CH—CH=CH— to form a naphthalene ring together with the carbon atoms to which they are bonded;
R$^2$ is hydrogen, halogen, C$_1$-C$_4$ alkyl or C$_1$-C$_4$haloalkyl;
L is a bond or —NR$^7$—; and
Y is Y-2, Y-3, Y-7, Y-8 or Y-9, wherein W and W$_1$ are O; R$^9$, R$^{10}$ and R$^{11}$ are independently hydrogen, C$_1$-C$_4$alkyl, C$_1$-C$_4$haloalkyl, C$_1$-C$_4$thioalkyl or C$_1$-C$_4$alkylthio C$_1$-C$_4$alkyl; R$^{12}$ and R$^{13}$ are hydrogen; and n is 1 or 2.

In another embodiment of formula (ID), A$^1$ and A$^3$ are independently chloro, fluoro or CF$_3$;
B$^1$ and B$^2$ are C—H;
R$^2$ is hydrogen, methyl or CF$_3$;
R$^3$ and R$^4$ are hydrogen or C$_1$-C$_4$alkyl;
L is a bond or —NH—; and
Y is methyl, ethyl, propyl, 1-methylethyl, butyl, 1-methylpropyl, 2-methylpropyl or 1,1-dimethylethyl.

In another embodiment of formula (ID), A$^1$ and A$^3$ are independently chloro, fluoro or CF$_3$;
B$^1$ and B$^2$ are C—X and each X together form —CH=CH—CH=CH— to form a naphthalene ring together with the carbon atoms to which they are bonded;
R$^2$ is hydrogen, methyl or CF$_3$;
R$^3$ and R$^4$ are hydrogen or C$_1$-C$_4$alkyl;
L is a bond or —NH—; and
Y is methyl, ethyl, propyl, 1-methylethyl, butyl, 1-methylpropyl, 2-methylpropyl or 1,1-dimethylethyl.

In another embodiment of formula (ID), A$^1$ and A$^3$ are independently chloro, fluoro or CF$_3$;
B$^1$ and B$^2$ are C—H;
R$^2$ is hydrogen, methyl or CF$_3$;
R$^3$ and R$^4$ together with the carbon atom to which they are bonded for the group C=O;
L is a bond or —NH—; and
Y is methyl, ethyl, propyl, 1-methylethyl, butyl, 1-methylpropyl, 2-methylpropyl or 1,1-dimethylethyl.

In another embodiment of formula (ID), A$^1$ and A$^3$ are independently chloro, fluoro or CF$_3$;
B$^1$ and B$^2$ are C—X and each X together form —CH=CH—CH=CH— to form a naphthalene ring together with the carbon atoms to which they are bonded;
R$^2$ is hydrogen, methyl or CF$_3$;
R$^3$ and R$^4$ together with the carbon atom to which they are bonded for the group C=O;
L is a bond or —NH—; and
Y is methyl, ethyl, propyl, 1-methylethyl, butyl, 1-methylpropyl, 2-methylpropyl or 1,1-dimethylethyl.

In another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ are hydrogen or $C_1$-$C_4$alkyl;
L is a bond or —NH—; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ are hydrogen or $C_1$-$C_4$alkyl;
L is a bond or —NH—; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ together with the carbon atom to which they are bonded for the group C=O;
L is a bond or —NH—; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ together with the carbon atom to which they are bonded for the group C=O;
L is a bond or —NH—; and
Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$.

In yet another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ are hydrogen or $C_1$-$C_4$alkyl;
L is a bond or —NH—; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ are hydrogen or $C_1$-$C_4$alkyl;
L is a bond or —NH—; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ together with the carbon atom to which they are bonded for the group C=O;
L is a bond or —NH—; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ together with the carbon atom to which they are bonded for the group C=O;
L is a bond or —NH—; and
Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In yet another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ are hydrogen or $C_1$-$C_4$alkyl;
L is a bond or —NH—; and
Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In yet another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ are hydrogen or $C_1$-$C_4$alkyl;
L is a bond or —NH—; and
Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In yet another embodiment of formula (ID), $A^1$ and $A^3$ are independently chloro, fluoro or $CF_3$;
$B^1$ and $B^2$ are C—H;
$R^2$ is hydrogen, methyl or $CF_3$;
$R^3$ and $R^4$ together with the carbon atom to which they are bonded for the group C=O;
L is a bond or —NH—; and
Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In yet another embodiment of formula (ID), $A^1$ and $A^3$ are independently chloro, fluoro or $CF_3$;
$B^1$ and $B^2$ are C—X and each X together form —CH=CH—CH=CH— to form a naphthalene ring together with the carbon atoms to which they are bonded;
$R^2$ is hydrogen, methyl or $CF_3$;
$R^3$ and $R^4$ together with the carbon atom to which they are bonded for the group C=O;
L is a bond or —NH—; and
Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In another embodiment, the invention provides compounds of formula (IE):

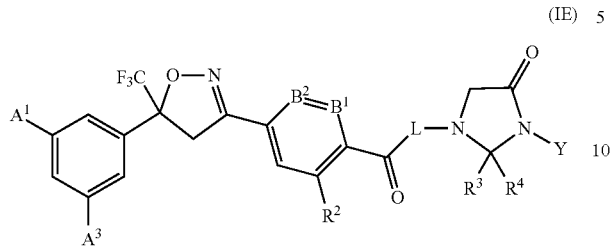

wherein:
$A^1$ and $A^3$ are independently halogen or $C_1$-$C_4$haloalkyl;
$B^1$ and $B^2$ are independently N or C—X;
each X is independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl, —CN or —NO$_2$; or two adjacent X together form a 5- or 6-membered ring together with the carbon atoms to which they are bonded by forming —CH$_2$CH$_2$CH$_2$—, —CH=CH—CH=CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—; and
$R^2$ is hydrogen, $C_1$-$C_4$alkyl or $C_1$-$C_4$ haloalkyl;
$R^3$ and $R^4$ are independently hydrogen, $C_1$-$C_4$alkyl, $C_1$-$C_4$haloalkyl or halogen; or $R^3$ and $R^4$ together with the carbon atom to which they are bonded for the group C=O;
Y is hydrogen, $C_1$-$C_4$alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

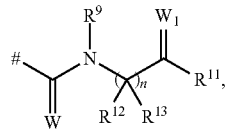
Y-1

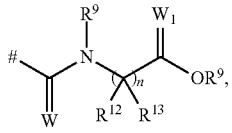
Y-2

Y-3

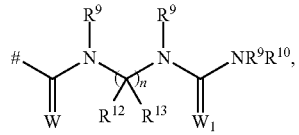
Y-4

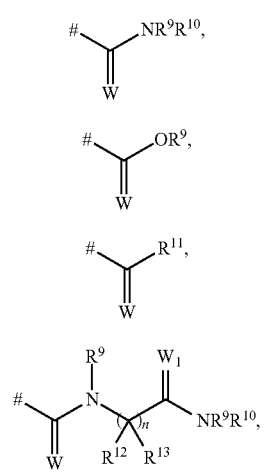

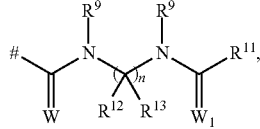
Y-5

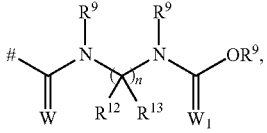
Y-6

Y-7

Y-8

Y-9

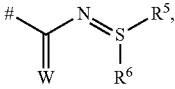
Y-10

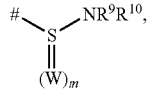
Y-11

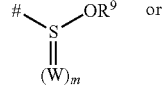
Y-12 or

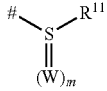
Y-13 wherein $R^7$ and $R^8$ are independently hydrogen, alkyl, haloalkyl, alkenyl, haloalkenyl, alkynyl, haloalkynyl, cycloalkyl, aryl, heteroaryl, heterocyclyl, thioalkyl, thiohaloalkyl, alkylthioalkyl, hydroxyalkyl or alkoxyalkyl;
$R^9$ and $R^{10}$ are independently hydrogen, $C_1$-$C_4$ alkyl, $C_1$-$C_4$haloalkyl, thio-$C_1$-$C_4$-alkyl or $C_1$-$C_4$alkylthio-$C_1$-$C_4$-alkyl;
each $R^{11}$ is independently hydrogen, $C_1$-$C_4$alkyl or $C_1$-$C_4$haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, thioalkyl or alkylthioalkyl;
each $R^{12}$ and $R^{13}$ is independently hydrogen or $C_1$-$C_4$alkyl;
W and $W_1$ are O;
L is a direct bond, —CR$^3$R$^4$—, —NR$^8$— or —O—;
n is 1, 2, 3 or 4; and
m is 0, 1 or 2.

In one embodiment of formula (IE), $R^3$ and $R^4$ are hydrogen. In another embodiment of formula (IE), $R^3$ and $R^4$ together with the carbon atom to which they are bonded for the group C=O.

In one embodiment of formula (IE), $A^1$ and $A^3$ are independently halogen, alkyl or haloalkyl. In an embodiment, $A^1$ and $A^3$ are independently halogen, $C_1$-$C_4$alkyl or $C_1$-$C_4$ haloalkyl.

In another embodiment of formula (IE), $A^1$ and $A^3$ are independently chloro, fluoro, $C_1$-$C_4$ alkyl or $C_1$-$C_4$ haloalkyl. In yet another embodiment of formula (IA), $A^1$ and $A^3$ are independently chloro, fluoro or $CF_3$.

In one embodiment of formula (IE), $A^1$ and $A^3$ are independently halogen, alkyl or haloalkyl; and $B^1$ and $B^2$ are C—H. In an embodiment, $A^1$ and $A^3$ are independently halogen, $C_1$-$C_4$alkyl or $C_1$-$C_4$ haloalkyl; and $B^1$ and $B^2$ are C—X and each X together form —CH=CH—CH=CH— to form a naphthalene ring together with the carbon atoms to which they are bonded.

In another embodiment of formula (IE), $A^1$ and $A^3$ are independently chloro, fluoro, $C_1$-$C_4$ alkyl or $C_1$-$C_4$ haloalkyl; and $B^1$ and $B^2$ are C—H. In yet another embodiment of formula (IA), $A^1$ and $A^3$ are independently chloro, fluoro or $CF_3$; and $B^1$ and $B^2$ are C—X and each X together form —CH=CH—CH=CH— to form a naphthalene ring together with the carbon atoms to which they are bonded.

In another embodiment of formula (IE), $R^2$ is hydrogen, halogen, alkyl or haloalkyl. In still another embodiment, $R^2$ is hydrogen, halogen, $C_1$-$C_4$ alkyl or $C_1$-$C_4$haloalkyl. In another embodiment, $R^2$ is methyl or $CF_3$.

In another embodiment of formula (IE), $A^1$ and $A^3$ are independently chloro, fluoro or $CF_3$; $B^1$ and $B^2$ are C—H; L is a bond or —$NR^7$—; and $R^2$ is methyl or $CF_3$.

In another embodiment of formula (IE), $A^1$ and $A^3$ are independently chloro, fluoro or $CF_3$; $B^1$ and $B^2$ are C—X and each X together form —CH=CH—CH=CH— to form a naphthalene ring together with the carbon atoms to which they are bonded; L is a bond or —$NR^8$—; and $R^2$ is methyl or $CF_3$.

In yet another embodiment of formula (IE), Y is $C_1$-$C_6$alkyl or $C_1$-$C_6$haloalkyl. In still another embodiment, Y is methyl, ethyl, propyl, 1-methylethyl, butyl, 1-methylpropyl, 2-methylpropyl or 1,1-dimethylethyl. In another embodiment of formula (IC), Y is $CF_3$, —$CH_2CF_3$, —$CF_2CF_3$, —$CH_2CH_2CF_3$, —$CH_2CF_2CF_3$, —$CF_2CF_2CF_3$, —$CH_2CH_2CH_2CF_3$, —$CH_2CH_2CF_2CF_3$, —$CH_2CF_2CF_2CF_3$ or —$CF_2CF_2CF_2CF_3$. In another embodiment of formula (IE), Y is Y-1, Y-2, Y-3, Y-4, Y-5, Y-6, Y-7, Y-8, Y-9, Y-10, Y-11, Y-12 or Y-13.

In still another embodiment of formula (IE), Y is Y-1, Y-4, Y-5, and Y-6. In another embodiment, Y is Y is Y-2, Y-3, Y-7, Y-8 or Y-9. In another embodiment, Y is Y-10, Y-11, Y-12 or Y-13.

In one embodiment of formula (IE), Y is Y-1, Y-4, Y-5 or Y-6, wherein W and $W_1$ are O; $R^9$, $R^{10}$ and $R^{11}$ are independently hydrogen, $C_1$-$C_4$alkyl, haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In another embodiment of formula (IE), Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In still another embodiment of formula (IE), Y is Y-1 wherein W is O; and $R^9$ and $R^{10}$ are independently hydrogen, $C_1$-$C_4$alkyl, $C_1$-$C_4$haloalkyl, $C_1$-$C_4$thioalkyl or $C_1$-$C_4$alkylthioalkyl. In yet another embodiment, Y is Y-1 wherein W is O; and $R^9$ and $R^{10}$ are independently hydrogen, —$CH_2CH_2SH$, —$CH_2CH_2SCH_3$ or —$CH_2CH_2SCF_3$.

In another embodiment of formula (IE), Y is Y-4, wherein W and $W_1$ are O; $R^9$ and $R^{10}$ are independently hydrogen, $C_1$-$C_4$alkyl or $C_1$-$C_4$haloalkyl; $R^{12}$ and $R^{13}$ are hydrogen; and n is 1 or 2. In another embodiment, Y is Y-4, wherein W and $W_1$ are O; $R^9$ and $R^{10}$ are independently hydrogen or $C_1$-$C_4$haloalkyl; $R^{12}$ and $R^{13}$ are hydrogen; and n is 1. In still another embodiment of formula (IE), Y is Y-4, wherein W and $W_1$ are O; $R^9$ and $R^{10}$ are independently hydrogen or —$CH_2CF_3$; $R^{12}$ and $R^{13}$ are hydrogen; and n is 1.

In an embodiment of formula (IE), $A^1$ and $A^3$ are independently halogen, $C_1$-$C_4$alkyl or $C_1$-$C_4$haloalkyl;
$B^1$ and $B^2$ are C—H;
$R^2$ is hydrogen, halogen, $C_1$-$C_4$alkyl or $C_1$-$C_4$haloalkyl;
L is a bond or —$NR^7$—; and
Y is $C_1$-$C_6$alkyl or $C_1$-$C_6$haloalkyl.

In another embodiment of formula (IE), $A^1$ and $A^3$ are independently halogen, $C_1$-$C_4$alkyl or $C_1$-$C_4$haloalkyl;
$R^2$ is halogen, $C_1$-$C_4$alkyl or $C_1$-$C_4$haloalkyl;
L is a bond or —$NR^7$—; and
Y is Y-1, Y-4, Y-5 or Y-6, in which W and $W_1$ are O, $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In an embodiment of formula (IE), $A^1$ and $A^3$ are independently halogen, $C_1$-$C_4$alkyl or $C_1$-$C_4$haloalkyl;
$B^1$ and $B^2$ are C—X and each X together form —CH=CH—CH=CH— to form a naphthalene ring together with the carbon atoms to which they are bonded;
$R^2$ is hydrogen, halogen, $C_1$-$C_4$alkyl or $C_1$-$C_4$haloalkyl;
L is a bond or —$NR^7$—; and
Y is $C_1$-$C_6$alkyl or $C_1$-$C_6$haloalkyl.

In another embodiment of formula (IE), $A^1$ and $A^3$ are independently halogen, $C_1$-$C_4$alkyl or $C_1$-$C_4$haloalkyl;
$R^2$ is halogen, $C_1$-$C_4$alkyl or $C_1$-$C_4$haloalkyl;
L is a bond or —$NR^7$—; and
Y is Y-1, Y-4, Y-5 or Y-6, in which W and $W_1$ are O, $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In yet another embodiment of formula (IE), $A^1$ and $A^3$ are independently halogen, $C_1$-$C_4$alkyl or $C_1$-$C_4$haloalkyl;
$B^1$ and $B^2$ are C—H;
$R^2$ is hydrogen, halogen, $C_1$-$C_4$alkyl or $C_1$-$C_4$haloalkyl;
$R^3$ and $R^4$ are hydrogen or $C_1$-$C_4$alkyl;
L is a bond or —$NR^7$—; and
Y is Y is Y-2, Y-3, Y-7, Y-8 or Y-9, in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In yet another embodiment of formula (IE), $A^1$ and $A^3$ are independently halogen, $C_1$-$C_4$alkyl or $C_1$-$C_4$haloalkyl;
$B^1$ and $B^2$ are C—X and each X together form —CH=CH—CH=CH— to form a naphthalene ring together with the carbon atoms to which they are bonded;
$R^2$ is hydrogen, halogen, $C_1$-$C_4$alkyl or $C_1$-$C_4$haloalkyl;
$R^3$ and $R^4$ are hydrogen or $C_1$-$C_4$alkyl;
L is a bond or —$NR^7$—; and
Y is Y is Y-2, Y-3, Y-7, Y-8 or Y-9, in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In yet another embodiment of formula (IE), $A^1$ and $A^3$ are independently halogen, $C_1$-$C_4$alkyl or $C_1$-$C_4$haloalkyl;

$B^1$ and $B^2$ are C—H;

$R^2$ is hydrogen, halogen, $C_1$-$C_4$alkyl or $C_1$-$C_4$haloalkyl;

$R^3$ and $R^4$ together with the carbon atom to which they are bonded for the group C=O;

L is a bond or —$NR^7$—; and

Y is Y is Y-2, Y-3, Y-7, Y-8 or Y-9, in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In yet another embodiment of formula (IE), $A^1$ and $A^3$ are independently halogen, $C_1$-$C_4$alkyl or $C_1$-$C_4$haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$alkyl or $C_1$-$C_4$haloalkyl;

$R^3$ and $R^4$ together with the carbon atom to which they are bonded for the group C=O;

L is a bond or —$NR^7$—; and

Y is Y is Y-2, Y-3, Y-7, Y-8 or Y-9, in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$-alkyl; $R^{12}$ and $R^{13}$ are hydrogen; and n is 1 or 2.

In still another embodiment of formula (IE), A and $A^3$ are independently halogen, $C_1$-$C_4$ alkyl or $C_1$-$C_4$haloalkyl;

$B^1$ and $B^2$ are C—H;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is $C_1$-$C_6$alkyl or $C_1$-$C_6$haloalkyl.

In still another embodiment of formula (IE), A and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is $C_1$-$C_6$alkyl or $C_1$-$C_6$haloalkyl.

In another embodiment of formula (IE), $A^1$ and $A^3$ are independently halogen, $C_1$-$C_4$ alkyl or $C_1$-$C_4$haloalkyl;

$B^1$ and $B^2$ are C—H;

$R^2$ is hydrogen, halogen, $C_1$-$C_4$ alkyl or $C_1$-$C_4$haloalkyl;

$R^3$ and $R^4$ together with the carbon atom to which they are bonded for the group C=O;

L is a bond or —$NR^7$—; and

Y is $C_1$-$C_6$alkyl or $C_1$-$C_6$haloalkyl.

In another embodiment of formula (IE), $A^1$ and $A^3$ are independently halogen, $C_1$-$C_4$ alkyl or $C_1$-$C_4$haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$ alkyl or $C_1$-$C_4$haloalkyl;

$R^3$ and $R^4$ together with the carbon atom to which they are bonded for the group C=O;

L is a bond or —$NR^7$—; and

Y is $C_1$-$C_6$alkyl or $C_1$-$C_6$haloalkyl.

In another embodiment of formula (IE), $A^1$ and $A^3$ are independently halogen, $C_1$-$C_4$ alkyl or $C_1$-$C_4$ haloalkyl;

$B^1$ and $B^2$ are C—H;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$alkyl; $R^{12}$ and $R^{13}$ are hydrogen; and n is 1 or 2.

In another embodiment of formula (IE), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$alkyl; $R^{12}$ and $R^{13}$ are hydrogen; and n is 1 or 2.

In another embodiment of formula (IE), $A^1$ and $A^3$ are independently halogen, $C_1$-$C_4$ alkyl or $C_1$-$C_4$ haloalkyl;

$B^1$ and $B^2$ are C—H;

$R^2$ is hydrogen, halogen, $C_1$-$C_4$ alkyl or $C_1$-$C_4$haloalkyl;

$R^3$ and $R^4$ together with the carbon atom to which they are bonded for the group C=O;

L is a bond or —$NR^7$—; and

Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$alkyl; $R^{12}$ and $R^{13}$ are hydrogen; and n is 1 or 2.

In another embodiment of formula (IE), $A^1$ and $A^3$ are independently halogen, $C_1$-$C_4$ alkyl or $C_1$-$C_4$haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$ alkyl or $C_1$-$C_4$haloalkyl;

$R^3$ and $R^4$ together with the carbon atom to which they are bonded for the group C=O;

L is a bond or —$NR^7$—; and

Y is Y-1, Y-4, Y-5 or Y-6 in which W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio-$C_1$-$C_4$alkyl; $R^{12}$ and $R^{13}$ are hydrogen; and n is 1 or 2.

In yet another embodiment of formula (IE), $A^1$ and $A^3$ are independently halogen, $C_1$-$C_4$ alkyl or $C_1$-$C_4$haloalkyl;

$B^1$ and $B^2$ are C—H;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IE), $A^1$ and $A^3$ are independently halogen, $C_1$-$C_4$ alkyl or $C_1$-$C_4$ haloalkyl;

$B^1$ and $B^2$ are C—X and each X together form —CH=CH—CH=CH— to form a naphthalene ring together with the carbon atoms to which they are bonded;

$R^2$ is hydrogen, halogen, $C_1$-$C_4$ alkyl or $C_1$-$C_4$haloalkyl;

$R^3$ and $R^4$ are hydrogen or $C_1$-$C_4$alkyl;

L is a bond or —$NR^7$—; and

Y is Y-2, Y-3, Y-7, Y-8 or Y-9, wherein W and $W_1$ are O; $R^9$, $R^{10}$ and $R^{11}$ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; $R^{12}$ and $R^{13}$ are hydrogen; and n is 1 or 2.

In yet another embodiment of formula (IE), $A^1$ and $A^3$ are independently halogen, $C_1$-$C_4$ alkyl or $C_1$-$C_4$ haloalkyl;

$B^1$ and $B^2$ are C—H;

$R^2$ is hydrogen, halogen, $C_1$-$C_4$ alkyl or $C_1$-$C_4$haloalkyl;

R³ and R⁴ together with the carbon atom to which they are bonded for the group C=O;

L is a bond or —NR⁷—; and

Y is Y-2, Y-3, Y-7, Y-8 or Y-9, wherein W and W₁ are O; R⁹, R¹⁰ and R¹¹ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; R¹² and R¹³ are hydrogen; and n is 1 or 2.

In yet another embodiment of formula (IE), A¹ and A³ are independently halogen, $C_1$-$C_4$ alkyl or $C_1$-$C_4$ haloalkyl;

B¹ and B² are C—X and each X together form —CH=CH—CH=CH— to form a naphthalene ring together with the carbon atoms to which they are bonded;

R² is hydrogen, halogen, $C_1$-$C_4$ alkyl or $C_1$-$C_4$haloalkyl;

R³ and R⁴ together with the carbon atom to which they are bonded for the group C=O;

L is a bond or —NR⁷—; and

Y is Y-2, Y-3, Y-7, Y-8 or Y-9, wherein W and W₁ are O; R⁹, R¹⁰ and R¹¹ are independently hydrogen, $C_1$-$C_4$alkyl, $C_1$-$C_4$haloalkyl, $C_1$-$C_4$thioalkyl or $C_1$-$C_4$alkylthio $C_1$-$C_4$alkyl; R¹² and R¹³ are hydrogen; and n is 1 or 2.

In another embodiment of formula (IE), A¹ and A³ are independently chloro, fluoro or CF₃;

B¹ and B² are C—H;

R² is hydrogen, methyl or CF₃;

R³ and R⁴ are hydrogen or $C_1$-$C_4$alkyl;

L is a bond or —NH—; and

Y is methyl, ethyl, propyl, 1-methylethyl, butyl, 1-methylpropyl, 2-methylpropyl or 1,1-dimethylethyl.

In another embodiment of formula (IE), A¹ and A³ are independently chloro, fluoro or CF₃;

B¹ and B² are C—X and each X together form —CH=CH—CH=CH— to form a naphthalene ring together with the carbon atoms to which they are bonded;

R² is hydrogen, methyl or CF₃;

R³ and R⁴ are hydrogen or $C_1$-$C_4$alkyl;

L is a bond or —NH—; and

Y is methyl, ethyl, propyl, 1-methylethyl, butyl, 1-methylpropyl, 2-methylpropyl or 1,1-dimethylethyl.

In another embodiment of formula (IE), A¹ and A³ are independently chloro, fluoro or CF₃;

B¹ and B² are C—H;

R² is hydrogen, methyl or CF₃;

R³ and R⁴ together with the carbon atom to which they are bonded for the group C=O;

L is a bond or —NH—; and

Y is methyl, ethyl, propyl, 1-methylethyl, butyl, 1-methylpropyl, 2-methylpropyl or 1,1-dimethylethyl.

In another embodiment of formula (IE), A¹ and A³ are independently chloro, fluoro or CF₃;

B¹ and B² are C—X and each X together form —CH=CH—CH=CH— to form a naphthalene ring together with the carbon atoms to which they are bonded;

R² is hydrogen, methyl or CF₃;

R³ and R⁴ together with the carbon atom to which they are bonded for the group C=O;

L is a bond or —NH—; and

Y is methyl, ethyl, propyl, 1-methylethyl, butyl, 1-methylpropyl, 2-methylpropyl or 1,1-dimethylethyl.

In another embodiment of formula (IE), A¹ and A³ are independently chloro, fluoro or CF₃;

B¹ and B² are C—H;

R² is hydrogen, methyl or CF₃;

R³ and R⁴ are hydrogen or $C_1$-$C_4$alkyl;

L is a bond or —NH—; and

Y is CF₃, —CH₂CF₃, —CF₂CF₃, —CH₂CH₂CF₃, —CH₂CF₂CF₃, —CF₂CF₂CF₃, —CH₂CH₂CH₂CF₃, —CH₂CH₂CF₂CF₃, —CH₂CF₂CF₂CF₃ or —CF₂CF₂CF₂CF₃.

In another embodiment of formula (IE), A¹ and A³ are independently chloro, fluoro or CF₃;

B¹ and B² are C—X and each X together form —CH=CH—CH=CH— to form a naphthalene ring together with the carbon atoms to which they are bonded;

R² is hydrogen, methyl or CF₃;

R³ and R⁴ are hydrogen or $C_1$-$C_4$alkyl;

L is a bond or —NH—; and

Y is CF₃, —CH₂CF₃, —CF₂CF₃, —CH₂CH₂CF₃, —CH₂CF₂CF₃, —CF₂CF₂CF₃, —CH₂CH₂CH₂CF₃, —CH₂CH₂CF₂CF₃, —CH₂CF₂CF₂CF₃ or —CF₂CF₂CF₂CF₃.

In another embodiment of formula (IE), A¹ and A³ are independently chloro, fluoro or CF₃;

B¹ and B² are C—H;

R² is hydrogen, methyl or CF₃;

R³ and R⁴ together with the carbon atom to which they are bonded for the group C=O;

L is a bond or —NH—; and

Y is CF₃, —CH₂CF₃, —CF₂CF₃, —CH₂CH₂CF₃, —CH₂CF₂CF₃, —CF₂CF₂CF₃, —CH₂CH₂CH₂CF₃, —CH₂CH₂CF₂CF₃, —CH₂CF₂CF₂CF₃ or —CF₂CF₂CF₂CF₃.

In another embodiment of formula (IE), A¹ and A³ are independently chloro, fluoro or CF₃;

B¹ and B² are C—X and each X together form —CH=CH—CH=CH— to form a naphthalene ring together with the carbon atoms to which they are bonded;

R² is hydrogen, methyl or CF₃;

R³ and R⁴ together with the carbon atom to which they are bonded for the group C=O;

L is a bond or —NH—; and

Y is CF₃, —CH₂CF₃, —CF₂CF₃, —CH₂CH₂CF₃, —CH₂CF₂CF₃, —CF₂CF₂CF₃, —CH₂CH₂CH₂CF₃, —CH₂CH₂CF₂CF₃, —CH₂CF₂CF₂CF₃ or —CF₂CF₂CF₂CF₃.

In yet another embodiment of formula (IE), A¹ and A³ are independently chloro, fluoro or CF₃; R¹ is CF₃;

B¹ and B² are C—H;

R² is hydrogen, methyl or CF₃;

R³ and R⁴ are hydrogen or $C_1$-$C_4$alkyl;

L is a bond or —NH—; and

Y is Y-1 wherein W is O; and R⁹ and R¹⁰ are independently hydrogen, —CH₂CH₂SH, —CH₂CH₂SCH₃ or —CH₂CH₂SCF₃.

In yet another embodiment of formula (IE), A¹ and A³ are independently chloro, fluoro or CF₃; R¹ is CF₃;

B¹ and B² are C—H;

R² is hydrogen, methyl or CF₃;

R³ and R⁴ are hydrogen or $C_1$-$C_4$alkyl;

L is a bond or —NH—; and

Y is Y-1 wherein W is O; and R⁹ and R¹⁰ are independently hydrogen, —CH₂CH₂SH, —CH₂CH₂SCH₃ or —CH₂CH₂SCF₃.

In yet another embodiment of formula (IE), A¹ and A³ are independently chloro, fluoro or CF₃;

B¹ and B² are C—H;

R¹ is CF₃;

R² is hydrogen, methyl or CF₃;

R³ and R⁴ together with the carbon atom to which they are bonded for the group C=O;

L is a bond or —NH—; and

Y is Y-1 wherein W is O; and $R^9$ and $R^{10}$ are independently hydrogen, —CH$_2$CH$_2$SH, —CH$_2$CH$_2$SCH$_3$ or —CH$_2$CH$_2$SCF$_3$.

In yet another embodiment of formula (IE), $A^1$ and $A^3$ are independently chloro, fluoro or CF$_3$;
$B^1$ and $B^2$ are C—X and each X together form —CH=CH—CH=CH— to form a naphthalene ring together with the carbon atoms to which they are bonded;
$R^1$ is CF$_3$;
$R^2$ is hydrogen, methyl or CF$_3$;
$R^3$ and $R^4$ together with the carbon atom to which they are bonded for the group C=O;
L is a bond or —NH—; and
Y is Y-1 wherein W is O; and $R^9$ and $R^{10}$ are independently hydrogen, —CH$_2$CH$_2$SH, —CH$_2$CH$_2$SCH$_3$ or —CH$_2$CH$_2$SCF$_3$.

In yet another embodiment of formula (IE), $A^1$ and $A^3$ are independently chloro, fluoro or CF$_3$;
$B^1$ and $B^2$ are C—H;
$R^2$ is hydrogen, methyl or CF$_3$;
$R^3$ and $R^4$ are hydrogen or $C_1$-$C_4$alkyl;
L is a bond or —NH—; and
Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In yet another embodiment of formula (IE), $A^1$ and $A^3$ are independently chloro, fluoro or CF$_3$;
$B^1$ and $B^2$ are C—X and each X together form —CH=CH—CH=CH— to form a naphthalene ring together with the carbon atoms to which they are bonded;
$R^2$ is hydrogen, methyl or CF$_3$;
$R^3$ and $R^4$ together with the carbon atom to which they are bonded for the group C=O;
L is a bond or —NH—; and
Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

$R^2$ is hydrogen, methyl or CF$_3$;
$R^3$ and $R^4$ are hydrogen or $C_1$-$C_4$alkyl;
L is a bond or —NH—; and
Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In yet another embodiment of formula (IE), $A^1$ and $A^3$ are independently chloro, fluoro or CF$_3$;
$B^1$ and $B^2$ are C—H;
$R^2$ is hydrogen, methyl or CF$_3$;
$R^3$ and $R^4$ together with the carbon atom to which they are bonded for the group C=O;
L is a bond or —NH—; and
Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In yet another embodiment of formula (IE), $A^1$ and $A^3$ are independently chloro, fluoro or CF$_3$;
$B^1$ and $B^2$ are C—X and each X together form —CH=CH—CH=CH— to form a naphthalene ring together with the carbon atoms to which they are bonded;
$R^2$ is hydrogen, methyl or CF$_3$;
$R^3$ and $R^4$ together with the carbon atom to which they are bonded for the group C=O;
L is a bond or —NH—; and
Y is Y-4, wherein W and $W_1$ are O; $R^9$ and $R^{10}$ are independently hydrogen or —CH$_2$CF$_3$; $R^{12}$ and $R^{13}$ are hydrogen; and n is 1.

In other embodiments, the invention provides the compounds in Table 1 below:

TABLE 1

| Compound | Structure |
|---|---|
| 67 | 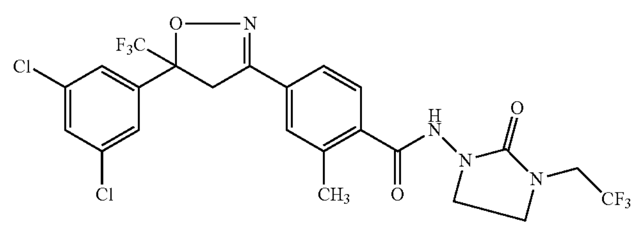 [SMILES: Cc1cc(C2=NOC(c3cc(Cl)cc(Cl)c3)(C(F)(F)F)C2)ccc1C(=O)NN1CCN(CC(F)(F)F)C1=O] |
| 70 | 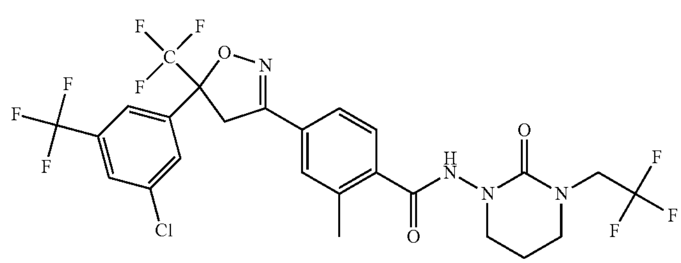 [SMILES: Cc1cc(C2=NOC(c3cc(Cl)cc(C(F)(F)F)c3)(C(F)(F)F)C2)ccc1C(=O)NN1CCCN(CC(F)(F)F)C1=O] |
| 90 | 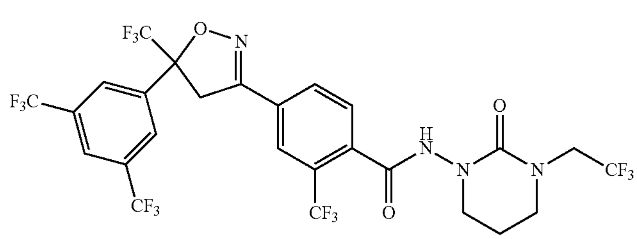 [SMILES: O=C(NN1CCCN(CC(F)(F)F)C1=O)c1ccc(C2=NOC(c3cc(C(F)(F)F)cc(C(F)(F)F)c3)(C(F)(F)F)C2)cc1C(F)(F)F] |

TABLE 1-continued

| Compound | Structure |
|---|---|
| 91 | 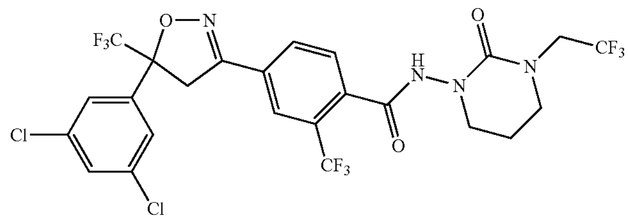 [SMILES: O=C(NN1CCCN(CC(F)(F)F)C1=O)c1ccc(C2=NOC(c3cc(Cl)cc(Cl)c3)(C(F)(F)F)C2)cc1C(F)(F)F] |
| 97 | 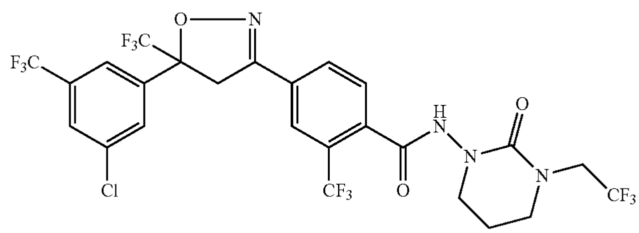 [SMILES: O=C(NN1CCCN(CC(F)(F)F)C1=O)c1ccc(C2=NOC(c3cc(Cl)cc(C(F)(F)F)c3)(C(F)(F)F)C2)cc1C(F)(F)F] |
| 69 | 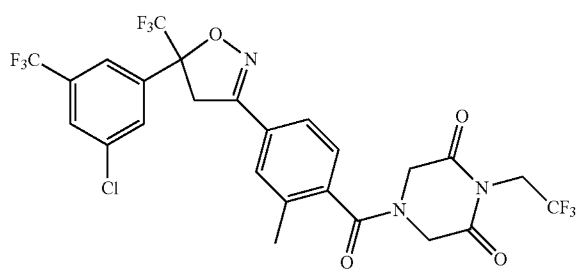 [SMILES: Cc1cc(C2=NOC(c3cc(Cl)cc(C(F)(F)F)c3)(C(F)(F)F)C2)ccc1C(=O)N1CC(=O)N(CC(F)(F)F)C(=O)C1] |
| 71 | 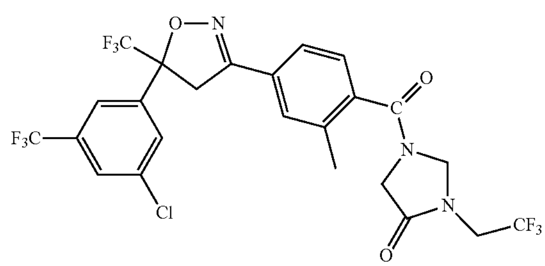 [SMILES: Cc1cc(C2=NOC(c3cc(Cl)cc(C(F)(F)F)c3)(C(F)(F)F)C2)ccc1C(=O)N1CC(=O)N(CC(F)(F)F)C1] |
| 79 | 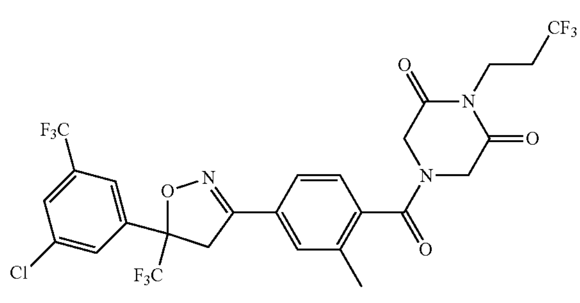 [SMILES: Cc1cc(C2=NOC(c3cc(Cl)cc(C(F)(F)F)c3)(C(F)(F)F)C2)ccc1C(=O)N1CC(=O)N(CCC(F)(F)F)C(=O)C1] |
| 80 | 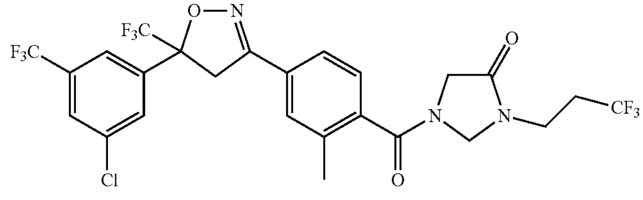 [SMILES: Cc1cc(C2=NOC(c3cc(Cl)cc(C(F)(F)F)c3)(C(F)(F)F)C2)ccc1C(=O)N1CC(=O)N(CCC(F)(F)F)C1] |

TABLE 1-continued
| Compound | Structure |
|---|---|
| 92 | 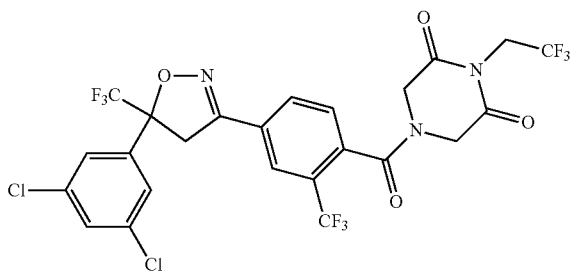 [SMILES: O=C(c1ccc(C2=NOC(c3cc(Cl)cc(Cl)c3)(C(F)(F)F)C2)cc1C(F)(F)F)N1CC(=O)N(CC(F)(F)F)C(=O)C1] |
| 93 | 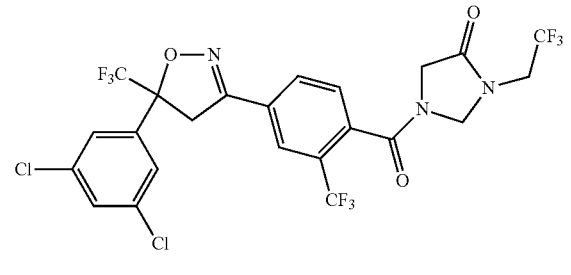 [SMILES: O=C1CN(C(=O)c2ccc(C3=NOC(c4cc(Cl)cc(Cl)c4)(C(F)(F)F)C3)cc2C(F)(F)F)CN1CC(F)(F)F] |
| 95 | 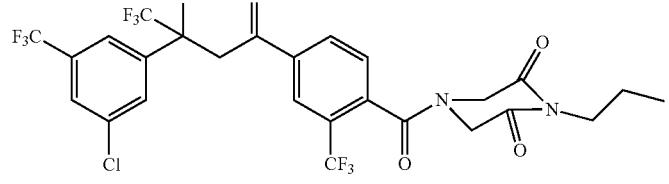 |
| 96 | 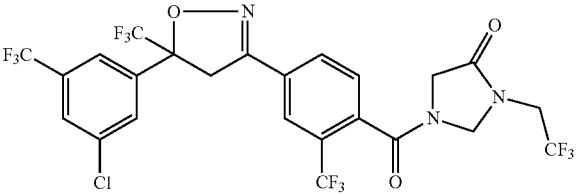 [SMILES: O=C1CN(C(=O)c2ccc(C3=NOC(c4cc(Cl)cc(C(F)(F)F)c4)(C(F)(F)F)C3)cc2C(F)(F)F)CN1CC(F)(F)F] |
| 98 | 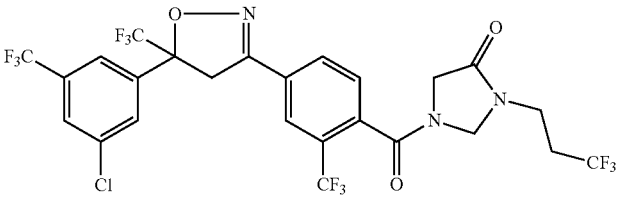 [SMILES: O=C1CN(C(=O)c2ccc(C3=NOC(c4cc(Cl)cc(C(F)(F)F)c4)(C(F)(F)F)C3)cc2C(F)(F)F)CN1CCC(F)(F)F] |
| 99 | 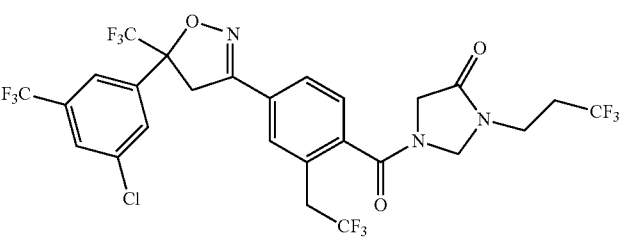 [SMILES: O=C1CN(C(=O)c2ccc(C3=NOC(c4cc(Cl)cc(C(F)(F)F)c4)(C(F)(F)F)C3)cc2CC(F)(F)F)CN1CCC(F)(F)F] |
| 9 | 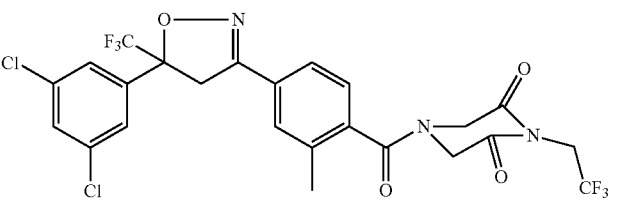 [SMILES: Cc1cc(C2=NOC(c3cc(Cl)cc(Cl)c3)(C(F)(F)F)C2)ccc1C(=O)N1CC(=O)N(CC(F)(F)F)C(=O)C1] |

TABLE 1-continued

| Compound | Structure |
|---|---|
| 9-10 | 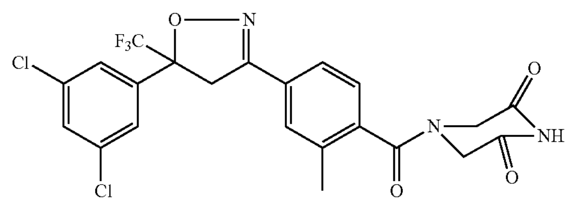 [SMILES: Cc1cc(C2=NOC(c3cc(Cl)cc(Cl)c3)(C(F)(F)F)C2)ccc1C(=O)N1CC(=O)NC(=O)C1] |
| 18 | 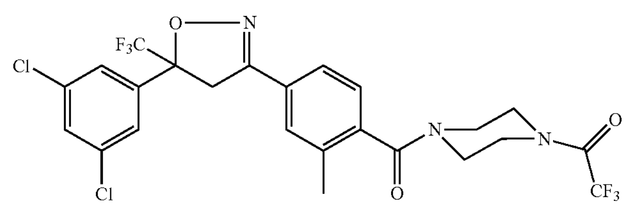 [SMILES: Cc1cc(C2=NOC(c3cc(Cl)cc(Cl)c3)(C(F)(F)F)C2)ccc1C(=O)N1CCN(C(=O)C(F)(F)F)CC1] |
| 18-1 | 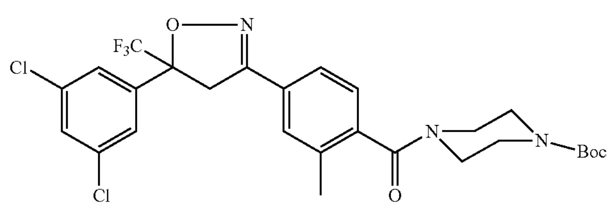 [SMILES: Cc1cc(C2=NOC(c3cc(Cl)cc(Cl)c3)(C(F)(F)F)C2)ccc1C(=O)N1CCN(C(=O)OC(C)(C)C)CC1] |
| 18-3 | 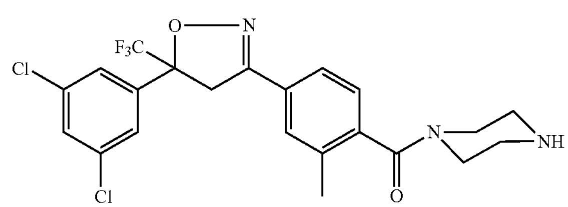 [SMILES: Cc1cc(C2=NOC(c3cc(Cl)cc(Cl)c3)(C(F)(F)F)C2)ccc1C(=O)N1CCNCC1] |
| 20 | 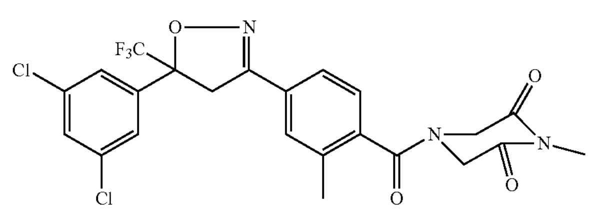 [SMILES: Cc1cc(C2=NOC(c3cc(Cl)cc(Cl)c3)(C(F)(F)F)C2)ccc1C(=O)N1CC(=O)N(C)C(=O)C1] |
| 21 | 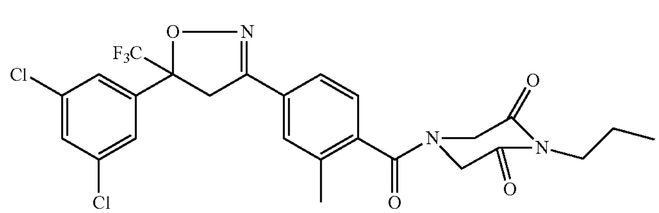 [SMILES: CCCN1C(=O)CN(C(=O)c2ccc(C3=NOC(c4cc(Cl)cc(Cl)c4)(C(F)(F)F)C3)cc2C)CC1=O] |
| 22 | 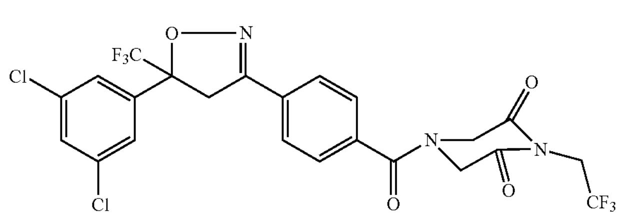 |

TABLE 1-continued

| Compound | Structure |
|---|---|
| 23 | 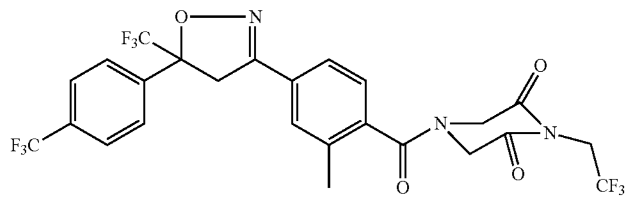 |
| 24 | 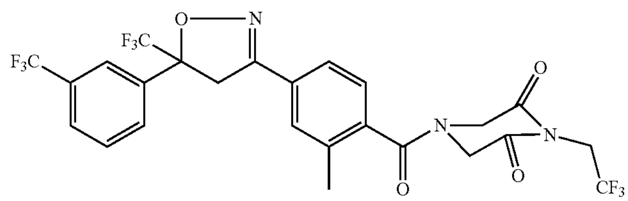 [SMILES: Cc1cc(C2=NOC(c3cccc(C(F)(F)F)c3)(C(F)(F)F)C2)ccc1C(=O)N1CC(=O)N(CC(F)(F)F)C(=O)C1] |
| 25 | 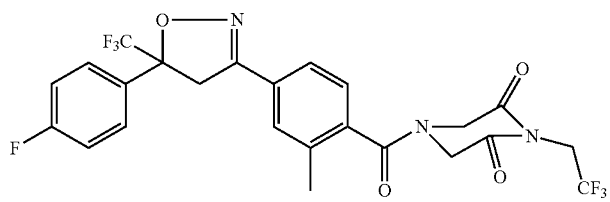 [SMILES: Cc1cc(C2=NOC(c3ccc(F)cc3)(C(F)(F)F)C2)ccc1C(=O)N1CC(=O)N(CC(F)(F)F)C(=O)C1] |
| 26 | 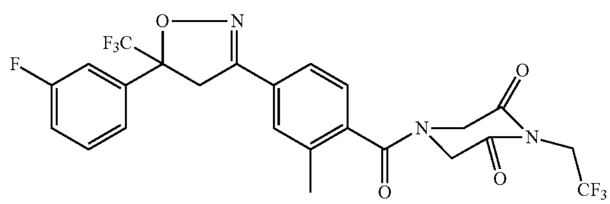 [SMILES: Cc1cc(C2=NOC(c3cccc(F)c3)(C(F)(F)F)C2)ccc1C(=O)N1CC(=O)N(CC(F)(F)F)C(=O)C1] |
| 27 | 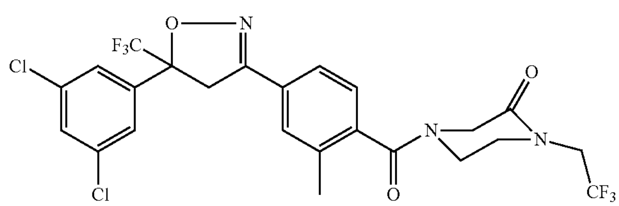 [SMILES: Cc1cc(C2=NOC(c3cc(Cl)cc(Cl)c3)(C(F)(F)F)C2)ccc1C(=O)N1CCN(CC(F)(F)F)C(=O)C1] |
| 28 | 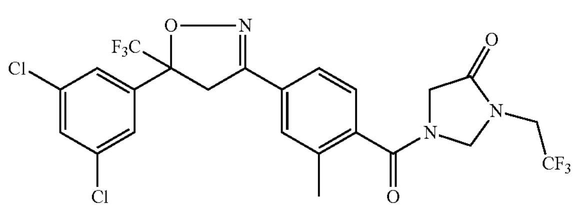 [SMILES: Cc1cc(C2=NOC(c3cc(Cl)cc(Cl)c3)(C(F)(F)F)C2)ccc1C(=O)N1CC(=O)N(CC(F)(F)F)C1] |
| 29 | 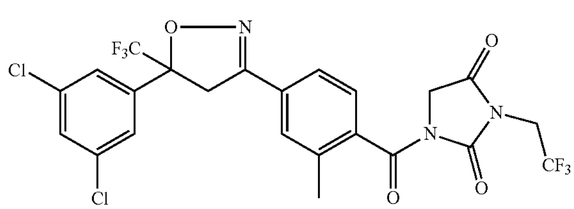 [SMILES: Cc1cc(C2=NOC(c3cc(Cl)cc(Cl)c3)(C(F)(F)F)C2)ccc1C(=O)N1CC(=O)N(CC(F)(F)F)C1=O] |

TABLE 1-continued

| Compound | Structure |
|---|---|
| 30 | 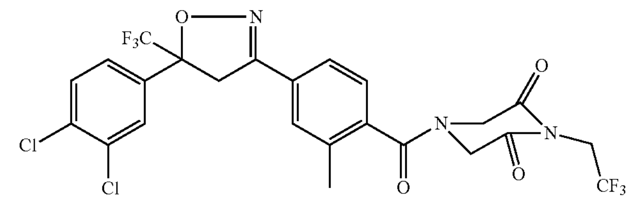 [SMILES: Cc1cc(C2=NOC(c3ccc(Cl)c(Cl)c3)(C(F)(F)F)C2)ccc1C(=O)N1CC(=O)N(CC(F)(F)F)C(=O)C1] |
| 31 | 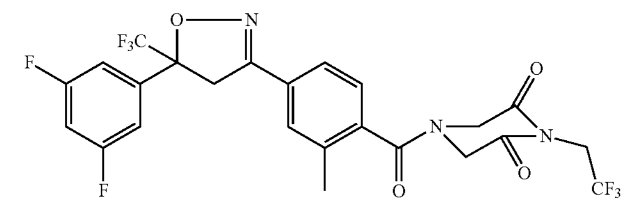 [SMILES: Cc1cc(C2=NOC(c3cc(F)cc(F)c3)(C(F)(F)F)C2)ccc1C(=O)N1CC(=O)N(CC(F)(F)F)C(=O)C1] |
| 32 | 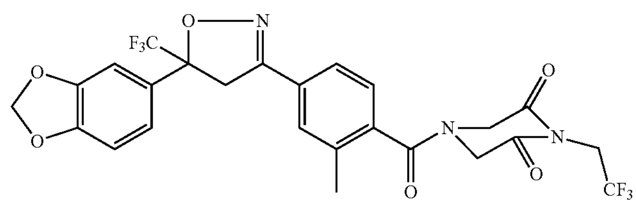 [SMILES: Cc1cc(C2=NOC(c3ccc4c(c3)OCO4)(C(F)(F)F)C2)ccc1C(=O)N1CC(=O)N(CC(F)(F)F)C(=O)C1] |
| 33 | 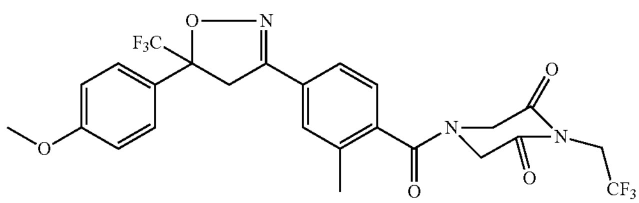 [SMILES: COc1ccc(C2(C(F)(F)F)CC(c3ccc(C(=O)N4CC(=O)N(CC(F)(F)F)C(=O)C4)c(C)c3)=NO2)cc1] |
| 34 | 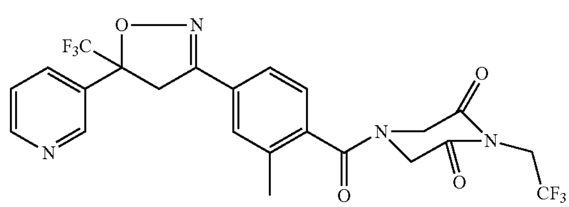 [SMILES: Cc1cc(C2=NOC(c3cccnc3)(C(F)(F)F)C2)ccc1C(=O)N1CC(=O)N(CC(F)(F)F)C(=O)C1] |
| 35 | 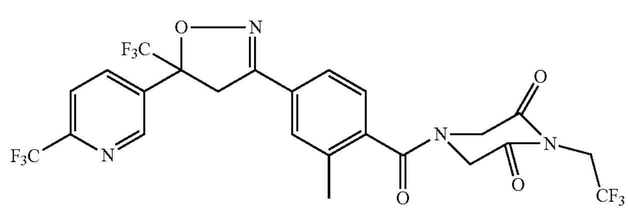 [SMILES: Cc1cc(C2=NOC(c3ccc(C(F)(F)F)nc3)(C(F)(F)F)C2)ccc1C(=O)N1CC(=O)N(CC(F)(F)F)C(=O)C1] |
| 36 | 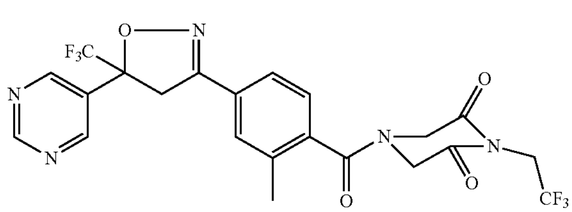 [SMILES: Cc1cc(C2=NOC(c3cncnc3)(C(F)(F)F)C2)ccc1C(=O)N1CC(=O)N(CC(F)(F)F)C(=O)C1] |

TABLE 1-continued
| Compound | Structure |
|---|---|
| 42 | 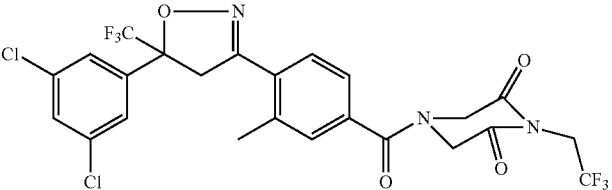 [SMILES: Cc1cc(C(=O)N2CC(=O)N(CC(F)(F)F)C(=O)C2)ccc1C1=NOC(c2cc(Cl)cc(Cl)c2)(C(F)(F)F)C1] |
| 43 | 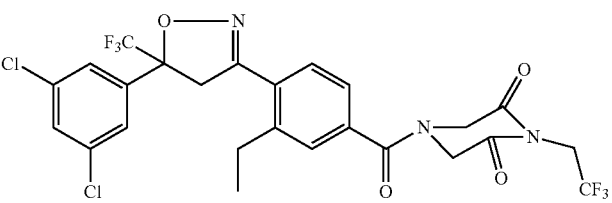 [SMILES: CCc1cc(C(=O)N2CC(=O)N(CC(F)(F)F)C(=O)C2)ccc1C1=NOC(c2cc(Cl)cc(Cl)c2)(C(F)(F)F)C1] |
| 44 | 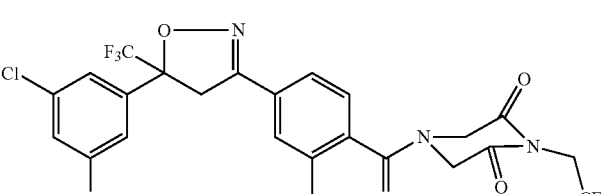 |
| 45 | 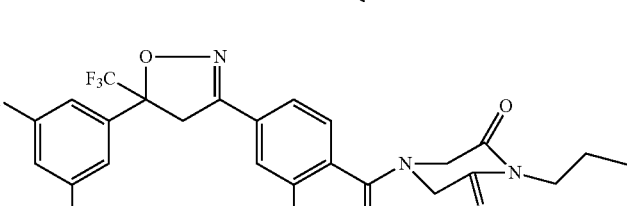 |
| 46 | 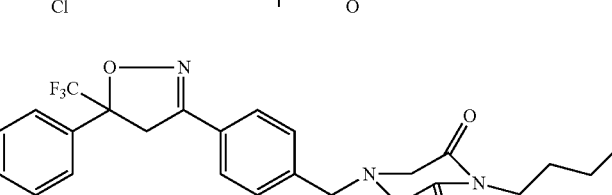 |
| 47 | 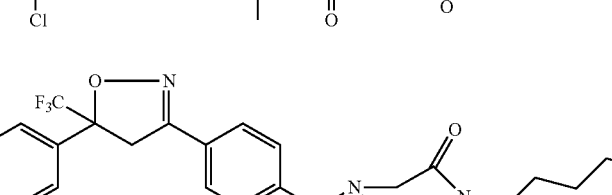 |
| 48 | 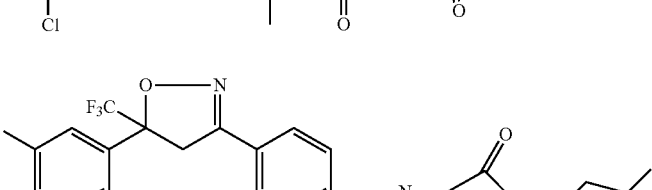 |

TABLE 1-continued
| Compound | Structure |
|---|---|
| 49 | 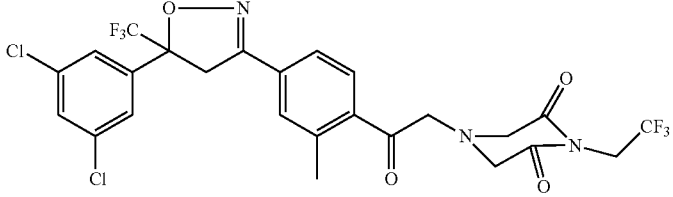 [SMILES: Cc1cc(C2=NOC(c3cc(Cl)cc(Cl)c3)(C(F)(F)F)C2)ccc1C(=O)CN1CC(=O)N(CC(F)(F)F)C(=O)C1] |
| 50 | 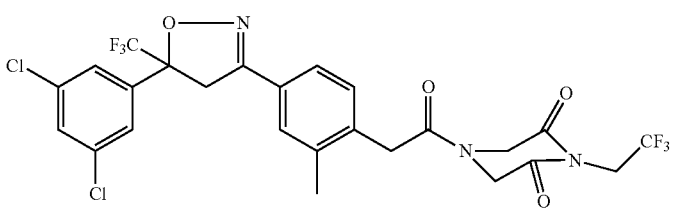 [SMILES: Cc1cc(C2=NOC(c3cc(Cl)cc(Cl)c3)(C(F)(F)F)C2)ccc1CC(=O)N1CC(=O)N(CC(F)(F)F)C(=O)C1] |
| 51 | 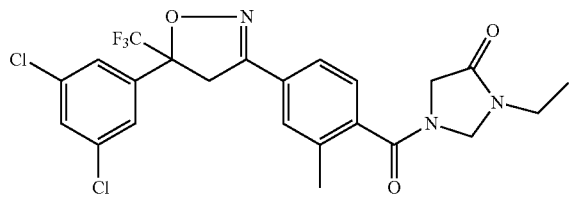 [SMILES: CCN1CN(C(=O)c2ccc(C3=NOC(c4cc(Cl)cc(Cl)c4)(C(F)(F)F)C3)cc2C)CC1=O] |
| 52 | 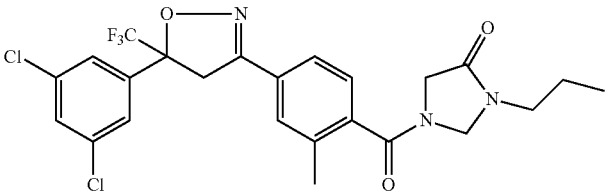 [SMILES: CCCN1CN(C(=O)c2ccc(C3=NOC(c4cc(Cl)cc(Cl)c4)(C(F)(F)F)C3)cc2C)CC1=O] |
| 53 | 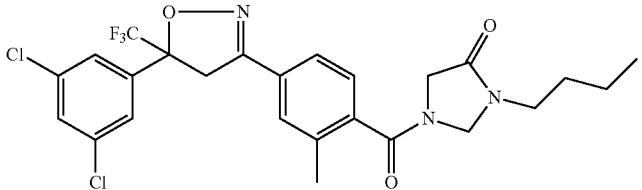 [SMILES: CCCCN1CN(C(=O)c2ccc(C3=NOC(c4cc(Cl)cc(Cl)c4)(C(F)(F)F)C3)cc2C)CC1=O] |
| 54 | 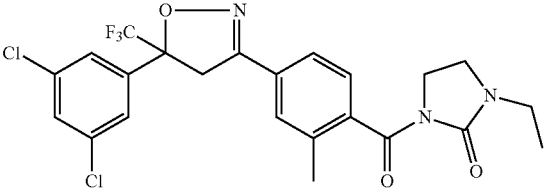 [SMILES: CCN1CCN(C(=O)c2ccc(C3=NOC(c4cc(Cl)cc(Cl)c4)(C(F)(F)F)C3)cc2C)C1=O] |
| 112 | 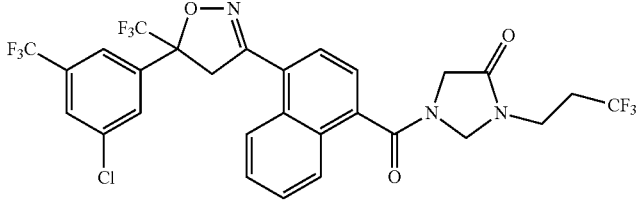 [SMILES: O=C1CN(C(=O)c2ccc(C3=NOC(c4cc(Cl)cc(C(F)(F)F)c4)(C(F)(F)F)C3)c3ccccc23)CN1CCC(F)(F)F] |

TABLE 1-continued

| Compound | Structure |
|---|---|
| 114 | (structure) |
| 115 | (structure) |

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I), (IA), (IB), (IC), (ID) and (IE) are also the subject of the invention.

Salts

In addition to the neutral compounds of formula (I), salt forms of the compounds are also active against animal pests. The terms "veterinarily acceptable salt" and "agriculturally acceptable salt" are used throughout the specification to describe any salts of the compounds that are acceptable for administration for veterinary and agricultural applications, and which provides the active compound upon administration.

In cases where compounds are sufficiently basic or acidic to form stable non-toxic acid or base salts, the compounds may be in the form of a veterinarily or agriculturally acceptable salt. Veterinarily or agriculturally acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily and agriculturally acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Definitions

For the purposes of this application, unless otherwise stated in the specification, the following terms have the terminology cited below:

(1) Alkyl refers to both straight, branched carbon chains and cyclic hydrocarbon groups. In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-6 or 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by the term "alkyl", may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10, 2-8 or 2-6. In yet another embodiment of alkenyl, the number of carbon atoms is 2-4. Other ranges of carbon-carbon double bonds and carbon numbers are also contemplated depending on the location of the alkenyl moiety on the molecule.

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronapthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or SFS. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetrahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means and isoxazoline compound of the invention.

The term "locus" is intended to mean a habitat, breeding ground, area, material or environment in which a parasite is growing or may grow. The term "locus" does not include the body of an animal.

Synthesis of Compounds

The isoxazoline compounds of formula (I), (IA), (IB), (IC), (ID) or (IE) may be prepared by processes described herein or by adaptation of these processes or process known in the art to prepare compounds with different substitution patterns. For example, the compounds of the invention may be prepared by adaptation of processes described in U.S. Pat. Nos. 7,951,828; 7,662,971; 7,662,972; 8,389,738; 8,217,180; 8,513,431 and U.S. Patent Publication No. 2010/0137612 (all incorporated herein by reference). Scheme 1 below describes one embodiment of the synthesis of certain compounds of the invention of formula (I), wherein $A^1$, $A^2$, $A^3$, $R^1$, $B^1$, $B^2$, $B^3$, $R^2$, $R^3$, $R^4$, $R^5$, $R^6$, $R^8$ L, Y, a and b are as described above, from carboxylic acid 1-1.

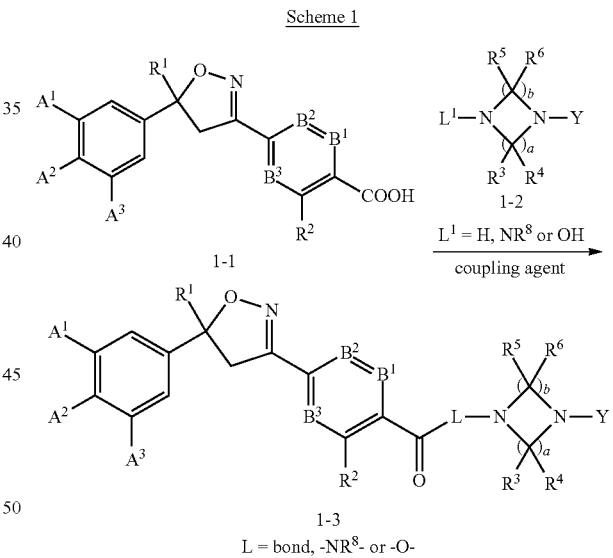

Scheme 1

The preparation of carboxylic acid 1-1 has been described previously in, for example, U.S. Pat. Nos. 7,951,828; 7,662,971; 7,662,972; 8,389,738; 8,217,180; 8,513,431 and U.S. Patent Publication No. 2010/0137612. Thus, carboxylic acid 1-1 is activated by addition of an appropriate activating agent such as a known peptide coupling agent including, but not limited to, a carbodiimide coupling agent, a phosphonium or uronium coupling agents and the like, to generate an activated acyl group, followed by reaction with compound 1-2 to provide the desired compound 1-3. A general description of this transformation is described in *March's Advanced Organic Chemistry*—Reactions, Mechanisms and Structure (6$^{th}$ Edition), ed. Michael B. Smith and Jerry March, Wiley Interscience (John Wiley & Sons, Inc.), page 1430-1434

(16-74—Acylation of Amines by Carboxylic Acids—Amino-de-hydroxylation), (2007). In another embodiment, the carboxylic acid 1-1 may be first converted to a reactive acyl halide compound or activated ester compound that is then reacted with compound 1-2 to form compound 1-3. Activated ester compounds include esters of phenols containing one or more electronic withdrawing groups on the phenyl ring such nitro, fluoro, chloro, and the like. Other active esters include succinimido esters (see for example, Amino Acid and Peptide Synthesis, second edition, by John Jones; Oxford University Press, 2002).

In another embodiment of the invention, certain compounds of the invention of formula (I), wherein $A^1$, $A^2$, $A^3$, $R^1$, $B^1$, $B^2$, $B^3$, $R^2$, $R^3$, $R^4$, $R^5$, $R^6$, $R^8$, L, Y, a and b are as described above, are prepared from carboxylic acid 1-1 according to the method shown in scheme 2 below.

or by use of column chromatography or reverse-phase column chromatography using a substantially optically active (or "chiral") stationary phase as known to those skilled in the art. The formation and/or isolation of specific enantiomers of a compound is not routine, and there are no general methods that may be used to obtain specific enantiomers of all compounds. The methods and conditions used to obtain specific enantiomers of a compound must be determined for each specific compound. Enantiomerically enriched compounds of the invention can also be obtained from enantiomerically enriched precursors.

Veterinary Compositions

Another aspect of the invention is the formation of parasiticidal compositions which comprise the isoxazoline compounds of the invention. The composition of the invention can also be in a variety of forms which include, but are

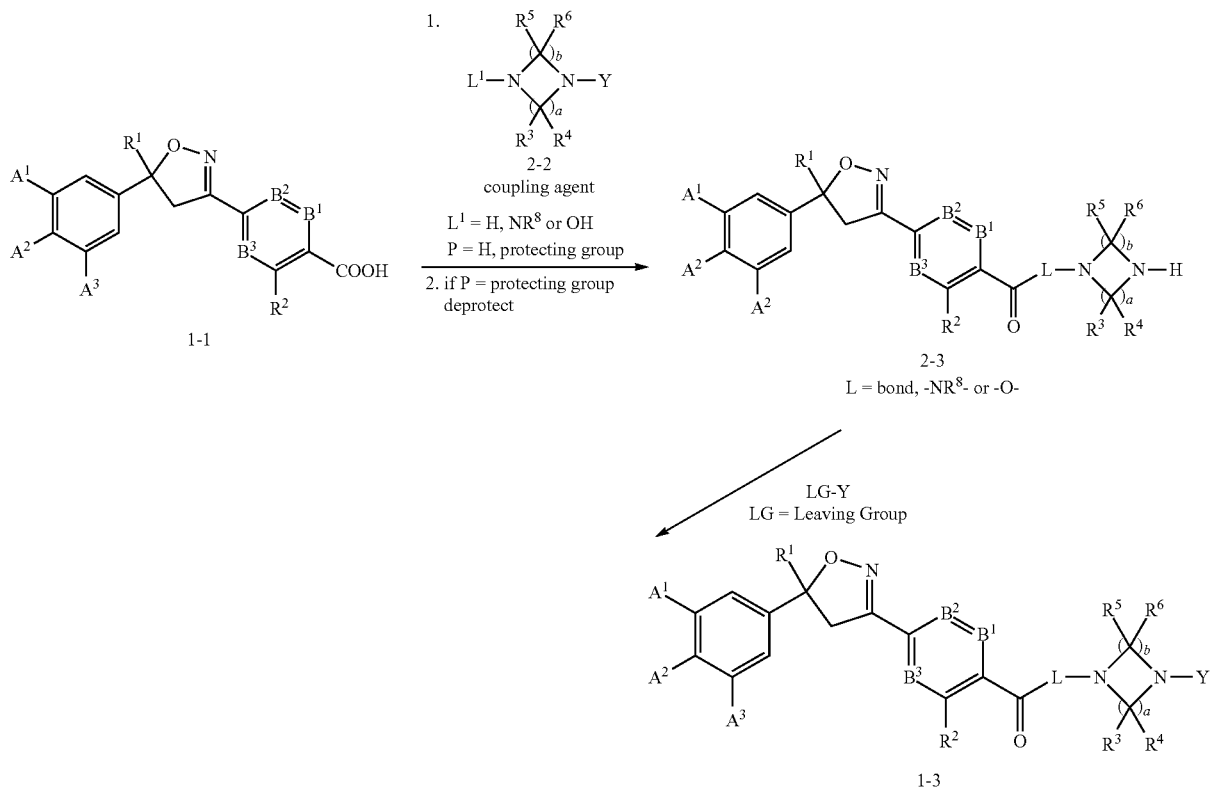

Scheme 2

In the embodiment shown in scheme 2, the carboxylic acid 1-1 is reacted with an unprotected (P=H) or nitrogen-protected compound 2-2 in the presence of a coupling agent. If compound 2-2 is protected with a nitrogen protecting group, the protecting group is removed to form compound 2-3. Compound 2-3 is then reacted with the group LG-Y to form the desired compound. Alternatively, the carboxylic acid 1-1 is first converted to an acyl halide or active ester and then reacted with compound 2-2 to form compound 2-3, which is then reacted further to form compound 1-3.

The invention further contemplates separating the enantiomers in whole or in part of the present invention or synthesizing enantiomerically enriched compounds of the invention. The composition may be prepared by separating the enantiomers in whole or in part by standard methods, for example by chemical resolution using optically active acid not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets or chewable dosage forms may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, polyethylene glycols (PEGs) and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the isoxazoline compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the isoxazoline compound into the carrier by mixing;
(b) adding the fumed silica to the carrier containing the dissolved isoxazoline compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing isoxazoline compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier including PEG 200, PEG 300, PEG 400, PEG 600, monoethanolamine, triethanolamine, glycerol, propylene glycol, polyoxyethylene (20) sorbitan monooleate (POLYSORBATE 80 or TWEEN 80), and poloxomers (e.g., PLURONIC L 81); an absorbent including magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension or an injectable solution. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic monoor diglycerides. In addition, fatty acids such as oleic acid find use in the preparation of injectables.

Topical, dermal and subdermal formulations can include emulsions, creams, ointments, gels, pastes, powders, shampoos, pour-on formulations, spot-on solutions and suspensions, dips and sprays. Topical application of an inventive compound or of a composition including at least one inventive compound among active agent(s) therein, in the form of a spot-on or pour-on composition, can allow for the inventive compound to be absorbed through the skin to achieve systemic levels, distributed through the sebaceous glands or on the surface of the skin achieving levels throughout the haircoat. When the compound is distributed through the sebaceous glands, they can act as a reservoir, whereby there can be a long-lasting effect (up to several months) effect. Spot-on formulations are typically applied in a localized region which refers to a relatively small area on the animal rather than to a large portion of the surface of the animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. In some embodiments, the pour-on formulations may be oily, and generally comprise a diluent or vehicle and also a solvent (e.g. an organic solvent) for the active ingredient if the latter is not soluble in the diluent. In other embodiments, the pour-on formulations may be non-oily, including alcohol-based formulations.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. In one embodiment, the emollient and/or spreading and/or film-forming agents are those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulfosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the isoxazoline compound and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution for localized topical application, including a spot-on formulation, as is described in U.S. Pat. No. 6,395,765, incorporated herein by reference. In addition to the isoxazoline compound, the solution may contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by the test in which 0.3 ml of a solution comprising 10% (w/v) of isoxazoline compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystals.

In one embodiment, the organic solvent has a dielectric constant of about 2 to about 35, about 10 to about 35 or about 20 to about 30. In other embodiments, the solvent will have a dielectric constant of between about 2 and about 20, or between about 2 and about 10. The content of this organic solvent in the overall composition will complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, the co-solvent may be present in the composition in an organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsufoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulfosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The non-active formulation components discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients are added.

The volume of the topical formulations applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal. In other embodiments, the volume applied may be about 5 ml to about 10 ml, about 5 ml to about 15 ml, about 10 ml to about 20 ml, or about 20 ml to about 30 ml, depending on the size of the animal treated and the concentration of the active agent in the formulation, among other factors.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference). In one embodiment, the spot-on formulation comprises a solvent and a cosolvent wherein the solvent may be acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents. In another embodiment, the spot-on formulations include a cosolvent that is absolute ethanol, isopropanol or methanol, or a mixture thereof. In another embodiment, the compositions include benzyl alcohol as a co-solvent.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent. More typically the dosage is about 1 mg to about 25 mg, 1 mg to about 50 mg, 10 mg to about 100 mg, or 20 mg to about 200 mg. In other embodiments, the dosage is about 50 mg to about 300 mg, 50 mg to about 400 mg, 50 mg to about 500 mg, 50 mg to about 600 mg, 50 mg to about 800 mg, or 100 mg to about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.01 mg/kg to about 100 mg/kg of weight of animal. In another embodiment, the dose is about 0.1 mg/kg to about 100 mg/kg of weight of animal. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.01 mg/kg to 5 mg/kg, 0.1 mg/kg to about 5 mg/kg, about 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Agricultural Compositions

The compounds of formula (I), (IA), (IB), (IC), (ID) and (IE) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I), (IA), (IB), (IC), (ID) and (IE) in wettable powders is, for example, about 10 to about 90% by weight, the remainder to 100% by weight being composed of customary formulation components. In the case of emulsifiable concentrates, the concentration of compounds of formula (I), (IA), (IB), (IC), (ID) and (IE) can amount to ranges selected from the group consisting of about 1% to about 90% and about 5% to about 80% by weight. Formulations in the form of dusts usually comprise in the range selected from the group consisting of about 1% to about 30% by weight of compounds of formula (I), (IA), (IB), (IC), (ID) and (IE) and about 5% to about 20% by weight of compounds of formula (I), (IA), (IB), (IC), (ID) and (IE). For sprayable solutions comprise a range selected from the group consisting of about 0.05% to about 80% by weight of compounds of formula (I), (IA), (IB), (IC), (ID) and (IE) and about 2% to about 50% by weight of compounds of formula (I). In the case of water-dispersible granules, the content of compounds of formula (I), (IA), (IB), (IC), (ID) and (IE) depends partly on whether the compounds of formula (I), (IA), (IB), (IC), (ID) and (IE) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I), (IA), (IB), (IC), (ID) and (IE) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The following are examples of agricultural compositions:
1. Products for dilution with water. For seed treatment purposes, such products may be applied to the seed diluted or undiluted.

A) Water-Soluble Concentrates 10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions 25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders 75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders 5 parts by weight of the active compound are ground finely and mixed intimately with 95 parts by weight of finely divided kaolin. This gives a dustable product having 5% (w/w) of active compound.

J) Granules 0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Methods of Treatment

In another aspect of the invention, a method for preventing or treating a parasite infestation/infection in an animal is provided, comprising administering to the animal at least one compound of formula (I), (IA), (IB), (IC), (ID) or (IE), optionally together with a pharmaceutically acceptable carrier. The compounds of the invention have long-lasting efficacy against ectoparasites (e.g. fleas and ticks) and in certain embodiments may also active against endoparasites that harm animals.

In one embodiment of the invention, methods for the treatment or prevention of a parasitic infestation or infection in a domestic animal are provided, which comprise administering to the animal an effective amount of at least one isoxazoline active agent of the invention to the animal. Ectoparasites against which the methods and compositions of the invention are effective include, but are not limited to, fleas, ticks, mites, mosquitoes, flies and lice. In certain embodiments wherein the compositions include one or more additional active agents that are active against internal parasites, the compositions and methods of the invention may also be effective against endoparasites including, but not limited to, cestodes, nematodes, hookworms and roundworms of the digestive tract of animals and humans. In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Hematobia* sp. including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In a preferred embodiment, the invention provides methods for the treatment or prevention of parasitic infections and infestations in companion animals including, but not limited to, cats and dogs. The methods of the invention are particularly effective for preventing or treating parasitic infestations of cats and dogs with fleas and ticks.

In another preferred embodiment, the methods of the invention are used for the treatment or prevention of parasitic infections and infestations in cattle or sheep. When treating livestock animals such as cattle or sheep, the methods and compositions are particularly effective against *Rhipicephalus (Boophilus) microplus, Haematobia irritans* (horn fly), *Stomoxys calcitrans* (stable fly), and sheep myiases such as *Lucilia sericata, Lucilia cuprina* (known as blowfly strike in Australia, New Zealand and South Africa).

The terms "treating" or "treat" or "treatment" are intended to mean the application or administration of an isoxazoline compound of the invention to an animal that has a parasitic infestation for the eradication of the parasite or the reduction of the number of the parasites infesting the animal undergoing treatment. It is noted that the compositions of the invention comprising an isoxazoline compound together with a pharmaceutically acceptable carrier may be used to prevent such a parasitic infestation.

The compounds and compositions of the invention are administered in parasiticidally effective amounts which are which are suitable to control the parasite in question to the desired extent, as described below. In each aspect of the invention, the compounds and compositions of the invention can be applied against a single pest or combinations thereof. The compounds and compositions of the invention may be administered continuously, for treatment or prevention of parasitic infections or infestations. In this manner, an effective amount of the active isoxazoline compounds of the invention are delivered to the animal in need thereof to control the target parasites. By "effective amount" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered is between about 0.1 to about 30 mg per kg of body weight. More typically the dose of the isoxazoline active agent administered is about 0.5 to about 20 mg/kg or about 0.5 to about 15 mg/kg body weight. Preferably, the dose of the isoxazoline active agent administered is about 0.5 to about 10 mg/kg, about 0.5 to about 8 mg/kg or about 0.5 to about 5 mg/kg of body weight.

In certain embodiments for the treatment and prevention of parasite infestations and infections in smaller animals (e.g. cats and other smaller mammals), the dose of the isoxazoline active agent administered will be about 0.5 to about 2 mg/kg of body weight, preferably about 1 mg/kg of bodyweight. In other embodiments for the very long lasting treatment and protection of smaller animals against parasitic infestations or infections a dose of about 2 to about 15 mg/kg of bodyweight or preferably about 5 to about 15 mg/kg of bodyweight will be administered.

In some embodiments for the treatment and protection of dogs from parasitic infestations and infections, a dose of about 2 to about 15 mg/kg of bodyweight of the isoxazoline active agent will be administered. In other embodiments, a dose of about 2 to about 8 mg/kg or about 2 to about 5 mg/kg of bodyweight will be administered.

In other embodiments for the treatment of livestock animals such as cattle or sheep, doses of the isoxazoline active agent administered may be about 1 to about 30 mg/kg of body weight. More typically the doses administered will be about 1 to about 20 mg/kg or about 1 to about 15 mg/kg. Preferably, a dose of the isoxazoline active agent administered to livestock animals will be about 1 to about 10 mg/kg of body weight.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal. More typically the dose of the isoxazoline for small-sized animals and birds is about 0.5 to about 15 mg/kg, about 0.5 to about 10 mg/kg of body weight, or about 0.5 mg/kg to about 5 mg/kg of body weight.

In one embodiment of the method of use in dogs or cats, a composition comprising an isoxazoline compound of the invention has an efficacy against fleas and/or ticks of at least about 90.0% or higher for about 1 month, or longer. In another embodiment, the compositions of the invention provide an efficacy against fleas and/or ticks of at least 95.0% or higher for about 30 days, or longer.

In another embodiment, the compounds and compositions of the invention provide an efficacy against fleas and/or ticks in cats and dogs of at least about 80% for two months, or longer. In another embodiment, the compounds and compositions provide efficacy against fleas and/or ticks in cats and dogs of about 90% for about two months, or longer. In still another embodiment, the compounds and compositions provide an efficacy of about 95% for about 2 months or longer. In other embodiments, the compounds and composition provide longer-lasting efficacy against fleas and/or ticks including for about 3 months, or longer.

In one embodiment of the invention, the isoxazoline compounds may be administered in the form of topical compositions to the animal. Topical compositions include dips, shampoos, sprays, spot-ons, pour-ons, and the like. Application of topical compositions is to animals to control parasites is well known in the art.

In some embodiments, the isoxazoline compounds may be administered in solutions using any means known in the art, including using an applicator gun or a metering flask, pipette, syringes, roll on, droppers, capsules, foil packages, vials, twist tip containers, metered-dose aerosols or sprays and other single dose and multi-dose containers.

In another aspect of the invention, a kit for the treatment or prevention of a parasitic infestation in an animal is provided, which comprises at least one isoxazoline active agent of the invention together with a pharmaceutically acceptable carrier and a dispensing device for application of the composition. The dispensing device may be a pipette, syringes, roll on, droppers, capsules, foil packages, vials, twist tip containers, metered-dose aerosols or sprays and other single dose and multi-dose containers, which includes an effective dose of each active agent in the pharmaceutically acceptable carrier or diluent.

In another embodiment of the invention, the compounds and compositions of the invention are suitable for controlling pests at a locus. Therefore, an additional embodiment of the invention is a method for controlling pests at a locus, comprising applying a pesticidally effective amount of compound of formula (I) or a composition comprising the compound to the locus. Pests that may be controlled with the compounds of the invention include insects such as *Blatella germanica, Heliothis virescens, Leptinotarsa decemlineata, Tetramorium caespitum* and combinations thereof.

In still another embodiment, the compounds and compositions of the invention are effective for protecting crops, plants and material made from wood against pests. Thus, the invention provides a method for protecting crops, plants, plant propagation material and material made from wood from pests that harm these materials comprising applying the compounds of the invention or compositions comprising the compounds to the crops, plants, plant propagation material and material made from wood.

In other embodiments, the compounds and compositions of the invention may be used against the phytoparasitic nematodes including, for example, *Anguina* spp., *Aphelenchoides* spp., *Belonoaimus* spp., *Bursaphelenchus* spp., *Ditylenchus dipsaci, Globodera* spp., *Helicotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans*, and *Xiphinema* spp.

In addition, the compounds and compositions of the invention can also be used against pests which include, but are not limited to, the following pests:

(1) from the order of Isopoda, for example *Oniscus asellus, Armadillidium vulgare* and *Porcellio scaber;*
(2) from the order of Diplopoda, for example *Blaniulus guttulatus;*
(3) from the order of Chilopoda, for example *Geophilus carpophagus* and *Scutigera* spp.;
(4) from the order of Symphyla, for example *Scutigerella immaculata;*
(5) from the order of Thysanura, for example *Lepisma saccharina;*
(6) from the order of Collembola, for example *Onychiurus armatus;*
(7) from the order of Blattaria, for example *Blatta orientalis, Periplaneta americana, Leucophaea maderae* and *Blattella germanica;*
(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalvia, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetoniajucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinellafrit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum,* Acylostoma *braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarvafimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda,*

*Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

Active Agent Combinations

The isoxazoline compounds of the invention or their salts can be employed as such or in the form of their preparations (formulations) as combinations with other active substances. For agricultural uses, the isoxazoline compounds of the invention may be used in combination with, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed with the isoxazoline compounds of the invention include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzothiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed with the isoxazoline compounds of the invention may also be from the classes of compounds described in U.S. Pat. Nos. 7,001,903 and 7,420,062, each incorporated herein by reference.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl(thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluroxypyr and picloram; quinoline carboxylic acid; phthalamate semicarbazone; qrylaminopropionic acid; qrylaminopropionic acid; organoarsenical.

Other herbicides that may optionally be admixed are compounds described in U.S. Pat. Nos. 7,432,226, 7,012, 041, and 7,365,082, all incorporated herein by reference.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001, 903, U.S. Patent publication 2008/0234331, each incorporated herein by reference, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

Veterinary compositions may include one or more isoxazoline compounds of the invention in combination with additional pharmaceutically or veterinarily active agents. In some embodiments, the additional active agent(s) may be one or more acaricide, anthelmintic, endectocide and insecticide active agent. Anti-parasitic agents can include both ectoparasiticidal and endoparasiticidal agents.

Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraaoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds, such as phenylpyrazoles, known in the art may be combined with the isoxazoline compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.). A particularly preferred arylpyrazole compound is fipronil.

In another embodiment of the invention, one or more macrocyclic lactones, which act as an acaricide, anthelmintic agent and/or insecticide, can be combined with the isoxazoline compounds of the invention. The macrocyclic lactones include, but are not limited to, avermectins such as abamectin, dimadectin, doramectin, emamectin, eprinomectin, ivermectin, latidectin, lepimectin, selamectin and ML-1, 694,554, and milbemycins such as milbemectin, milbemycin D, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag, or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569 (both incorporated herein by reference). Mention is also made of U.S. Pat. Nos. 4,468,390, 5,824,653, EP 0 007 812 A1, U.K. Patent Specification 1 390 336, EP 0 002 916, and New Zealand Patent No. 237 086 (all incorporated by reference), inter alia. Naturally occurring milbemycins are described in U.S. Pat. No. 3,950,360, which is incorporated herein by reference, as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054 (all incorporated by reference).

In another embodiment, the isoxazoline compounds of the invention may be combined with a class of compounds known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be combined with the isoxazoline compounds of the invention. These include pyrethrins (which include cinerin I, cinerin II, jasmolin I, jasmolin II, pyrethrin I, pyrethrin II and mixtures thereof) and pyrethroids (including permethrin cyhalothrin, cypermethrin, deltamethrin, fenvalerate, flucythrinate), and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the isoxazoline compounds of the invention may be combined with one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the isoxazoline compounds of the invention may be combined with an imidazothiazole compounds including, but not limited to, tetramisole, levamisole and butamisole. In still other embodiments, the isoxazoline compounds of the invention may be combined with tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the isoxazoline compounds of the invention may be combined with the antinematodal compounds phenothiazine and piperazine as the neutral compound, or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the isoxazoline compounds of the invention may be combined with antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously combined with isoxazoline compounds of the invention including, but not limited to, arecoline in various salt forms, bunamidine, niclosamide, nitroscanate, paromomycin and paromomycin II.

In yet other embodiments, the isoxazoline compounds of the invention may be combined with other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, the isoxazoline compounds of the invention be combined with pyrethroid active agents including, but not limited to, permethrin, deltamethrin, cypermethrin, cyphenothrin, etofenprox, fenvalerate and cyfluthrin.

Another antiparasitic agent that can be combined with the isoxazoline compounds of the invention include a biologically active peptide or protein including, but not limited to, depsipeptides, which act at the neuromuscular junction by stimulating presynaptic receptors belonging to the secretin receptor family resulting in the paralysis and death of parasites. In one embodiment, the depsipeptide is emodepside (see Willson et al., *Parasitology*, January 2003, 126(Pt 1):79-86). In another embodiment, the depsipeptide is PF1022a In another embodiment, the isoxazoline compounds of the invention may be combined with an active agent from the neonicotinoid class of pesticides. The neonicotinoids bind and inhibit insect specific nicotinic acetylcholine receptors. In one embodiment, the neonicotinoid insecticidal agent is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060 (incorporated herein by reference).

In another embodiment, the neonicotinoid active agent is nitenpyram. Nitenpyram is the active ingredient in the oral product CAPSTAR™ Tablets sold by Novartis Animal Health. Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day.

In certain embodiments, an insecticidal agent that can be combined with the isoxazoline compounds of the invention is a semicarbazone, such as metaflumizone.

In another embodiment, the isoxazoline compounds of the invention may advantageously be combined with another isoxazoline compounds known in the art. These active agents are described in U.S. Pat. No. 7,964,204, U.S. Pat. No. 8,410,153, US 2011/0152312, US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. No. 8,119,671; U.S. Pat. No. 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. No. 7,897,630, U.S. Pat. No. 7,951,828 and U.S. Pat. No. 7,662,972, all of which are incorporated herein by reference in their entirety.

In another embodiment of the invention, nodulisporic acid and its derivatives (a class of known acaricidal, anthelmintic, anti-parasitic and insecticidal agents) may be combined with the isoxazoline compounds of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety.

In another embodiment, anthelmintic compounds of the amino acetonitrile class (AAD) of compounds such as monepantel (ZOLVIX), and the like, may be combined with the isoxazoline compounds of the invention. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The isoxazoline compounds of the invention may also be combined with aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621, also incorporated herein by reference.

The isoxazoline compounds of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In general, the additional active agent is included in the composition in an amount of between about 0.1 μg and about 1000 mg. More typically, the additional active agent may be included in an amount of about 10 μg to about 500 mg, about 1 mg to about 300 mg, about 10 mg to about 200 mg or about 10 mg to about 100 mg.

In other embodiments of the invention, the additional active agent may be included in the composition to deliver a dose of about 5 μg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 μg/kg to about 200 μg/kg or about 0.1 mg/kg to about 1 mg/kg of weight of animal. In still another embodiment of the invention, the additional active agent is included in a dose between about 0.5 mg/kg to about 50 mg/kg.

The invention will now be further described by way of the following non-limiting examples.

EXAMPLES

All temperatures are given in degrees Centigrade; room temperature means 20 to 25° C. Reagents were purchased from commercial sources or prepared following literature procedures.
DCM=dichloromethane
THF=tetrahydrofuran
MeOH=methanol
EtOH=ethanol
EtOAc=ethyl acetate
DMF=dimethylformamide
TFAA=trifluoroacetic anhydride
EDCI=1-Ethyl-3-(3-dimethylaminopropyl)carbodiimide
HATU=1-[Bis(dimethylamino)methylene]-1H-1,2,3-triazolo[4,5-b]pyridinium 3-oxide hexafluorophosphate
TLC=thin-layer chromatography
TEA=triethylamine
DIEA=diisopropylethylamine
LAH=lithium aluminum hydride
HOBt=1-hydroxybenzotriazole
PCC=pyridinium chlorochromate
NBS=N-bromosuccinimide
rt=room temperature
Pd(dppf)Cl$_2$=[1,1'-Bis(diphenylphosphino)ferrocene]dichloropalladium(II)
Py/TEA=pyridine/triethylamine Proton and fluorine magnetic resonance (respectively $^1$H NMR and $^{19}$F NMR) spectra were recorded on a Varian INOVA NMR spectrometer [400 MHz (1H) or 500 MHz ($^1$H) and 377 MHz ($^{19}$F)]. All spectra were determined in the solvents indicated. Chemical shifts are reported in ppm downfield of tetramethylsilane (TMS), referenced to the residual proton peak of the respective solvent peak for $^1$H NMR. Interproton coupling constants are reported in Hertz (Hz).

LC-MS spectra were obtained using two different systems. For LCMS method 1, LC-MS spectra were obtained using an Agilent 1200SL HPLC equipped with a 6130 mass spectrometer operating with electrospray ionization; chromatographic data were obtained using a Shimadzu Shim-pack XR-ODS, 3.0×30 mm, 2.2 micron particle size column and a water:methanol gradient from 15% methanol to 95% methanol in 2.2 minutes under a 1.5 mL/min flow; a hold at 95% methanol was applied at the end of the gradient for 0.8 minutes; and both water and methanol mobile phases contained 0.1% formic acid. For LCMS method 2, LCMS spectra were obtained using a Waters ACQUITY UPLC™ equipped with a Thermofinnigan AQA™ mass spectrometer operating with electrospray ionization; chromatographic data were obtained using a Supelco® Analytical Ascentis® Express, 2.1×50 mm, 2.7 micron particle size column (C$_{18}$) and a water:acetonitrile gradient from 5% acetonitrile to 100% acetonitrile in 0.8 minute under a 1.5 mL/min flow; a hold at 100% methanol was applied at the end of the gradient for 0.05 minutes; and water mobile phase was buffered with ammonium acetate (10 mmolar) and 0.1% v./v. acetic acid. When LCMS retention times are reported as RT, LCMS method 1 or 2 is then specified.

When semi-preparative HPLC was carried out to purify reaction mixture, a modified Gilson HPLC system was used with offline regeneration; chromatographic data were obtained using a Varian Pursuit™ XRS, 21.4×50 mm, 10 micron particle size column (C18) and a water:methanol gradient from 40% methanol to 100% methanol in 5 minutes under a 28 mL/min flow; and water mobile phase was buffered with ammonium acetate (10 mmolar) and 0.1% v./v. ammonium hydroxide.

Example 1

4-[5-(3,5-dichlorophenyl)-5-(trifluoromethyl)-4,5-dihydro-1,2-oxazol-3-yl]-2-methyl-N-[2-oxo-3-(2,2,2-trifluoroethyl)imidazolidin-1-yl]benzamide, Compound No 67

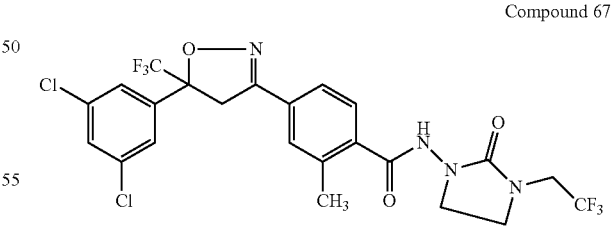

Compound 67

Compound 67 was prepared according to the procedure shown in scheme 3 and described below.

Scheme 3

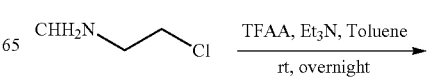

115

-continued

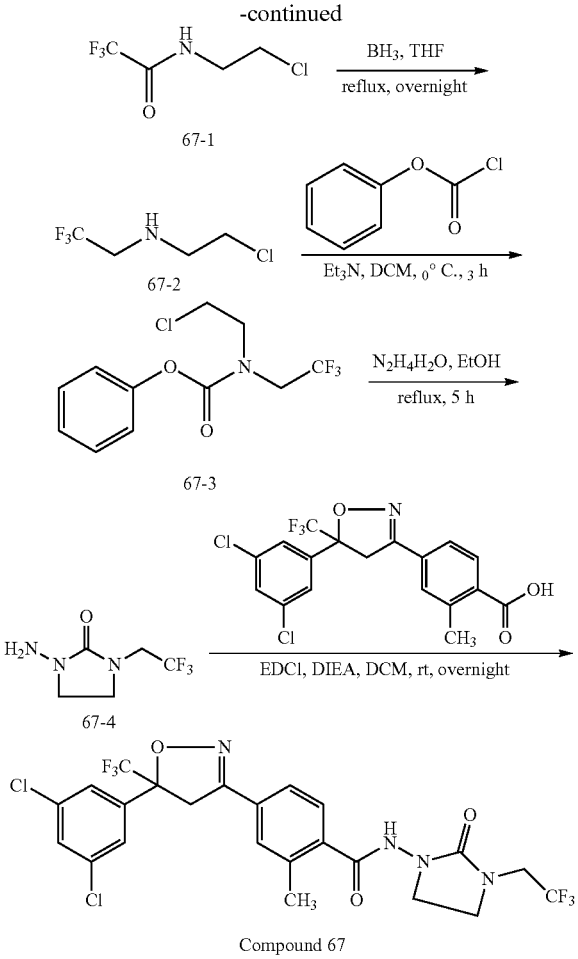

Compound 67

Step 1

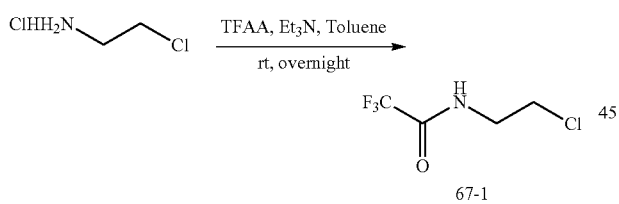

N-(2-chloroethyl)-2,2,2-trifluoroacetamide

Into a 1000-mL round-bottom flask, was placed a solution of 2-chloroethan-1-amine hydrochloride (15 g, 129.32 mmol, 1.00 equiv) in dichloromethane (500 mL). This was followed by the addition of triethylamine (19.5 g, 192.71 mmol, 1.49 equiv) dropwise with stirring. To this was added TFAA (32.6 g, 155.22 mmol, 1.20 equiv) dropwise with stirring at 0° C. The resulting solution was stirred overnight at room temperature. The reaction was then quenched by the addition of 200 mL of 1M HCl. The resulting solution was extracted with 100 mL of dichloromethane and the organic layers combined and dried over anhydrous sodium sulfate and concentrated under vacuum. This resulted in 20 g (crude) of N-(2-chloroethyl)-2,2,2-trifluoroacetamide as a off-white solid. (ES, m/z): 177 [M+H]+

116

Step 2

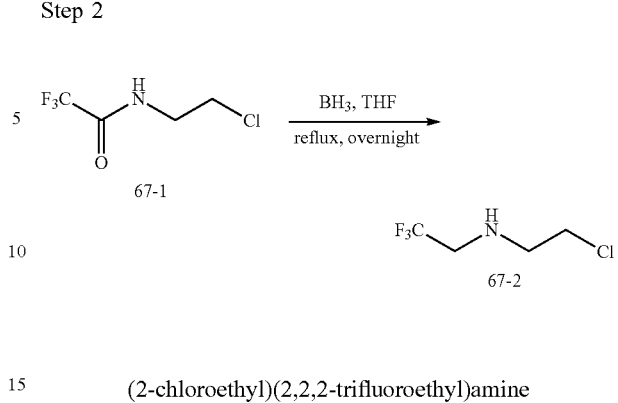

(2-chloroethyl)(2,2,2-trifluoroethyl)amine

Into a 500-mL round-bottom flask, was placed a solution of N-(2-chloroethyl)-2,2,2-trifluoroacetamide (17.6 g, 100.26 mmol, 1.00 equiv) in tetrahydrofuran (50 mL). This was followed by the addition of $BH_3$.THF (200 mL) dropwise with stirring. The resulting solution was heated to reflux overnight in an oil bath. The resulting mixture was concentrated under vacuum. The resulting solution was diluted with 200 mL of $H_2O$. The resulting solution was extracted with 3×100 mL of ethyl acetate and the organic layers combined and dried over anhydrous sodium sulfate and concentrated under vacuum. This resulted in 15 g (crude) of (2-chloroethyl)(2,2,2-trifluoroethyl)amine as yellow oil. (ES, m/z): 163 [M+H]+

Step 3

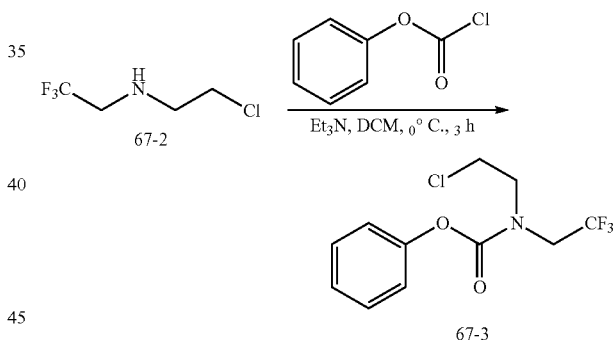

Phenyl N-(2-chloroethyl)-N-(2,2,2-trifluoroethyl) carbamate

Into a 500-mL round-bottom flask, was placed (2-chloroethyl)(2,2,2-trifluoroethyl)amine (15 g, 92.85 mmol, 1.00 equiv), a solution of triethylamine (16.4 g, 162.07 mmol, 1.75 equiv) in dichloromethane (200 mL). This was followed by the addition of phenyl chloroformate (20.3 g, 129.66 mmol, 1.40 equiv) dropwise with stirring at 0° C. The resulting solution was stirred overnight at room temperature. The reaction was then quenched by the addition of 100 mL of 1M HCl. The resulting mixture was washed with 2×100 mL of sodium bicarbonate (sat.). The organic phase was dried over anhydrous sodium sulfate and concentrated under vacuum. The residue was applied onto a silica gel column with petroleum ether. This resulted in 10 g (22%) of phenyl N-(2-chloroethyl)-N-(2,2,2-trifluoroethyl)carbamate as light yellow oil. (ES, m/z): 283 [M+H]+

Step 4

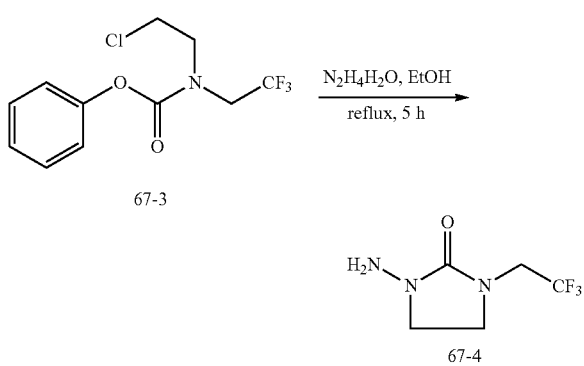

1-amino-3-(2,2,2-trifluoroethyl)imidazolidin-2-one

Into a 250-mL round-bottom flask, was placed a solution of phenyl N-(2-chloroethyl)-N-(2,2,2-trifluoroethyl)carbamate (5.6 g, 19.88 mmol, 1.00 equiv) in ethanol (100 mL), NH$_2$NH$_2$.H$_2$O (10 mL, 80%). The resulting solution was heated to reflux overnight in an oil bath. The resulting mixture was concentrated under vacuum. The residue was applied onto a silica gel column with ethyl acetate (1:1). This resulted in 0.8 g (22%) of 1-amino-3-(2,2,2-trifluoroethyl)imidazolidin-2-one as colorless oil. (ES, m/z): 184 [M+H]$^+$ Step 5

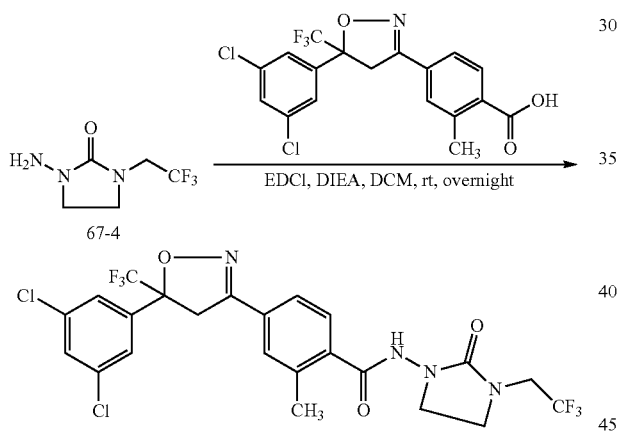

Compound 67

4-[5-(3,5-dichlorophenyl)-5-(trifluoromethyl)-4,5-dihydro-1,2-oxazol-3-yl]-2-methyl-N-[2-oxo-3-(2,2,2-trifluoroethyl)imidazolidin-1-yl]benzamide Into a 25-mL round-bottom flask, was placed 1-amino-3-(2,2,2-trifluoroethyl)imidazolidin-2-one (90 mg, 0.49 mmol, 1.00 equiv), 4-[5-(3,5-dichlorophenyl)-5-(trifluoromethyl)-4,5-dihydro-1,2-oxazol-3-yl]-2-methylbenzoic acid (200 mg, 0.48 mmol, 0.97 equiv), EDCI (192 mg, 1.00 mmol, 2.04 equiv), HOBT (135 mg, 1.00 mmol, 2.03 equiv), triethylamine (303 mg, 2.99 mmol, 6.09 equiv), dichloromethane (10 mL). The resulting solution was stirred for 30 h at room temperature. The resulting mixture was concentrated under vacuum. The residue was applied onto a silica gel column with ethyl acetate/petroleum ether (1:1). This resulted in 39 mg (13%) of 4-[5-(3,5-dichlorophenyl)-5-(trifluoromethyl)-4,5-dihydro-1,2-oxazol-3-yl]-2-methyl-N-[2-oxo-3-(2,2,2-trifluoroethyl)imidazolidin-1-yl]benzamide as a white solid. (ES, m/z): 583 [M−H]$^−$; $^1$H NMR (300 MHz, CDCl$_3$) δ 7.89 (s, 1H), 7.43-7.62 (m, 6H), 4.06-4.12 (m, 1H), 3.54-3.89 (m, 7H), 2.47 (s, 3H).

Example 2

4-[5-[3-chloro-5-(trifluoromethyl)phenyl]-5-(trifluoromethyl)-2,5-dihydro-1,3-oxazol-4-yl]-2-methyl-N-[2-oxo-3-(2,2,2-trifluoroethyl)-1,3-diazinan-1-yl]benzamide, Compound 70

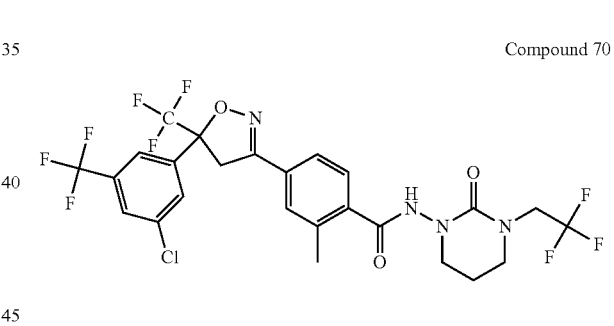

Compound 70

Compound 70 was prepared by the method described below and depicted in scheme 4:

Scheme 4

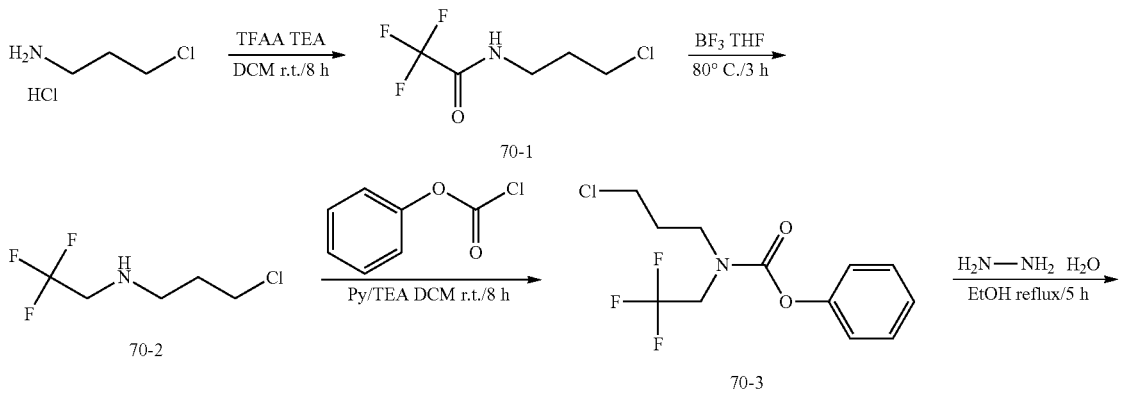

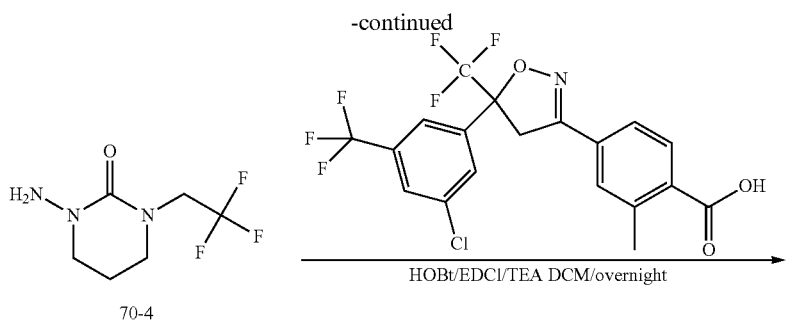

Compound 70

Step 1

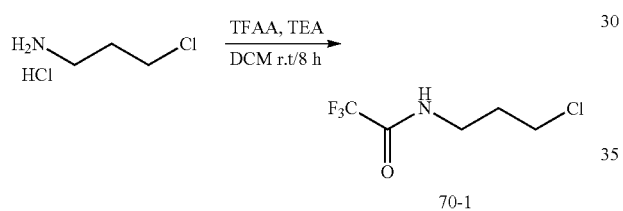

N-(3-chloropropyl)-2,2,2-trifluoroacetamide

Into a 500-mL round-bottom flask, was placed 3-chloropropan-1-amine hydrochloride (10 g, 76.91 mmol, 1.00 equiv), dichloromethane (300 mL), TEA (15.6 g, 154.17 mmol, 2.00 equiv). This was followed by the addition of pyridine (2 mL) dropwise with stirring at 0° C. To this was added trifluoroacetyl 2,2,2-trifluoroacetate (16.2 g, 77.13 mmol, 1.00 equiv). The resulting solution was stirred for 8 h at room temperature. The resulting mixture was washed with 2×200 mL of 0.1N hydrogen chloride and 2×200 mL of sodium bicarbonate aq. The resulting mixture was washed with 2×200 mL of brine. The mixture was dried over anhydrous sodium sulfate. The solids were filtered out. The resulting mixture was concentrated under vacuum. This resulted in 6 g (41%) of N-(3-chloropropyl)-2,2,2-trifluoroacetamide as a white solid. H-NMR (CDCl$_3$, ppm): 6.564 (s, 1H), 3.634-3.535 (m, 4H), 2.135-2.050 (m, 2H)

Step 2

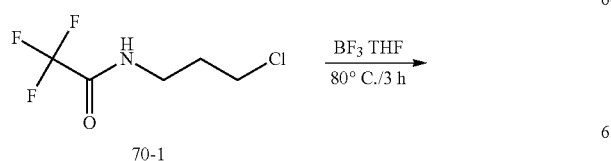

(3-chloropropyl)(2,2,2-trifluoroethyl)amine

Into a 250-mL round-bottom flask, was placed N-(3-chloropropyl)-2,2,2-trifluoroacetamide (6 g, 31.65 mmol, 1.00 equiv), tetrahydrofuran (30 mL), BH$_3$/THF (80 mL). The resulting solution was stirred for 3 h at 80° C. in an oil bath. The resulting mixture was concentrated under vacuum. The resulting solution was diluted with 200 mL of H$_2$O. The resulting solution was extracted with 4×100 mL of ethyl acetate and the organic layers combined. The resulting mixture was washed with 2×100 mL of brine. The mixture was dried over anhydrous sodium sulfate. This resulted in 5 g (90%) of (3-chloropropyl)(2,2,2-trifluoroethyl)amine as a light yellow liquid.

Step 3

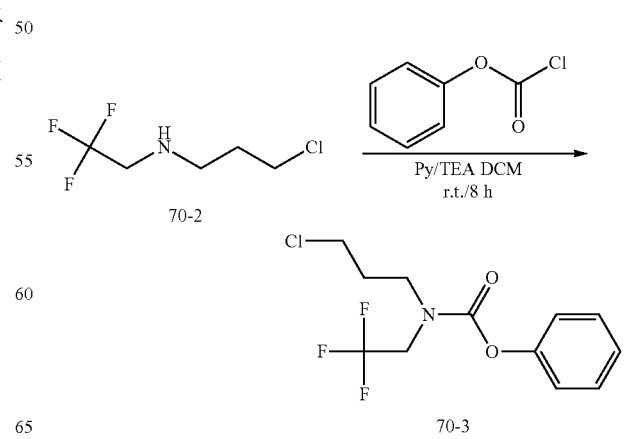

Phenyl N-(3-chloropropyl)-N-(2,2,2-trifluoroethyl) carbamate

Into a 500-mL round-bottom flask, was placed (3-chloropropyl)(2,2,2-trifluoroethyl)amine (5 g, 28.48 mmol, 1.00 equiv), dichloromethane (300 mL), TEA (5.8 g, 57.32 mmol, 2.00 equiv), pyridine (0.5 mL). To this was added dropwise phenyl chloroformate (4.4 g, 28.10 mmol, 1.00 equiv) at 0° C. The resulting solution was stirred for 3 h at room temperature. The resulting mixture was washed with 2×100 mL of H₂O. The resulting mixture was washed with 2×100 mL of brine. The mixture was dried over sodium sulfate. The resulting mixture was concentrated under vacuum. This resulted in 1.4 g (crude) of phenyl N-(3-chloropropyl)-N-(2,2,2-trifluoroethyl)carbamate as a colorless liquide.

Step 4

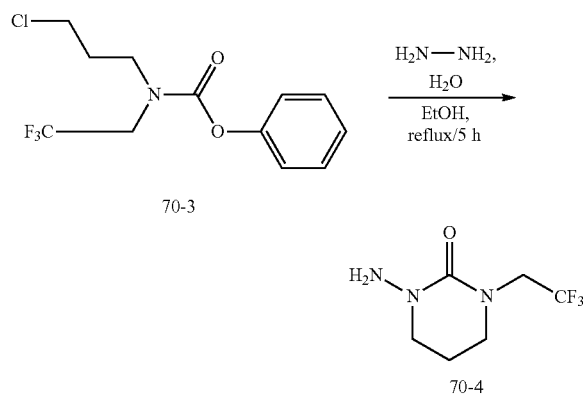

1-amino-3-(2,2,2-trifluoroethyl)-1,3-diazinan-2-one

Into a 100-mL round-bottom flask, was placed phenyl N-(3-chloropropyl)-N-(2,2,2-trifluoroethyl)carbamate (1.4 g, 4.73 mmol, 1.00 equiv), NH₂NH₂·H₂O (6 mL), ethanol (40 mL). The resulting solution was stirred for 5 h at 90° C. in an oil bath. The resulting mixture was concentrated under vacuum. The resulting solution was diluted with 50 mL of H₂O. The resulting solution was extracted with 3×30 mL of ethyl acetate and the organic layers combined. The resulting mixture was washed with 2×30 mL of brine. The mixture was dried over anhydrous sodium sulfate. The resulting mixture was concentrated under vacuum. This resulted in 200 mg (crude) of 1-amino-3-(2,2,2-trifluoroethyl)-1,3-diazinan-2-one as a light yellow solid.

Step 5

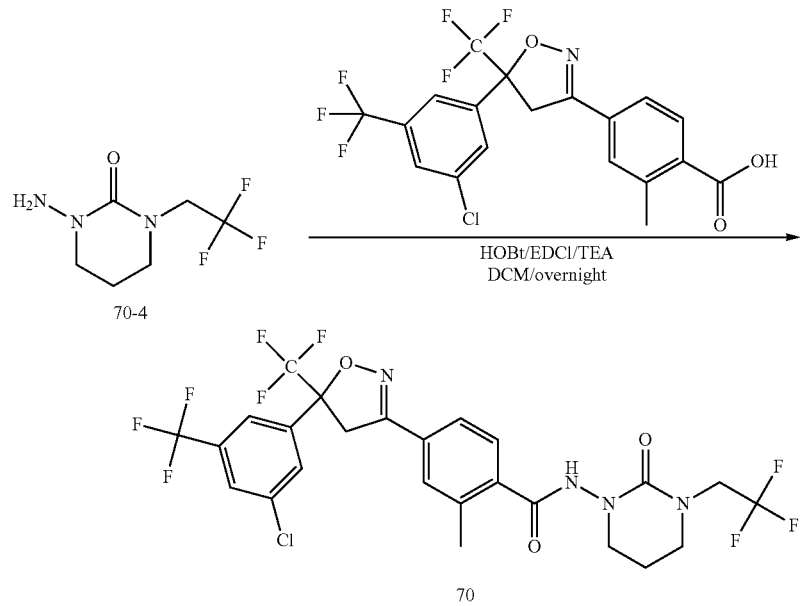

4-[5-[3-chloro-5-(trifluoromethyl)phenyl]-5-(trifluoromethyl)-2,5-dihydro-1,3-oxazol-4-yl]-2-methyl-N-[2-oxo-3-(2,2,2-trifluoroethyl)-1,3-diazinan-1-yl]benzamide Into a 50-mL round-bottom flask, was placed 4-[5-[3-chloro-5-(trifluoromethyl)phenyl]-5-(trifluoromethyl)-2,5-dihydro-1,3-oxazol-4-yl]-2-methylbenzoic acid (50 mg, 0.11 mmol, 1.00 equiv), dichloromethane (20 mL), EDCI (25 mg, 0.13 mmol, 1.20 equiv), HOBt (18 mg, 0.13 mmol, 1.20 equiv), TEA (30 mg, 0.30 mmol, 3.00 equiv), 1-amino-3-(2,2,2-trifluoroethyl)-1,3-diazinan-2-one (22 mg, 0.11 mmol, 1.00 equiv). The resulting solution was stirred overnight at room temperature. The resulting solution was diluted with 40 mL of DCM. The resulting mixture was washed with 3×20 mL of brine. The mixture was dried over anhydrous sodium sulfate. The resulting mixture was concentrated under vacuum. The residue was applied onto a silica gel column with ethyl acetate/petroleum ether (1:1). This resulted in 12 mg (17.2%) of 4-[5-[3-chloro-5-(trifluoromethyl)phenyl]-5-(trifluoromethyl)-2,5-dihydro-1,3-oxazol-4-yl]-2-methyl-N-[2-oxo-3-(2,2,2-trifluoroethyl)-1,3-diazinan-1-yl]benzamide as a white solid. (ES, m/z): 631 [M+H]⁺ ¹H-NMR (CDCl₃, ppm): 7.82 (s, 1H), 7.76-7.73 (m, 2H), 7.69 (s, 1H), 7.61-7.50 (m, 3H), 4.14 (d, J=18.6 Hz, 1H), 4.07-3.98 (m, 2H), 3.80-3.69 (m, 3H), 3.58-3.52 (m, 2H), 2.51 (s, 3H), 2.25-2.17 (m, 2H).

Example 3

4-[5-[3,5-bis(trifluoromethyl)phenyl]-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide, Compound 90

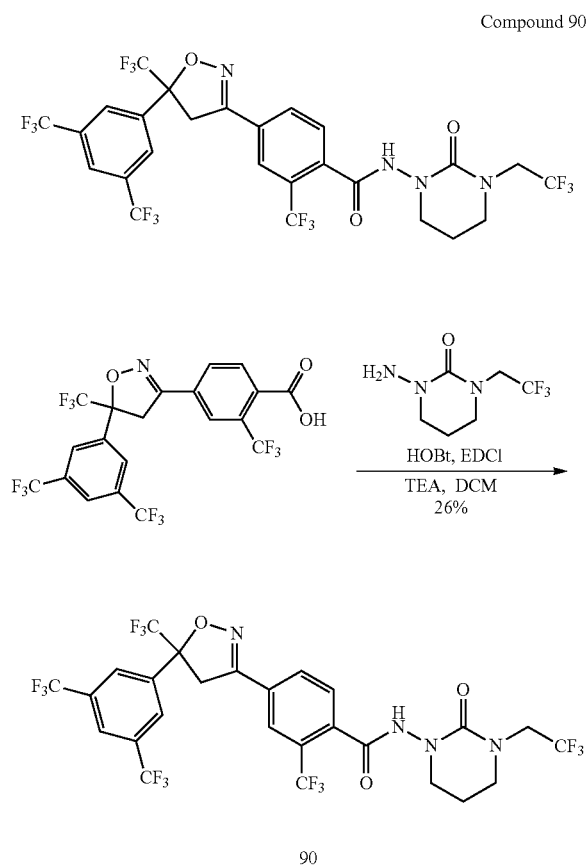

90

Into a 25-mL round-bottom flask, was placed 4-[5-[3,5-bis(trifluoromethyl)phenyl]-5-(trifluoromethyl)-4,5-dihydro-1,2-oxazol-3-yl]-2-(trifluoromethyl)benzoic acid (100 mg, 0.19 mmol, 1.00 equiv), N,N-dimethylformamide (5 mL), HATU (141 mg, 0.37 mmol, 2.00 equiv), DIEA (96 mg, 0.74 mmol, 4.00 equiv), 1-amino-3-(2,2,2-trifluoroethyl)-1,3-diazinan-2-one (40 mg, 0.20 mmol, 1.10 equiv). The resulting solution was stirred for 3 h at room temperature. The resulting solution was diluted with 20 mL of water. The resulting solution was extracted with 3×20 mL of ethyl acetate and the organic layers combined. The resulting mixture was washed with 1×20 mL of brine. The mixture was dried over anhydrous sodium sulfate. The residue was purified by preparative TLC (EtOAc/ether=1:2). This resulted in 34.3 mg (26%) of 4-[5-[3,5-bis(trifluoromethyl)phenyl]-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide as a white solid; (ES, m/z): [M+H]$^+$ 719.00, $^1$H NMR (300 MHz, DMSO): δ 10.72 (s, 1H), 8.37 (s, 1H), 8.23 (s, 2H), 8.16-8.14 (d, J=6 Hz, 1H), 8.08 (s, 1H), 7.74-7.72 (d, 1H), 4.70-4.49 (dd, J=21 Hz, J=45 Hz, 2H), 4.17-4.11 (q, J=9 Hz, 2H), 3.58-3.54 (t, J=6 Hz, 2H), 3.48-3.45 (t, J=5.1 Hz), 2.07-2.05 (m, 2H).

Example 4

4-[5-(3,5-dichlorophenyl)-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide, Compound 91

Compound 91 was prepared according to the method described below.

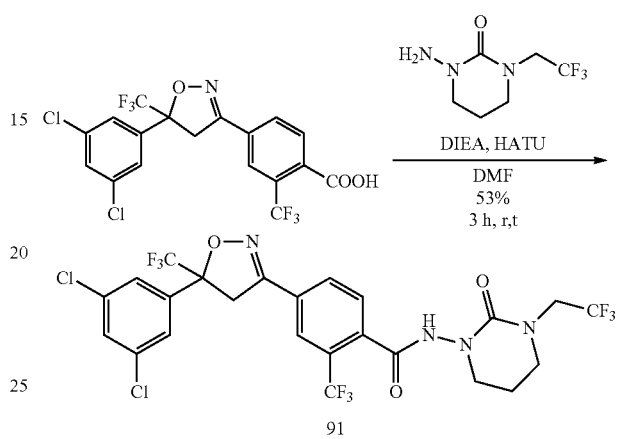

91

Into a 50-mL round-bottom flask, was placed 4-[5-(3,5-dichlorophenyl)-5-(trifluoromethyl)-4,5-dihydro-1,2-oxazol-3-yl]-2-(trifluoromethyl)benzoic acid (100 mg, 0.21 mmol, 1.00 equiv), HATU (161 mg, 0.42 mmol, 2.00 equiv), DIEA (54 mg, 0.42 mmol, 2.00 equiv), 1-amino-3-(2,2,2-trifluoroethyl)-1,3-diazinan-2-one (84 mg, 0.43 mmol, 2.00 equiv). The resulting solution was stirred for 3 h at 20° C. The resulting solution was diluted with 50 of brine. The resulting solution was extracted with 3×20 mL of ethyl acetate and the organic layers combined. The mixture was dried over sodium sulfate and concentrated under vacuum. The residue was applied onto TLC with ethyl acetate/petroleum ether (1:10). This resulted in 72.5 mg (53%) of 4-[5-(3,5-dichlorophenyl)-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide as an off-white solid; (ES, m/z): [M+H]$^+$ 651; $^1$H NMR (300 MHz, CDCl$_3$) δ: 8.03 (s, 1H), 7.88-7.91 (m, 1H), 7.78-7.84 (m, 2H), 7.46-7.53 (dd, J=1.2 Hz, J=1.8 Hz, 3H), 3.99-4.15 (m, 3H), 3.76-3.80 (m, 3H), 3.53-3.91 (m, 2H), 2.20-2.24 (m, 2H)

Example 5

4-[5-[3-chloro-5-(trifluoromethyl)phenyl]-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide, Compound 97

125

Compound 97 was prepared by the method described below starting from the appropriately substituted carboxylic acid

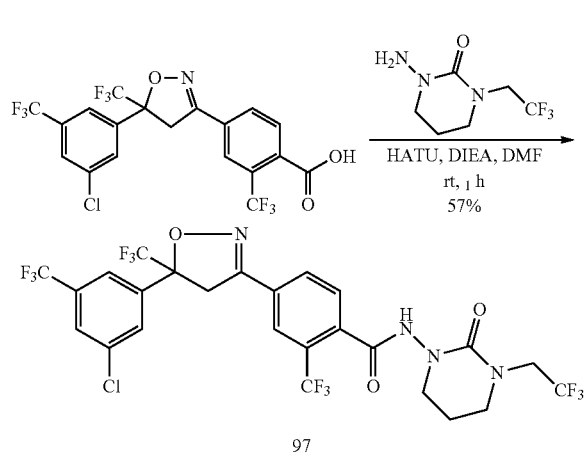

97

Into a 25-mL round-bottom flask, was placed a solution of 4-[5-[3-chloro-5-(trifluoromethyl)phenyl]-5-(trifluoromethyl)-4,5-dihydro-1,2-oxazol-3-yl]-2-(trifluoromethyl)benzoic acid (60 mg, 0.12 mmol, 1.00 equiv) in N,N-dimethylformamide (2 mL), 1-amino-3-(2,2,2-trifluoroethyl)-1,3-diazinan-2-one (43 mg, 0.22 mmol, 2.00 equiv), HATU (90 mg, 0.24 mmol, 2.00 equiv), DIEA (31 mg, 0.24 mmol, 2.00 equiv). The resulting solution was stirred for 1 h at r t. The reaction was then quenched by the addition of water. The resulting solution was extracted with 2×10 mL of ethyl acetate and the organic layers combined and concentrated under vacuum. The residue was applied onto a silica gel column with ethyl acetate/petroleum ether (2:3). This resulted in 46.3 mg (57%) of 4-[5-[3-chloro-5-(trifluoromethyl)phenyl]-5-(trifluoromethyl)-4,5-dihydro-1,2-oxazol-3-yl]-N-[2-oxo-3-(2,2,2-trifluoroethyl)-1,3-diazinan-1-yl]-2-(trifluoromethyl)benzamide as a white solid. (ES, m/z): [M+H]+ 685.0; $^1$H NMR (300 MHz, CDCl$_3$): δ8.18 (s, 1H), 8.08 (d, J=8.1 Hz, 1H), 7.99 (s, 1H), 7.89 (d, J=7.8 Hz, 4H), 4.314-4.859 (m, 1H), 4.07-4.20 (m, 3H), 3.68 (t, J=6.0 Hz, 2H), 3.57 (t, J=5.7 Hz, 2H), 2.16-2.24 (m, 2H).

Example 6

4-[(5-[5-[3-chloro-5-(trifluoromethyl)phenyl]-5-(trifluoromethyl)-4,5-dihydro-1,2-oxazol-3-yl]-2-methylphenyl)carbonyl]-1-(2,2,2-trifluoroethyl)piperazine-2,6-dione, Compound 69

Compound 69

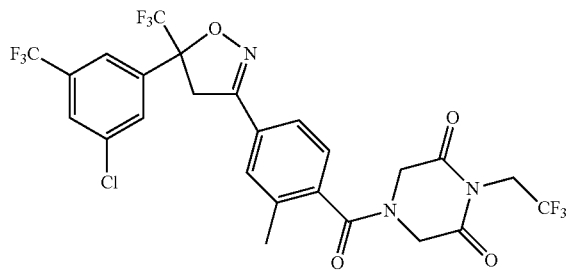

126

Compound 69 was prepared by the method described below.

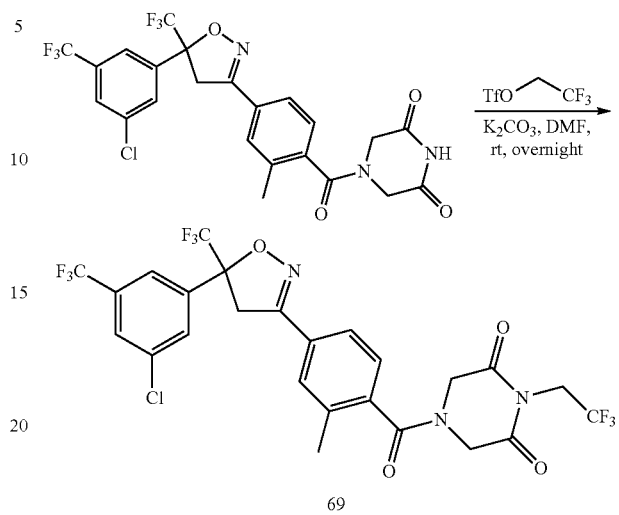

69

Into a 250-mL round-bottom flask, was placed 4-[(5-[5-[3-chloro-5-(trifluoromethyl)phenyl]-5-(trifluoromethyl)-4,5-dihydro-1,2-oxazol-3-yl]-2-methylphenyl)carbonyl]piperazine-2,6-dione (120 mg, 0.22 mmol, 1.00 equiv), 1,1,1-trifluoropropane (102 mg, 1.04 mmol, 2.00 equiv), potassium carbonate (75 mg, 2.00 equiv), N,N-dimethylformamide (10 mL). The resulting solution was stirred overnight at room temperature. The resulting solution was diluted with 50 mL of H$_2$O. The resulting solution was extracted with 3×50 mL of ethyl acetate and the organic layers combined. The resulting mixture was washed with 1×100 mL of brine. The mixture was dried over anhydrous sodium sulfate and concentrated under vacuum. This resulted in 37.4 mg (27%) of 4-[(5-[5-[3-chloro-5-(trifluoromethyl)phenyl]-5-(trifluoromethyl)-4,5-dihydro-1,2-oxazol-3-yl]-2-methylphenyl)carbonyl]-1-(2,2,2-trifluoroethyl)piperazine-2,6-dione as a off-white solid; (ES, m/z): [M−H]− 628.25; $^1$H NMR (300 MHz, CCl$_3$D): δ 8.10 (s, 1H), 7.98 (s, 1H), 7.86 (s, 1H), 7.68 (m, 2H), 7.36 (d, J=8.1 Hz, 1H), 4.75 (brs, 2H), 4.45 (m, 4H), 4.23 (s, 2H), 2.20 (s, 3H).

Example 7

1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(2,2,2-trifluoroethyl)imidazolidin-4-one, Compound 71

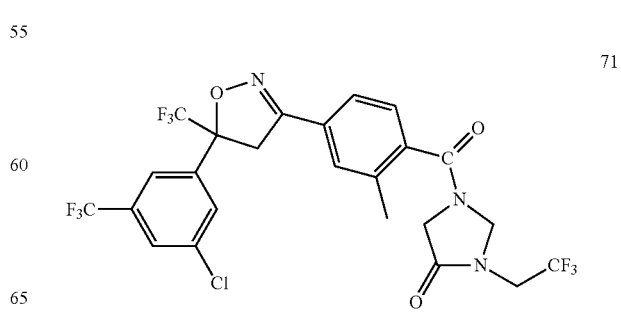

71

Compound 71 was prepared by the method described below and depicted in scheme 5:

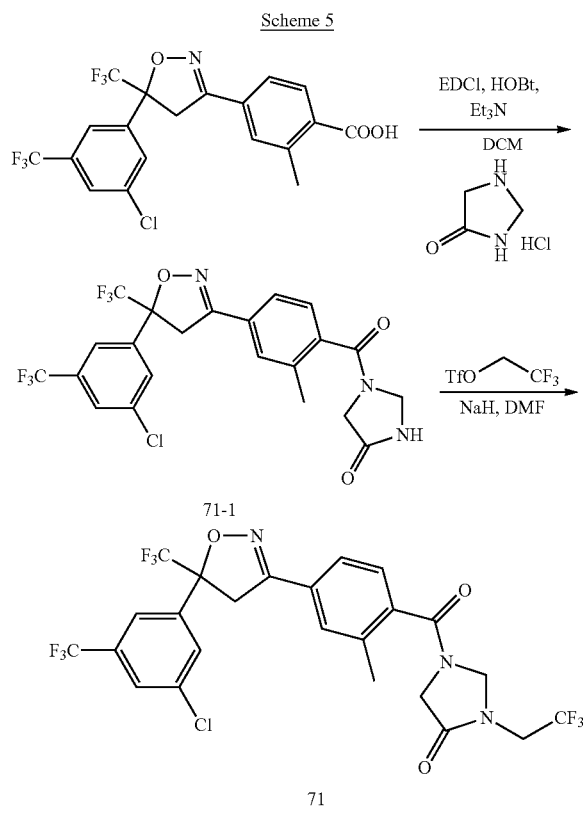

Step 1

1-[(4-[5-[3-chloro-5-(trifluoromethyl)phenyl]-5-methyl-4,5-dihydro-1,2-oxazol-3-yl]-2-methylphenyl)carbonyl]imidazolidin-4-one Into a 100-mL 3-necked round-bottom flask, was placed a solution of 4-[5-[3-chloro-5-(trifluoromethyl)phenyl]-5-methyl-4,5-dihydro-1,2-oxazol-3-yl]-2-methylbenzoic acid (100 mg, 0.25 mmol, 1.00 equiv) in dichloromethane (5 mL), imidazolidin-4-one hydrochloride (27.05 mg, 0.22 mmol, 1.00 equiv), HOBt (32.92 mg, 0.24 mmol, 1.10 equiv), triethylamine (33.59 mg, 0.33 mmol, 2.10 equiv), EDCI (63.85 mg, 0.33 mmol, 1.50 equiv). The resulting solution was stirred overnight at room temperature. The resulting solution was diluted with 20 mL of water. The resulting solution was extracted with 3×10 mL of dichloromethane and the organic layers combined and dried over anhydrous sodium sulfate and concentrated under vacuum. The residue was applied onto a silica gel column with ethyl acetate/petroleum ether (1:5-1:1). This resulted in 80 mg (68%) of 1-[(4-[5-[3-chloro-5-(trifluoromethyl)phenyl]-5-methyl-4,5-dihydro-1,2-oxazol-3-yl]-2-methylphenyl)carbonyl]imidazolidin-4-one as a white solid.

Step 2

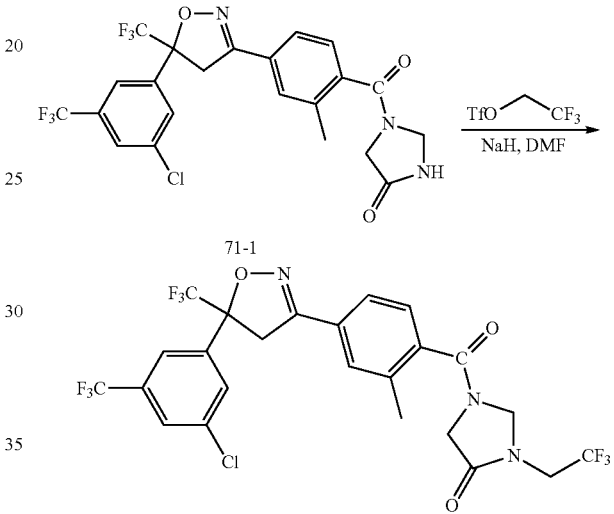

1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(2,2,2-trifluoroethyl)imidazolidin-4-one Into a 100-mL 3-necked round-bottom flask purged and maintained with an inert atmosphere of nitrogen, was placed 1-[(4-[5-[3-chloro-5-(trifluoromethyl)phenyl]-5-(trifluoromethyl)-4,5-dihydro-1,2-oxazol-3-yl]-2-methylphenyl)carbonyl]imidazolidin-4-one (80 mg, 0.15 mmol, 1.00 equiv), N,N-dimethylformamide (5 mL). This was followed by the addition of NaH (60%) (12.3 mg, 0.51 mmol, 2.00 equiv) in several batches at 0° C. The resulting solution was stirred for 30 min at 0° C. To this was added 2,2,2-trifluoroethyl trifluoromethanesulfonate (71 mg, 0.31 mmol, 2.00 equiv). The resulting solution was allowed to react, with stirring, for an additional 3 h at room temperature. The reaction was then quenched by the addition of 20 mL of water/ice. The resulting solution was extracted with 3×10 mL of ethyl acetate and the organic layers combined. The mixture was dried over anhydrous sodium sulfate. This resulted in 14 mg (15%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(2,2,2-trifluoroethyl)imidazolidin-4-one as a light yellow solid. (ES, m/z): [M+CH$_3$CN]$^+$ 643; $^1$H NMR (300 MHz, CDCl$_3$): δ 7.82 (s, 1H), 7.76 (s, 1H), 7.697 (s, 1H), 7.58-7.61 (m, 2H), 7.28-7.34 (m, 1H), 5.196 (s, 1H), 4.911 (s, 1H), 4.646 (s, 1H), 4.03-4.18 (m, 2H), 3.998 (s, 1H), 3.70-3.76 (m, 1H), 2.399 (s, 3H).

Example 8

4-[(4-[5-[3-chloro-5-(trifluoromethyl)phenyl]-5-(trifluoromethyl)-4,5-dihydro-1,2-oxazol-3-yl]-2-methylphenyl)carbonyl]-1-(3,3,3-trifluoropropyl)piperazine-2,6-dione, Compound 79

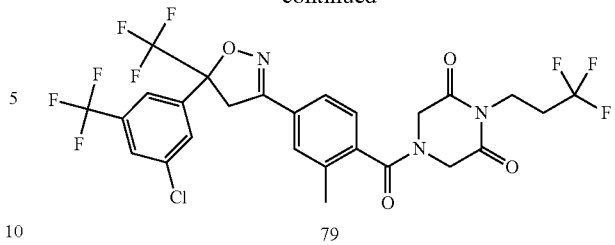

Compound 79 is prepared according to the method described below and depicted in scheme 6.

Scheme 6

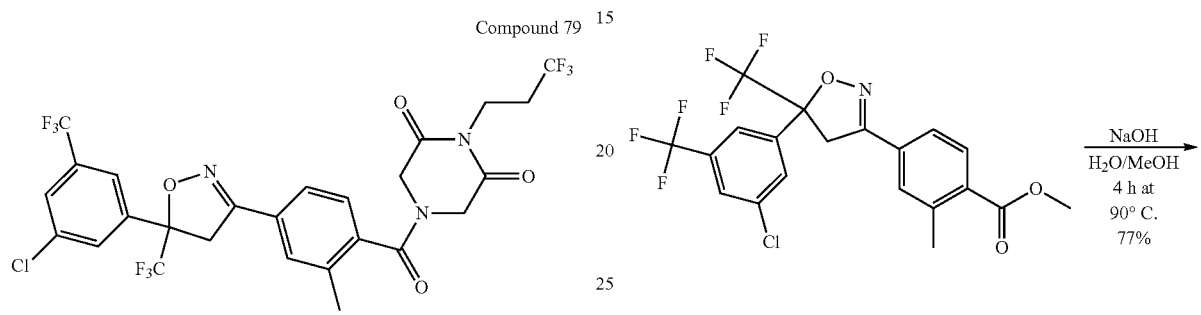

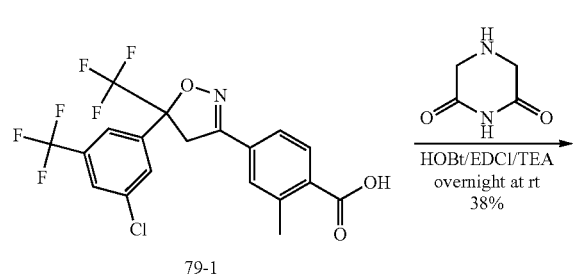

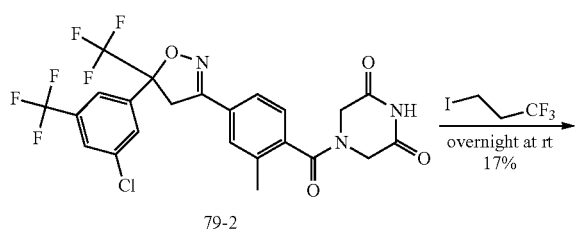

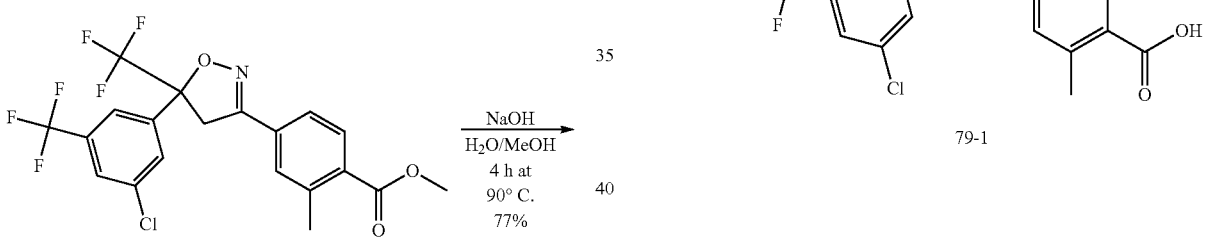

Step 1

4-[5-[3-chloro-5-(trifluoromethyl)phenyl]-5-(trifluoromethyl)-4,5-dihydro-1,2-oxazol-3-yl]-2-methylbenzoic acid Into a 500-mL round-bottom flask, was placed ethyl 4-[5-[3-chloro-5-(trifluoromethyl)phenyl]-5-(trifluoromethyl)-4,5-dihydro-1,2-oxazol-3-yl]-2-methylbenzoate (7 g, 14.59 mmol, 1.00 equiv), methanol (100 mL), water (100 mL), sodium hydroxide (1.75 g, 43.75 mmol, 3.00 equiv). The resulting solution was stirred for 4 h at 90° C. in an oil bath. The resulting mixture was concentrated under vacuum. The resulting solution was extracted with 2×50 mL of ethyl acetate and the aqueous layers combined. The pH value of the solution was adjusted to 1-2 with hydrogen chloride aq. The resulting solution was extracted with 3×50 mL of ethyl acetate and the organic layers combined. The resulting mixture was washed with 2×50 mL of brine. The mixture was dried over anhydrous sodium sulfate. The solids were filtered out. The resulting mixture was concentrated under vacuum. This resulted in 5.1 g (77%) of 4-[5-[3-chloro-5-(trifluoromethyl)phenyl]-5-(trifluoromethyl)-4,5-dihydro-1,2-oxazol-3-yl]-2-methylbenzoic acid as a light yellow solid.

Step 2

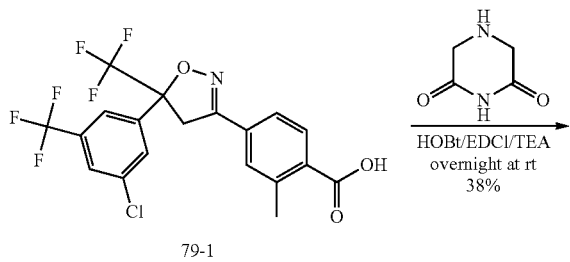

79-1

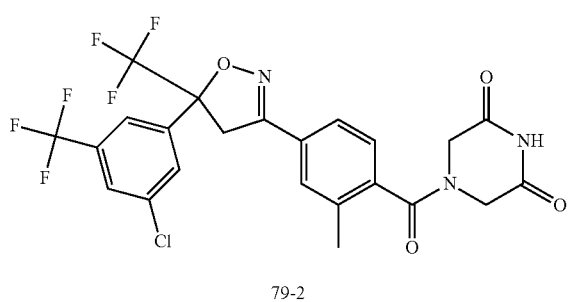

79-2

4-[(4-[5-[3-chloro-5-(trifluoromethyl)phenyl]-5-(trifluoromethyl)-4,5-dihydro-1,2-oxazol-3-yl]-2-methylphenyl)carbonyl]piperazine-2,6-dione Into a 100-mL round-bottom flask, was placed 4-[5-[3-chloro-5-(trifluoromethyl)phenyl]-5-(trifluoromethyl)-4,5-dihydro-1,2-oxazol-3-yl]-2-methylbenzoic acid (452 mg, 1.00 mmol, 1.00 equiv), dichloromethane (50 mL), TEA (202 mg, 2.00 mmol, 2.00 equiv), EDCI (384 mg, 2.00 mmol, 2.00 equiv), HOBt (270 mg, 2.00 mmol, 2.00 equiv). The mixture was stirred for 0.5 h at room temperature. This was followed by the addition of piperazine-2,6-dione (125 mg, 1.10 mmol, 1.10 equiv). The resulting solution was stirred overnight at room temperature. The resulting solution was diluted with 100 mL of DCM. The resulting mixture was washed with 3×50 mL of brine. The mixture was dried over anhydrous sodium sulfate. The resulting mixture was concentrated under vacuum. The residue was applied onto a silica gel column with ethyl acetate/petroleum ether (1:2). This resulted in 210 mg (38%) of 4-[(4-[5-[3-chloro-5-(trifluoromethyl)phenyl]-5-(trifluoromethyl)-4,5-dihydro-1,2-oxazol-3-yl]-2-methylphenyl)carbonyl]piperazine-2,6-dione as a light yellow solid.

Step 3

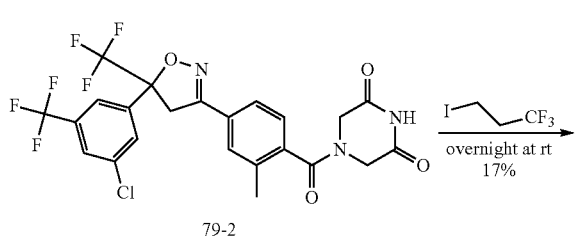

79-2

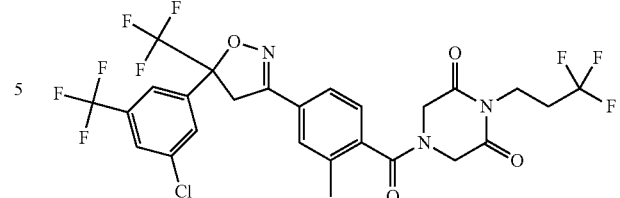

79

4-[(4-[5-[3-chloro-5-(trifluoromethyl)phenyl]-5-(trifluoromethyl)-4,5-dihydro-1,2-oxazol-3-yl]-2-methylphenyl)carbonyl]-1-(3,3,3-trifluoropropyl)piperazine-2,6-dione Into a 50-mL round-bottom flask, was placed 4-[(4-[5-[3-chloro-5-(trifluoromethyl)phenyl]-5-(trifluoromethyl)-4,5-dihydro-1,2-oxazol-3-yl]-2-methylphenyl)carbonyl]piperazine-2,6-dione (200 mg, 0.36 mmol, 1.00 equiv), 1,1,1-trifluoro-3-iodopropane (163.5 mg, 0.73 mmol, 2.00 equiv), N,N-dimethylformamide (10 mL), potassium carbonate (100.7 mg, 0.73 mmol, 2.00 equiv). The resulting solution was stirred overnight at room temperature. The resulting solution was diluted with 60 mL of H$_2$O. The resulting solution was extracted with 3×20 mL of ethyl acetate and the organic layers combined. The resulting mixture was washed with 4×40 mL of brine. The mixture was dried over anhydrous sodium sulfate. The resulting mixture was concentrated under vacuum. The crude product (85 mg) was purified by Prep-HPLC. This resulted in 39.5 g (17%) of 4-[(4-[5-[3-chloro-5-(trifluoromethyl)phenyl]-5-(trifluoromethyl)-4,5-dihydro-1,2-oxazol-3-yl]-2-methylphenyl)carbonyl]-1-(3,3,3-trifluoropropyl)piperazine-2,6-dione as a white solid. (ES, m/z): [M+CH$_3$CN]$^+$ 685.0; $^1$H NMR (300 MHz, CDCl$_3$): δ 7.85 (s, 1H), 7.78 (s, 1H), 7.72 (s, 1H), 7.61 (d, J=8.7 Hz, 2H), 7.28-7.23 (m, 1H), 4.79 (s, 2H), 4.19-4.10 (m, 5H), 3.75 (d, J=17.4 Hz, 1H), 2.49-2.41 (m, 2H), 2.32 (s, 3H)

Example 9

1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(3,3,3-trifluoropropyl)imidazolidin-4-one, Compound 80

Compound 80

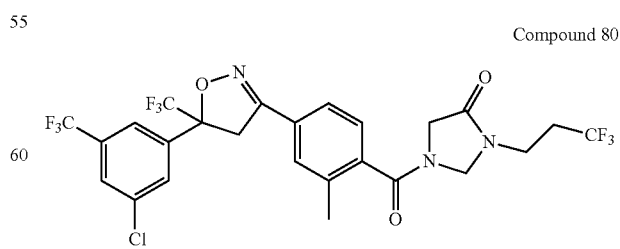

Compound 80 was prepared according to the method described below and depicted in scheme 7.

Scheme 7

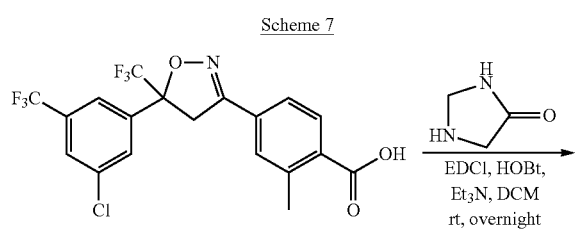

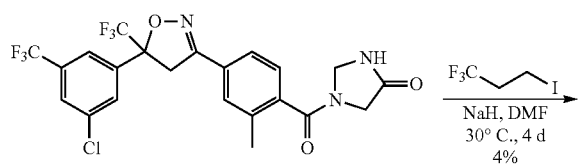

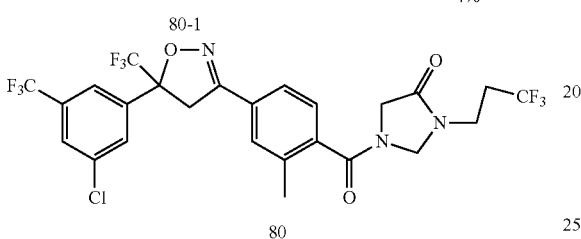

Step 1.

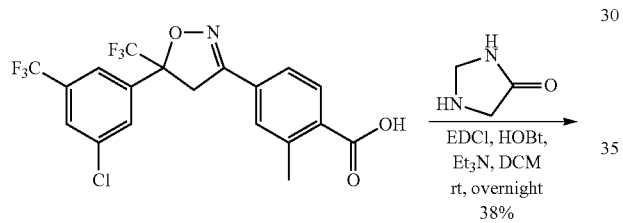

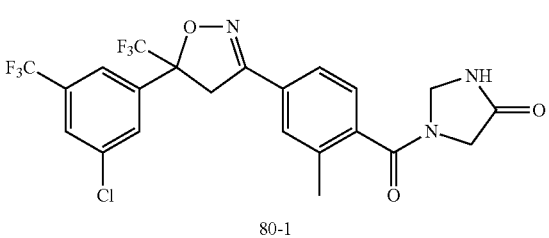

1-[(4-[5-[3-chloro-5-(trifluoromethyl)phenyl]-5-(trifluoromethyl)-4,5-dihydro-1,2-oxazol-3-yl]-2-methylphenyl)carbonyl]imidazolidin-4-one Into a 100-mL round-bottom flask, was placed 4-[5-[3-chloro-5-(trifluoromethyl)phenyl]-5-(trifluoromethyl)-4,5-dihydro-1,2-oxazol-3-yl]-2-methylbenzoic acid (452 mg, 1.00 mmol, 1.00 equiv), dichloromethane (50 mL), EDCI (384 mg, 2.00 mmol, 2.00 equiv), HOBt (270 mg, 2.00 mmol, 2.00 equiv), TEA (303 mg, 2.99 mmol, 3.00 equiv), imidazolidin-4-one hydrochloride (135 mg, 1.10 mmol, 1.00 equiv). The resulting solution was stirred overnight at room temperature. The resulting solution was diluted with 100 mL of DCM. The resulting mixture was washed with 3×50 mL of brine. The mixture was dried over anhydrous sodium sulfate. The resulting mixture was concentrated under vacuum. The residue was applied onto a silica gel column with ethyl acetate/petroleum ether (1:2). This resulted in 200 mg (38%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]imidazolidin-4-one as a light yellow solid.
Step 2.

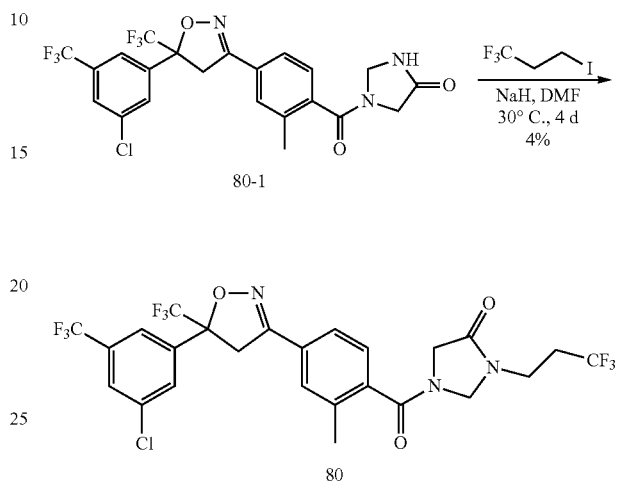

1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(3,3,3-trifluoropropyl)imidazolidin-4-one Into a 50-mL 3-necked round-bottom flask purged and maintained with an inert atmosphere of nitrogen, was placed 1-[(4-[5-[3-chloro-5-(trifluoromethyl)phenyl]-5-(trifluoromethyl)-4,5-dihydro-1,2-oxazol-3-yl]-2-methylphenyl)carbonyl]imidazolidin-4-one (200 mg, 0.38 mmol, 1.00 equiv), N,N-dimethylformamide (5 mL). This was followed by the addition of sodium hydride (46 mg, 1.15 mmol, 3.00 equiv, 60%), in portions at 0° C. The resulting solution was stirred for 30 min at 0° C. To this was added 1,1,1-trifluoro-3-iodopropane (863 mg, 3.85 mmol, 10.00 equiv). The resulting solution was allowed to react, with stirring, for an additional 4 days at 30° C. The reaction was then quenched by the addition of 10 ml of water. The resulting solution was extracted with 3×10 ml of ethyl acetate and the organic layers combined. The resulting mixture was washed with 3×20 mL of brine. The resulting mixture was concentrated under vacuum. The residue was applied onto a TLC plate with EA/PE (5:1). This resulted in 10.9 mg (4%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(3,3,3-trifluoropropyl)imidazolidin-4-one as a light yellow semi solid. (ES, m/z): [M+H]$^+$ 616; $^1$H NMR (300 MHz, CDCl$_3$) δ: 7.97 (s, 1H), 7.88 (d, J=6.0 Hz, 2H), 7.69-7.71 (m, 2H), 7.43 (d, J=7.8 Hz, 1H), 5.12 (s, 1H), 4.69 (s, 1H), 4.05-4.39 (m, 3H), 3.87 (s, 1H), 3.70 (t, J=7.2 Hz, 1H), 3.56 (t, J=7.2 Hz, 1H), 2.46-2.65 (m, 3H), 2.39 (s, 3H).

Example 10

4-([4-[5-(3,5-dichlorophenyl)-5-(trifluoromethyl)-4,5-dihydro-1,2-oxazol-3-yl]-2-(trifluoromethyl)phenyl]carbonyl)-1-(2,2,2-trifluoroethyl)piperazine-2,6-dione, Compound 92

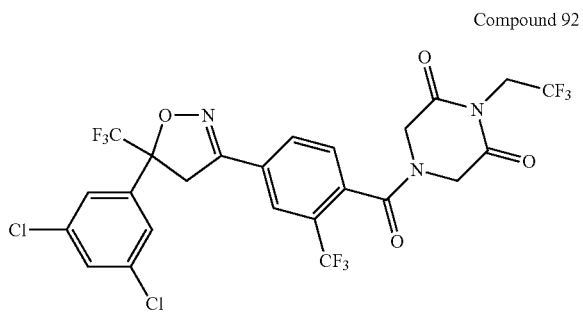 [SMILES: O=C(c1ccc(C2=NOC(c3cc(Cl)cc(Cl)c3)(C(F)(F)F)C2)cc1C(F)(F)F)N1CC(=O)N(CC(F)(F)F)C(=O)C1]

Compound 92

Compound 92 was prepared according to the description provided below and depicted in scheme 8.

Scheme 8

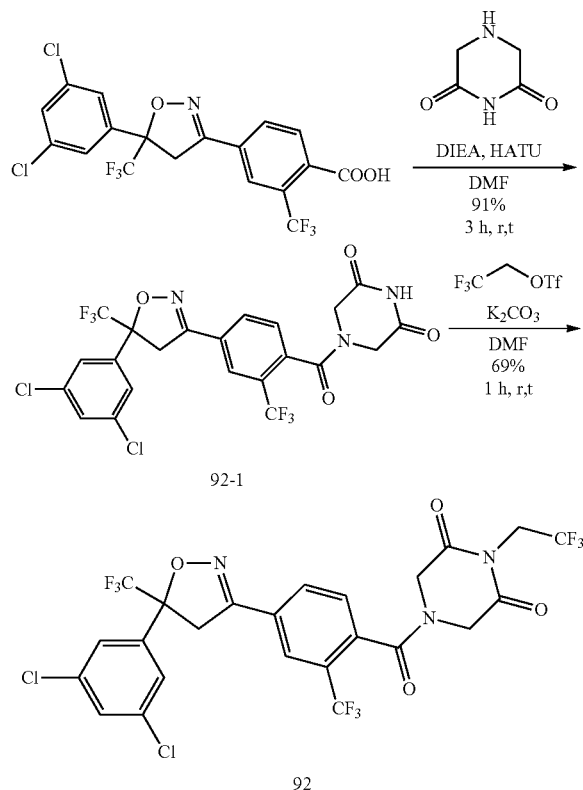

Step 1

4-([4-[5-(3,5-dichlorophenyl)-5-(trifluoromethyl)-4,5-dihydro-1,2-oxazol-3-yl]-2-(trifluoromethyl)phenyl]carbonyl)piperazine-2,6-dione Into a 50-mL round-bottom flask, was placed a solution of 4-[5-(3,5-dichlorophenyl)-5-(trifluoromethyl)-4,5-dihydro-1,2-oxazol-3-yl]-2-(trifluoromethyl)benzoic acid (300 mg, 0.64 mmol, 1.00 equiv) in N,N-dimethylformamide (2 mL), HATU (483 mg, 1.27 mmol, 2.00 equiv), DIEA (164 mg, 1.27 mmol, 2.00 equiv), piperazine-2,6-dione (145 mg, 1.27 mmol, 2.00 equiv). The resulting solution was stirred for 3 h at 20° C. The resulting solution was diluted with 50 mL of brine. The resulting solution was extracted with 3×50 mL of ethyl acetate and the organic layers combined. The mixture was dried over sodium sulfate and concentrated under vacuum. The residue was applied onto a silica gel column with PE/EA (10:1). This resulted in 330 mg (91%) of 4-([4-[5-(3,5-dichlorophenyl)-5-(trifluoromethyl)-4,5-dihydro-1,2-oxazol-3-yl]-2-(trifluoromethyl)phenyl]carbonyl)piperazine-2,6-dione as a white solid.

Step 2

4-([4-[5-(3,5-dichlorophenyl)-5-(trifluoromethyl)-4,5-dihydro-1,2-oxazol-3-yl]-2-(trifluoromethyl)phenyl]carbonyl)-1-(2,2,2-trifluoroethyl)piperazine-2,6-dione Into a 50-mL round-bottom flask, was placed a solution of 4-([4-[5-(3,5-dichlorophenyl)-5-(trifluoromethyl)-4,5-dihydro-1,2-oxazol-3-yl]-2-(trifluoromethyl)phenyl]carbonyl)piperazine-2,6-dione (300 mg, 0.53 mmol, 1.00 equiv) in N,N-dimethylformamide (5 mL), $K_2CO_3$ (140 mg, 1.01 mmol, 2.00 equiv), 2,2,2-trifluoroethyl trifluoromethanesulfonate (240 mg, 1.03 mmol, 2.00 equiv). The resulting solution was stirred for 1 h at 20° C. The resulting solution was diluted with 50 mL of brine. The resulting solution was extracted with 3×50 mL of ethyl acetate and the organic layers combined. The mixture was dried over sodium sulfate and concentrated under vacuum. The residue was applied onto a silica gel column with ethyl acetate/petroleum ether (1/5). This resulted in 235.9 mg (69%) of 4-([4-[5-(3,5-dichlorophenyl)-5-(trifluoromethyl)-4,5-dihydro-1,2-oxazol-3-yl]-2-(trifluoromethyl)phenyl]carbonyl)-1-(2,2,2-trifluoroethyl)piperazine-2,6-dione as a off-white solid. (ES, m/z): [M−H]⁻ 648; $^1$H NMR (300 MHz, $CDCl_3$) δ: 8.00-8.05 (m, 2H), 7.44-7.53 (m, 4H), 4.94-5.01 (m, 1H), 4.68 (s, 1H), 4.50-4.56 (m, 2H), 4.10-4.16 (m, 3H), 3.76 (d, J=17.4 Hz, 1H)

Example 11

1-([4-[5-(3,5-dichlorophenyl)-5-(trifluoromethyl)-4,5-dihydro-1,2-oxazol-3-yl]-2-(trifluoromethyl)phenyl]carbonyl)-3-(2,2,2-trifluoroethyl)imidazolidin-4-one, Compound 93

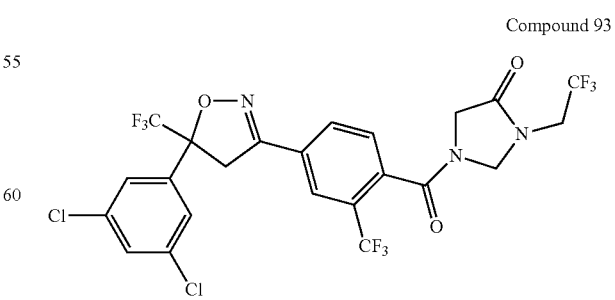

Compound 93

Compound 93 was prepared according to the description provided below and depicted in scheme 9.

Scheme 9

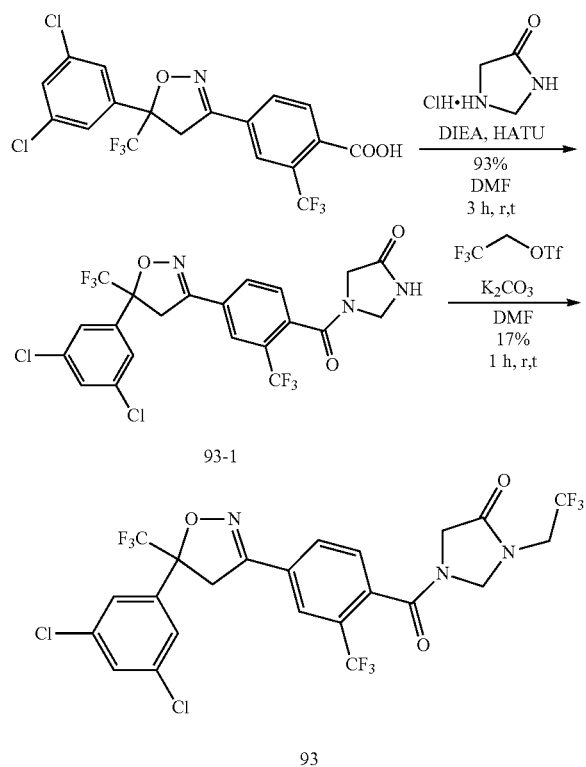

Step 1

1-([4-[5-(3,5-dichlorophenyl)-5-(trifluoromethyl)-4,5-dihydro-1,2-oxazol-3-yl]-2-(trifluoromethyl)phenyl]carbonyl)imidazolidin-4-one Into a 50-mL round-bottom flask, was placed a solution of 4-[5-(3,5-dichlorophenyl)-5-(trifluoromethyl)-4,5-dihydro-1,2-oxazol-3-yl]-2-(trifluoromethyl)benzoic acid (300 mg, 0.64 mmol, 1.00 equiv) in N,N-dimethylformamide (2 mL), HATU (483 mg, 1.27 mmol, 2.00 equiv), DIEA (164 mg, 1.27 mmol, 2.00 equiv), imidazolidin-4-one hydrochloride (155 mg, 1.26 mmol, 2.00 equiv). The resulting solution was stirred for 3 h at 20° C. The resulting solution was diluted with 50 mL of brine. The resulting solution was extracted with 3×50 mL of ethyl acetate and the organic layers combined. The mixture was dried over sodium sulfate and concentrated under vacuum. The residue was applied onto a silica gel column with PE/EA (10:1). This resulted in 320 mg (93%) of 1-([4-[5-(3,5-dichlorophenyl)-5-(trifluoromethyl)-4,5-dihydro-1,2-oxazol-3-yl]-2-(trifluoromethyl)phenyl]carbonyl)imidazolidin-4-one as light yellow oil.

Step 2

1-([4-[5-(3,5-dichlorophenyl)-5-(trifluoromethyl)-4,5-dihydro-1,2-oxazol-3-yl]-2-(trifluoromethyl)phenyl]carbonyl)-3-(2,2,2-trifluoroethyl)imidazolidin-4-one Into a 50-mL round-bottom flask, was placed a solution of 1-([4-[5-(3,5-dichlorophenyl)-5-(trifluoromethyl)-4,5-dihydro-1,2-oxazol-3-yl]-2-(trifluoromethyl)phenyl]carbonyl)imidazolidin-4-one (300 mg, 0.56 mmol, 1.00 equiv) in N,N-dimethylformamide (5 mL), sodium hydride (26 mg, 1.08 mmol, 2.00 equiv), 2,2,2-trifluoroethyl trifluoromethanesulfonate (260 mg, 1.12 mmol, 2.00 equiv). The resulting solution was stirred for 2 h at 20° C. The resulting solution was diluted with 50 mL of brine. The resulting solution was extracted with 3×50 mL of ethyl acetate and the organic layers combined and dried over sodium sulfate and concentrated under vacuum. The residue was applied onto a silica gel column with ethyl acetate/petroleum ether (1/5). This resulted in 58.8 mg (17%) of 1-([4-[5-(3,5-dichlorophenyl)-5-(trifluoromethyl)-4,5-dihydro-1,2-oxazol-3-yl]-2-(trifluoromethyl)phenyl]carbonyl)-3-(2,2,2-trifluoroethyl)imidazolidin-4-one as a off-white solid. (ES, m/z): [M−H]⁻ 620; $^1$H NMR (300 MHz, CDCl$_3$) δ: 8.01-8.03 (m, 2H), 7.53 (s, 3H), 7.47 (s, 1H), 5.20 (s, 1H), 4.65 (s, 1H), 4.32 (s, 1H), 4.17 (s, 1H), 4.02-4.11 (m, 2H), 3.73-3.84 (m, 2H)

Example 12

4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-1-propylpiperazine-2,6-dione, Compound 95

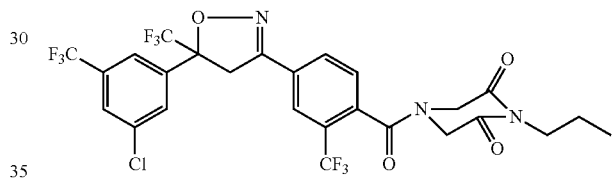

Compound 95 was prepared according to the description provided below and depicted in scheme 10.

Scheme 10

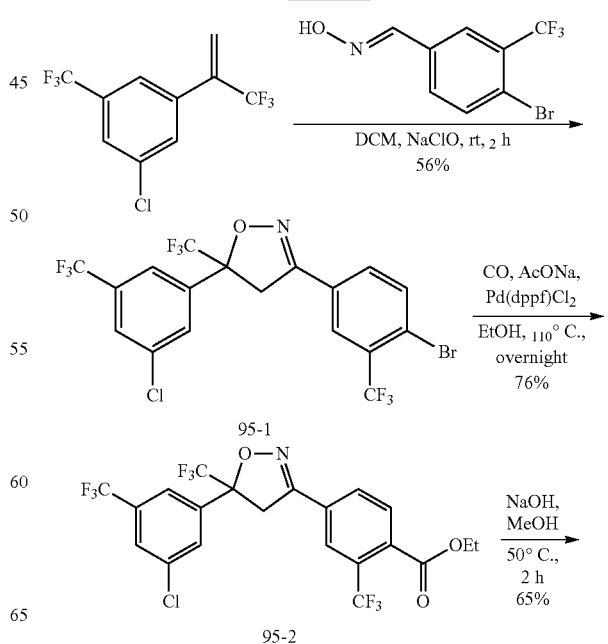

139

-continued

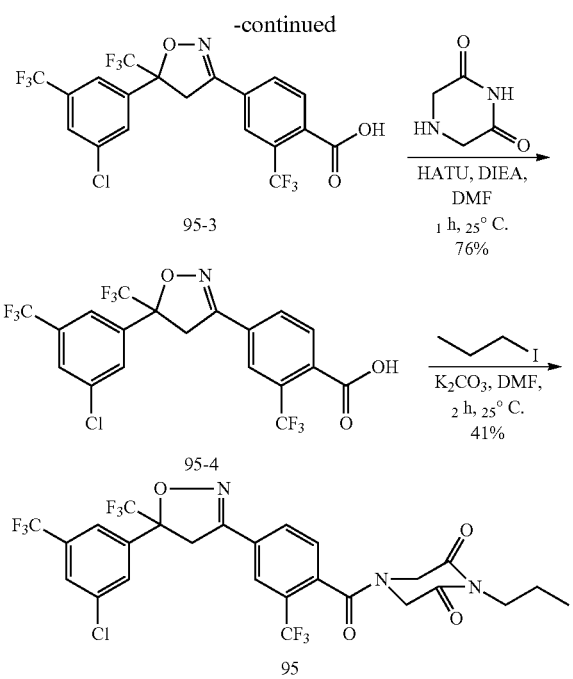

Step 1

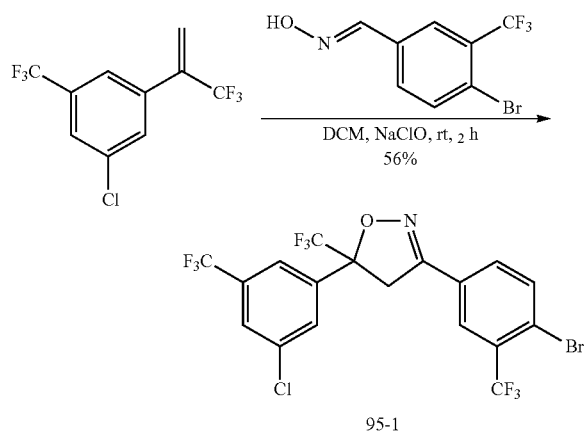

3-[4-bromo-3-(trifluoromethyl)phenyl]-5-[3-chloro-5-(trifluoromethyl)phenyl]-5-(trifluoromethyl)-4,5-dihydro-1,2-oxazole Into a 50-mL round-bottom flask, was placed (E)-N-[[4-bromo-3-(trifluoromethyl)phenyl]methylidene]hydroxylamine (1.5 g, 5.60 mmol, 1.00 equiv), dichloromethane (20 mL), 1-chloro-3-(trifluoromethyl)-5-(3,3,3-trifluoroprop-1-en-2-yl)benzene (1.6 g, 5.83 mmol, 1.10 equiv), NaOCl (10 mL). The resulting solution was stirred for 2 h at room temperature. The resulting solution was diluted with 30 mL of H$_2$O. The resulting solution was extracted with 3×50 mL of dichloromethane and the organic layers combined. The resulting mixture was washed with 3×50 mL of brine. The mixture was dried over anhydrous sodium sulfate. The solids were filtered out. The resulting mixture was concentrated under vacuum. The residue was applied onto a silica gel column with ethyl acetate/petroleum ether (1:100).

140

This resulted in 1.7 g (56%) of 3-[4-bromo-3-(trifluoromethyl)phenyl]-5-[3-chloro-5-(trifluoromethyl)phenyl]-5-(trifluoromethyl)-4,5-dihydro-1,2-oxazole as a light yellow solid.

Step 2

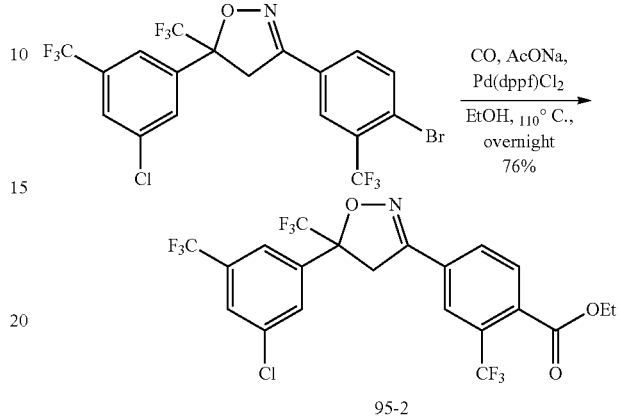

Ethyl 4-[5-[3-chloro-5-(trifluoromethyl)phenyl]-5-(trifluoromethyl)-4,5-dihydro-1,2-oxazol-3-yl]-2-(trifluoromethyl)benzoate Into a 30-mL pressure tank reactor (10 atm), was placed 3-[4-bromo-3-(trifluoromethyl)phenyl]-5-[3-chloro-5-(trifluoromethyl)phenyl]-5-(trifluoromethyl)-4,5-dihydro-1,2-oxazole (600 mg, 1.11 mmol, 1.00 equiv), ethanol (20 g, 434.12 mmol, 391.15 equiv), Pd(dppf)Cl$_2$ (40 mg, 0.05 mmol, 0.05 equiv), NaOAc (179 mg, 2.00 equiv). The resulting solution was stirred overnight at 110° C. in an oil bath under CO (gas). The resulting mixture was concentrated under vacuum. The residue was applied onto a silica gel column with ethyl acetate/petroleum ether (1:50). This resulted in 450 mg (76%) of ethyl 4-[5-[3-chloro-5-(trifluoromethyl)phenyl]-5-(trifluoromethyl)-4,5-dihydro-1,2-oxazol-3-yl]-2-(trifluoromethyl)benzoate as brown oil.

Step 3

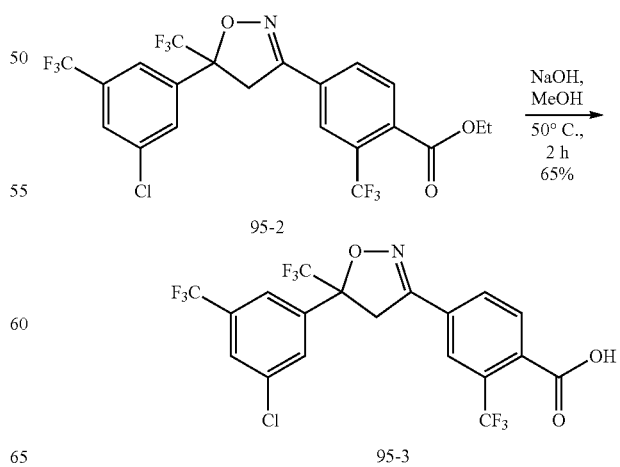

4-[5-[3-chloro-5-(trifluoromethyl)phenyl]-5-(trifluoromethyl)-4,5-dihydro-1,2-oxazol-3-yl]-2-(trifluoromethyl)benzoic acid Into a 25-mL round-bottom flask, was placed ethyl 4-[5-[3-chloro-5-(trifluoromethyl)phenyl]-5-(trifluoromethyl)-4,5-dihydro-1,2-oxazol-3-yl]-2-(trifluoromethyl)benzoate (680 mg, 1.27 mmol, 1.00 equiv), water (5 mL), methanol (10 mL), LiOH (153 mg, 6.39 mmol, 5.00 equiv). The resulting solution was stirred for 2 h at 50° C. The resulting mixture was concentrated under vacuum. The resulting solution was diluted with 30 mL of $H_2O$. The resulting solution was extracted with 3×20 mL of ethyl acetate and the organic layers combined. The resulting mixture was washed with 2×20 mL of brine. The mixture was dried over anhydrous sodium sulfate and concentrated under vacuum. This resulted in 420 mg (65%) of 4-[5-[3-chloro-5-(trifluoromethyl)phenyl]-5-(trifluoromethyl)-4,5-dihydro-1,2-oxazol-3-yl]-2-(trifluoromethyl)benzoic acid as a light yellow solid.

Step 4

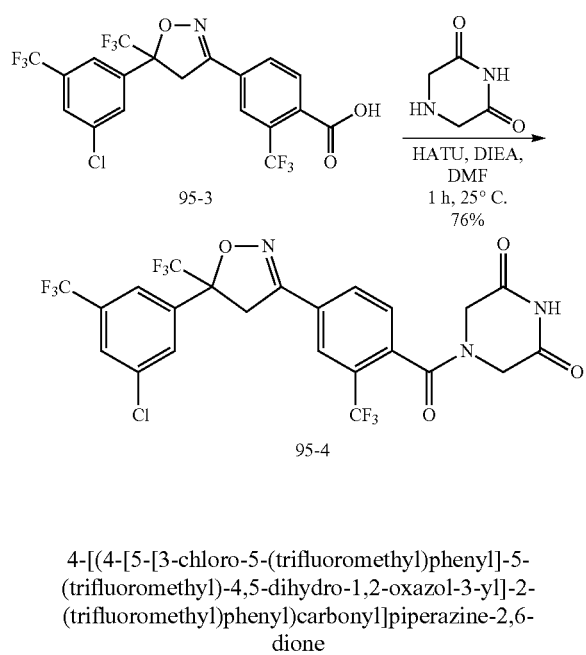

4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]piperazine-2,6-dione Into a 25-mL round-bottom flask, was placed 4-[5-[3-chloro-5-(trifluoromethyl)phenyl]-5-(trifluoromethyl)-4,5-dihydro-1,2-oxazol-3-yl]-2-(trifluoromethyl)benzoic acid (70 mg, 0.14 mmol, 1.00 equiv), N,N-dimethylformamide (3 mL), HATU (105 mg, 0.28 mmol, 2.00 equiv), DIEA (36 mg, 0.28 mmol, 1.96 equiv), piperazine-2,6-dione (32 mg, 0.28 mmol, 1.99 equiv). The resulting solution was stirred for 1 h at 25° C. The reaction was then quenched by the addition of 10 ml of water. The resulting solution was extracted with 2×10 mL of ethyl acetate and the organic layers combined. The resulting mixture was washed with 3×20 mL of brine. The resulting mixture was concentrated under vacuum. The residue was applied onto a TLC plate with ethyl acetate/petroleum ether (1/1). This resulted in 70 mg (76%) of 4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]piperazine-2,6-dione as colorless oil.

Step 5

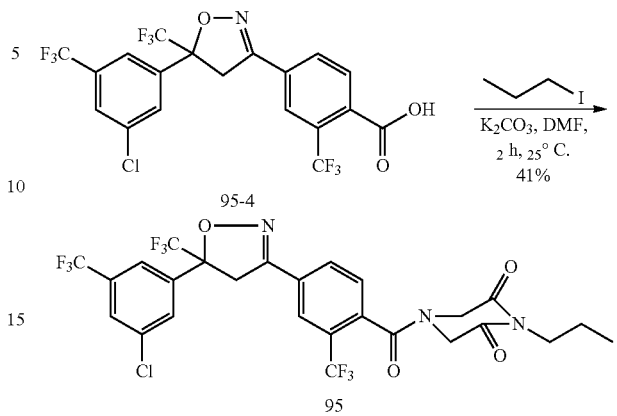

4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-1-propylpiperazine-2,6-dione Into a 25-mL round-bottom flask, was placed a solution of 4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]piperazine-2,6-dione (70 mg, 0.12 mmol, 1.00 equiv) in N,N-dimethylformamide (2 mL), 1-iodopropane (32 mg, 0.19 mmol, 2.00 equiv), potassium carbonate (59 mg, 0.43 mmol, 3.00 equiv). The resulting solution was stirred for 2 h at 25° C. The reaction was then quenched by the addition of 10 mL of water. The resulting solution was extracted with 2×10 mL of ethyl acetate and the organic layers combined and concentrated under vacuum. The residue was applied onto a silica gel column with ethyl acetate/petroleum ether (1:2). This resulted in 31 mg (41%) of 4-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-1-propylpiperazine-2,6-dione as a white solid. (ES, m/z): $[M+CH_3CN]^+$ 685.0; $^1H$ NMR (300 MHz, $CDCl_3$): δ 7.79-7.84 (m, 2H), 7.73-7.87 (m, 3H), 7.46 (d, J=7.8 Hz, 1H), 4.86 (d, J=19.4 Hz, 1H), 4.56 (d, J=18.3 Hz, 1H), 4.19 (d, J=17.4 Hz, 1H), 4.05 (s, 2H), 3.75-3.81 (m, 3H), 1.52-1.64 (m, 2H), 0.93 (t, J=7.2 Hz, 3H).

Example 13

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(2,2,2-trifluoroethyl)imidazolidin-4-one, Compound 96

Compound 96

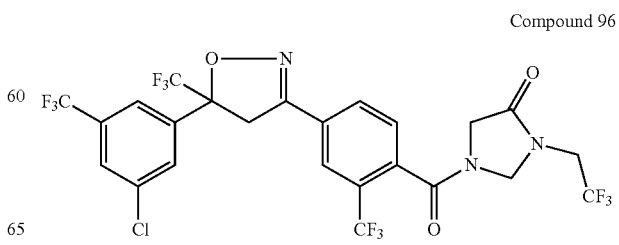

Compound 96 was prepared according to the description below depicted in scheme 11.

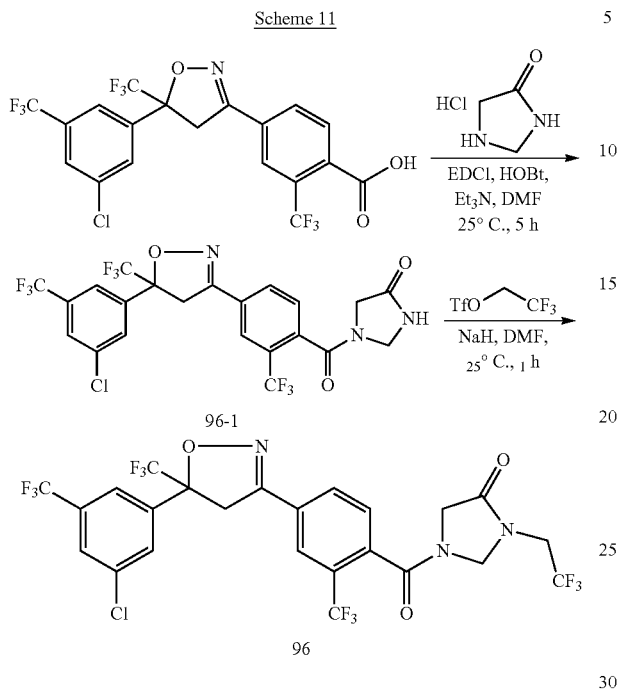

Step 1

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one Into a 50-mL round bottom flask, was placed 4-[5-[3-chloro-5-(trifluoromethyl)phenyl]-5-(trifluoromethyl)-4,5-dihydro-1,2-oxazol-3-yl]-2-(trifluoromethyl)benzoic acid (50 mg, 0.10 mmol, 1.00 equiv), N,N-dimethylformamide (2 mL), EDCI (38 mg, 0.20 mmol, 2.00 equiv), HOBt (27 mg, 0.20 mmol, 2.02 equiv), TEA (50 mg, 0.49 mmol, 5.00 equiv), imidazolidin-4-one (17 mg, 0.20 mmol, 2.00 equiv). The resulting solution was stirred for 30 min at 25° C. The resulting solution was allowed to react, with stirring, for an additional 5 h at 25° C. The reaction was then quenched by the addition of 10 ml of water. The resulting solution was extracted with 2×10 ml of ethyl acetate and the organic layers combined. The resulting mixture was washed with 3×10 mL of brine. The resulting mixture was concentrated under vacuum. The residue was applied onto a TLC plate with PE/EA (1/1). This resulted in 50 mg (79%) of 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one as yellow oil.

Step 2

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(2,2,2-trifluoroethyl)imidazolidin-4-one Into a 50-mL round bottom flask, was placed 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one (50 mg, 0.09 mmol, 1.00 equiv), N,N-dimethylformamide (1 mL), sodium hydride (7 mg, 0.17 mmol, 2.00 equiv, 60%), The resulting solution was stirred for 20 min at 25° C. Added 2,2,2-trifluoroethyl trifluoromethanesulfonate (40 mg, 0.17 mmol, 1.98 equiv). The resulting solution was allowed to react, with stirring, for an additional 1 h at r t. The reaction was then quenched by the addition of 10 ml of water. The resulting solution was extracted with 2×10 ml of ethyl acetate and the organic layers combined. The resulting mixture was washed with 3×10 mL of brine. The resulting mixture was concentrated under vacuum. The residue was applied onto a TLC plate with PE/EA (2/1). This resulted in 23.7 mg (37%) of 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(2,2,2-trifluoroethyl)imidazolidin-4-one as yellow oil. ES, m/z): [M+CH$_3$CN]$^+$697.0; $^1$H NMR (300 MHz, CDCl$_3$): δ8.12-8.22 (m, 2H), 7.98 (s, 1H), 7.86 (d, J=7.8 Hz, 2H), 7.73 (d, J=7.8 Hz, 1H), 5.17 (s, 1H), 4.79 (s, 1H), 4.44 (d, J=18.0 Hz, 1H), 4.01-4.31 (m, 4H), 3.93 (s, 1H).

Example 14

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(3,3,3-trifluoropropyl)imidazolidin-4-one, Compound 98

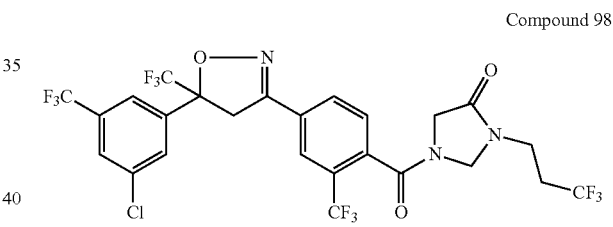

Compound 98

Compound 98 was prepared according to the description provided below and depicted in scheme 12.

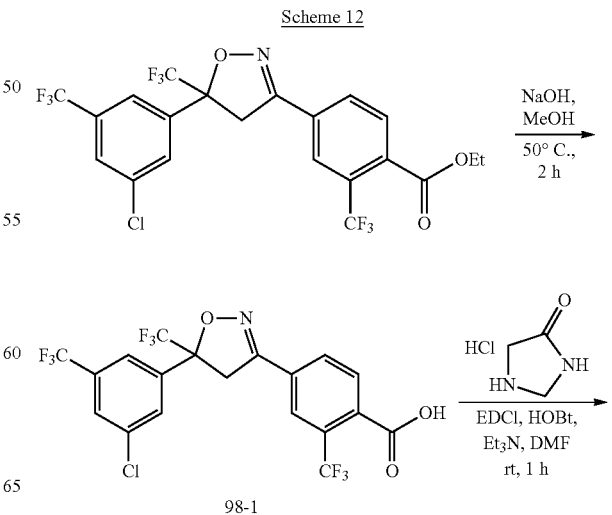

-continued

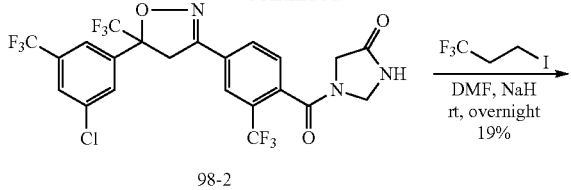
98-2

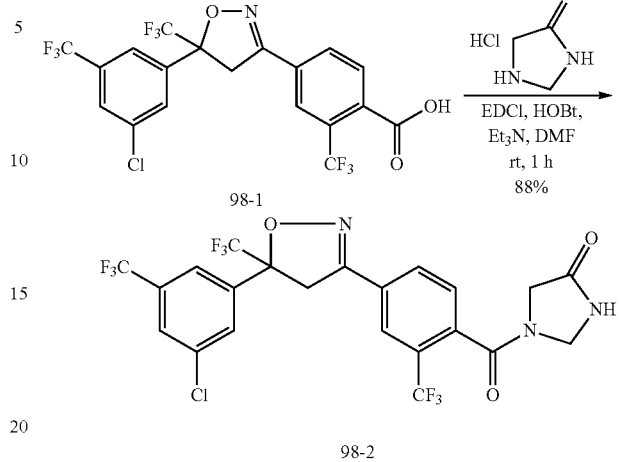

Step 2

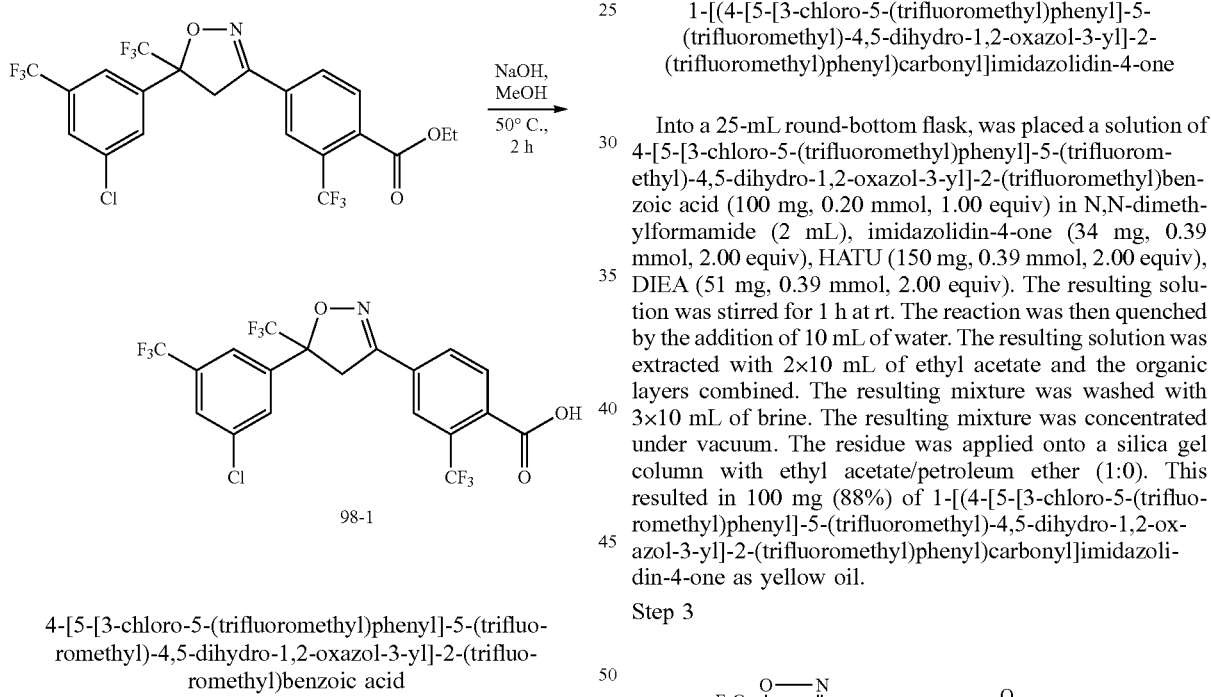

98

Step 1

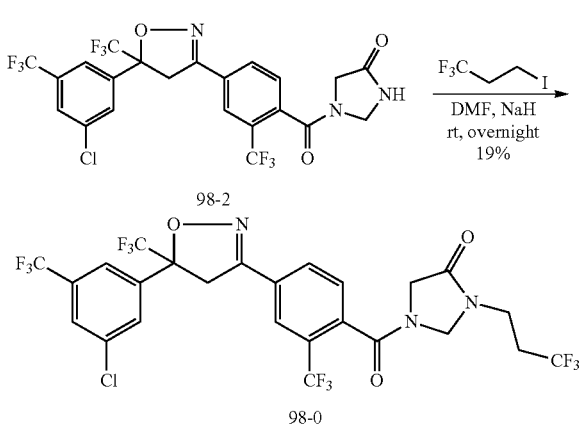

98-1

4-[5-[3-chloro-5-(trifluoromethyl)phenyl]-5-(trifluoromethyl)-4,5-dihydro-1,2-oxazol-3-yl]-2-(trifluoromethyl)benzoic acid Into a 100-mL round-bottom flask, was placed a solution of ethyl 4-[5-[3-chloro-5-(trifluoromethyl)phenyl]-5-(trifluoromethyl)-4,5-dihydro-1,2-oxazol-3-yl]-2-(trifluoromethyl)benzoate (400 mg, 0.75 mmol, 1.00 equiv) in methanol (5 mL), a solution of sodium hydroxide (400 mg) in water (5 mL). The resulting solution was stirred for 2 h at 50° C. The pH value of the solution was adjusted to 5 with hydrogen chloride (2 mol/L). The resulting solution was extracted with 2×10 mL of ethyl acetate and the organic layers combined. The resulting mixture was washed with 3×10 mL of brine. The mixture was dried over anhydrous sodium sulfate and concentrated under vacuum. This resulted in 380 mg (crude) of 4-[5-[3-chloro-5-(trifluoromethyl)phenyl]-5-(trifluoromethyl)-4,5-dihydro-1,2-oxazol-3-yl]-2-(trifluoromethyl)benzoic acid as yellow oil.

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one Into a 25-mL round-bottom flask, was placed a solution of 4-[5-[3-chloro-5-(trifluoromethyl)phenyl]-5-(trifluoromethyl)-4,5-dihydro-1,2-oxazol-3-yl]-2-(trifluoromethyl)benzoic acid (100 mg, 0.20 mmol, 1.00 equiv) in N,N-dimethylformamide (2 mL), imidazolidin-4-one (34 mg, 0.39 mmol, 2.00 equiv), HATU (150 mg, 0.39 mmol, 2.00 equiv), DIEA (51 mg, 0.39 mmol, 2.00 equiv). The resulting solution was stirred for 1 h at rt. The reaction was then quenched by the addition of 10 mL of water. The resulting solution was extracted with 2×10 mL of ethyl acetate and the organic layers combined. The resulting mixture was washed with 3×10 mL of brine. The resulting mixture was concentrated under vacuum. The residue was applied onto a silica gel column with ethyl acetate/petroleum ether (1:0). This resulted in 100 mg (88%) of 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one as yellow oil.

Step 3

1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(3,3,3-trifluoropropyl)imidazolidin-4-one Into a 50-mL round-bottom flask, was placed a solution of 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]imidazolidin-4-one (80 mg, 0.14 mmol, 1.00 equiv) in N,N-dimethylformamide (5 ml), sodium hydride (11 mg, 0.28 mmol, 2.00 equiv, 60%), 1,1,1-trifluoro-3-iodopropane (153 mg, 0.68 mmol, 5.00 equiv). The resulting solution was stirred overnight at r t. The reaction was then quenched by the addition of 10 mL of water. The resulting solution was extracted with 2×10 mL of ethyl acetate and the organic layers combined. The resulting mixture was washed with 3×10 mL of brine. The resulting mixture was concentrated under vacuum. The residue was applied onto a silica gel column with ethyl acetate/petroleum ether (1:1). This resulted in 17.8 mg (19%) of 1-[(4-[5-[3-chloro-5-(trifluoromethyl)phenyl]-5-(trifluoromethyl)-4,5-dihydro-1,2-oxazol-3-yl]-2-(trifluoromethyl)phenyl)carbonyl]-3-(3,3,3-trifluoropropyl)imidazolidin-4-one as a light yellow solid. (ES, m/z): [M+CH$_3$CN]$^+$ 711.0; $^1$H NMR (300 MHz, CD$_3$OD): δ8.12-8.22 (m, 2H), 7.99 (s, 1H), 7.89 (d, J=5.4 Hz, 2H), 7.71 (d, J=5.1 Hz, 1H), 5.12 (s, 1H), 4.70 (s, 1H), 4.16-4.47 (m, 3H), 3.86 (s, 1H), 3.57-3.74 (m, 2H), 2.39-2.67 (m, 2H).

Example 15

1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]-3-(3,3,3-trifluoropropyl)imidazolidin-4-one, Compound 99

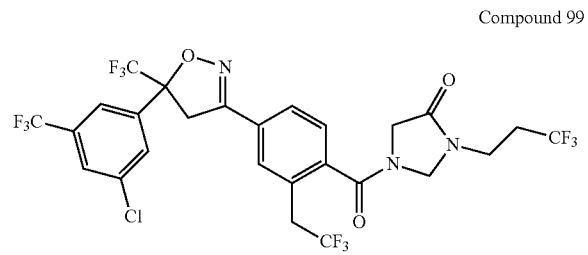 [SMILES: O=C1CN(C(=O)c2ccc(C3=NOC(c4cc(Cl)cc(C(F)(F)F)c4)(C(F)(F)F)C3)cc2CC(F)(F)F)CN1CCC(F)(F)F]

Compound 99

Compound 99 was prepared according to the description provided below and depicted in scheme 13.

Scheme 13

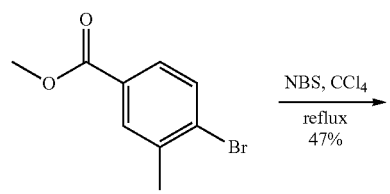

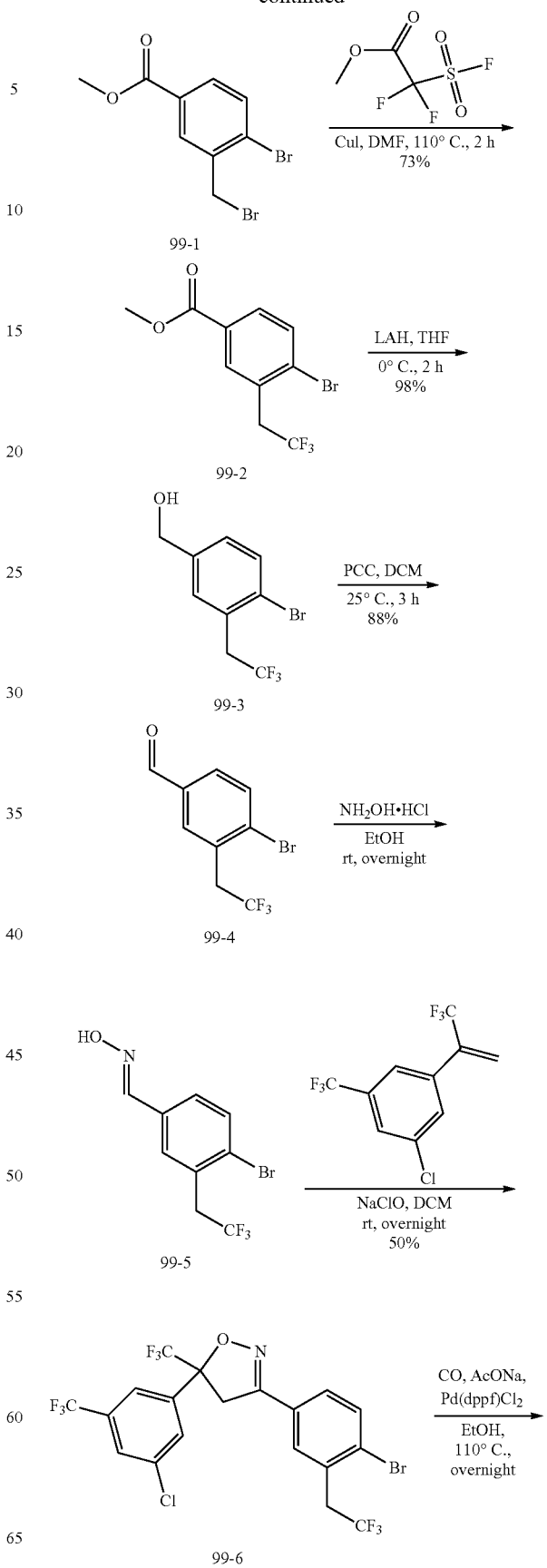

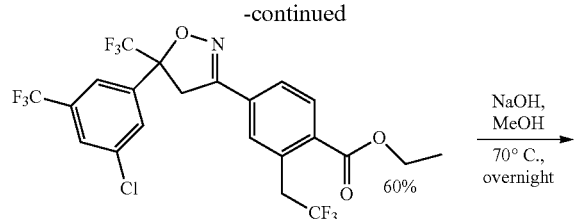

99-7

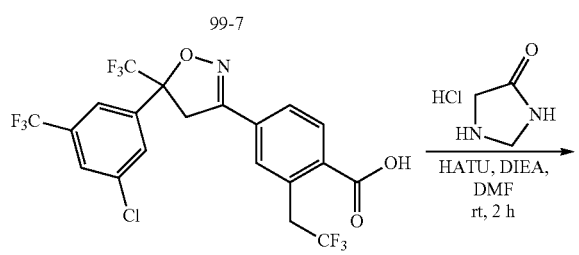

99-8

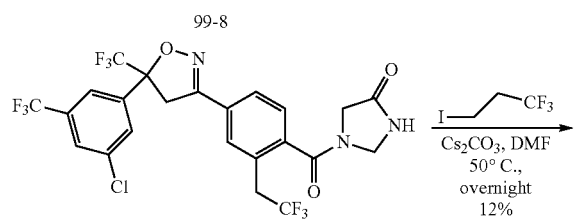

99-9

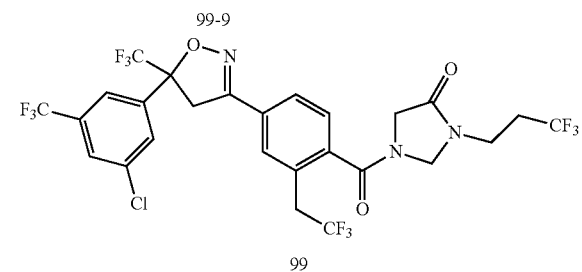

99

Step 1

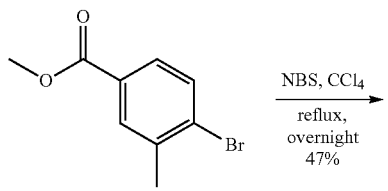

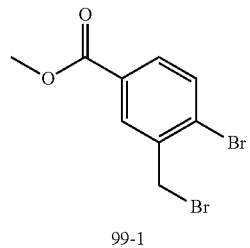

99-1

Methyl 4-bromo-3-(bromomethyl)benzoate

Into a 500-mL round-bottom flask, was placed a solution of methyl 4-bromo-3-methylbenzoate (10 g, 43.65 mmol, 1.00 equiv) in CCl₄ (150 ml), NBS (8.12 g, 45.62 mmol, 1.05 equiv). The resulting solution was heated to reflux overnight under 100 w incandescent bulb. The solids were filtered out. The resulting mixture was concentrated under vacuum. The residue was applied onto a silica gel column with ethyl acetate/petroleum ether (1:30-1:10). This resulted in 6 g (47%) of methyl 4-bromo-3-(bromomethyl)benzoate as a off-white solid.

Step 2

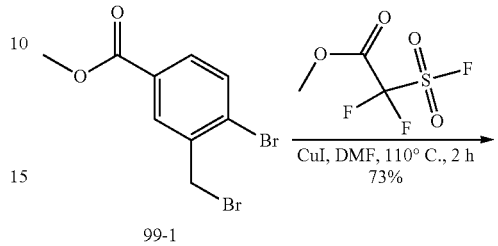

99-1

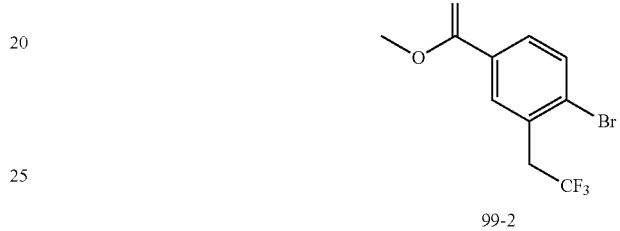

99-2

Methyl 4-bromo-3-(2,2,2-trifluoroethyl)benzoate

Into a 50-mL round-bottom flask purged and maintained with an inert atmosphere of nitrogen, was placed a solution of methyl 4-bromo-3-(bromomethyl)benzoate (2 g, 6.49 mmol, 1.00 equiv) in N,N-dimethylformamide (20 mL), CuI (2.5 g, 13.13 mmol, 2.00 equiv), methyl 2,2-difluoro-2-(fluorosulfonyl)acetate (2.5 g, 13.01 mmol, 2.00 equiv). The resulting solution was stirred for 2 h at 110° C. The reaction was then quenched by the addition of 10 mL of water. The resulting solution was extracted with 2×20 mL of ethyl acetate and the organic layers combined. The resulting mixture was washed with 3×30 mL of water. The resulting mixture was concentrated under vacuum. The residue was applied onto a silica gel column with ethyl acetate/petroleum ether (1:30-1:10). This resulted in 1.4 g (73%) of methyl 4-bromo-3-(2,2,2-trifluoroethyl)benzoate as yellow oil.

Step 3

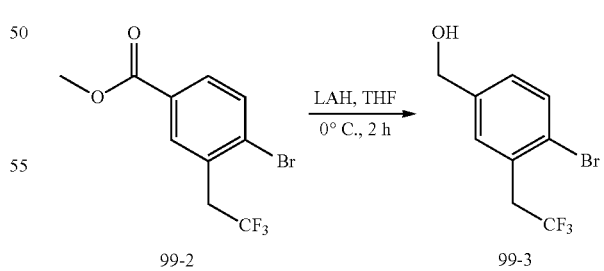

99-2    99-3

[4-bromo-3-(2,2,2-trifluoroethyl)phenyl]methanol

Into a 100-mL round-bottom flask, was placed a solution of methyl 4-bromo-3-(2,2,2-trifluoroethyl)benzoate (900 mg, 3.03 mmol, 1.00 equiv) in tetrahydrofuran (30 mL). This was followed by the addition of LAH (231 mg, 6.09 mmol, 2.00 equiv), in portions at 0° C. The resulting solution was stirred for 2 h at 0° C. The reaction was then quenched by the addition of 5 g of sodium sulfate.10H₂O. The solids were filtered out. The resulting mixture was concentrated under vacuum. This resulted in 800 mg (98%) of [4-bromo-3-(2,2,2-trifluoroethyl)phenyl]methanol as yellow oil.

Step 4

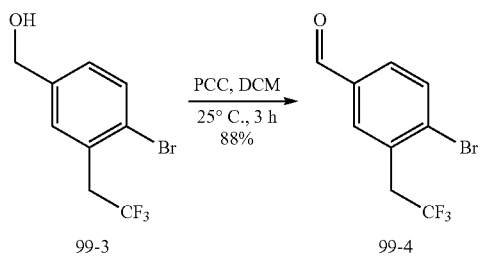 [SMILES: OCc1ccc(Br)c(CC(F)(F)F)c1 ; O=Cc1ccc(Br)c(CC(F)(F)F)c1]

4-bromo-3-(2,2,2-trifluoroethyl)benzaldehyde

Into a 100-mL round-bottom flask, was placed a solution of [4-bromo-3-(2,2,2-trifluoroethyl)phenyl]methanol (800 mg, 2.97 mmol, 1.00 equiv) in dichloromethane (20 mL), PCC (1.3 g, 6.03 mmol, 2.00 equiv). The resulting solution was stirred for 3 h at 25° C. The resulting mixture was concentrated under vacuum. The residue was applied onto a silica gel column with ethyl acetate/petroleum ether (1:30-1:10). This resulted in 700 mg (88%) of 4-bromo-3-(2,2,2-trifluoroethyl)benzaldehyde as yellow oil.

Step 5

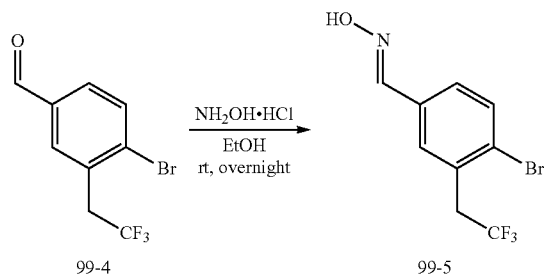

N-[[4-bromo-3-(2,2,2-trifluoroethyl)phenyl]methylidene]hydroxylamine

Into a 100-mL round-bottom flask, was placed a solution of 4-bromo-3-(2,2,2-trifluoroethyl)benzaldehyde (700 mg, 2.62 mmol, 1.00 equiv) in ethanol:H2O (20:5 mL), NH₂OH. hydrogen chloride (235 mg, 3.41 mmol, 1.30 equiv), NaOAc (279 mg, 3.40 mmol, 1.30 equiv). The resulting solution was stirred overnight at room temperature. The reaction was then quenched by the addition of 10 mL of water. The resulting solution was extracted with 3×20 mL of ethyl acetate and the organic layers combined. The resulting mixture was washed with 2×20 mL of brine. The mixture was dried over anhydrous sodium sulfate and concentrated under vacuum. This resulted in 700 mg (crude) of N-[[4-bromo-3-(2,2,2-trifluoroethyl)phenyl]methylidene]hydroxylamine as yellow oil.

Step 6

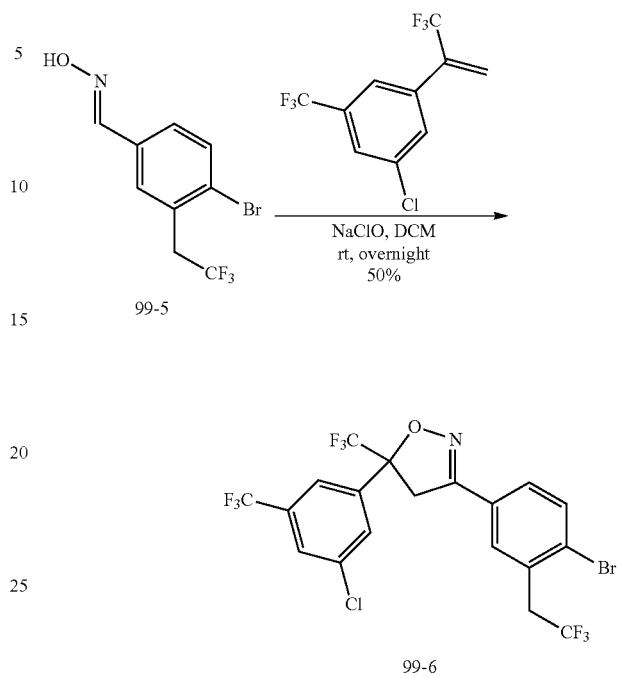

3-[4-bromo-3-(2,2,2-trifluoroethyl)phenyl]-5-[3-chloro-5-(trifluoromethyl)phenyl]-4,5-dihydro-1,2-oxazole Into a 100-mL round-bottom flask, was placed 1-chloro-3-(trifluoromethyl)-5-(3,3,3-trifluoroprop-1-en-2-yl)benzene (680 mg, 2.48 mmol, 1.00 equiv), a solution of N-[[4-bromo-3-(2,2,2-trifluoroethyl)phenyl]methylidene] hydroxylamine (700 mg, 2.48 mmol, 1.10 equiv) in dichloromethane (20 mL), NaClO (10 mL). The resulting solution was stirred overnight at room temperature. The reaction was then quenched by the addition of 10 mL of water. The resulting solution was extracted with 3×20 mL of dichloromethane and the organic layers combined. The resulting mixture was washed with 3×20 mL of brine. The resulting mixture was concentrated under vacuum. The residue was applied onto a silica gel column with ethyl acetate/petroleum ether (1:30-1:10). This resulted in 600 mg (50%) of 3-[4-bromo-3-(2,2,2-trifluoroethyl)phenyl]-5-[3-chloro-5-(trifluoromethyl)phenyl]-4,5-dihydro-1,2-oxazole as yellow oil.

Step 7

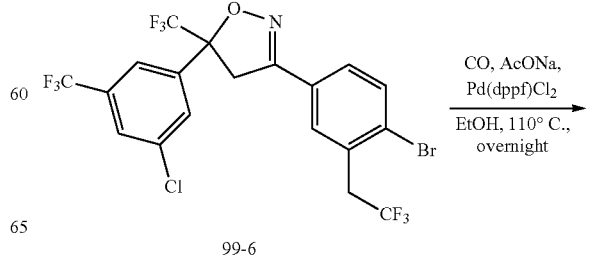

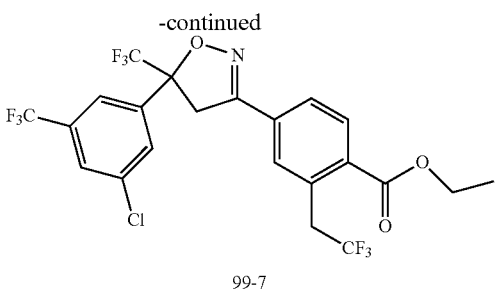

99-7

Ethyl 4-[5-[3-chloro-5-(trifluoromethyl)phenyl]-5-(trifluoromethyl)-4,5-dihydro-1,2-oxazol-3-yl]-2-(2,2,2-trifluoroethyl)benzoate Into a 50-mL pressure tank reactor (10 atm), was placed 3-[4-bromo-3-(2,2,2-trifluoroethyl)phenyl]-5-[3-chloro-5-(trifluoromethyl)phenyl]-5-(trifluoromethyl)-4,5-dihydro-1,2-oxazole (600 mg, 1.08 mmol, 1.00 equiv), ethanol (20 mL), Pd(dppf)Cl$_2$ (158 mg, 0.22 mmol, 0.20 equiv), NaOAc (177 mg, 2.16 mmol, 2.00 equiv), CO (10 atm). The resulting solution was stirred overnight at 110° C. The resulting mixture was concentrated under vacuum. The residue was applied onto a silica gel column with ethyl acetate/petroleum ether (1:30-1:10). This resulted in 300 mg (46%) of ethyl 4-[5-[3-chloro-5-(trifluoromethyl)phenyl]-5-(trifluoromethyl)-4,5-dihydro-1,2-oxazol-3-yl]-2-(2,2,2-trifluoroethyl)benzoate as yellow oil.
Step 8

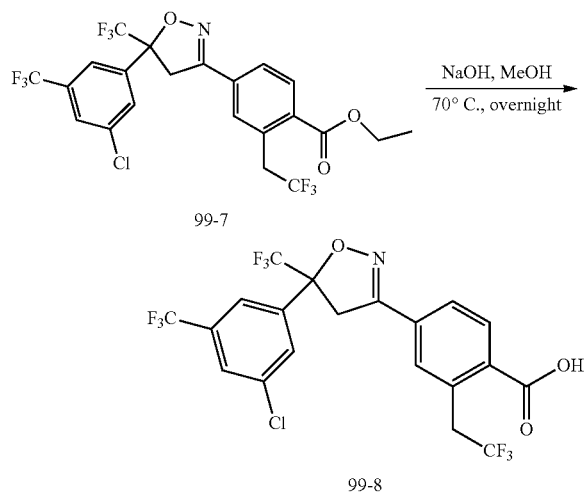

4-[5-[3-chloro-5-(trifluoromethyl)phenyl]-5-(trifluoromethyl)-4,5-dihydro-1,2-oxazol-3-yl]-2-(2,2,2-trifluoroethyl)benzoic acid Into a 50-mL pressure tank reactor (10 atm), was placed ethyl 4-[5-[3-chloro-5-(trifluoromethyl)phenyl]-5-(trifluoromethyl)-4,5-dihydro-1,2-oxazol-3-yl]-2-(2,2,2-trifluoroethyl)benzoate (300 mg, 0.55 mmol, 1.00 equiv), methanol (5 mL), sodium hydroxide (600 mg, 15.00 mmol, 13.69 equiv), water (5 mL). The resulting solution was stirred overnight at 70° C. The pH value of the solution was adjusted to 5 with hydrogen chloride (3 mol/L). The resulting solution was extracted with 3×10 ml of ethyl acetate and the organic layers combined. The resulting mixture was washed with 3×10 mL of brine. The mixture was dried over sodium sulfate and concentrated under vacuum. This resulted in 200 mg (crude) of 4-[5-[3-chloro-5-(trifluoromethyl)phenyl]-5-(trifluoromethyl)-4,5-dihydro-1,2-oxazol-3-yl]-2-(2,2,2-trifluoroethyl)benzoic acid as yellow oil.
Step 9

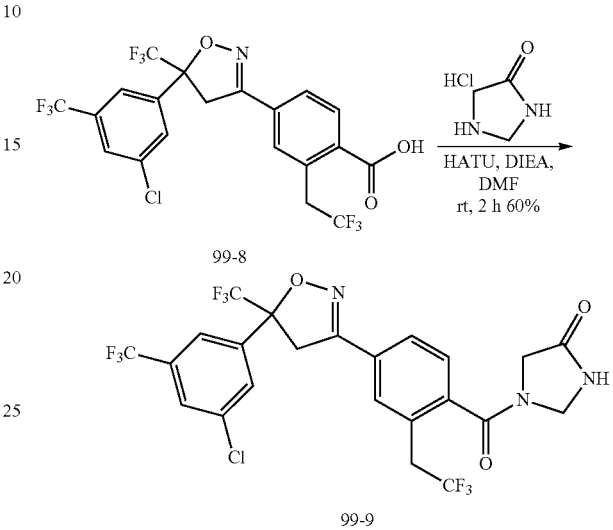

1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]imidazolidin-4-one Into a 25-mL round-bottom flask, was placed 4-[5-[3-chloro-5-(trifluoromethyl)phenyl]-5-(trifluoromethyl)-4,5-dihydro-1,2-oxazol-3-yl]-2-(2,2,2-trifluoroethyl)benzoic acid (200 mg, 0.38 mmol, 1.00 equiv), N,N-dimethylformamide (10 mL), HATU (292 mg, 0.77 mmol, 2.00 equiv), DIEA (99 mg, 0.77 mmol, 1.94 equiv), imidazolidin-4-one hydrochloride (94 mg, 0.77 mmol, 1.98 equiv). The resulting solution was stirred for 2 h at r t. The reaction was then quenched by the addition of 10 mL of water. The resulting solution was extracted with 2×10 mL of ethyl acetate and the organic layers combined. The resulting mixture was washed with 3×20 mL of brine. The resulting mixture was concentrated under vacuum. The residue was applied onto a TLC plate with ethyl acetate/petroleum ether (2:1). This resulted in 150 mg (60%) of 1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]imidazolidin-4-one as yellow oil.
Step 10

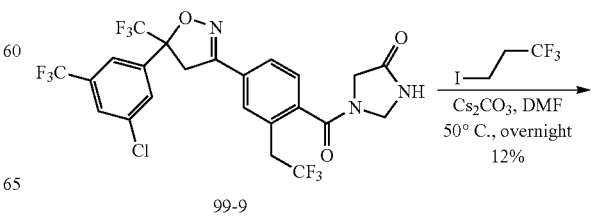

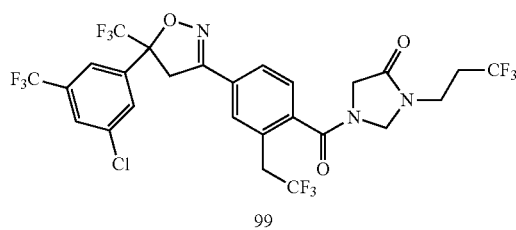

99

1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]-3-(3,3,3-trifluoropropyl)imidazolidin-4-one Into a 25-mL round-bottom flask, was placed 1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]imidazolidin-4-one (150 mg, 0.26 mmol, 1.00 equiv), N,N-dimethylformamide (10 mL), 1,1,1-trifluoro-3-iodopropane (114 mg, 0.51 mmol, 2.01 equiv), Cs2CO3 (166 mg, 0.51 mmol, 1.98 equiv). The resulting solution was stirred overnight at 50° C. The reaction was then quenched by the addition of 10 mL of water. The resulting solution was extracted with 3×10 mL of ethyl acetate and the organic layers combined. The resulting mixture was washed with 3×10 mL of brine. The resulting mixture was concentrated under vacuum. The residue was applied onto a TLCplate with ethyl acetate/petroleum ether (1:1). This resulted in 22.3 mg (12%) of 1-[(4-[5-[3-chloro-5-(trifluoromethyl)phenyl]-5-(trifluoromethyl)-4,5-dihydro-1,2-oxazol-3-yl]-2-(2,2,2-trifluoroethyl)phenyl)carbonyl]-3-(3,3,3-trifluoropropyl)imidazolidin-4-one as a light yellow solid. (ES, m/z): [M+CH$_3$CN]$^-$ 726.0; $^1$H NMR (300 MHz, CDCl$_3$): δ7.86-7.98 (m, 5H), 7.63 (d, J=8.1 Hz, 1H), 5.14 (s, 1H), 4.78 (s, 1H), 4.15-4.42 (m, 3H), 3.57-3.92 (m, 5H), 2.40-2.66 (m, 2H).

Example 16

1-[(4-[5-[3-chloro-5-(trifluoromethyl)phenyl]-5-(trifluoromethyl)-4,5-dihydro-1,2-oxazol-3-yl]naphthalen-1-yl)carbonyl]-3-(3,3,3-trifluoropropyl)imidazolidin-4-one, Compound 112

Compound 112

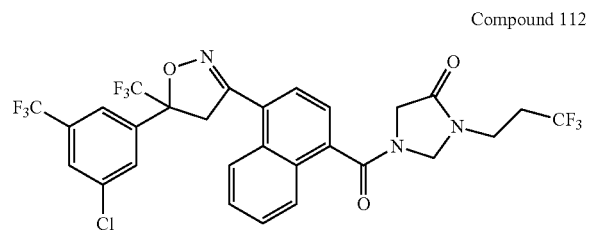 [SMILES: O=C1CN(C(=O)c2ccc(C3=NOC(c4cc(Cl)cc(C(F)(F)F)c4)(C(F)(F)F)C3)c3ccccc23)CN1CCC(F)(F)F]

Compound 112 was prepared using a method as described below and depicted in Scheme 14:

Scheme 14

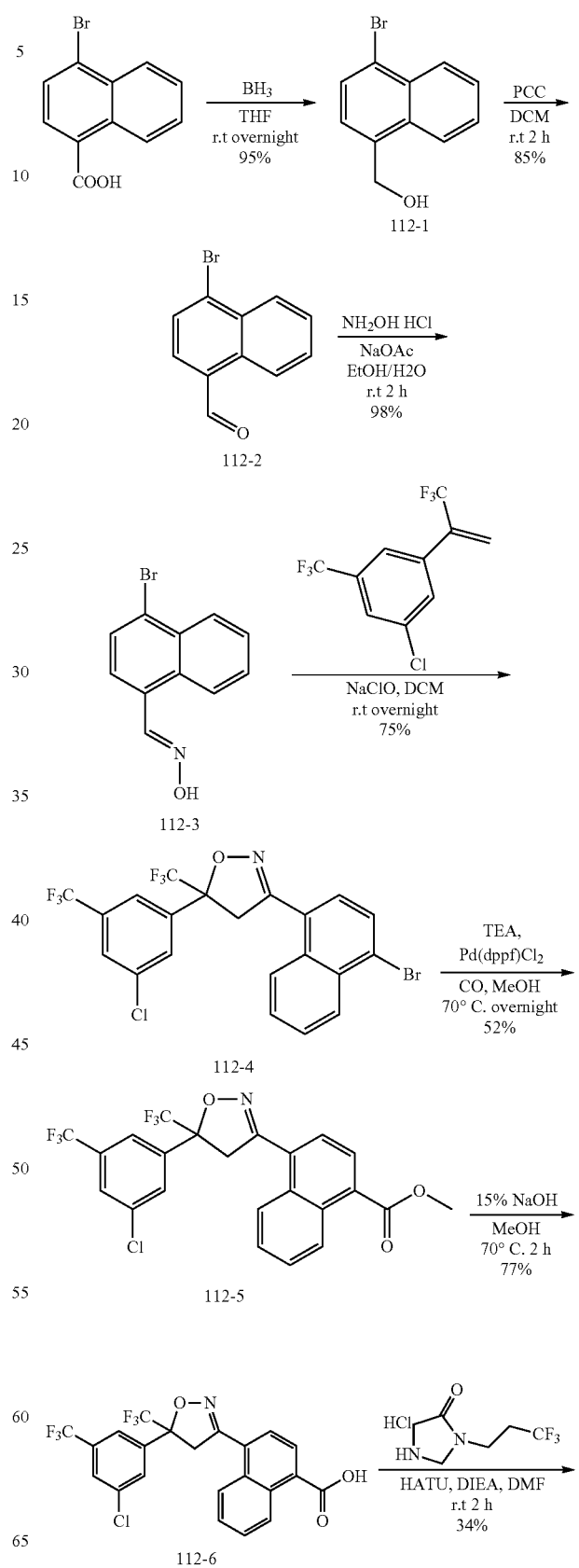

-continued

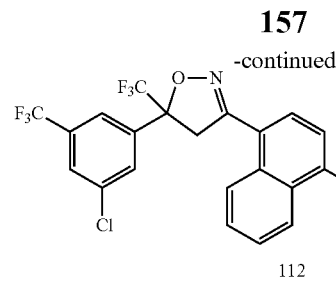

112

Step 1.

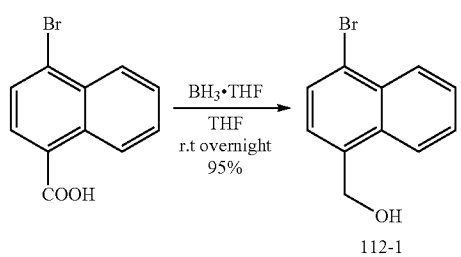 [SMILES: O=C(O)c1ccc(Br)c2ccccc12 ; OCc1ccc(Br)c2ccccc12 ; "BH3·THF"]

(4-bromonaphthalen-1-yl)methanol

Into a 250-mL 3-necked round-bottom flask, was placed tetrahydrofuran (200 mL), 4-bromonaphthalene-1-carboxylic acid (7 g, 27.88 mmol, 1.00 equiv). This was followed by the addition of BH₃.THF (55.7 mL, 2.00 equiv) dropwise with stirring. The resulting solution was stirred overnight at room temperature. The reaction was then quenched by the addition of hydrogen chloride. The pH was adjusted to 6. The resulting solution was diluted with 200 mL of ethyl acetate. The resulting mixture was washed with 3×100 mL of brine. The organic phase was dried over anhydrous sodium sulfate and concentrated under vacuum. The resulting residue was washed with 30 mL of n-hexane. This resulted in 6.3 g (95%) of (4-bromonaphthalen-1-yl)methanol as a white solid.

Step 2.

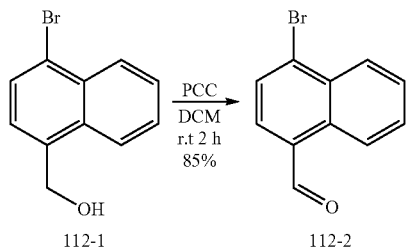

4-bromonaphthalene-1-carbaldehyde

Into a 250-mL round-bottom flask, was placed dichloromethane (150 mL), (4-bromonaphthalen-1-yl)methanol (6.3 g, 26.57 mmol, 1.00 equiv), PCC (11.4 g, 183.72 mmol, 2.00 equiv) and 20 g Silicon dioxide. The resulting solution was stirred for 2 h at room temperature. The resulting mixture was concentrated under vacuum. The residue was applied onto a silica gel column and washed with ethyl acetate/petroleum ether (1/10-1/5). This resulted in 5.3 g (85%) of 4-bromonaphthalene-1-carbaldehyde as a white solid.

Step 3.

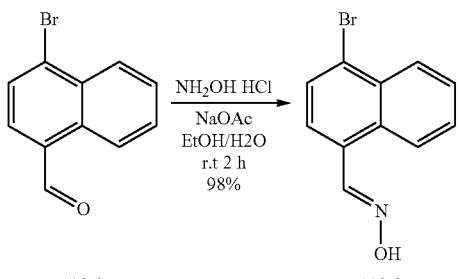

(E)-N-[(4-bromonaphthalen-1-yl)methylidene]hydroxylamine

Into a 250-mL round-bottom flask, was placed ethanol (100 mL), water (40 mL), 4-bromonaphthalene-1-carbaldehyde (4.3 g, 18.29 mmol, 1.00 equiv), hydroxylamine hydrochloride (1.52 g, 21.87 mmol, 1.20 equiv), sodium acetate (2.25 g, 27.43 mmol, 1.50 equiv). The resulting solution was stirred for 2 h at room temperature. The resulting mixture was concentrated under vacuum. The solids were collected by filtration and washed with enough water. The solid was dried in an oven under reduced pressure. This resulted in 4.5 g (98%) of (E)-N-[(4-bromonaphthalen-1-yl)methylidene]hydroxylamine as a white solid.

Step 4.

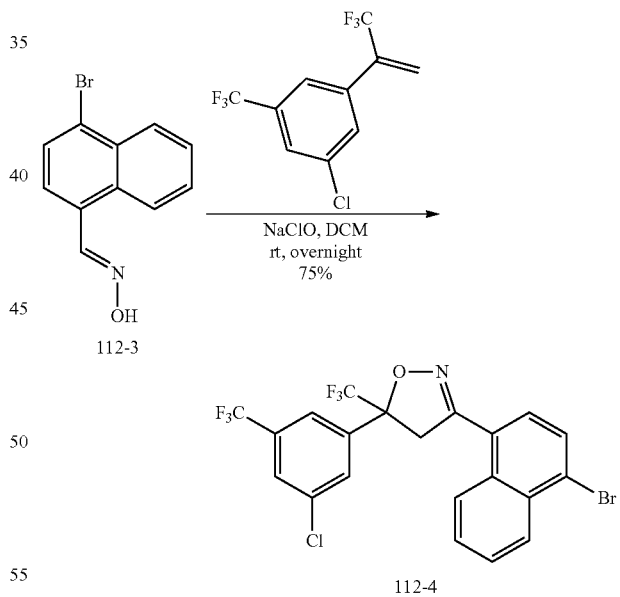

3-(4-bromonaphthalen-1-yl)-5-[3-chloro-5-(trifluoromethyl)phenyl]-5-(trifluoromethyl)-4,5-dihydro-1,2-oxazole Into a 250-mL round-bottom flask purged and maintained with an inert atmosphere of nitrogen, was placed dichloromethane (100 mL), (E)-N-[(4-bromonaphthalen-1-yl)methylidene]hydroxylamine (4.5 g, 17.99 mmol, 1.00 equiv), 1-chloro-3-(trifluoromethyl)-5-(3,3,3-trifluoroprop- 1-en-2-yl)benzene (4.9 g, 17.84 mmol, 1.00 equiv), chlorosylsodium (30 mL). The resulting solution was stirred overnight at room temperature. The aqueous layer was extracted with 3×20 mL of dichloromethane and the organic layers combined and washed with 3×40 mL of brine. The organic phase was dried over anhydrous sodium sulfate and concentrated under vacuum. The residue was applied onto a silica gel column and washed with ethyl acetate/petroleum ether (1/10-1/5). This resulted in 7.1 g (75%) of 3-(4-bromonaphthalen-1-yl)-5-[3-chloro-5-(trifluoromethyl)phenyl]-5-(trifluoromethyl)-4,5-dihydro-1,2-oxazole as a off-white solid.
Step 5.

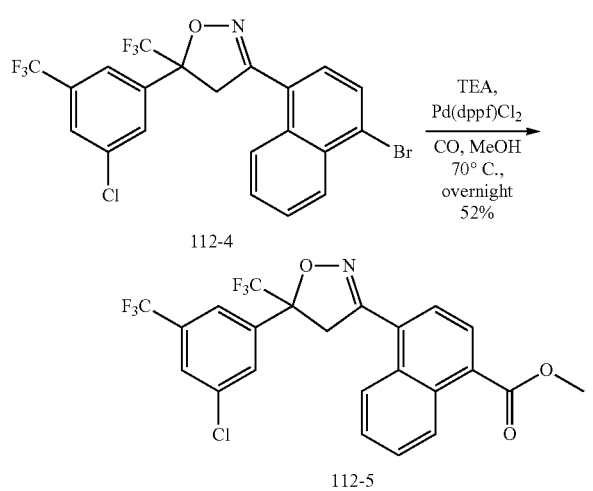

Methyl 4-[5-[3-chloro-5-(trifluoromethyl)phenyl]-5-(trifluoromethyl)-4,5-dihydro-1,2-oxazol-3-yl]naphthalene-1-carboxylate Into a 50-mL pressure tank reactor (10 atm), was placed methanol (10 mL), 3-(4-bromonaphthalen-1-yl)-5-[3-chloro-5-(trifluoromethyl)phenyl]-5-(trifluoromethyl)-4,5-dihydro-1,2-oxazole (400 mg, 0.77 mmol, 1.00 equiv), TEA (232 mg, 2.29 mmol, 30.00 equiv), Pd(dppf)Cl$_2$ (56 mg, 0.08 mmol, 0.10 equiv), CO (10 atm). The resulting solution was stirred overnight at 70° C. in an oil bath. The reaction mixture was cooled. The resulting mixture was concentrated under vacuum. The residue was purified by preparative TLC (EtOAc:PE=1/20). This resulted in 200 mg (52%) of methyl 4-[5-[3-chloro-5-(trifluoromethyl)phenyl]-5-(trifluoromethyl)-4,5-dihydro-1,2-oxazol-3-yl]naphthalene-1-carboxylate as colorless oil.
Step 6.

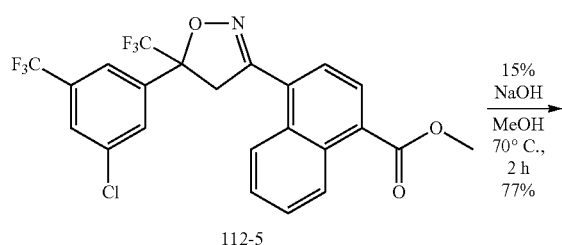

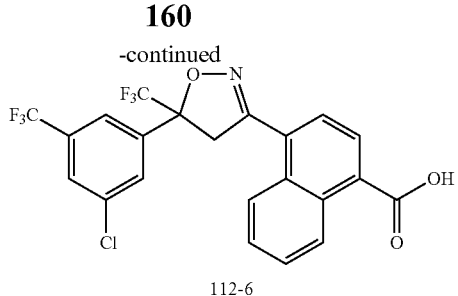

4-[5-[3-chloro-5-(trifluoromethyl)phenyl]-5-(trifluoromethyl)-4,5-dihydro-1,2-oxazol-3-yl]naphthalene-1-carboxylic acid Into a 50-mL round-bottom flask, was placed methanol (20 mL), methyl 4-[5-[3-chloro-5-(trifluoromethyl)phenyl]-5-(trifluoromethyl)-4,5-dihydro-1,2-oxazol-3-yl]naphthalene-1-carboxylate (200 mg, 0.40 mmol, 1.00 equiv), 15% NaOH (5 mL). The resulting solution was stirred for 2 h at 70° C. in an oil bath. The reaction mixture was cooled. The resulting mixture was concentrated under vacuum. The solids were collected by filtration and washed with 10 mL H$_2$O. Then the solid was dried under infrared light. This resulted in 150 mg (77%) of 4-[5-[3-chloro-5-(trifluoromethyl)phenyl]-5-(trifluoromethyl)-4,5-dihydro-1,2-oxazol-3-yl]naphthalene-1-carboxylic acid as a white solid.
Step 7.

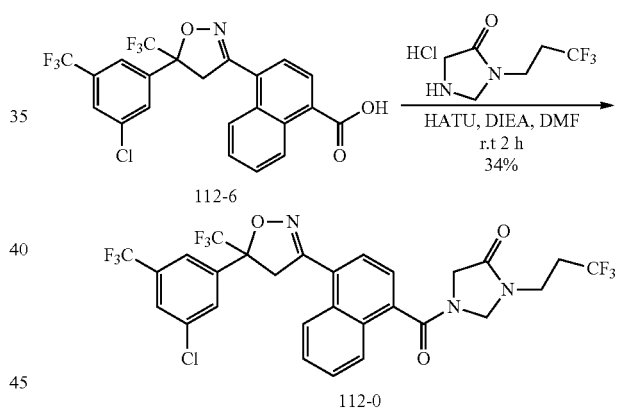

1-[(4-[5-[3-chloro-5-(trifluoromethyl)phenyl]-5-(trifluoromethyl)-4,5-dihydro-1,2-oxazol-3-yl]naphthalen-1-yl)carbonyl]-3-(3,3,3-trifluoropropyl)imidazolidin-4-one Into a 50-mL round-bottom flask purged and maintained with an inert atmosphere of nitrogen, was placed N,N-dimethylformamide (10 mL), 4-[5-[3-chloro-5-(trifluoromethyl)phenyl]-5-(trifluoromethyl)-4,5-dihydro-1,2-oxazol-3-yl]naphthalene-1-carboxylic acid (70 mg, 0.14 mmol, 1.00 equiv), HATU (74 mg, 0.19 mmol, 4.00 equiv), DIEA (218 mg, 1.69 mmol, 4.00 equiv), 3-(3,3,3-trifluoropropyl)imidazolidin-4-one (31 mg, 0.17 mmol, 1.00 equiv). The resulting solution was stirred for 2 h at room temperature. The crude product was purified by Prep-HPLC. This resulted in 32 mg (34%) of 1-[(4-[5-[3-chloro-5-(trifluoromethyl)phenyl]-5-(trifluoromethyl)-4,5-dihydro-1,2-oxazol-3-yl]naphthalen-1-yl)carbonyl]-3-(3,3,3-trifluoropropyl)imidazolidin-4-one as a light brown solid. (ES, m/z): 693 [M+41]$^+$;

(300 MHz, CD₃OD, ppm): δ 8.98-8.95 (m, 1H), 8.04-7.96 (m, 3H), 7.92-7.85 (m, 2H), 7.74-7.65 (m, 3H), 5.26 (s, 1H), 4.88-4.52 (m, 2H), 4.36-4.29 (m, 2H), 3.82 (s, 1H), 3.73 (t, J=6.6 Hz, 1H), 3.50 (t, J=7.5 Hz, 1H), 2.68-2.60 (m, 1H), 2.43-2.37 (m, 1H).

Example 17

1-[(4-[5-[3-Chloro-5-(trifluoromethyl)phenyl]-5-(trifluoromethyl)-4,5-dihydro-1,2-oxazol-3-yl]-2-methylphenyl)carbonyl]-3-(methanesulfonylmethyl)imidazolidin-4-one, Compound 114

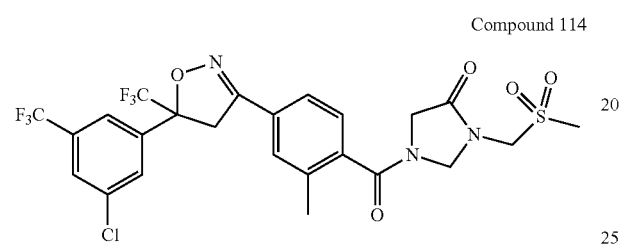

Compound 114

Compound 114 was prepared using a method as described below and depicted in Scheme 15:

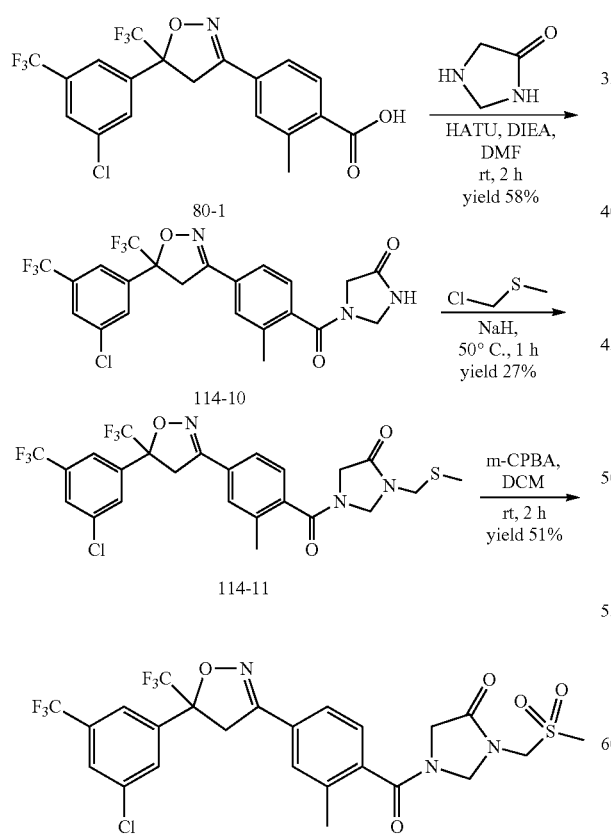

Scheme 15

Step 1.

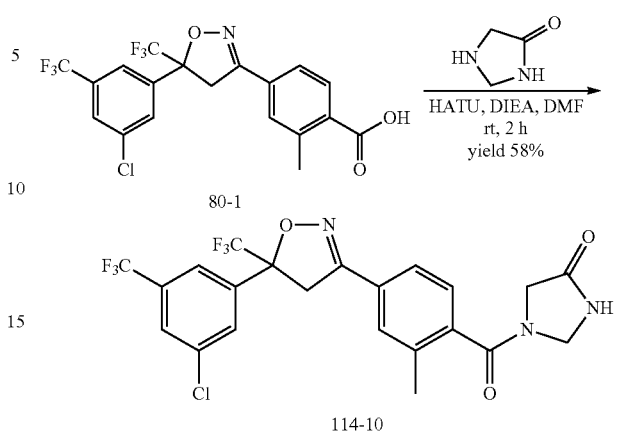

1-[(4-[5-[3-Chloro-5-(trifluoromethyl)phenyl]-5-(trifluoromethyl)-4,5-dihydro-1,2-oxazol-3-yl]-2-methylphenyl)carbonyl]imidazolidin-4-one Into a 100-mL round-bottom flask, was placed 4-[5-[3-chloro-5-(trifluoromethyl)phenyl]-5-(trifluoromethyl)-4,5-dihydro-1,2-oxazol-3-yl]-2-methylbenzoic acid (900 mg, 1.99 mmol, 1.00 equiv), N,N-dimethylformamide (10 mL), HATU (1.1 g, 2.89 mmol, 1.45 equiv), DIEA (770 mg, 5.96 mmol, 2.99 equiv), imidazolidin-4-one hydrochloride (489 mg, 3.99 mmol, 2.00 equiv). The resulting solution was stirred for 2 h at rt. The reaction was then quenched by the addition of 10 mL of water. The resulting solution was extracted with 3×10 mL of ethyl acetate and the organic layers combined. The resulting mixture was washed with 3×20 mL of brine. The resulting organic phase was concentrated under vacuum. The residue was applied onto a silica gel column with ethyl acetate/petroleum ether (1/30-1/10). This resulted in 600 mg (58%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]imidazolidin-4-one as a light yellow solid.

Step 2.

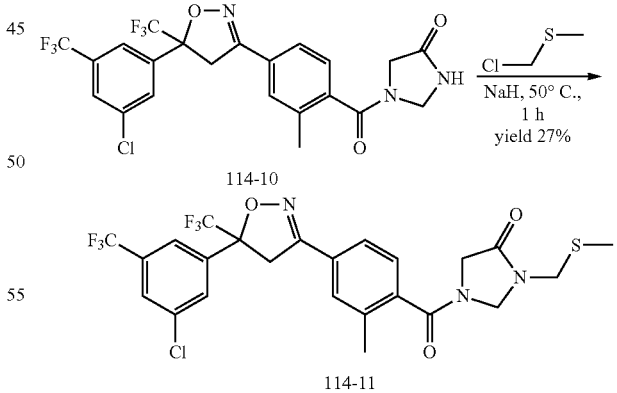

1-[(4-[5-[3-Chloro-5-(trifluoromethyl)phenyl]-5-(trifluoromethyl)-4,5-dihydro-1,2-oxazol-3-yl]-2-methylphenyl)carbonyl]-3-[(methylsulfanyl)methyl]imidazolidin-4-one Into a 100-mL round-bottom flask purged and maintained with an inert atmosphere of nitrogen, was placed 1-[(4-[5-

[3-chloro-5-(trifluoromethyl)phenyl]-5-(trifluoromethyl)-4,5-dihydro-1,2-oxazol-3-yl]-2-methylphenyl)carbonyl]imidazolidin-4-one (200 mg, 0.38 mmol, 1.00 equiv), tetrahydrofuran (10 mL), sodium hydride (30 mg, 0.75 mmol, 2.00 equiv, 60%), chloro(methylsulfanyl)methane (149 mg, 1.54 mmol, 4.00 equiv). The resulting solution was stirred for 1 h at 50° C. The reaction was then quenched by the addition of 10 mL of water. The resulting solution was extracted with 3×10 mL of ethyl acetate and the organic layers combined. The resulting mixture was washed with 3×20 mL of brine. The resulting mixture was concentrated under vacuum. The residue was applied onto a silica gel TLC-plate with ethyl acetate/petroleum ether (1/1). This resulted in 60 mg (27%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]-3-[(methylsulfanyl)methyl]imidazolidin-4-one as yellow oil.
Step 3.

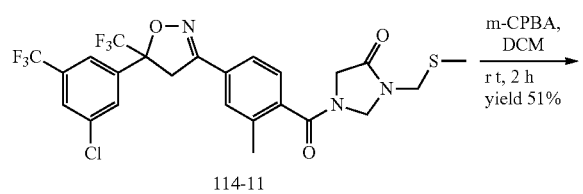

1-[(4-[5-[3-Chloro-5-(trifluoromethyl)phenyl]-5-(trifluoromethyl)-4,5-dihydro-1,2-oxazol-3-yl]-2-methylphenyl)carbonyl]-3-(methanesulfonylmethyl)imidazolidin-4-one Into a 100-mL round-bottom flask purged and maintained with an inert atmosphere of nitrogen, was placed 1-[(4-[5-[3-chloro-5-(trifluoromethyl)phenyl]-5-(trifluoromethyl)-4,5-dihydro-1,2-oxazol-3-yl]-2-methylphenyl)carbonyl]-3-[(methylsulfanyl)methyl]imidazolidin-4-one (50 mg, 0.09 mmol, 1.00 equiv), dichloromethane (2 mL), m-CPBA (44 mg, 0.25 mmol, 2.96 equiv). The resulting solution was stirred for 2 h at rt. The resulting mixture was concentrated under vacuum. The residue was purified by Prep-TLC with ethyl acetate/petroleum ether (1/1). This resulted in 27 mg (51%) of 1-[(4-[5-[3-chloro-5-(trifluoromethyl)phenyl]-5-(trifluoromethyl)-4,5-dihydro-1,2-oxazol-3-yl]-2-methylphenyl)carbonyl]-3-(methanesulfonylmethyl)imidazolidin-4-one as an off-white solid. (ES, m/z): [M+CH$_3$CN+H]$^+$ 653; $^1$H NMR (CD$_3$OD, 300 MHz) δ: 7.96 (s, 1H), 7.87 (d, J=9.3 Hz, 2H), 7.72-7.67 (m, 2H), 7.44-7.40 (m, 1H), 5.30 (s, 1H), 4.87 (s, 2H), 4.71 (s, 1H), 4.39-4.27 (m, 2H), 4.11-3.96 (m, 2H), 3.03 (m, 3H), 2.41 (s, 3H).

Example 18

1-([4-[5-(3,5-dichloro-4-fluorophenyl)-5-(trifluoromethyl)-4,5-dihydro-1,2-oxazol-3-yl]-2-methylphenyl]carbonyl)-3-(3,3,3-trifluoropropyl)imidazolidin-4-one, Compound 115

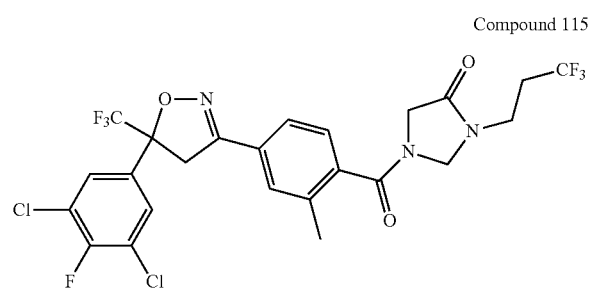 [SMILES: Cc1cc(C2=NOC(c3cc(Cl)c(F)c(Cl)c3)(C(F)(F)F)C2)ccc1C(=O)N1CC(=O)N(CCC(F)(F)F)C1]

Compound 115 was prepared using a method as described below and depicted in Scheme 16:

Scheme 16

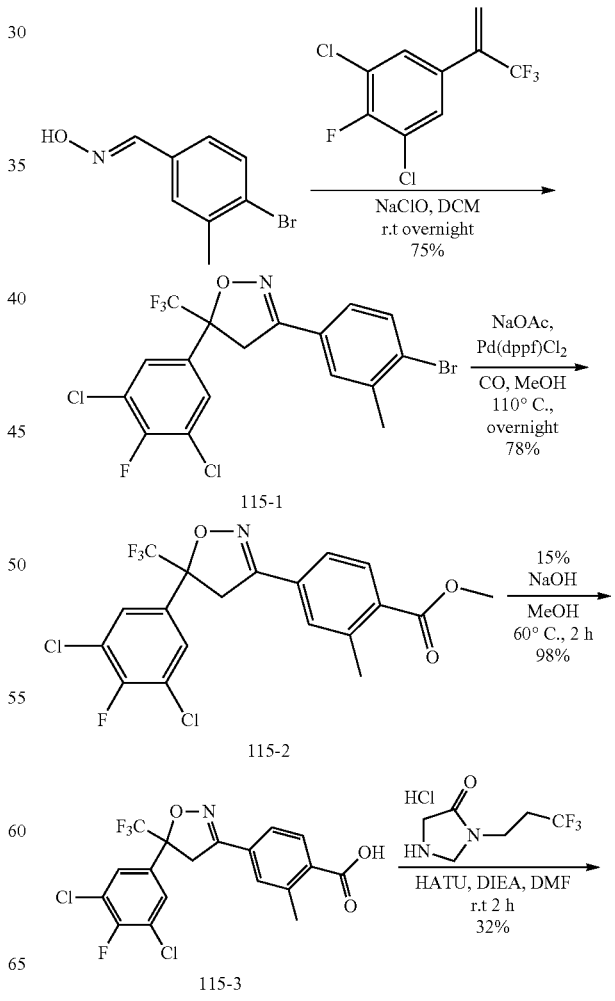

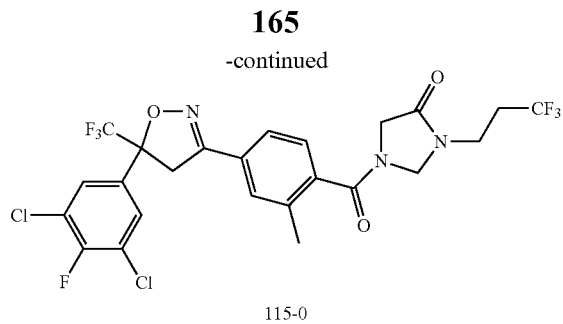

115-0

Step 1.

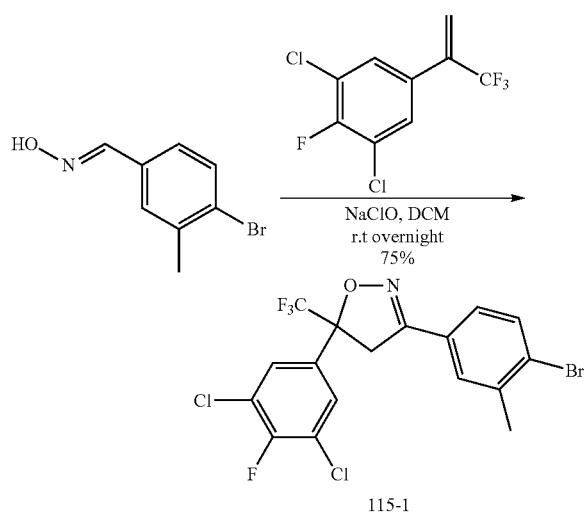

115-1

3-(4-bromo-3-methylphenyl)-5-(3,5-dichloro-4-fluorophenyl)-5-(trifluoromethyl)-4,5-dihydro-1,2-oxazole Into a 50-mL round-bottom flask purged and maintained with an inert atmosphere of nitrogen, was placed dichloromethane (10 mL), (E)-N-[(4-bromo-3-methylphenyl)methylidene]hydroxylamine (50 mg, 0.23 mmol, 1.00 equiv), 1,3-dichloro-2-fluoro-5-(3,3,3-trifluoroprop-1-en-2-yl)benzene (60 mg, 0.23 mmol, 1.00 equiv), chlorosylsodium (5 mL). The resulting solution was stirred overnight at room temperature. The resulting solution was diluted with 50 mL of DCM. The resulting mixture was washed with 3×10 mL of brine. The organic phase was dried over anhydrous sodium sulfate and concentrated under vacuum. This resulted in 82 mg (75%) of 3-(4-bromo-3-methylphenyl)-5-(3,5-dichloro-4-fluorophenyl)-5-(trifluoromethyl)-4,5-dihydro-1,2-oxazole as a white solid.

Step 2.

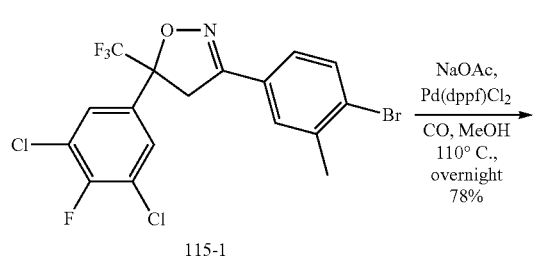

115-1

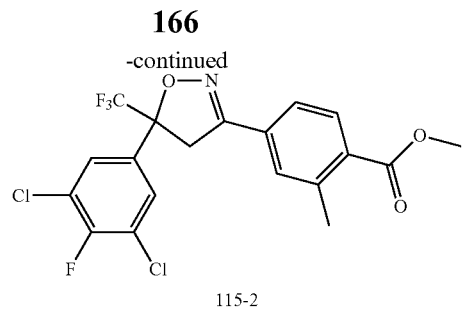

115-2

Methyl 4-[5-(3,5-dichloro-4-fluorophenyl)-5-(trifluoromethyl)-4,5-dihydro-1,2-oxazol-3-yl]-2-methylbenzoate Into a 30-mL pressure tank reactor (20 atm), was placed methanol (10 mL), 3-(4-bromo-3-methylphenyl)-5-(3,5-dichloro-4-fluorophenyl)-5-(trifluoromethyl)-4,5-dihydro-1,2-oxazole (80 mg, 0.17 mmol, 1.00 equiv), sodium acetate (41 mg, 0.50 mmol, 3.00 equiv), Pd(dppf)Cl$_2$ (12 mg, 0.02 mmol, 0.10 equiv), CO (20 atm). The resulting solution was stirred overnight at 110° C. in an oil bath. The reaction mixture was cooled. The residue was purified by Prep-TLC (EtOAc:PE=10:1). This resulted in 60 mg (78%) of methyl 4-[5-(3,5-dichloro-4-fluorophenyl)-5-(trifluoromethyl)-4,5-dihydro-1,2-oxazol-3-yl]-2-methylbenzoate as colorless oil.

Step 3.

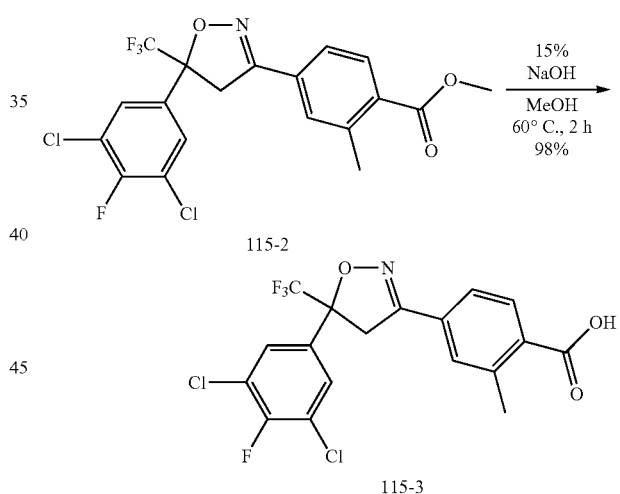

115-2

115-3

4-[5-(3,5-dichloro-4-fluorophenyl)-5-(trifluoromethyl)-4,5-dihydro-1,2-oxazol-3-yl]-2-methylbenzoic acid Into a 50-mL round-bottom flask, was placed methanol (5 mL), methyl 4-[5-(3,5-dichloro-4-fluorophenyl)-5-(trifluoromethyl)-4,5-dihydro-1,2-oxazol-3-yl]-2-methylbenzoate (60 mg, 0.13 mmol, 1.00 equiv), 15% NaOH (2 mL). The resulting solution was stirred for 2 h at 60° C. in an oil bath. The reaction mixture was cooled. The resulting mixture was concentrated under vacuum. The pH value of the solution was adjusted to 3-4 with hydrogen chloride (3 mol/L). The resulting solution was extracted with 3×10 mL of ethyl acetate and the organic layers combined. The resulting mixture was washed with 3×5 mL of Brine. The organic phase was dried over anhydrous sodium sulfate and concentrated under vacuum. This resulted in 57 mg (98%) of 4-[5-(3,5-dichloro-4-fluorophenyl)-5-(trifluoromethyl)-4,5-dihydro-1,2-oxazol-3-yl]-2-methylbenzoic acid as a white solid.

Step 4.

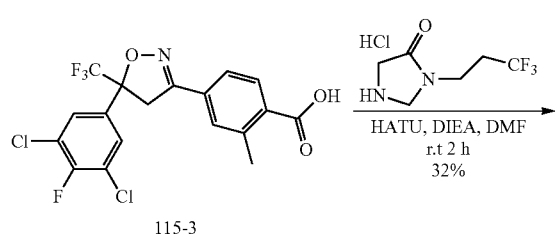

115-3

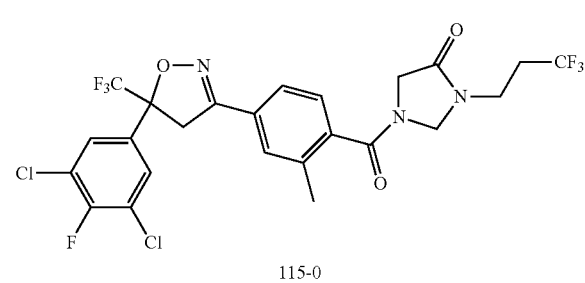

115-0

1-([4-[5-(3,5-dichloro-4-fluorophenyl)-5-(trifluoromethyl)-4,5-dihydro-1,2-oxazol-3-yl]-2-methylphenyl]carbonyl)-3-(3,3,3-trifluoropropyl)imidazolidin-4-one Into a 50-mL round-bottom flask purged and maintained with an inert atmosphere of nitrogen, was placed N,N-dimethylformamide (2 mL), 4-[5-(3,5-dichloro-4-fluorophenyl)-5-(trifluoromethyl)-4,5-dihydro-1,2-oxazol-3-yl]-2-methylbenzoic acid (50 mg, 0.11 mmol, 1.00 equiv), HATU (174 mg, 0.46 mmol, 4.00 equiv), DIEA (60 mg, 0.46 mmol, 4.00 equiv), 3-(3,3,3-trifluoropropyl)imidazolidin-4-one (25 g, 137.25 mmol, 1.00 equiv). The resulting solution was stirred for 2 h at room temperature. The crude product was purified by Prep-HPLC. This resulted in 22.1 mg (32%) of 1-([4-[5-(3,5-dichloro-4-fluorophenyl)-5-(trifluoromethyl)-4,5-dihydro-1,2-oxazol-3-yl]-2-methylphenyl]carbonyl)-3-(3,3,3-trifluoropropyl)imidazolidin-4-one as a white solid. 641 [Ms+CH$_3$CN+H]$^+$; (300 MHz, CD$_3$OD, ppm): δ7.77-7.64 (m, 4H), 7.45-7.28 (m, 1H), 5.12-4.69 (m, 1H), 4.32-4.22 (m, 1H), 4.08-4.01 (m, 1H), 3.87-3.54 (m, 2H), 3.14-2.87 (m, 3H), 2.70-2.31 (m, 4H).

Biological Activity Against Parasites

Example 19

Efficacy of Compounds Against Fleas Following Ingestion

A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocephalides felis* was held at 20-22° C. and 40-60% relative humidity while the well part containing the treated blood was held at 37° C. and 40-60% relative humidity. Assessment was performed at 72 hours after application in comparison with untreated controls. Using this test, compounds 69, 77, 84, 95, 82, 92, 87, 83, 100, 114, 54 and 72 were found to have EC$_{50}$ values of ≤10 parts per million (ppm). Compounds 90, 98, 99, 96, 97, 94, 91, 93, 61, 70, 78, 67 and 68 were found to have EC$_{50}$ values of ≤1 ppm; and compounds 80, 89, 88, 57, 71, 74, 75, 76, 112 and 115 were found to have EC$_{50}$ values of ≤0.1 ppm.

Example 20

Effect of Carbonyl Substituent

It was found that inclusion of at least one carbonyl substituent in the dinitrogen-containing heterocyclic ring of the compounds of formula (I) resulted in a surprising enhancement of efficacy against fleas. In this regard, the efficacy of the compounds of the invention having at least one carbonyl group in Ring D against fleas was compared with the efficacy of corresponding compounds that are not substituted with a carbonyl group in Ring D using the method of Example 19. The table below demonstrates the surprising effect of the substitution on Ring D.

| Compound | EC$_{50}$ (ppm) |
|---|---|
| 80 | <0.1 |

-continued
| Compound | EC$_{50}$ (ppm) |
|---|---|
| 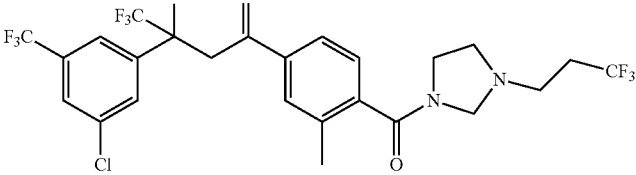<br>100 | 1-10 |
| 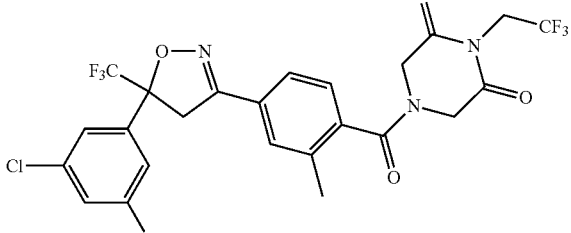<br>9 | <0.1 |
| 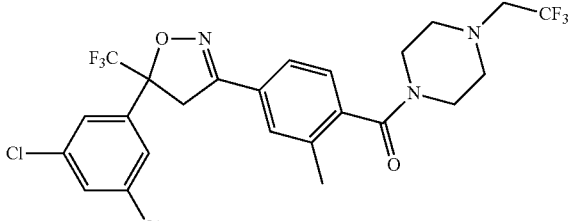<br>102 | 10-20 |
| 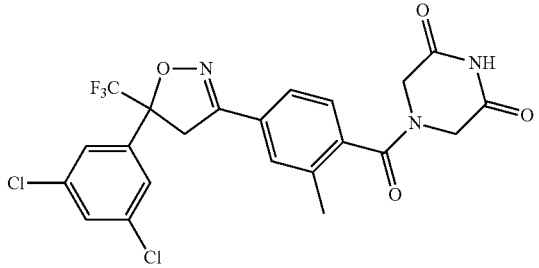<br>09-10 | <0.1 |
| 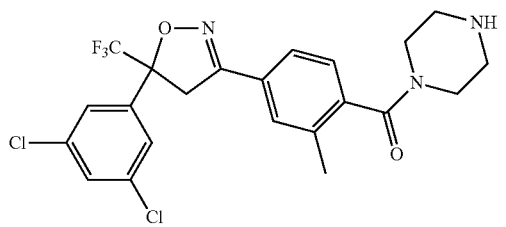<br>18-3 | 1-10 |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:
1. A parasiticidal and pesticidal isoxazoline compound of formula (I):

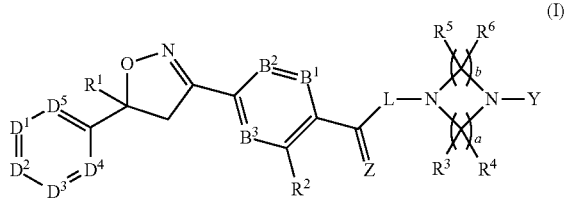

wherein:
- each of $D^1$, $D^2$, $D^3$, $D^4$ and $D^5$ are independently N or C-$A^1$, C-$A^2$, C-$A^3$, C-$A^4$ and C-$A^5$, respectively, with the proviso that at most only three of $D^1$, $D^2$, $D^3$, $D^4$ and $D^5$ may be simultaneously N;
- $R^1$ is halogen, alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of hydroxy, amino, alkyl- or di(alkyl)amino, alkoxy, haloalkoxy, alkylthio or haloalkylthio;
- $A^1$, $A^2$, $A^3$, $A^4$ and $A^5$ are independently hydrogen, halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, —CN or —$NO_2$;
- $B^1$, $B^2$ and $B^3$ are independently N or C—X;
- each X is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl, —CN or —$NO_2$; or two adjacent X together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—,
- $R^2$ is hydrogen, halogen, alkyl, haloalkyl, alkenyl, haloalkenyl, alkynyl, haloalkynyl, hydroxy, alkoxy, amino, alkyl- or dialkylamino, —CN or —$NO_2$;
- $R^3$, $R^4$, $R^5$ and $R^6$ are each independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl; or
- $R^5$ and $R^6$ together with the carbon atom to which they are bonded together form C=W, with the proviso that at least one of $R^5$ and $R^6$ together form the group C=W;
- $R^7$ and $R^8$ are independently hydrogen, alkyl, haloalkyl, alkenyl, haloalkenyl, alkynyl, haloalkynyl, cycloalkyl, aryl, heteroaryl, heterocyclyl, alkyl substituted by thiol, haloalkyl substituted by thiol, alkylthioalkyl, hydroxyalkyl or alkoxyalkyl;
- Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$— or —CN; or Y is Y-1, Y-2, Y-3, Y-4, Y-5, Y-6, Y-7, Y-8, Y-9, Y-10, Y-11, Y-12 or Y-13, wherein # signifies the point of attachment;

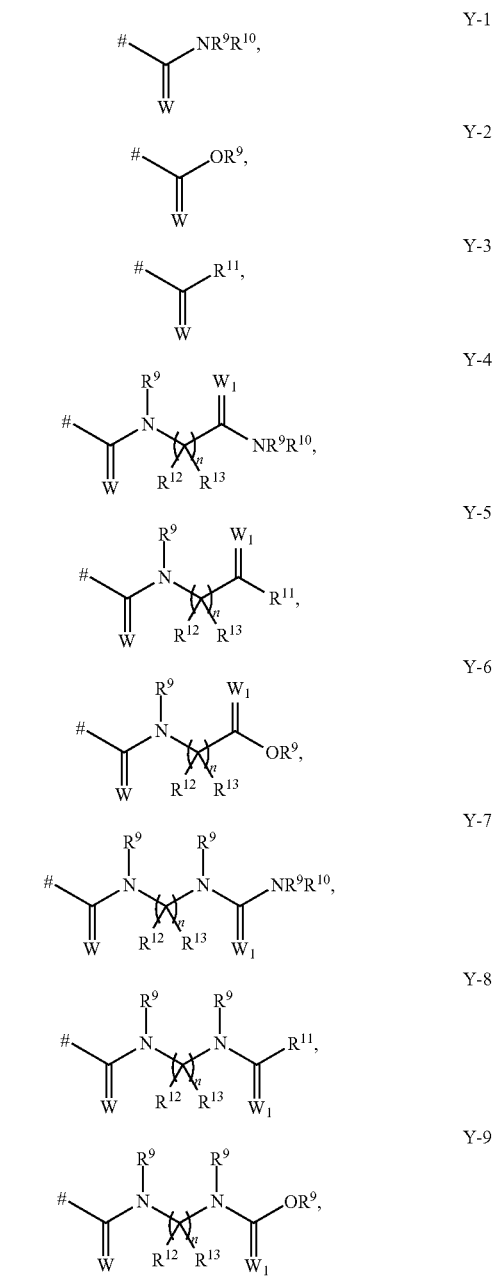

-continued

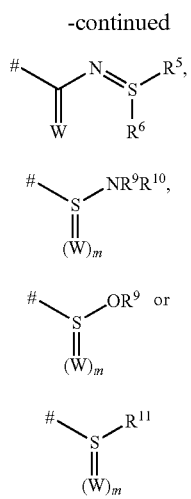

Y-10

Y-11

Y-12

Y-13 wherein each $R^9$, $R^{10}$ are independently hydrogen, alkyl, haloalkyl, alkyl substituted by thiol, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)$—, $R_7S(O)_2$—, $R_7C(O)$—, $R_7R_8NC(O)$—, $R_7OC(O)$—, $R_7C(O)O$—, $R_7C(O)NR_8$—;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl; or $R^{12}$ and $R^{13}$ together with the carbon atom to which they are bonded together form C=W;

W, $W_1$ and Z are independently O, S or $NR^7$;

L is a direct bond, —$CR^3R^4$—, —$NR^8$— or —O—;

a is 1, 2 or 3;

b is 2 or 3;

n is 1, 2, 3 or 4; and m is 0, 1 or 2.

2. The isoxazoline compound of claim 1, wherein $D^1$, $D^2$, $D^3$, $D^4$ and $D^5$ are each respectively $C-A^1$, $C-A^2$, $C-A^3$, $C-A^4$ and $C-A^5$.

3. The isoxazoline compound of claim 1, wherein $B^1$, $B^2$ and $B^3$ are C—H.

4. The isoxazoline compound of claim 1, wherein $B^1$ and $B^2$ are C—X wherein the two Xs together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—.

5. The isoxazoline compound of claim 4, wherein the two Xs together form —CH=CH—CH=CH— to form a naphthalene ring together with the carbon atoms to which they are bonded.

6. The isoxazoline compound of claim 1, wherein $D^1$, $D^2$, $D^3$, $D^4$ and $D^5$ are respectively $C-A^1$, $C-A^2$, $C-A^3$, $C-A^4$ and $C-A^5$; $A^2$, $A^4$ and $A^5$ are hydrogen; and $A^1$ and $A^3$ are independently halogen, alkyl or haloalkyl.

7. The isoxazoline compound of claim 1, wherein the compound has the structure of formula (IA):

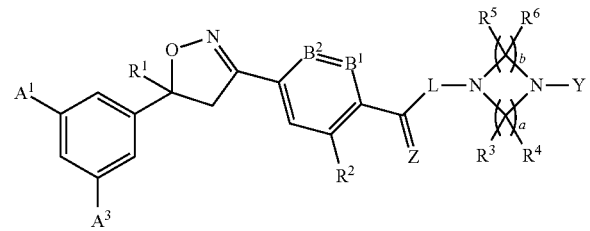

(IA)

wherein:

$R^1$ is halogen, alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of hydroxy, amino, alkyl- or di(alkyl)amino, alkoxy, haloalkoxy, alkylthio or haloalkylthio;

$A^1$ and $A^3$ are independently hydrogen, halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, —CN or —$NO_2$;

$B^1$ and $B^2$ are independently N or C—X;

each X is independently hydrogen, halogen, alkyl or haloalkyl; or two adjacent X together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—;

$R^2$ is hydrogen, halogen, alkyl, haloalkyl, alkenyl, haloalkenyl, alkynyl, haloalkynyl, hydroxy, alkoxy, amino, alkyl- or dialkylamino, —CN or —$NO_2$;

$R^3$, $R^4$, $R^5$ and $R^6$ are each independently hydrogen, halogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl; or $R^5$ and $R^6$ together with the carbon atom to which they are bonded together form C=W, with the proviso that at least one of $R^5$ and $R^6$ together form the group C=W;

$R^7$ and $R^8$ are independently hydrogen, alkyl, haloalkyl, alkenyl, haloalkenyl, alkynyl, haloalkynyl, cycloalkyl, aryl, heteroaryl, heterocyclyl, alkyl substituted by thiol, haloalkyl substituted by thiol, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R₇S(O)—, R₇S(O)₂—, R₇C(O)—, R₇R₈NC(O)—, R₇OC(O)—, R₇C(O)O—, R₇C(O)NR₈—, —CN or —NO₂; or Y is Y-1, Y-2, Y-3, Y-4, Y-5, Y-6, Y-7, Y-8, Y-9, Y-10, Y-11, Y-12 or Y-13, wherein # signifies the point of attachment;

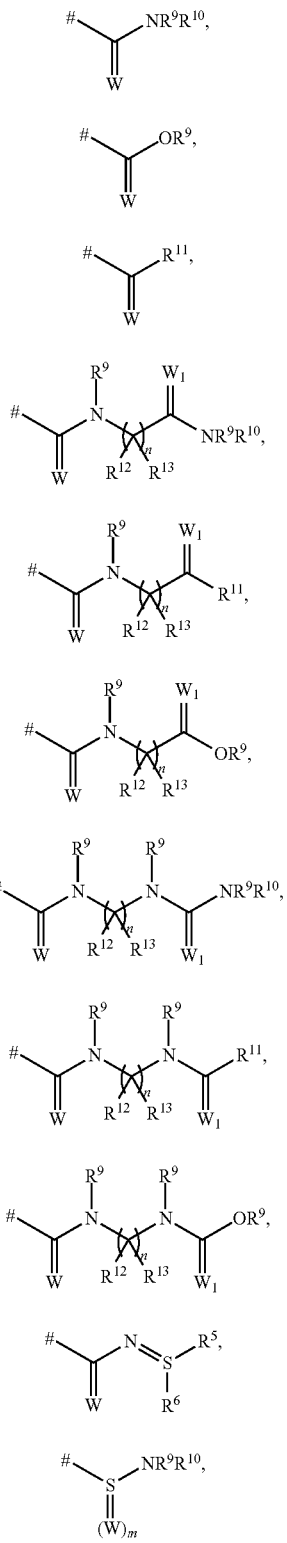

Y-1
Y-2
Y-3
Y-4
Y-5
Y-6
Y-7
Y-8
Y-9
Y-10
Y-11

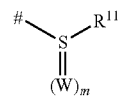

Y-12

Y-13 wherein each $R^9$, $R^{10}$ are independently hydrogen, alkyl, haloalkyl, alkyl substituted by thiol, alkylthioalkyl, hydroxyalkyl, alkoxylakyl, alkenyl, haloalkenyl, alkynyl, haloalkynyl, cycloalkyl, aryl, heteroaryl, heterocyclyl, R₇S(O)—, R₇S(O)₂—, R₇C(O)—, R₇R₈NC(O)—, R₇OC(O)—, R₇C(O)O—, R₇C(O)NR₈—;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl; or $R^{12}$ and $R^{13}$ together with the carbon atom to which they are bonded together form C=W;

W, W₁ and Z are independently O, S or NR';
L is a direct bond, —CR³R⁴—, —NR⁸— or —O—;
a is 1, 2 or 3;
b is 2 or 3;
n is 1, 2, 3 or 4; and
m is 0, 1 or 2.

8. An isoxazoline compound of formula (IB):

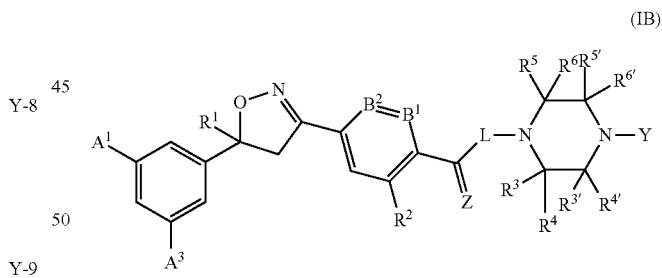

(IB)

wherein:
R₁ is alkyl, haloalkyl, alkenyl, haloalkenyl, alkynyl, haloalkynyl;
A¹ and A³ are independently hydrogen, halogen, alkyl, haloalkyl, alkenyl, haloalkenyl, alkynyl or haloalkynyl;
B¹ and B² are independently N or C—X;
each X is independently hydrogen, halogen, alkyl or haloalkyl; or two adjacent X together form a 5- or 6-membered ring together with the carbon atoms to which they are bonded by forming —CH₂CH₂CH₂—, —CH=CH—CH=CH—, —CH₂CH₂O— —CH₂OCH₂—, —OCH₂O—, —CH₂CH₂S—, —CH₂SCH₂—, —SCH₂S—, —CH₂CH₂CH₂—, —CH₂CH₂CH₂O—, —CH₂CH₂OCH₂—, —CH$_2$OCH$_2$O—, —OCH$_2$CH$_2$O—, —OCH$_2$CH$_2$S—, —SCH$_2$CH$_2$S—, —OCH=N— or —SCH=N—;

R$^2$ is hydrogen, halogen, alkyl, haloalkyl, alkenyl, haloalkenyl, alkynyl or haloalkynyl;

R$^3$, R$^4$, R$^{3'}$, R$^{4'}$, R$^5$, R$^6$, R$^{5'}$ and R$^{6'}$ are each independently hydrogen, halogen, alkyl, haloalkyl, alkenyl, haloalkenyl, alkynyl or haloalkynyl; or R$^3$ and R$^4$ and/or R$^{3'}$ and R$^{4'}$ together with the carbon atom to which they are bonded together form C=W; and/or R$^5$ and R$^6$ and/or R$^{5'}$ and R$^{6'}$ together with the carbon atom to which they are bonded together form C=W, with the proviso that at least one of R$^3$ and R$^4$, R$^{3'}$ and R$^{4'}$, R$^5$ and R$^6$, or R$^{5'}$ and R$^{6'}$, together with the carbon atom to which they are attached form the group C=W;

R$^7$ and R$^8$ are independently hydrogen, alkyl, haloalkyl, alkenyl, haloalkenyl, alkynyl, haloalkynyl, cycloalkyl, aryl, heteroaryl, heterocyclyl, alkyl substituted by thiol, haloalkyl substituted by thiol, alkylthioalkyl, hydroxyalkyl or alkoxyalkyl;

Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

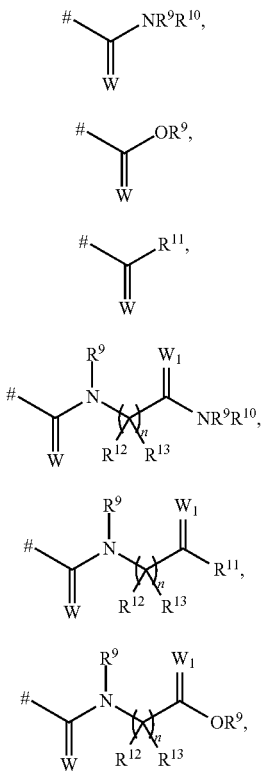

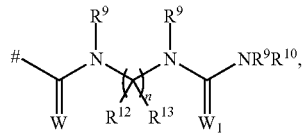
Y-7

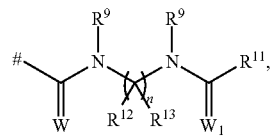
Y-8

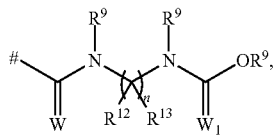
Y-9

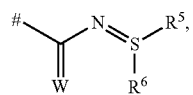
Y-10

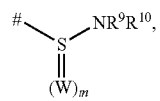
Y-11

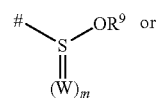
Y-12

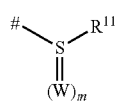
Y-13 wherein each R$^9$, R$^{10}$ are independently hydrogen, alkyl, haloalkyl, alkyl substituted by thiol, alkylthioalkyl, hydroxyalkyl, alkoxylakyl, alkenyl, haloalkenyl, alkynyl, haloalkynyl, cycloalkyl, aryl, heteroaryl, heterocyclyl, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—;

each R$^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl;

each R$^{12}$ and R$^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl alkyl substituted by thiol or alkylthioalkyl; or R$^{12}$ and R$^{13}$ together with the carbon atom to which they are bonded together form C=W;

W, W$_1$ and Z are independently O, S or NR$^7$;

L is a direct bond, —CR$^3$R$^4$—, —NR$^8$— or —O—;

n is 1, 2, 3 or 4; and m is 0, 1 or 2.

9. The isoxazoline compound of claim 1, wherein the compound has the structure of formula (IC)

wherein:
R$_1$ is alkyl, haloalkyl, alkenyl, haloalkenyl, alkynyl, haloalkynyl;
A$^1$ and A$^3$ are independently hydrogen, halogen, alkyl, haloalkyl, alkenyl, haloalkenyl, alkynyl or haloalkynyl;
B$^1$ and B$^2$ are independently N or C—X;
each X is independently hydrogen, halogen, alkyl or haloalkyl; or two adjacent X together form a 5- or 6-membered ring together with the carbon atoms to which they are bonded by forming —CH$_2$CH$_2$CH$_2$—, —CH=CH—CH=CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—;
R$^2$ is hydrogen, halogen, alkyl, haloalkyl, alkenyl, haloalkenyl, alkynyl or haloalkynyl;
R$^3$, R$^4$, R$^5$, R$^6$, R$^{5'}$ and R$^{6'}$ are each independently hydrogen, halogen, alkyl, haloalkyl, alkenyl, haloalkenyl, alkynyl or haloalkynyl;
R$^5$ and R$^6$ together with the carbon atom to which they are bonded together form C=W; and/or
R$^{5'}$ and R$^{6'}$ together with the carbon atom to which they are bonded together form C=W, with the proviso that at least one of R$^5$ and R$^6$ or R$^{5'}$ and R$^{6'}$, together with the carbon atom to which they are attached form the group C=W;
R$^7$ and R$^8$ are independently hydrogen, alkyl, haloalkyl, alkenyl, haloalkenyl, alkynyl, haloalkynyl, cycloalkyl, aryl, heteroaryl, heterocyclyl, alkyl substituted by thiol, haloalkyl substituted by thiol, alkylthioalkyl, hydroxyalkyl or alkoxyalkyl;
Y is hydrogen, alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

Y-1

Y-2

Y-3

Y-4

Y-5

Y-6

Y-7

Y-8

Y-9

Y-10

Y-11

Y-12

Y-13 wherein each R$^9$, R$^{10}$ are independently hydrogen, alkyl, haloalkyl, alkyl substituted by thiol, alkylthioalkyl, hydroxyalkyl, alkoxylakyl, alkenyl, haloalkenyl, alkynyl, haloalkynyl, cycloalkyl, aryl, heteroaryl, heterocyclyl, $R_7S(O)$—, $R_7S(O)_2$—, $R_7C(O)$—, $R_7R_8NC(O)$—, $R_7OC(O)$—, $R_7C(O)O$—, $R_7C(O)NR_8$—;

each $R^{11}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl, alkyl substituted by thiol or alkylthioalkyl;

each $R^{12}$ and $R^{13}$ is independently hydrogen, alkyl, haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl alkyl substituted by thiol or alkylthioalkyl; or $R^{12}$ and $R^{13}$ together with the carbon atom to which they are bonded together form C=W;

W, $W_1$ and Z are independently O, S or $NR^7$;

L is a direct bond, —$CR^3R^4$—, —$NR^8$— or —O—;

n is 1, 2, 3 or 4; and m is 0, 1 or 2.

10. An isoxazoline compound of formula (ID):

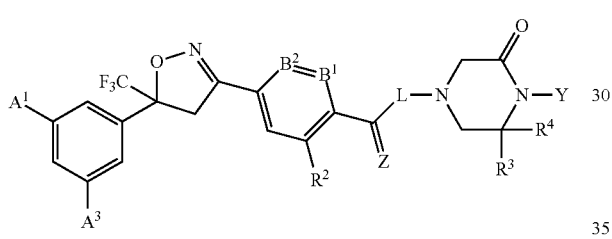

(ID)

wherein:

$A^1$ and $A^3$ are independently halogen or $C_1$-$C_4$haloalkyl;

$B^1$ and $B^2$ are independently N or C—X;

each X is independently hydrogen, halogen, alkyl or haloalkyl; or two adjacent X together form a 5- or 6-membered ring together with the carbon atoms to which they are bonded by forming —$CH_2CH_2CH_2$—, —CH=CH—CH=CH—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N— or —SCH=N—;

$R^2$ is $C_1$-$C_4$alkyl or $C_1$-$C_4$ haloalkyl;

$R^3$ and $R^4$ are independently hydrogen, $C_1$-$C_4$alkyl, $C_1$-$C_4$haloalkyl or halogen; or $R^3$ and $R^4$ together with the carbon atom to which they are bonded for the group C=O;

Y is hydrogen, $C_1$-$C_4$alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13, wherein # signifies the point of attachment;

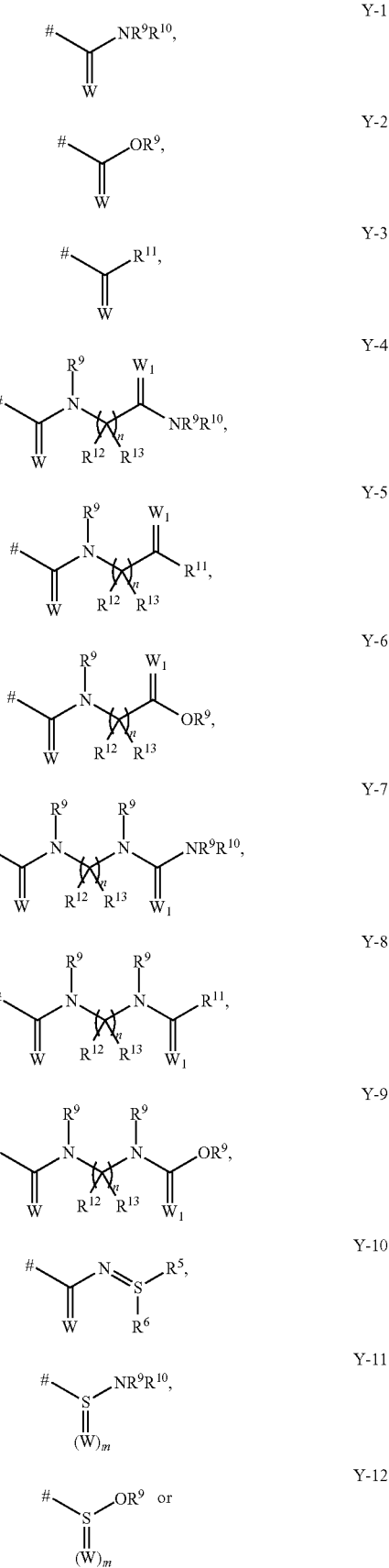

-continued

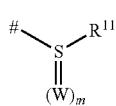
Y-13 wherein $R^7$ and $R^8$ are independently hydrogen, alkyl, haloalkyl, alkenyl, haloalkenyl, alkynyl, haloalkynyl, cycloalkyl, aryl, heteroaryl, heterocyclyl alkyl substituted by thiol, haloalkyl substituted by thiol, alkylthioalkyl, hydroxyalkyl or alkoxyalkyl;

$R^9$ and $R^{10}$ are independently hydrogen, $C_1$-$C_4$ alkyl, $C_1$-$C_4$haloalkyl, thio-$C_1$-$C_4$-alkyl or $C_1$-$C_4$alkylthio-$C_1$-$C_4$-alkyl;

each $R^{11}$ is independently hydrogen, $C_1$-$C_4$alkyl or $C_1$-$C_4$haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl alkyl substituted by thiol or alkylthioalkyl;

each $R^{12}$ and $R^{13}$ is independently hydrogen or $C_1$-$C_4$alkyl;

W and $W_1$ are O;

L is a direct bond, —$CR^3R^4$—, —$NR^8$— or —O—;

n is 1, 2, 3 or 4; and m is 0, 1 or 2.

11. An isoxazoline compound of formula (IE):

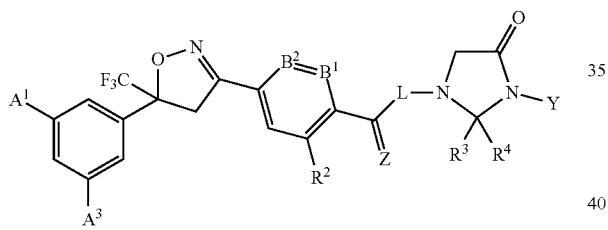
(IE)

wherein:

$A^1$ and $A^3$ are independently halogen or $C_1$-$C_4$haloalkyl;

$B^1$ and $B^2$ are independently N or C—X;

each X is independently hydrogen, halogen, alkyl or haloalkyl; or two adjacent X together form a 5- or 6-membered ring together with the carbon atoms to which they are bonded by forming —CH$_2$CH$_2$CH$_2$—, —CH═CH—CH═CH—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH═N— or —SCH═N—;

$R^2$ is hydrogen, $C_1$-$C_4$alkyl or $C_1$-$C_4$ haloalkyl;

$R^3$ and $R^4$ are independently hydrogen, $C_1$-$C_4$alkyl, $C_1$-$C_4$haloalkyl or halogen; or $R^3$ and $R^4$ together with the carbon atom to which they are bonded for the group C═O;

Y is hydrogen, $C_1$-$C_4$alkyl, haloalkyl, alkenyl, haloalkenyl, alkynyl, haloalkynyl, cycloalkyl, alkylcycloalkyl, cycloalkylalkyl, aryl, heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13, wherein # signifies the point of attachment;

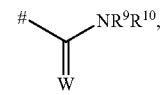
Y-1

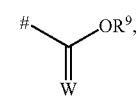
Y-2

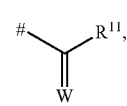
Y-3

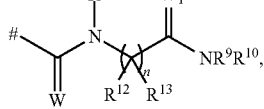
Y-4

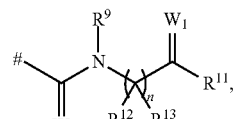
Y-5

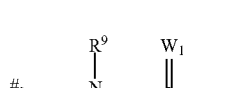
Y-6

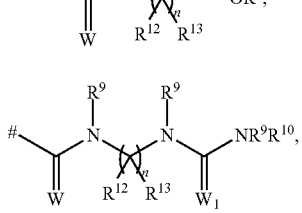
Y-7

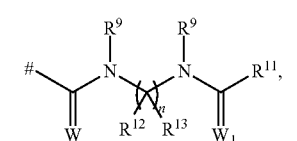
Y-8

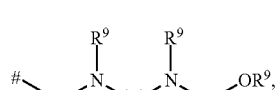
Y-9

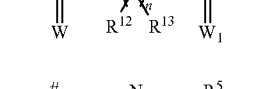
Y-10

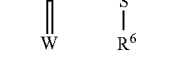
Y-11

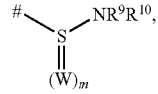

-continued

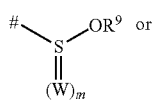
Y-12

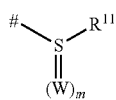
Y-13 wherein $R^7$ and $R^8$ are independently hydrogen, alkyl, haloalkyl, alkenyl, haloalkenyl, alkynyl, haloalkynyl, cycloalkyl, aryl, heteroaryl, heterocyclyl alkyl substituted by thiol, haloalkyl substituted by thiol, alkylthioalkyl, hydroxyalkyl or alkoxyalkyl;

$R^9$ and $R^{10}$ are independently hydrogen, $C_1$-$C_4$ alkyl, $C_1$-$C_4$haloalkyl, thio-$C_1$-$C_4$-alkyl or $C_1$-$C_4$alkylthio-$C_1$-$C_4$-alkyl;

each $R^{11}$ is independently hydrogen, $C_1$-$C_4$alkyl or $C_1$-$C_4$haloalkyl, alkenyl, haloalkenyl, alkynyl, haloalkynyl, alkoxy, haloalkoxy, alkylthio, haloalkylthio, amino, alkylamino, haloalkylamino, dialkylamino, dihaloalkylamino, hydroxyalkyl, alkoxyalkyl alkyl substituted by thiol or alkylthioalkyl;

each $R^{12}$ and $R^{13}$ is independently hydrogen or $C_1$-$C_4$alkyl;

W and $W_1$ are O;

L is a direct bond, —$CR^3R^4$—, —$NR^8$— or —O—;

n is 1, 2, 3 or 4; and m is 0, 1 or 2.

12. The isoxazoline compound of claim 11, wherein $B^1$ and $B^2$ are C—H.

13. The isoxazoline compound of claim 11, wherein $B^1$ and $B^2$ are C—X where each X together form —CH=CH—CH=CH— thereby forming a naphthalene ring together with the carbon atoms to which they are attached.

14. A composition for the treatment or prevention of a parasitic infection or infestation in an animal comprising an effective amount of an isoxazoline compound of formula (I) of claim 1 in combination with a pharmaceutically acceptable carrier.

15. A composition for the protection of crops, plants, plant propagation material or material made from wood from pests comprising a pesticidally effective amount of an isoxazoline compound of formula (I) of claim 1 in combination with an agriculturally acceptable carrier or diluent.

16. A method for the treatment or prevention of a parasitic infection or infestation in an animal, comprising administering to the animal a parasiticidally effective amount of an isoxazoline compound of formula (I) of claim 1 to the animal.

17. A method for protecting crops and growing plants from attack or infestation by insect pests, comprising contacting a plant, or soil or water in which the plant is growing, with an isoxazoline compound of formula (I) of claim 1.

18. An isoxazoline compound wherein the compound has the structure

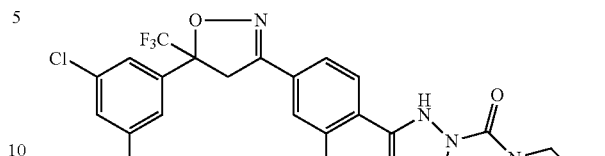

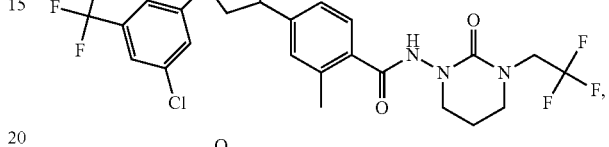

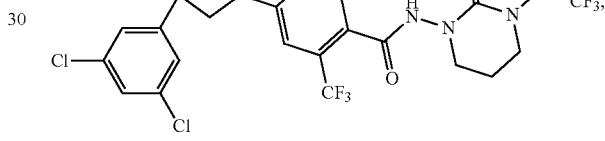

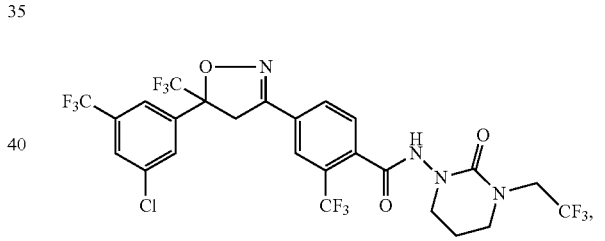

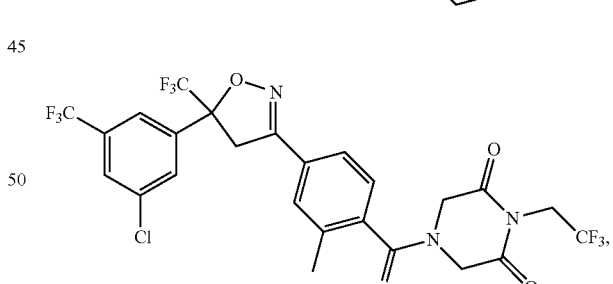

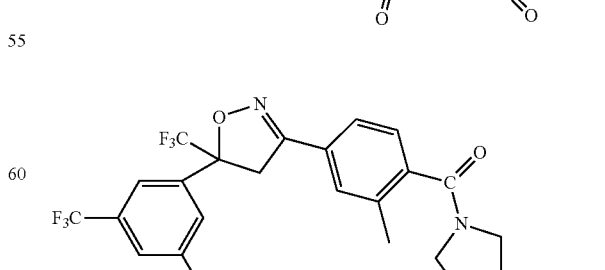

187
-continued
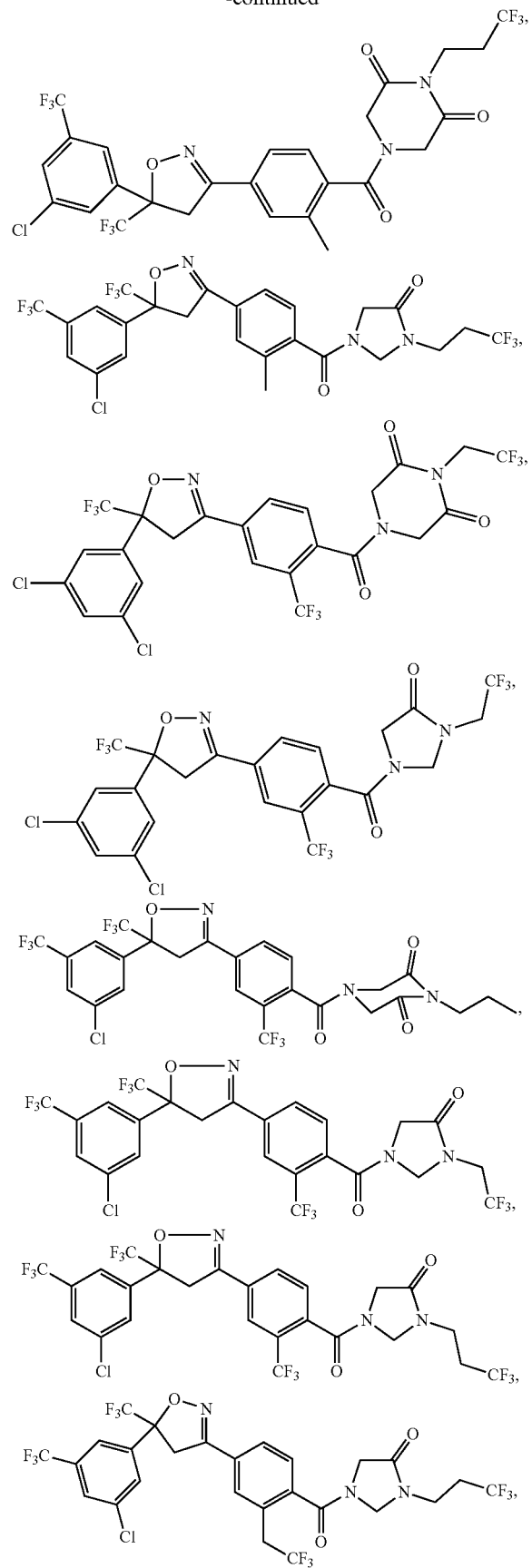
188
-continued
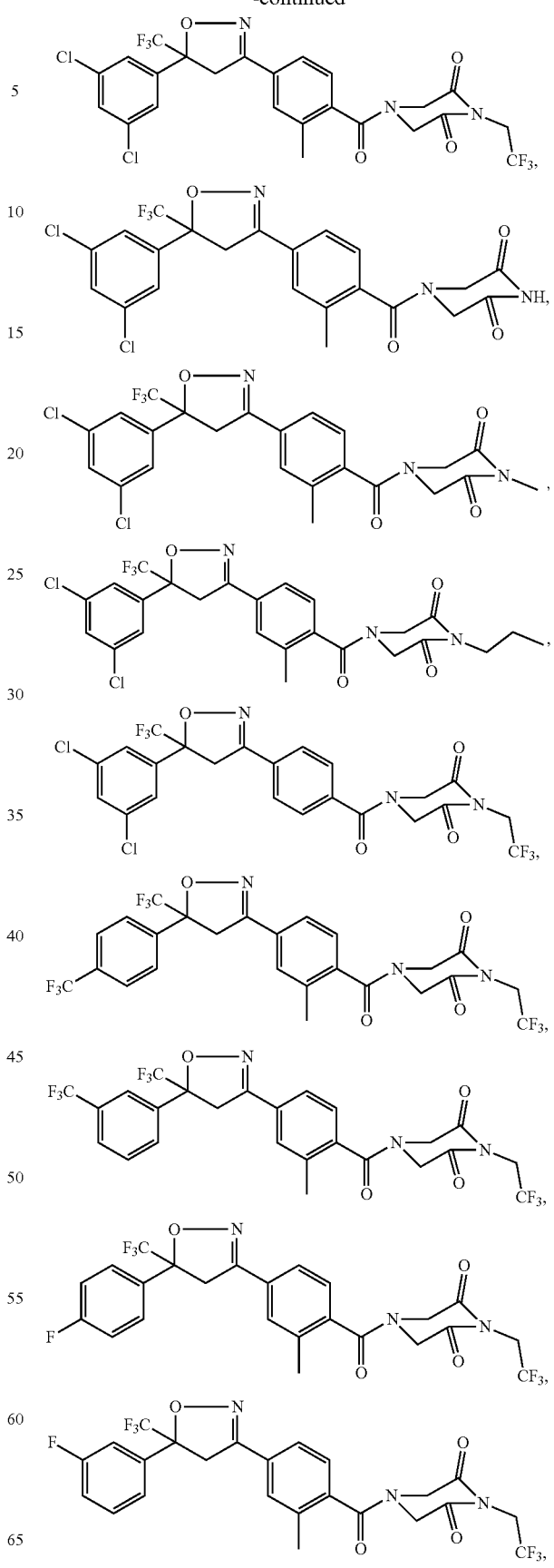

189
-continued
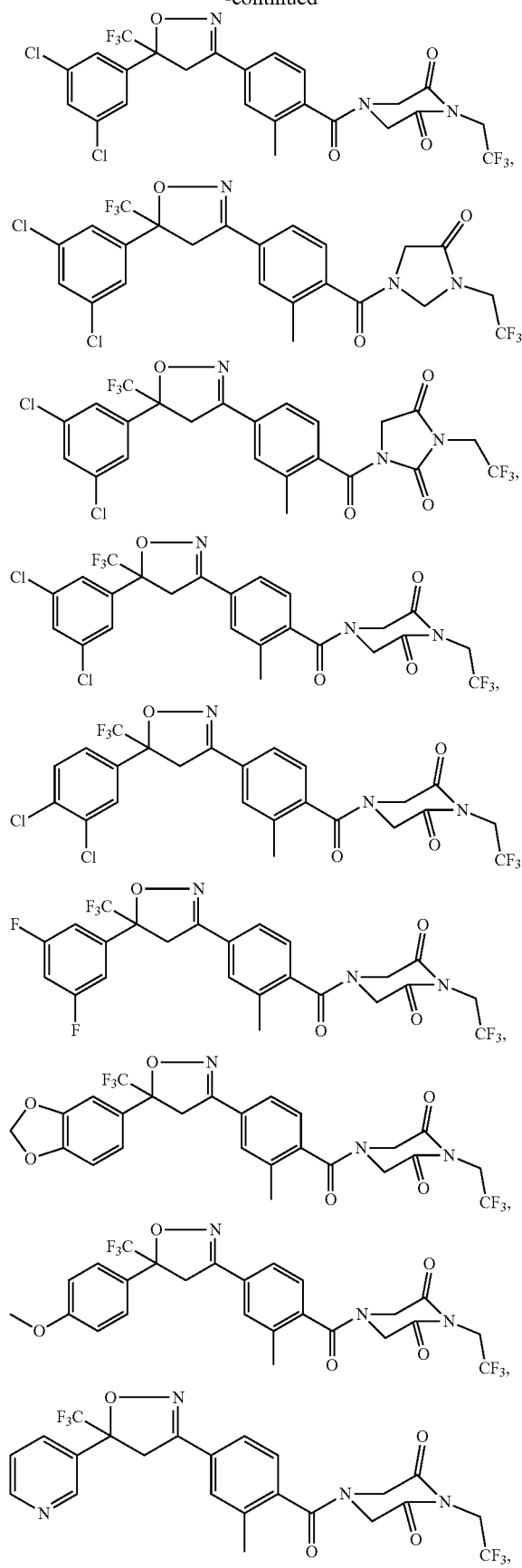
190
-continued
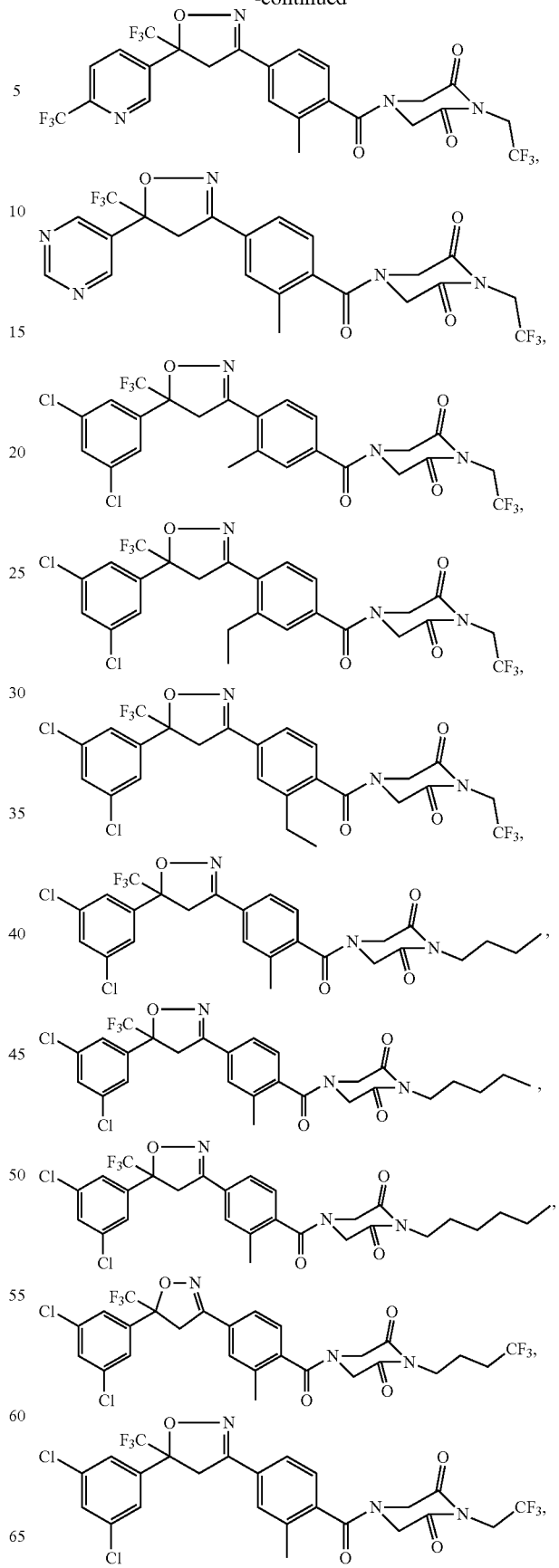

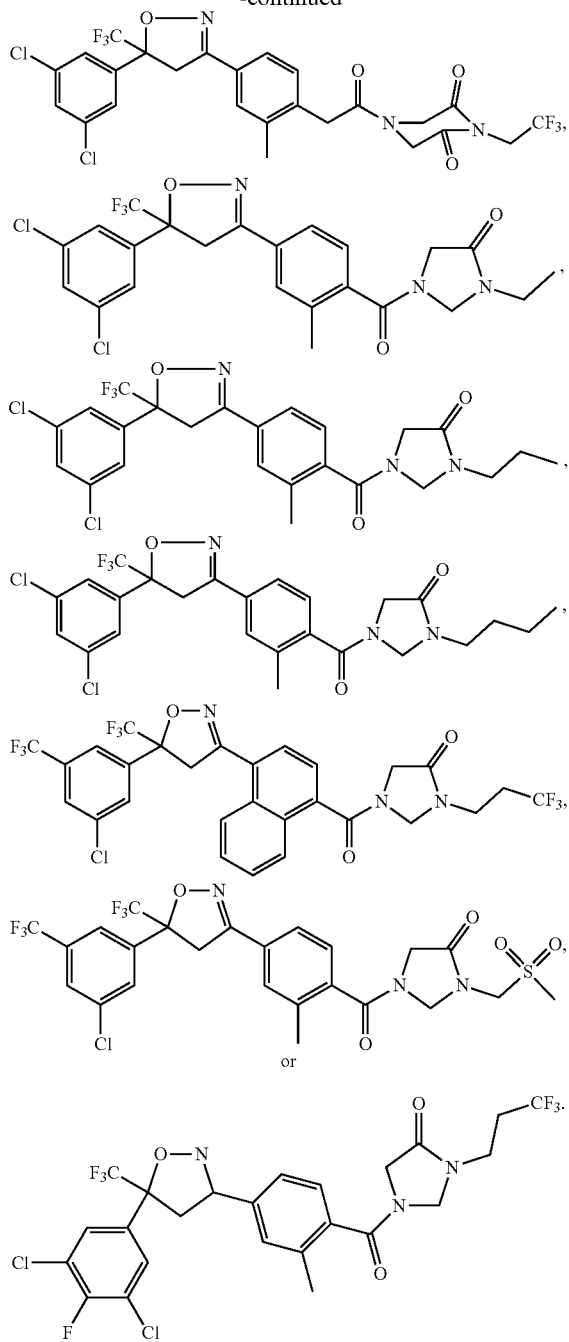

19. A composition for the treatment or prevention of a parasitic infection or infestation in an animal comprising an effective amount of an isoxazoline compound of formula (IB) of claim 8 in combination with a pharmaceutically acceptable carrier.

20. A composition for the treatment or prevention of a parasitic infection or infestation in an animal comprising an effective amount of an isoxazoline compound of formula (ID) of claim 10 in combination with a pharmaceutically acceptable carrier.

21. A composition for the treatment or prevention of a parasitic infection or infestation in an animal comprising an effective amount of an isoxazoline compound of formula (IE) of claim 11 in combination with a pharmaceutically acceptable carrier.

22. A composition for the protection of crops, plants, plant propagation material or material made from wood from pests comprising a pesticidally effective amount of an isoxazoline compound of formula (IB) of claim 8 in combination with an agriculturally acceptable carrier or diluent.

23. A composition for the protection of crops, plants, plant propagation material or material made from wood from pests comprising a pesticidally effective amount of an isoxazoline compound of formula (ID) of claim 10 in combination with an agriculturally acceptable carrier or diluent.

24. A composition for the protection of crops, plants, plant propagation material or material made from wood from pests comprising a pesticidally effective amount of an isoxazoline compound of formula (IE) of claim 11 in combination with an agriculturally acceptable carrier or diluent.

25. A method for the treatment or prevention of a parasitic infection or infestation in an animal, comprising administering to the animal a parasiticidally effective amount of an isoxazoline compound of formula (IB) of claim 8 to the animal.

26. A method for the treatment or prevention of a parasitic infection or infestation in an animal, comprising administering to the animal a parasiticidally effective amount of an isoxazoline compound of formula (ID) of claim 10 to the animal.

27. A method for the treatment or prevention of a parasitic infection or infestation in an animal, comprising administering to the animal a parasiticidally effective amount of an isoxazoline compound of formula (IE) of claim 11 to the animal.

28. A method for protecting crops and growing plants from attack or infestation by insect pests, comprising contacting a plant, or soil or water in which the plant is growing, with an isoxazoline compound of formula (IB) of claim 8.

29. A method for protecting crops and growing plants from attack or infestation by insect pests, comprising contacting a plant, or soil or water in which the plant is growing, with an isoxazoline compound of formula (ID) of claim 10.

30. A method for protecting crops and growing plants from attack or infestation by insect pests, comprising contacting a plant, or soil or water in which the plant is growing, with an isoxazoline compound of formula (IE) of claim 11.

* * * * *

UNITED STATES PATENT AND TRADEMARK OFFICE
CERTIFICATE OF CORRECTION

| | | |
|---|---|---|
| PATENT NO. | : 9,447,084 B2 | Page 1 of 2 |
| APPLICATION NO. | : 14/528172 | |
| DATED | : September 20, 2016 | |
| INVENTOR(S) | : Charles Q. Meng | |

It is certified that error appears in the above-identified patent and that said Letters Patent is hereby corrected as shown below:

In the Claims

In Column 189, Lines 1-8 Claim 18, please delete the first compound in the column having the following structure:

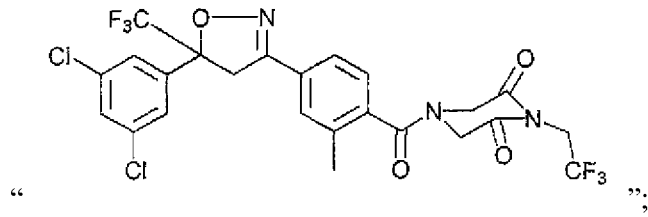
" ";

And insert the following compound structure in its place:

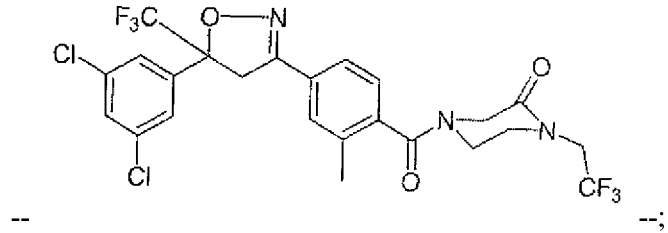
-- --;

Signed and Sealed this
Thirteenth Day of June, 2017

Joseph Matal
*Performing the Functions and Duties of the
Under Secretary of Commerce for Intellectual Property and
Director of the United States Patent and Trademark Office*

In the Column 189, Lines 22-29 Claim 18, please delete the fourth compound having the following structure:
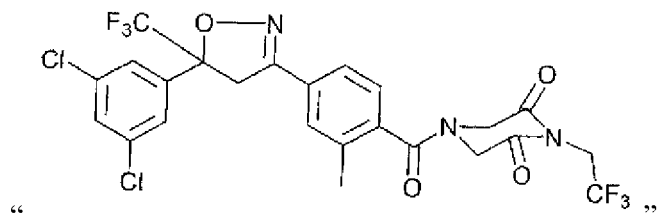
" ".
In Column 190, Lines 60-65 Claim 18, please delete the last compound in the column having the following structure:
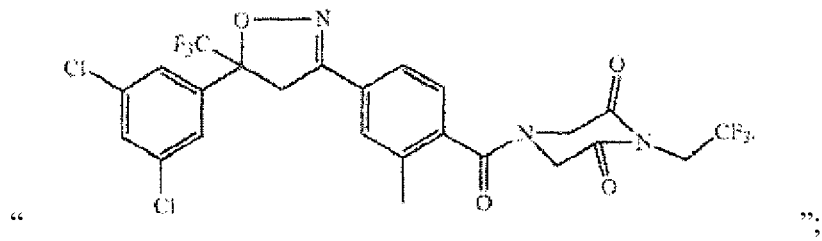
" ";
And insert in its place the compound structure shown below:
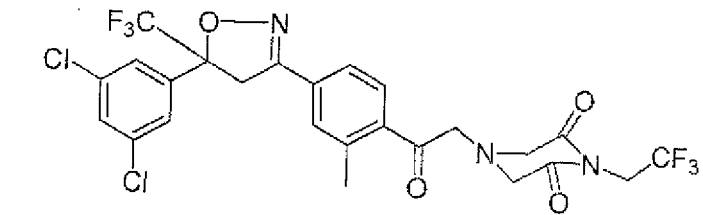
-- --.